US010501552B2

(12) United States Patent
Moore et al.

(10) Patent No.: US 10,501,552 B2
(45) Date of Patent: Dec. 10, 2019

(54) MULTIVALENT MOLECULES COMPRISING DR5-BINDING DOMAINS

(71) Applicant: MacroGenics, Inc., Rockville, MD (US)

(72) Inventors: Paul A. Moore, North Potomac, MD (US); Leslie S. Johnson, Darnestown, MD (US); Jonathan C. Li, Millbrae, CA (US); Kalpana Shah, Boyds, MD (US)

(73) Assignee: MacroGenics, Inc., Rockville, MD (US)

(*) Notice: Subject to any disclaimer, the term of this patent is extended or adjusted under 35 U.S.C. 154(b) by 0 days.

(21) Appl. No.: 15/545,871

(22) PCT Filed: May 29, 2015

(86) PCT No.: PCT/US2015/033099
§ 371 (c)(1),
(2) Date: Jul. 24, 2017

(87) PCT Pub. No.: WO2016/122702
PCT Pub. Date: Aug. 4, 2016

(65) Prior Publication Data
US 2018/0016344 A1 Jan. 18, 2018

Related U.S. Application Data

(60) Provisional application No. 62/149,139, filed on Apr. 17, 2015, provisional application No. 62/107,871, filed on Jan. 26, 2015.

(51) Int. Cl.
A61K 39/395 (2006.01)
C07K 16/28 (2006.01)
C07K 16/30 (2006.01)
A61K 39/00 (2006.01)

(52) U.S. Cl.
CPC .......... C07K 16/2878 (2013.01); C07K 16/30 (2013.01); A61K 2039/505 (2013.01); C07K 2317/24 (2013.01); C07K 2317/35 (2013.01); C07K 2317/622 (2013.01); C07K 2317/73 (2013.01); C07K 2317/92 (2013.01)

(58) Field of Classification Search
None
See application file for complete search history.

(56) References Cited

U.S. PATENT DOCUMENTS

| | | |
|---|---|---|
| 4,105,603 A | 8/1978 | Vale, Jr. et al. |
| 4,526,938 A | 7/1985 | Churchill et al. |
| 4,816,567 A | 3/1989 | Cabilly et al. |
| 4,880,078 A | 11/1989 | Inoue et al. |
| 4,928,535 A | 5/1990 | Dang et al. |
| 4,980,286 A | 12/1990 | Morgan |
| 5,128,326 A | 7/1992 | Leshchiner et al. |
| 5,290,540 A | 3/1994 | Prince et al. |
| 5,565,332 A | 10/1996 | Baier et al. |
| 5,580,717 A | 12/1996 | Dower et al. |
| 5,624,821 A | 4/1997 | Winter |
| 5,679,377 A | 10/1997 | Bernstein |
| 5,733,743 A | 3/1998 | Winter et al. |
| 5,807,715 A | 9/1998 | Morrison et al. |
| 5,814,056 A | 9/1998 | Liu et al. |
| 5,855,913 A | 1/1999 | Hanes et al. |
| 5,866,692 A | 2/1999 | Shitara et al. |
| 5,874,064 A | 2/1999 | Lotan et al. |
| 5,885,573 A | 3/1999 | Bluestone |
| 5,888,553 A | 3/1999 | Dunn |
| 5,912,015 A | 6/1999 | Bernstein et al. |
| 5,916,597 A | 6/1999 | Lee et al. |
| 5,934,272 A | 8/1999 | Lloyd et al. |
| 5,945,155 A | 8/1999 | Grill et al. |
| 5,985,309 A | 11/1999 | Wang et al. |
| 5,985,320 A | 11/1999 | Edwards et al. |
| 5,989,463 A | 11/1999 | Tracy et al. |

(Continued)

FOREIGN PATENT DOCUMENTS

| | | |
|---|---|---|
| CN | 102924600 | 2/2013 |
| EP | 0359096 | 11/1997 |

(Continued)

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Abdulghani, J. et al. (2010) "*TRAIL Receptor Signaling and Therapeutics*," Expert Opin. Ther. Targets 14(10):1091-1108.
Alegre, M.L. et al. (1994) "*A Non Activating "Humanized" Anti-CD3 Monoclonal Antibody Retains Immunosuppressive Properties in Vivo*," Transplantation 57:1537-1543.

(Continued)

Primary Examiner — Joanne Hama
Assistant Examiner — Jon M Lockard
(74) Attorney, Agent, or Firm — AuerbachSchrot LLC; William C. Schrot; Jeffrey I. Auerbach

(57) ABSTRACT

The present invention is directed to multivalent DR5-Binding Molecules that comprise Binding Domain(s) of anti-DR5 antibodies, and particularly Binding Domain(s) of anti-human DR5 antibodies. The DR5-Binding Molecules of the present invention include bivalent and tetravalent molecules having two, three or four DR5-Binding Domains each capable of binding human DR5. In particular, the present invention is directed to multivalent DR5-Binding Molecules that comprise diabodies, and more particularly, diabodies that comprise a covalently bonded complex of two or more polypeptide chains. The invention particularly pertains to such multivalent DR5-Binding Molecules that comprise of the anti-DR5 antibodies DR5 mAb 1 and/or DR5 mAb 2, and/or humanized and chimeric versions of such antibodies.

26 Claims, 44 Drawing Sheets
Specification includes a Sequence Listing.

(56) References Cited

U.S. PATENT DOCUMENTS

| | | |
|---|---|---|
| 5,997,867 A | 12/1999 | Sims |
| 6,019,968 A | 2/2000 | Eljamal et al. |
| 6,054,297 A | 4/2000 | Carter |
| 6,180,377 B1 | 1/2001 | Morgan et al. |
| 6,194,551 B1 | 2/2001 | Presta |
| 6,218,149 B1 | 4/2001 | Morrison et al. |
| 6,265,150 B1 | 7/2001 | Logtenberg et al. |
| 6,331,415 B1 | 12/2001 | Cabilly et al. |
| 6,472,511 B1 | 10/2002 | Qu et al. |
| 6,946,292 B2 | 9/2005 | Kanda et al. |
| 7,122,646 B2 | 10/2006 | Winter et al. |
| 7,129,330 B1 | 10/2006 | Little et al. |
| 7,276,586 B2 | 10/2007 | Goddard |
| 7,476,383 B2 | 1/2009 | Zhou et al. |
| 7,507,796 B2 | 3/2009 | Little et al. |
| 7,704,502 B2 | 4/2010 | Zhou et al. |
| 7,893,216 B2 | 2/2011 | Liu et al. |
| 7,897,730 B2 | 3/2011 | Yu et al. |
| 7,981,421 B2 | 7/2011 | Ohsumi et al. |
| 8,029,783 B2 | 10/2011 | Adams et al. |
| 8,030,023 B2 | 10/2011 | Adams et al. |
| 8,067,001 B2 | 11/2011 | Zhou et al. |
| 8,097,704 B2 | 1/2012 | Kim et al. |
| 8,148,496 B2 | 4/2012 | Little et al. |
| 8,173,128 B2 | 5/2012 | Nasoff et al. |
| 8,329,180 B2 | 12/2012 | Zhou et al. |
| 8,372,396 B2 | 2/2013 | Liu et al. |
| 8,409,570 B2 | 4/2013 | Adams et al. |
| 8,461,311 B2 | 6/2013 | Spitzer et al. |
| 8,703,712 B2 | 4/2014 | Zhou et al. |
| 8,715,668 B2 | 5/2014 | Zhou et al. |
| 9,127,070 B2 | 9/2015 | Oguni et al. |
| 9,284,375 B2 | 3/2016 | Huang et al. |
| 9,296,816 B2 | 3/2016 | Johnson et al. |
| 9,481,730 B2 | 11/2016 | Bruenker et al. |
| 9,528,993 B2 | 12/2016 | Zhou et al. |
| 9,700,618 B2 | 7/2017 | Zhou et al. |
| 9,889,197 B2 | 2/2018 | Johnson et al. |
| 2002/0004587 A1 | 1/2002 | Miller et al. |
| 2002/0028486 A1 | 3/2002 | Morrison |
| 2004/0220388 A1 | 11/2004 | Mertens et al. |
| 2005/0079170 A1 | 4/2005 | Little et al. |
| 2009/0060910 A1 | 3/2009 | Huang et al. |
| 2009/0175854 A1 | 7/2009 | Ashkenazi |
| 2009/0208483 A1 | 8/2009 | Zhou et al. |
| 2009/0317384 A1 | 12/2009 | Ashkenazi et al. |
| 2011/0070248 A1 | 3/2011 | Ichikawa et al. |
| 2011/0318366 A1 | 12/2011 | Cromie et al. |
| 2012/0070432 A1 | 3/2012 | Wiezorek et al. |
| 2013/0064838 A1 | 3/2013 | Huang et al. |
| 2013/0189263 A1 | 7/2013 | Little et al. |
| 2013/0280282 A1 | 10/2013 | Yada et al. |
| 2013/0295121 A1 | 11/2013 | Johnson et al. |
| 2014/0010812 A1 | 1/2014 | Li et al. |
| 2014/0105898 A1 | 4/2014 | Zauli et al. |
| 2014/0370019 A1 | 12/2014 | Bruenker et al. |

FOREIGN PATENT DOCUMENTS

| | | |
|---|---|---|
| EP | 1293514 | 11/2006 |
| EP | 1078004 | 10/2007 |
| EP | 1958959 | 8/2008 |
| EP | 2046836 | 4/2009 |
| EP | 2158221 | 3/2010 |
| EP | 1576179 | 9/2010 |
| EP | 1506285 | 12/2010 |
| EP | 2292794 | 7/2011 |
| EP | 2376109 | 10/2011 |
| EP | 2287285 | 5/2012 |
| EP | 2480230 | 8/2012 |
| EP | 2059533 | 11/2012 |
| EP | 2569336 | 3/2013 |
| EP | 2371866 | 6/2013 |
| EP | 2601216 | 6/2013 |
| EP | 2021370 | 10/2013 |
| EP | 2684896 | 1/2014 |
| EP | 1790663 | 3/2014 |
| EP | 2714079 | 4/2014 |
| EP | 2350641 | 9/2014 |
| EP | 2368910 | 2/2016 |
| EP | 2636736 | 3/2016 |
| EP | 2361936 | 4/2016 |
| WO | WO 1991/003493 | 3/1991 |
| WO | WO 1991/005548 | 5/1991 |
| WO | WO 1992/019244 | 11/1992 |
| WO | WO 1992/022583 | 12/1992 |
| WO | WO 1996/020698 | 7/1996 |
| WO | WO 1997/032572 | 9/1997 |
| WO | WO 1997/044013 | 11/1997 |
| WO | WO 1998/002463 | 1/1998 |
| WO | WO 1998/031346 | 7/1998 |
| WO | WO 1999/015154 | 4/1999 |
| WO | WO 1999/020253 | 4/1999 |
| WO | WO 1999/057150 | 11/1999 |
| WO | WO 1999/058572 | 11/1999 |
| WO | WO 1999/066903 | 12/1999 |
| WO | WO 2000/042072 | 7/2000 |
| WO | WO 2002/002781 | 1/2002 |
| WO | WO 2003/012069 | 2/2003 |
| WO | WO 2003/025018 | 3/2003 |
| WO | WO 2003/035835 | 5/2003 |
| WO | WO 2005/070966 | 8/2005 |
| WO | WO 2006/107617 | 10/2006 |
| WO | WO 2006/107786 | 10/2006 |
| WO | WO 2007/024715 | 3/2007 |
| WO | WO 2007/046893 | 4/2007 |
| WO | WO 2007/075270 | 7/2007 |
| WO | WO 2007/146968 | 12/2007 |
| WO | WO 2008/003103 | 1/2008 |
| WO | WO 2008/003116 | 1/2008 |
| WO | WO 2008/004760 | 1/2008 |
| WO | WO 2008/024188 | 2/2008 |
| WO | WO 2008/027236 | 3/2008 |
| WO | WO 2008/091908 | 7/2008 |
| WO | WO 2008/145142 | 12/2008 |
| WO | WO 2008/157379 | 12/2008 |
| WO | WO 2009/018386 | 2/2009 |
| WO | WO 2009/132876 | 11/2009 |
| WO | WO 2010/028795 | 3/2010 |
| WO | WO 2010/028796 | 3/2010 |
| WO | WO 2010/028797 | 3/2010 |
| WO | WO 2010/080538 | 7/2010 |
| WO | WO 2010/108127 | 9/2010 |
| WO | WO 2010/136172 | 12/2010 |
| WO | WO 2011/038159 | 3/2011 |
| WO | WO 2011/086091 | 7/2011 |
| WO | WO 2011/133886 | 10/2011 |
| WO | WO 2011/143614 | 11/2011 |
| WO | WO 2012/009544 | 1/2012 |
| WO | WO 2012/018687 | 2/2012 |
| WO | WO 2012/156430 | 11/2012 |
| WO | WO 2012/162068 | 11/2012 |
| WO | WO 2012/162583 | 11/2012 |
| WO | WO 2013/003652 | 1/2013 |
| WO | WO 2013/006544 | 1/2013 |
| WO | WO 2013/013700 | 1/2013 |
| WO | WO 2013/070565 | 5/2013 |
| WO | WO 2013/119903 | 8/2013 |
| WO | WO 2013/148877 | 10/2013 |
| WO | WO 2013/163229 | 10/2013 |
| WO | WO 2013/163427 | 10/2013 |
| WO | WO 2013/174873 | 11/2013 |
| WO | WO 2014/009358 | 1/2014 |
| WO | WO 2014/022540 | 2/2014 |
| WO | WO 2014/035474 | 3/2014 |
| WO | WO 2014/050779 | 4/2014 |
| WO | WO 2014/159562 | 10/2014 |
| WO | WO 2014/161845 | 10/2014 |

(56) References Cited

FOREIGN PATENT DOCUMENTS

| WO | WO 2014/180754 | 11/2014 |
|---|---|---|
| WO | WO 2015/184203 | 12/2015 |

OTHER PUBLICATIONS

Alison, M.R. et al. (2009) "*Stem Cells and Lung Cancer: Future Therapeutic Targets?*" Expert Opin. Biol. Ther. 9(9):1127-1141.
Allen, J.E. et al. (2012) "*Regulation of the Human TRAIL Gene*," Cancer Biol. Ther. 13(12):1143-1151.
Alt et al. (1999) "*Novel tetravalent and bispecific IgG-like antibody molecules combining single-chain diabodies with the immunoglobulin γl Fc or CH3 region*" FEBS Lett. 454(1-2):90-94.
Andera, L. (2009) "*Signaling Activated by the Death Receptors of the TNFR Family*," Biomed. Pap. Med. Fac. Univ. Palacky Olomouc Czech. Repub. 153(3):173-180.
Apostolovic, B. et al. (2008) "*pH-Sensitivity of the E3/K3 Heterodimeric Coiled Coil*," Biomacromolecules 9:3173-3180.
Armour, K.L. et al. (1999) "*Recombinant human IgG Molecules Lacking Fcgamma Receptor I Binding and Monocyte Triggering Activities*," Eur. J. Immunol. 29:2613-24.
Arndt, K.M. et al. (2001) "*Helix-stabilized Fv (hsFv) Antibody Fragments: Substituting the Constant Domains of a Fab Fragment for a Heterodimeric Coiled-coil Domain*," J. Molec. Biol. 312:221-228.
Arndt, K.M. et al. (2002) "*Comparison of in Vivo Selection and Rational Design of Heterodimeric Coiled Coils*," Structure 10:1235-1248.
Aruffo, A. et al. (1987) "*Molecular Cloning of a CD28 cDNA by a High-Efficiency COS Cell Expression System*," Proc. Natl. Acad. Sci. (U.S.A.) 84:8573-8577.
Asano et al. (2004) "*A Diabody for Cancer Immunotherapy and Its Functional Enhancement by Fusion of Human Fc Domain*," Abstract 3P-683, J. Biochem. 76(8):992.
Atwell et al. (1997) "*Stable Heterodimers From Remodeling the Domain Interface of a Homodimer Using a Phage Display Library*," J. Mol. Biol. 270: 26-35.
Baeuerle, P.A. et al. (2009) "*Bispecific T-Cell Engaging Antibodies for Cancer Therapy*," Cancer Res. 69(12):4941-4944.
Bajaj, M. et al. (2011) "*Conatumumab: A Novel Monoclonal Antibody Against Death Receptor 5 for the Treatment of Advanced Malignancies in Adults*," Expert Opin. Biol. Ther. 11(11):1519-1524.
Bedzyk, W.D. et al. (1989) "*Comparison of Variable Region Primary Structures Within an Anti-Fluorescein Idiotype Family*," J. Biol. Chem. 264(3): 1565-1569.
Benedict, C.A. et al. (2012) "*TRAIL: Not Just for Tumors Anymore?,* " J. Exp. Med. 209(11):1903-1906.
Bird et al. (1988) "*Single-Chain Antigen-Binding Proteins*," Science 242:423-426.
Boucher, C. et al. (2010) "*Protein Detection by Western Blot Via Coiled—Coil Interactions*," Analytical Biochemistry 399:138-140.
Brown et al. (1987) "*Tumor-Specific Genetically Engineered Murine/ Human Chimeric Monoclonal Antibody*," Cancer Res. 47:3577-3583.
Brüggemann et al. (1987) "*Comparison of the effector functions of human immunoglobulins using a matched set of chimeric antibodies*". J. Exp. Med 166:1351-1361.
Buchsbaum, D.J. et al. (2003) "*Antitumor Efficacy of TRA-8 Anti-DR5 Monoclonal Antibody Alone or in Combination With Chemotherapy and/or Radiation Therapy in a Human Breast Cancer Model*," Clin. Cancer Res. 9:3731-3741.
Buchsbaum, D.J. et al. (2006) "*TRAIL Receptor-Targeted Therapy*," Future Oncol. 2(4):493-508.
Buchwald et al. (1980) "*Long-Term, Continuous Intravenous Heparin Administration by an Implantable Infusion Pump in Ambulatory Patients With Recurrent Venous Thrombosis*," Surgery 88:507-516.

Butler et al. (2006) "*The histone deacetylase inhibitor, suberoylanilide hydroxamic acid, overcomes resistance of human breast cancer cells to Apo2L/TRAIL*," Int J Cancer. 15:944-54.
Cachia, P.J. et al. (2004) "*Synthetic Peptide Vaccine Development: Measurement of Polyclonal Antibody Affinity and Cross Reactivity Using a New Peptide Capture and Release System for Surface Plasmon Resonance Spectroscopy*," J. Mol. Recognit. 17:540-557.
Camidge, D. et al. (2007) "*A Phase I Safety and Pharmacokinetic Study of Apomab, a Human DR5 Agonist Antibody, in Patients With Advanced Cancer*," 2007 ASCO Annual Meeting Proceedings (Post-Meeting Edition), J. Clin. Oncol. 25(18S):3582 (Abstract).
Canafax, D.M. et al. (1987) "*Monoclonal Antilymphocyte Antibody (OKT3) Treatment of Acute Renal Allograft Rejection*," Pharmacotherapy 7(4):121-124.
Carlo-Stella, C. et al. (2007) "*Targeting TRAIL Agonistic Receptors for Cancer Therapy*," Clin, Cancer 13(8):2313-2317.
Caron, P.C. et al. (1992) "*Engineered Humanized Dimeric Forms of IgG Are More Effective Antibodies*," J. Exp. Med. 176:1191-1195.
Carter, P. et al. (1992) "*Humanization of an Anti-p185her2 Antibody for Human Cancer Therapy*," Proc. Natl. Acad. Sci. (U.S.A.) 89:4285-4289.
Chan, C.E. et al. (2009) "*The Use of Antibodies in the Treatment of Infectious Diseases*," Singapore Med. J. 50(7):663-666.
Chan, F.K.-M. (2007) "*Three is Better Than One: Pre-Ligand Receptor Assembly in the Regulation of TNF Receptor Signaling*," Cytokine 37(2):101-107.
Chappel et al. (1991) "*Identification of the Fc gamma receptor class I binding site in human IgG through the use of recombinant IgG1/IgG2 hybrid and point-mutated antibodies*" Proc. Natl. Acad. Sci. (U.S.A.) 88:9036-9040.
Chappel et al. (1993) "*Identification of a Secondary FcgammaRI Binding Site within a Genetically Engineered Human IgG Antibody*," J. Biol. Chem. 33:25124-25131.
Charafe-Jauffret, E. et al. (2009) "*Breast Cancer Stem Cells: Tools and Models to Rely On*," BMC Cancer 9:202.
Chaudhari, B.R. et al. (2006) "*Following the TRAIL to Apoptosis*," Immunologic Res. 35(3):249-262.
Co, M. S. et al. (1991) "*Humanized Antibodies for Antiviral Therapy*," Proc. Natl. Acad. Sci. (U.S.A.) 88:2869-2873.
Co, M.S. et al. (1992) "*Chimeric and Humanized Antibodies With Specificity for the CD33 Antigen*," J. Immunol. 148:1149-1154.
Daugherty et al. (1991) "*Polymerase Chain Reaction Facilitates the Cloning, CDR-Grafting, and Rapid Expression of a Murine Monoclonal Antibody Directed Against the CD18 Component of Leukocyte Integrins*," Nucl. Acids Res. 19:2471-2476.
De Bruyn, M. et al. (2013) "*Antibody-Based Fusion Proteins to Target Death Receptors in Cancer*," Cancer Lett. 332:175-183.
De Crescenzo, G.D. et al. (2003) "*Real-Time Monitoring of the Interactions of Two-Stranded de novo Designed Coiled-Coils: Effect of Chain Length on the Kinetic and Thermodynamic Constants of Binding*," Biochemistry 42:1754-1763.
Dimberg, L.Y. et al. (2013) "*On the TRAIL to Successful Cancer Therapy? Predicting and Counteracting Resistance Against TRAIL-Based Therapeutics*," Oncogene 32:1341-1350.
Du, Y.-W. et al. (2011) "*A Novel Agonistic Anti-Human Death Receptor 5 Monoclonal Antibody With Tumoricidal Activity Induces Caspase- and Mitochondrial-Dependent Apoptosis in Human Leukemia Jurkat Cells*," Cancer Biother. Radiopharmaceut. 26(2):143-152.
Duncan, A.R. et al. (1988) "*Localization of the Binding Site for the Human High-Affinity Fc Receptor on IgG*," Nature 332:563-564.
During et al. (1989) "*Controlled Release of Dopamine From a Polymeric Brain Implant: in Vivo Characterization*," Ann. Neurol. 25:351-356.
Falschlehner, C. et al. (2007) "*TRAIL Signalling: Decisions Between Life and Death*," Intl. J. Biochem. Cell Biol. 39:1462-1475.
Falschlehner, C. et al. (2009) "*TRAIL and Other TRAIL Receptor Agonists as Novel Cancer Therapeutics*," in: Therapeutic Targets of the TNF Superfamily (Grewal, I.S., Ed.) Landes Bioscience and Springer Science+Business Media, NY; pp. 195-206.
Fernandez-Rodriquez, J. et al. (2012) "*Induced Heterodimerization and Purification of Two Target Proteins by a Synthetic Coiled-Coil Tag*," Protein Science 21:511-519.

(56) References Cited

OTHER PUBLICATIONS

Finnberg, N. et al. (2008) "*TRAIL Death Receptors as Tumor Suppressors and Drug Targets*," Cell Cycle 7(11):1525-1528.
Fitzgerald et al. (1997) "*Improved Tumour Targeting by Disulphide Stabilized Diabodies Expressed in Pichia pastoris*," Protein Eng. 10:1221.
Flesch, B.K. et al. (2000) "*Functions of the Fc Receptors for Immunoglobulin G*," J. Clin. Lab. Anal. 14:141-156.
Ganesan, A. (2006) "*Solid-Phase Synthesis in the Twenty-First Century*," Mini Rev. Med. Chem. 6(1):3-10.
Ghosh, T.S. et al. (2009) "*End-To-End and End-To-Middle Interhelical Interactions: New Classes of Interacting Helix Pairs in Protein Structures*," Acta Crystallographica D65:1032-1041.
Ghotra, V.P. et al. (2009) "*The Cancer Stem Cell Microenvironment and Anti-Cancer Therapy*," Int. J. Radiat. Biol. 85(11):955-962.
Gorman, S. D. et al. (1991) "*Reshaping a Therapeutic CD4 Antibody*," Proc. Natl. Acad. Sci. (U.S.A.) 88:4181-4185.
Greco, F.A. et al. (2008) "*Phase 2 Study of Mapatumumab, a Fully Human Agonistic Monoclonal Antibody Which Targets and Activates the TRAIL Receptor-1, in Patients With Advanced Non-Small Cell Lung Cancer*," Lung Cancer 61:82-90.
Grigoryan, G. et al. (2008) "*Structural Specificity in Coiled-Coil Interactions*," Curr. Opin. Struc. Biol. 18:477-483.
Gruber, M. et al. (1994) "*Efficient Tumor Cell Lysis Mediated by a Bispecific Single Chain Antibody Expressed in Escherichia coli*," J. Immunol. 152(11):5368-5374.
Guicciardi, M.E. et al. (2009) "*Life and Death by Death Receptors*," FASEB J. 23:1625-1637.
Gupta, P.B. et al. (2009) "*Cancer Stem Cells: Mirage or Reality?*" Nat. Med. 15(9):1010-1012.
Hellwig, C.T. et al. (2012) "*Trail Signaling and Synergy Mechanisms Used in TRAIL-Based Combination Therapies*," Molec. Cancer Ther. 11(1):3-13.
Henson, E.S. et al. (2008) "*The Role of TRAIL Death Receptors in the Treatment of Hematological Malignancies*," Leukemia & Lymphoma 49(1):27-35.
Hermann, P.C. et al. (2009) "*Pancreatic Cancer Stem Cells—Insights and Perspectives*," Expert. Opin. Biol. Ther. 9(10):1271-1278.
Holliger et al. (1993) "*Diabodies': Small Bivalent and Bispecific Antibody Fragments*," Proc. Natl. Acad. Sci. (U.S.A.) 90:6444-6448.
Holliger et al. (1996) "*Specific Killing of Lymphoma Cells by Cytotoxic T-Cells Mediated by a Bispecific Diabody*," Protein Eng. 9:299-305.
Hollstein, M. et al. (1994) "*Database of p53 Gene Somatic Mutations in Human Tumors and Cell Lines*," Nucleic Acids Res. 22:3551-3555.
Houghten, R.A. (1985) "*General Method for the Rapid Solid-Phase Synthesis of Large Numbers of Peptides: Specificity of Antigen-Antibody Interaction at the Level of Individual Amino Acids*," Proc. Natl. Acad. Sci. (U.S.A.) 82(15):5131-5135.
Howard et al. (1989) "*Intracerebral Drug Delivery in Rats With Lesion-Induced Memory Deficits*," J. Neurosurg. 7(1):105-112.
Huang, Y. et al. (2007) "*TRAIL Death Receptors and Cancer Therapeutics*," Toxicol. Appl. Pharmacol. 224:284-289.
Humphreys, R.C. et al. (2008) "*Trail Receptors: Targets for Cancer Therapy*," in: Programmed Cell Death in Cancer Progression and Therapy Khosravi-Far, R. and White, E. (Eds.) Springer, NY; pp. 127-158.
Hutchins et al. (1995) "*Improved Biodistribution, Tumor Targeting, and Reduced Immunogenicity in Mice With a Gamma 4 Variant of Campath-1H*," Proc. Natl. Acad. Sci. (U.S.A.) 92:11980-84.
Ichikawa, K. et al. (2001) "*Tumoricidal Activity of a Novel Anti-Human DR5 Monoclonal Antibody Without Hepatocyte Cytotoxicity*," Nat. Med. 7:954-960.
Idusogie, E.E. et al. (2000) "*Mapping of the C1q Binding Site on Rituxan, a Chimeric Antibody With a Human IgG Fc*," J. Immunol. 164:4178-84.
Idusogie, E.E. et al. (2001) "*Engineered Antibodies With Increased Activity to Recruit Complement*," J. Immunol. 166:2571-75.
Jefferis, B.J. et al. (2002) "*Interaction Sites on Human IgG-Fc for FcgammaR: Current Models*," Immunol. Lett. 82:57-65.
Jefferis, R. et al. (1995) "*Recognition Sites on Human IgG for Fc Gamma Receptors: The Role of Glycosylation*," Immunol. Lett. 44:111-17.
Jefferis, R. et al. (1996) "*Modulation of Fc(Gamma)R and Human Complement Activation by IgG3-Core Oligosaccharide Interactions*," Immunol. Lett. 54:101-04.
Jennings, V.M. (1995) "*Review of Selected Adjuvants Used in Antibody Production*," ILAR J. 37(3):119-125.
Jo, M. M et al. (2000) "*Apoptosis Induced in Normal Human Hepatocytes by Tumor Necrosis Factor-Related Apoptosis Inducing Ligand*," Nat. Med. 6:564-567.
Johansson, M.U. et al. (2002) "*Structure, Specificity, and Mode of Interaction for Bacterial Albumin-Binding Modules*," J. Biol. Chem. 277(10):8114-8120.
Johnson, S. et al. (2010) "*Effector Cell Recruitment With Novel Fv-Based Dual-Affinity Re-Targeting Protein Leads to Potent Tumor Cytolysis and in vivo B-Cell Depletion*," J. Mol. Biol. 399(3):436-449.
Johnstone, R.W. et al. (2008) "*The TRAIL Apoptotic Pathway in Cancer Onset, Progression and Therapy*," Nat. Rev. Cancer 8:782-798.
Joliot et al. (1991) "*Antennapedia Homeobox Peptide Regulates Neural Morphogenesis,*" Proc. Natl. Acad. Sci. (U.S.A.) 88:1864-1868.
Jones et al. (1986) "*Replacing the Complementarity-Determining Regions in a Human Antibody With Those From a Mouse*," Nature 321:522-525.
Kandasamy, K. et al. (2003) "*Involvement of Proapoptotic Molecules Bax and Bak in Tumor Necrosis Factor-Related Apoptosis-Inducing Ligand (TRAIL)-Induced Mitochondrial Disruption and Apoptosis: Differential Regulation of Cytochrome C and Smac/DIABLO Release*," Cancer Res. 63:1712-1721.
Kang, Z. et al. (2011) "*Drozitumab, a Human Antibody to Death Receptor 5, Has Potent Antitumor Activity Against Rhabdomyosarcoma With the Expression of Caspase-8 Predictive of Response*," Clin. Cancer Res. 17(10):3181-3192.
Kelley, S.K. et al. (2004) "*Targeting Death Receptors in Cancer With Apo2L/TRAIL*," Curr. Opin. Pharmacol. 4:333-339.
Kettleborough, C. A. et al. (1991) "*Humanization of a Mouse Monoclonal Antibody by CDR-Grafting: The Importance of Framework Residues on Loop Conformation*," Protein Engineering 4:773-3783.
Kischkel, F.C. et al. (2000) "*Apo2L/TRAIL-Dependent Recruitment of Endogenous FADD and Caspase-8 to Death Receptors 4 and 5*," Immunity 12:611-620.
Kohler, G. et al. (1975) "*Continuous Cultures of Fused Cells Secreting Antibody of Predefined Specificity,*" Nature 256:495-497.
Koschny, R. et al. (2007) "*The Promise of TRAIL—Potential and Risks of a Novel Anticancer Therapy*," J. Molec. Med. 85:923-935.
Kruyt, F.A.E. (2008) "*TRAIL and Cancer Therapy*," Cancer Lett. 263 14-25.
Kuhns, M.S. et al. (2006) "*Deconstructing the Form and Function of the TCR/CD3 Complex*," Immunity. Feb. 2006;24(2):133-139.
Kuijlen, J.M.A. et al. (2010) "*Review: On TRAIL for Malignant Glioma Therapy?,*" Neuropathol. Appl. Neurobiol. 36:168-182.
Langer (1990), "*New Methods of Drug Delivery*," Science 249:1527-1533.
Lawrence, D, et al. (2001) "*Differential Hepatocyte Toxicity of Recombinant Apo2L/TRAIL Versions*," Nat. Med. 7:383-385.
Lawson, J.C. et al. (2009) "*Cancer Stem Cells in Breast Cancer and Metastasis*," Breast Cancer Res. Treat. 118(2):241-254.
Levy et al. (1985) "*Inhibition of Calcification of Bioprosthetic Heart Valves by Local Controlled-Release Diphosphonate*," Science 228:190-192.
Li, J. et al. (2008) "*LBY135, a Novel Anti-DR5 Agonistic Antibody Induces Tumor Cell-Specific Cytotoxic Activity in Human Colon Tumor Cell Lines and Xenografts*," Drug Dev. Res. 69:69-82.
Litowski, J.R. et al. (2002) "*Designing Heterodimeric Two-Stranded α-Helical Coiled-Coils: The Effects of Hydrophobicity*

(56) References Cited

OTHER PUBLICATIONS and α-Helical Propensity on Protein Folding, Stability, and Specificity," J. Biol. Chem. 277:37272-37279.
LoBuglio, A.F. et al. (1989) "Mouse/Human Chimeric Monoclonal Antibody in Man: Kinetics and Immune Response," Proc. Natl. Acad. Sci. (U.S.A.) 86:4220-4224.
Lonberg, N. et al. (1995) "Human Antibodies From Transgenic Mice," Int. Rev. Immunol 13:65-93.
LoRusso, P. et al. (2007) "First-In-Human Study of AMG 655, a Pro-Apoptotic TRAIL Receptor-2 Agonist, in Adult Patients With Advanced Solid Tumors," 2007 ASCO Annual Meeting Proceedings Part I. J. Clin. Oncol. 25(18S):3534 (Abstract).
Lu et al., (2008) "The Effect of a Point Mutation on the Stability of IgG4 as Monitored by Analytical Ultracenfrifugation," J Pharmaceutical Sciences 97:960-969.
Lu, D. et al. (2005) "A Fully Human Recombinant IgG-Like Bispecific Antibody to Both the Epidermal Growth Factor Receptor and the Insulin-Like Growth Factor Receptor for Enhanced Antitumor Activity," J. Biol. Chem. 280(20):19665-19672.
Lund et al. (1991) "Human Fc Gamma RI and Fc Gamma RII Interact With Distinct But Overlapping Sites on Human IgG," J. Immunol. 147:2657-2662.
Lund et al. (1992) "Multiple Binding Sites on the CH2 Domain of IgG for Mouse Fc Gamma RII," Mol. Immunol. 29:53-59.
Lund, J. et al. (1995) "Oligosaccharide-Protein Interactions in IgG Can Modulate Recognition by Fc Gamma Receptors," FASEB J. 9:115-19.
Lund, J. et al. (1996) "Multiple Interactions of IgG With Its Core Oligosaccharide Can Modulate Recognition by Complement and Human Fc Gamma Receptor I and Influence the Synthesis of Its Oligosaccharide Chains," J. Immunol. 157:4963-4969.
Maeda, H. et al. (1991) "Construction of Reshaped Human Antibodies With HIV-Neutralizing Activity," Human Antibodies Hybridoma 2:124-134.
Mahmood, Z. et al. (2010) "Death Receptors: Targets for Cancer Therapy," Exper. Cell. Res. 316:887-899.
Maksimovic-Ivanic, D. et al. (2012) "Resistance to TRAIL and How to Surmount It," Immunol. Res. 52:157-168.
Martin-Ventura, J.L. et al. (2007) "TRAIL and Vascular Injury," Frontiers in Bioscience 12:3656-3667.
Marvin et al. (2005) "Recombinant Approaches to IgG-Like Bispecific Antibodies," Acta Pharmacol. Sin. 26:649-658.
Mellier, G. et al. (2010) "TRAILing Death in Cancer," Molec. Aspects Med. 31:93-112.
Merrifield, B. (1986) "Solid Phase Synthesis," Science 232(4748):341-347.
Micheau, O. et al. (2013) "Death Receptors as Targets in Cancer," Br. J. Pharmacol. 169:1723-1744.
Mittal, S. et al. (2009) "Cancer Stem Cells: The Other Face of Janus," Amer. J. Med. Sci. 338(2):107-112.
Moore, P.A. et al. (2011) "Application of Dual Affinity Retargeting Molecules to Achieve Optimal Redirected T-Cell Killing of B-Cell Lymphoma," Blood 117(17):4542-4551.
Mori, E. et al. (2004) "Human Normal Hepatocytes Are Susceptible to Apoptosis Signal Mediated by Both TRAIL-R1 and TRAIL-R2," Cell. Death Differ. 11:203-207.
Motoki, K. et al. (2005) "Enhanced Apoptosis and Tumor Regression Induced by a Direct Agonist Antibody to Tumor Necrosis Factor-Related Apoptosis Inducing Ligand Receptor 2," Clin. Cancer Res. 11(8):3126-3135.
Nagane, M. et al. (2010) "Predominant Antitumor Effects by Fully Human Anti-TRAIL-Receptor 2 (DR5) Monoclonal Antibodies in Human Glioma Cells in Vitro and in Vivo," Neuro. Oncol. 12(7):687-700.
Nakata et al. (2004) "Histone deacetylase inhibitors upregulate death receptor 5/TRAIL-R2 and sensitize apoptosis induced by TRAIL/APO2-L in human malignant tumor cells," Oncogene 19:6261-71.
Ning et al. (1996) "Intratumoral Radioimmunotheraphy of a Human Colon Cancer Xenograft Using a Sustained Release Gel," Radiotherapy & Oncology 39:179 189.
Norman, D.J. (1995) "Mechanisms of Action and Overview of OKT3," Ther. Drug Monit. 17(6):615-620.
Oikonomou, E. et al. (2013) "The TRAIL of Oncogenes to Apoptosis," Intl. J Union Biochem. Molec. Biol. 39(4):343-354.
Olafsen et al. (2004) "Covalent Disulfide-Linked Anti-CEA Diabody Allows Site-Specific Conjugation and Radiolabeling for Tumor Targeting Applications," Prot. Engr. Des. Sel. 17:21-27.
Oldenhuis, C.N.A.M. et al. (2008) "Targeting TRAIL Death Receptors," Curr. Opin. Pharmacol. 8:433-439.
Papenfuss, K. et al. (2008) "Death Receptors as Targets for Anti-Cancer Therapy," J. Cell. Mol. Med. 12:2566-2585.
Peeters et al. (2001) "Production of Antibodies and Antibody Fragments in Plants," Vaccine 19:2756.
Peters, P et al., (2012) "Engineering an Improved IgG4 Molecule with Reduced Disulfide Bond Heterogeneity and Increased Fab Domain Thermal Stability," J. Biol. Chem. 287:24525-24533.
Plummer, R. et al. (2007) "Phase 1 and Pharmacokinetic Study of LEXATUMUM4B in Patients With Advanced Cancers," Clin. Cancer Res. 13:6187-6194.
Pollock et al. (1999) "Transgenic Milk as a Method for the Production of Recombinant Antibodies," J. Immunol Methods 231:147-157.
Presta, L.G. et al. (2002) "Engineering Therapeutic Antibodies for Improved Function," Biochem. Soc. Trans. 30:487-90.
Qin, J. et al. (2001) "Avoiding Premature Apoptosis of Normal Epidermal Cells," Nat. Med. 7:385-386.
Rahman, M. et al. (2009) "The TRAIL to Targeted Therapy of Breast Cancer," Adv. Cancer Res. 103:43-73.
Reddy, M.P. et al. (2000) "Elimination of Fc Receptor-Dependent Effector Functions of a Modified IgG4 Monoclonal Antibody to Human CD4," J. Immunol. 164:1925-1933.
Ridgway et al. (1996) "Knobs-Into-Holes' Engineering of Antibody CH3 Domains for Heavy Chain Heterodimerization," Protein Engr. 9:617-621.
Riechmann, L. et al. (1988) "Reshaping Human Antibodies for Therapy," Nature 332:323-327.
Rudner, J. et al. (2005) "Type I and Type II Reactions in TRAIL-Induced Apoptosis—Results From Dose-Response Studies," Oncogene 24:130-140.
Saleh, M.N. et al. (2008) "A Phase I Study of CS-1008 (Humanized Monoclonal Antibody Targeting Death Receptor 5 or DR5), Administered Weekly to Patients With Advanced Solid Tumors or Lymphomas," 2008 ASCO Annual Meeting Proceedings, J. Clin. Oncol. 26(15S):3537 (Abstract).
Sato, K. et al. (1993) "Reshaping a human antibody to inhibit the interleukin 6-dependent tumor cell growth". Cancer Res 53:851-856.
Saudek et al. (1989) "A Preliminary Trial of the Programmable Implantable Medication System for Insulin Delivery," N. Engl. J. Med. 321:574-579.
Schatton, T. et al. (2009) "Identification and Targeting of Cancer Stem Cells," Bioessays 31(10):1038-1049.
Schneider-Brachert, W. et al. (2013) "Membrane Trafficking of Death Receptors: Implications on Signalling," Int. J. Mol. Sci. 14:14475-14503.
Scopelliti, A. et al. (2009) "Therapeutic Implications of Cancer Initiating Cells," Expert Opin. Biol. Ther. 9(8):1005-1016.
Sefton, (1987) "Implantable Pumps," CRC Crit. Rev. Biomed. Eng. 14:201-240 (Abstract).
Shankar et al. (2009) "Suberoylanilide hydroxamic acid (Zolinza/vorinostat) sensitizes TRAIL-resistant breast cancer cells orthotopically implanted in BALB/c nude mice," Mol Cancer Ther. 8:1596-605.
Sharma, S. et al. (2008) "Phase I Trial of LBY135, a Monoclonal Antibody Agonist to DR5, Alone and in Combination With Capecitabine in Advanced Solid Tumors," 2008 ASCO Annual Meeting Proceedings. J. Clin. Oncol. 26(15S):3538 (Abstract).
Shaw et al. (1987) "Characterization of a Mouse/Human Chimeric Monoclonal Antibody (17-1A) to a Colon Cancer Tumor Associated Antigen," J. Immunol. 138:4534-4538.

(56) References Cited

OTHER PUBLICATIONS

Shields, R.L. et al. (2001) "*High Resolution Mapping of the Binding Site on Human IgG1 for Fc Gamma RI, Fc Gamma RII, Fc Gamma RIII, and FcRn and Design of IgG1 Variants With Improved Binding to the Fc gamma R*," J. Biol. Chem. 276:6591-6604.
Shopes, B. (1992) "*A Genetically Engineered Human IgG Mutant With Enhanced Cytolytic Activity*," J. Immunol. 148(9):2918-2922.
Sondermann et al. (2000) "*The 3.2-Å Crystal Structure of the Human IgG1 Fc Fragment-FcgammaRIII Complex*," Nature 406:267-273.
Song et al. (1995) "*Antibody Mediated Lung Targeting of Long Circulating Emulsions*," PDA Journal of Pharmaceutical Science & Technology 50:372 397.
Staerz et al. (1985) "*Hybrid Antibodies Can Target Sites for Attack by T Cells*," Nature 314:628-631.
Steinkruger, J.D. et al. (2012) "*The d'—d—d' Vertical Triad is Less Discriminating Than the a'—a—a' Vertical Triad in the Antiparallel Coiled-coil Dimer Motif*," J. Amer. Chem. Soc. 134(5):2626-2633.
Stephan, J. et al. (1999) "*Selective Cloning of Cell Surface Proteins Involved in Organ Development: Epithelial Glycoprotein Is Involved in Normal Epithelial Diffferentiation*," Endocrinol. 140:5841-5854.
Stern, H.M. et al. (2010) "*Development of Immunohistochemistry Assays to Assess GALNT14 and FUT3/6 in Clinical Trials of Dulanermin and Drozitumab*," Clin. Cancer Res. 16(5):1587-1596.
Stevenson, G.T. et al. (1989) "*A Chimeric Antibody With Dual Fc Regions (bisFabFc) Prepared by Manipulations at the IgG Hinge*," Anti-Cancer Drug Design 3:219-230 (Abstract).
Straussman, R. et al. (2007) "*Kinking the Coiled Coil—Negatively Charged Residues at the Coiled-coil Interface*," J. Molec. Biol. 366:1232-1242.
Sun, Z. J. et al. (2001) "*Mechanisms Contributing to T Cell Receptor Signaling and Assembly Revealed by the Solution Structure of an Ectodomain Fragment of the CD3ε:γ Heterodimer*," Cell 105(7):913-923.
Swinnen, L.J. et al. (1993) "*OKT3 Monoclonal Antibodies Induce Interleukin-6 and Interleukin-10: A Possible Cause of Lymphoproliferative Disorders Associated With Transplantation*," Curr. Opin. Nephrol. Hypertens. 2(4):670-678.
Takemura, S. et al. (2000) "*Construction of a Diabody (Small Recombinant Bispecific Antibody) Using a Refolding System*," Protein Eng. 13(8):583-588.
Tempest, P.R. et al. (1991) "*Reshaping a Human Monoclonal Antibody to Inhibit Human Respiratory Syncytial Virus Infection* in vivo," Bio/Technology 9:266-271.
Thomas, S. et al. (2010) "*Molecular Immunology Lessons From Therapeutic T-Cell Receptor Gene Transfer*," Immunology 129(2):170-177.
Thorburn, A. et al. (2008) "*TRAIL Receptor-Targeted Therapeutics: Resistance Mechanisms and Strategies to Avoid Them*," Drug Resist. Updat. 11(1-2):17-24.
Trarbach, T. et al. (2010) "*Phase II Trial of Mapatumumab, a Fully Human Agonistic Monoclonal Antibody That Targets and Activates the Tumour Necrosis Factor Apoptosis-Inducing Ligand Receptor-1 (TRAIL-R1), in Patients With Refractory Colorectal Cancer*," Br. J. Cancer 102:506-512.
Tripet, B. et al. (2002) "*Kinetic Analysis of the Interactions between Troponin C and the C-terminal Troponin I Regulatory Region and Validation of a New Peptide Delivery/Capture System used for Surface Plasmon Resonance*," J. Molec. Biol. 323:345-362.
Van Roosmalen, I.A.M. et al. (2014) "*Two Death-Inducing Human TRAIL Receptors to Target in Cancer: Similar or Distinct Regulation and Function?*," Biochem. Pharamcol. 91:447-456.

Verhoeyen, M. et al. (1988) "*Reshaping Human Antibodies: Grafting an Antilysozyme Activity*," Science 239:1534-1536.
Veri, M.C. et al. (2010) "*Therapeutic Control of B Cell Activation Via Recruitment of Fcgamma Receptor IIb (Cd32B) Inhibitory Function With a Novel Bispecific Antibody Scaffold*," Arthritis Rheum. 62(7):1933-1943.
Voelkel-Johnson, C.(2011) "*TRAIL-Mediated Signaling in Prostate, Bladder and Renal Cancer*," Nat. Rev. Urol. 8:417-427.
Wajant, H. et al. (2013) "*Engineering Death Receptor Ligands for Cancer Therapy*," Canc. Lett. 332:163-174.
Walczak, H. (2013) "*Death Receptor—Ligand Systems in Cancer, Cell Death, and Inflammation*," Cold Spring Harb. Perspect. Biol. 2013;5:a008698; pp. 1-19.
Walczak, H. et al. (1999) "*Tumoricidal Activity of Tumor Necrosis Factor-Related Apoptosis-Inducing Ligand* in Vivo," Nat. Med. 5:157-163.
Whiteside, T.L. (2007) "*The Role of Death Receptor Ligands in Shaping Tumor Microenvironment*," Immunol. Investig. 36:25-46.
Winter et al. (1991) "*Man-made Antibodies*," Nature 349:293-299.
Winter, G. et al. (1994) "*Making Antibodies by Phage Display Technology*," Annu. Rev. Immunol. 12.433-455.
Wolff, E.A. et al. (1993) "*Monoclonal Antibody Homodimers: Enhanced Antitumor Activity in Nude Mice*," Cancer Research 53:2560-2565.
Woolfson, D.N. (2005) "*The Design of Coiled-Coil Structures and Assemblies*," Adv. Prot. Chem. 70:79-112.
Wu et al. (1987) "*Receptor-Mediated* in Vitro *Gene Transformation by a Soluble DNA Carrier System*," J. Biol. Chem. 262:4429-4432.
Wu, A. et al. (2001) "*Multimerization of a Chimeric Anti-CD20 Single Chain Fv-Fv Fusion Protein Is Mediated Through Variable Domain Exchange*," Protein Engineering 14(2):1025-1033.
Wucherpfennig, K.W. et al. (2010) "*Structural Biology of the T-Cell Receptor: Insights Into Receptor Assembly, Ligand Recognition, and Initiation of Signaling*," Cold Spring Harb. Perspect. Biol. 2(4):a005140; pp. 1-14.
Xiang, H. et al. (2013) "*Death Receptor 5 Agonistic Antibody PRO95780: Preclinical Pharmacokinetics and Concentration-Effect Relationship Support Clinical Dose and Regimen Selection*," Cancer Chemother. Pharmacol. 72(2):405-415.
Xie et al. (2005) "*A New Format of Bispecific Antibody: Highly Efficient Heterodimerization, Expression and Tumor Cell Lysis*," J. Immunol. Methods 296:95-101.
Xu, D. et al. (2000) "In Vitro *Characterization of Five Humanized OKT3 Effector Function Variant Antibodies*," Cell. Immunol. 200:16-26.
Zeng, Y. et al. (2008) "*A Ligand-Pseudoreceptor System Based on* de novo *Designed Peptides for the Generation of Adenoviral Vectors With Altered Tropism*," J. Gene Med. 10:355-367.
Zinonos, I. et al. (2014) "*Doxorubicin Overcomes Resistance to Drozitumab by Antagonizing Inhibitor of Apoptosis Proteins (IAPs)*," Anticancer Res. 34(12):7007-7020.
International Search Report PCT/US2015/033099 (WO 2016/122702) (2015) (4 pages).
Written Opinion of the International Searching Authority PCT/US2015/033099 (WO 2016/122702) (2015) (4 pages).
European Search Report (Application EP15880591; 4 pages).
Huet, HA et al. (2014) *Multivalent nanobodies targeting death receptor 5 elicit superior tumour cell killing through efficient caspase induction*, MAbs, 6(6):1560-1570.
Frew, AJ et al. (2008) *Combination therapy of established cancer using a histone deacetylase inhibitor and a TRAIL receptor agonist*, PNAS, 105(32):11317-11322.
Singapore Search Report (Application 11201706024Y; 3 pages).

\* cited by examiner

- ● - DR5 mAb 1 x DR5 mAb 2 Fc Diabody (AA)
- ■ - DR5 mAb 1 x DR5 mAb 1 Fc Diabody (AA)
- ▲ - DR5 mAb 2 x DR5 mAb 2 Fc Diabody (AA)
- ◇ - DR5 mAb 8 (AA)
- ▼ - DR5 mAb 4 (AA)
- ▽ - DR5 mAb 4 (AA)+αhFc
- —— R&D TRAIL/His

SEQUENCE LISTING

```
<160> NUMBER OF SEQ ID NOS: 168

<210> SEQ ID NO 1
<211> LENGTH: 217
<212> TYPE: PRT
<213> ORGANISM: Homo sapiens
<220> FEATURE:
<221> NAME/KEY: MISC_FEATURE
<222> LOCATION: (1)..(218)
<223> OTHER INFORMATION: Human Wild-Type IgG CH2-CH3 Domain

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

```
Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 2
<211> LENGTH: 440
<212> TYPE: PRT
<213> ORGANISM: Mus musculus
<220> FEATURE:
<221> NAME/KEY: MISC_FEATURE
<222> LOCATION: (1)..(440)
<223> OTHER INFORMATION: human Death Receptor 5 precursor protein
<220> FEATURE:
<221> NAME/KEY: mat_peptide
<222> LOCATION: (1)..(440)
<220> FEATURE:
<221> NAME/KEY: SIGNAL
<222> LOCATION: (1)..(55)

<400> SEQUENCE: 2

Met Glu Gln Arg Gly Gln Asn Ala Pro Ala Ala Ser Gly Ala Arg Lys
1                5                  10                  15

Arg His Gly Pro Gly Pro Arg Glu Ala Arg Gly Ala Arg Pro Gly Leu
                20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
        50                  55                  60

Gln Arg Val Ala Pro Gln Gln Lys Arg Ser Ser Pro Ser Glu Gly Leu
 65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
            115                 120                 125
```

Cys Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Asp Pro Glu
                245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
        275                 280                 285

Met Glu Val Gln Glu Pro Ala Glu Pro Thr Gly Val Asn Met Leu Ser
290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Arg Gln Cys Phe Asp Asp Phe Ala Asp Leu Val Pro Phe Asp
            340                 345                 350

Ser Trp Glu Pro Leu Met Arg Lys Leu Gly Leu Met Asp Asn Glu Ile
        355                 360                 365

Lys Val Ala Lys Ala Glu Ala Ala Gly His Arg Asp Thr Leu Tyr Thr
370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Gln
                405                 410                 415

Lys Ile Glu Asp His Leu Leu Ser Ser Gly Lys Phe Met Tyr Leu Glu
            420                 425                 430

Gly Asn Ala Asp Ser Ala Met Ser
        435                 440

<210> SEQ ID NO 3
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: Anti-DR5 Antibody mAb 1 Light Chain Variable
    Region

<400> SEQUENCE: 3

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

```
Gly Tyr Ser Tyr Met His Trp Tyr Gln Gln Lys Pro Gly Gln Pro Pro
             35                  40                  45

Lys Val Leu Ile Phe Leu Ser Ser Asn Leu Asp Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Asp Gly Asp Ala Ala Thr Tyr Tyr Cys Gln His Ser Arg
                 85                  90                  95

Asp Leu Pro Pro Thr Phe Gly Gly Gly Thr Lys Leu Glu Ile Lys
            100                 105                 110
```

<210> SEQ ID NO 4
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: Anti-DR5 Antibody mAb 1 Light Chain Variable
      Region CDRL1

<400> SEQUENCE: 4

```
Arg Ala Ser Lys Ser Val Ser Ser Ser Gly Tyr Ser Tyr Met His
 1               5                  10                  15
```

<210> SEQ ID NO 5
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Anti-DR5 Antibody mAb 1 Light Chain Variable
      Region CDRL2

<400> SEQUENCE: 5

```
Leu Ser Ser Asn Leu Asp Ser
 1               5
```

<210> SEQ ID NO 6
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Anti-DR5 Antibody mAb 1 Light Chain Variable
      Region CDRL3

<400> SEQUENCE: 6

```
Gln His Ser Arg Asp Leu Pro Pro Thr
 1               5
```

<210> SEQ ID NO 7
<211> LENGTH: 333
<212> TYPE: DNA
<213> ORGANISM: Mus musculus
<220> FEATURE:
<221> NAME/KEY: misc_feature
<222> LOCATION: (1)..(333)
<223> OTHER INFORMATION: Polynucleotide Encoding Anti-DR5 Antibody mAb 1
      Light Chain Variable Region

<400> SEQUENCE: 7

```
gacattgtgc tgacacagtc tcctgcttcc ttagctgtat ctctcgggca gagggccacc      60
atctcatgca gggccagcaa aagtgtcagt tcctctggct atagttatat gcactggtac     120
```

```
caacagaaac caggacagcc acccaaagtc ctcatctttc tttcatccaa cctagattct    180
ggggtccctg ccaggttcag tggcagtggg tctgggacag acttcaccct caacatccat    240
cctgtggagg atggggatgc tgcaacctat tactgtcagc acagtaggga tcttcctccg    300
acgttcggtg gaggcaccaa gctggaaatc aaa                                 333
```

```
<210> SEQ ID NO 8
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: Anti-DR5 Antibody mAb 1 Heavy Chain Variable
      Region

<400> SEQUENCE: 8
```

Glu Val Lys Phe Leu Glu Ser Gly Gly Gly Leu Val Gln Pro Gly Gly
1               5                   10                  15

Ser Leu Lys Leu Ser Cys Val Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Asn Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Thr Arg Arg Ala Tyr Tyr Gly Asn Pro Ala Trp Phe Ala Tyr Trp Gly
            100                 105                 110

Gln Gly Thr Leu Val Thr Val Ser Ser
        115                 120

```
<210> SEQ ID NO 9
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Anti-DR5 Antibody mAb 1 Light Chain Variable
      Region CDRH1
<220> FEATURE:
<221> NAME/KEY: MISC_FEATURE
<222> LOCATION: (1)..(10)
<223> OTHER INFORMATION: Anti-DR5 Antibody mAb 1 Heavy Chain Variable
      Region CDRH1

<400> SEQUENCE: 9
```

Gly Phe Asp Phe Ser Arg Tyr Trp Met Ser
1               5                   10

```
<210> SEQ ID NO 10
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Anti-DR5 Antibody mAb 1 Heavy Chain Variable
      Region CDRH2

<400> SEQUENCE: 10
```

```
Glu Ile Asn Pro Asp Ser Asn Thr Ile Asn Tyr Thr Pro Ser Leu Lys
1               5                   10                  15

Asp

<210> SEQ ID NO 11
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: Anti-DR5 Antibody mAb 1 Heavy Chain Variable
      Region CDRH3

<400> SEQUENCE: 11

Arg Ala Tyr Tyr Gly Asn Pro Ala Trp Phe Ala Tyr
1               5                   10

<210> SEQ ID NO 12
<211> LENGTH: 363
<212> TYPE: DNA
<213> ORGANISM: Mus musculus
<220> FEATURE:
<221> NAME/KEY: misc_feature
<223> OTHER INFORMATION: Polynucleotide Encoding Anti-DR5 Antibody mAb 1
      Heavy Chain Variable Region

<400> SEQUENCE: 12
gaggtgaagt tctcgagtc tggaggtggc ctggtgcagc ctggaggatc cctgaaactc        60
tcctgtgtag cctcaggatt cgattttagt agatactgga tgagttgggt ccggcaggct      120
ccagggaaag gctagaatg gattggagaa attaatccag atagcaatac gataaactat      180
acgccatctc taaggataa attcatcatc tccagagaca cgccaaaaa tacgctgtat       240 ctgcaaatga ccaaagtgag atctgaggac acagcccttt attattgtac aagaagggcc      300
tactatggta acccggcctg gtttgcttac tggggccaag ggactctggt cactgtctct      360
tcc                                                                   363

<210> SEQ ID NO 13
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: Anti-DR5 Antibody mAb 2 Light Chain Variable
      Region

<400> SEQUENCE: 13

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Lys Ser Val Gln Ala
65                  70                  75                  80

Glu Asp Leu Thr Leu Tyr Tyr Cys Gln Gln His Tyr Ile Thr Pro Trp
                85                  90                  95
```

Thr Phe Gly Gly Gly Thr Lys Leu Glu Ile Lys
            100                 105

<210> SEQ ID NO 14
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: Anti-DR5 Antibody mAb 2 Light Chain Variable
      Region CDRL1

<400> SEQUENCE: 14

Lys Ala Ser Gln Asp Val Asn Thr Ala Val Ala
1               5                   10

<210> SEQ ID NO 15
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Anti-DR5 Antibody mAb 2 Light Chain Variable
      Region CDRL2

<400> SEQUENCE: 15

Trp Ala Ser Thr Arg His Thr
1               5

<210> SEQ ID NO 16
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Anti-DR5 Antibody mAb 2 Light Chain Variable
      Region CDRL3

<400> SEQUENCE: 16

Gln Gln His Tyr Ile Thr Pro Trp Thr
1               5

<210> SEQ ID NO 17
<211> LENGTH: 321
<212> TYPE: DNA
<213> ORGANISM: Mus musculus
<220> FEATURE:
<221> NAME/KEY: misc_feature
<222> LOCATION: (1)..(321)
<223> OTHER INFORMATION: Polynucleotide Encoding Anti-DR5 Antibody mAb 2
      Light Chain Variable Region

<400> SEQUENCE: 17
gacattgtga tgacccagtc tcacaaattc atgtccactt cagtaggaga cagggtcagc    60
atcacctgca aggccagtca ggatgtgaat actgctgtag cctggtatca acaaaaacca   120
gggcaatctc ctaaactact gatttactgg gcatccaccc ggcacactgg agtccctgat   180
cgcttcacag gcagtggatc tgggacagat tatacactca ccatcaaaag tgtgcaggct   240
gaagacctga cactttatta ctgtcagcaa cactatatca ctccgtggac gttcggtgga   300
ggcaccaagc tggaaatcaa a                                             321

<210> SEQ ID NO 18
<211> LENGTH: 119

```
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: Anti-DR5 Antibody mAb 2 Heavy Chain Variable
      Region

<400> SEQUENCE: 18

Lys Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Glu Tyr
            20                  25                  30

Ile Leu His Trp Val Lys Gln Lys Ser Gly Gln Gly Leu Glu Trp Ile
        35                  40                  45

Gly Trp Phe Tyr Pro Gly Asn Asn Asn Ile Lys Tyr Asn Glu Lys Phe
    50                  55                  60

Lys Asp Lys Ala Thr Leu Thr Ala Asp Lys Ser Ser Ser Thr Val Tyr
65                  70                  75                  80

Met Glu Leu Ser Arg Leu Thr Ser Glu Asp Ser Ala Val Tyr Phe Cys
                85                  90                  95

Ala Arg His Glu Gln Gly Pro Tyr Phe Asp Tyr Trp Gly Gln Gly
            100                 105                 110

Thr Thr Leu Thr Val Ser Ser
        115

<210> SEQ ID NO 19
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Anti-DR5 Antibody mAb 2 Heavy Chain Variable
      Region CDRH1

<400> SEQUENCE: 19

Gly Tyr Thr Phe Thr Glu Tyr Ile Leu His
1               5                   10

<210> SEQ ID NO 20
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Anti-DR5 Antibody mAb 2 Heavy Chain Variable
      Region CDRH2

<400> SEQUENCE: 20

Trp Phe Tyr Pro Gly Asn Asn Asn Ile Lys Tyr Asn Glu Lys Phe Lys
1               5                   10                  15

Asp

<210> SEQ ID NO 21
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Anti-DR5 Antibody mAb 2 Heavy Chain Variable
      Region CDRH3
```

<400> SEQUENCE: 21

His Glu Gln Gly Pro Gly Tyr Phe Asp Tyr
1               5                   10

<210> SEQ ID NO 22
<211> LENGTH: 357
<212> TYPE: DNA
<213> ORGANISM: Mus musculus
<220> FEATURE:
<221> NAME/KEY: misc_feature
<222> LOCATION: (1)..(357)
<223> OTHER INFORMATION: Polynucleotide Encoding Anti-DR5 Antibody mAb 2
      Heavy Chain Variable Region

<400> SEQUENCE: 22
aaggtccagc tgcagcagtc tggagctgaa ctggtgaaac ccggggcatc agtgaagctg      60
tcctgcaagg cttctgggta caccttcact gagtatattt tacactgggt aaagcagaag     120
tctggacagg gtcttgagtg gattgggtgg ttttatcctg gaaataataa tataaagtac     180
aatgagaaat tcaaggacaa ggccacactg actgcgcaca atcctccag cacagtctat      240 atggaactta gtagattgac atctgaagac tctgcggtct atttctgtgc aagacacgaa     300
caaggaccag gttactttga ctactggggc caaggcacca ctctcacagt ctcctcc       357

<210> SEQ ID NO 23
<211> LENGTH: 107
<212> TYPE: PRT
<213> ORGANISM: Artificial Sequence
<220> FEATURE:
<223> OTHER INFORMATION: Humanized Anti-DR5 mAb 2 Light Chain Variable
      Region Variant 2

<400> SEQUENCE: 23

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Tyr Ile Thr Pro Trp
                85                  90                  95

Thr Phe Gly Gly Gly Thr Lys Leu Glu Ile Lys
            100                 105

<210> SEQ ID NO 24
<211> LENGTH: 321
<212> TYPE: DNA
<213> ORGANISM: Artificial Sequence
<220> FEATURE:
<223> OTHER INFORMATION: Polynucleotide Encoding Humanized Anti-DR5 mAb
      2 Light Chain Variable Region Variant 2

<400> SEQUENCE: 24
gatattcaga tgacccagag tccctcattt ctgtccgcct ccgtcggtga ccgcgtgact      60
attacttgta aagcttctca ggatgtcaac accgccgtgg cttggtacca gcagaagccc     120
ggtaaagcac ctaagctgct gatctattgg gccagcactc ggcacaccgg agtcccatct     180

```
aggttctctg gcagtggatc agggacagac tttaccctga caattagctc cctgcagccc    240
gaggatgtgg ctacttacta ttgtcagcag cactacatca ctccttggac cttcggcggg    300
ggcacaaaac tggaaatcaa a                                              321
```

<210> SEQ ID NO 25
<211> LENGTH: 107
<212> TYPE: PRT
<213> ORGANISM: Artificial Sequence
<220> FEATURE:
<223> OTHER INFORMATION: Humanized Anti-DR5 mAb 2 Light Chain Variable
      Region Variant 3

<400> SEQUENCE: 25

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Tyr Ile Thr Pro Trp
                85                  90                  95

Thr Phe Gly Gly Gly Thr Lys Leu Glu Ile Lys
            100                 105
```

<210> SEQ ID NO 26
<211> LENGTH: 321
<212> TYPE: DNA
<213> ORGANISM: Artificial Sequence
<220> FEATURE:
<223> OTHER INFORMATION: Polynucleotide Encoding Humanized Anti-DR5 mAb
      2 Light Chain Variable Region Variant 3

<400> SEQUENCE: 26

```
gatattcaga tgacccagag tccctcattt ctgtccgcct ccgtcggtga ccgcgtgact    60
attacttgtc gggcttctca ggatgtcaac accgccgtgg cttggtacca gcagaagccc    120
ggtaaagcac ctaagctgct gatctattgg gccagcactc ggcacaccgg agtcccagat    180
aggttctctg gcagtggatc agggacagac tttaccctga caattagctc cctgcagccc    240
gaggatgtgg ctacttacta ttgtcagcag cactacatca ctccttggac cttcggcggg    300
ggcacaaaac tggaaatcaa a                                              321
```

<210> SEQ ID NO 27
<211> LENGTH: 107
<212> TYPE: PRT
<213> ORGANISM: Artificial Sequence
<220> FEATURE:
<223> OTHER INFORMATION: Humanized Anti-DR5 mAb 2 Light Chain Variable
      Region Variant 4

<400> SEQUENCE: 27

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
```

```
              35                  40                  45
Tyr Trp Ala Ser Thr Arg His Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln Gln His Tyr Ile Thr Pro Trp
                 85                  90                  95

Thr Phe Gly Gly Gly Thr Lys Leu Glu Ile Lys
            100                 105
```

<210> SEQ ID NO 28
<211> LENGTH: 321
<212> TYPE: DNA
<213> ORGANISM: Artificial Sequence
<220> FEATURE:
<223> OTHER INFORMATION: Polynucleotide Encoding Humanized Anti-DR5 mAb
       2 Light Chain Variable Region Variant 4

<400> SEQUENCE: 28

```
gatattcaga tgacccagag tccctcattt ctgtccgcct ccgtcggtga ccgcgtgact    60
attacttgtc gggcttctca ggatgtcaac accgccgtgg cttggtacca gcagaagccc   120
ggtaaagcac ctaagctgct gatctattgg gccagcactc ggcacaccgg agtcccatct   180
aggttctctg gcagtggatc agggacagac tttacccctga caattagctc cctgcagcca   240
gaggatatcg ctacatacta ttgtcagcag cactacatca ctccttggac cttcggcggg   300
ggcacaaaac tggaaatcaa a                                             321
```

<210> SEQ ID NO 29
<211> LENGTH: 107
<212> TYPE: PRT
<213> ORGANISM: Artificial Sequence
<220> FEATURE:
<223> OTHER INFORMATION: Humanized Anti-DR5 mAb 2 Light Chain Variable
       Region Variant 5

<400> SEQUENCE: 29

```
Asp Ile Gln Met Thr Gln Ser Pro Ser Phe Leu Ser Ala Ser Val Gly
  1               5                  10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
             35                  40                  45

Tyr Trp Ala Ser Thr Arg His Thr Gly Val Pro Asp Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln Gln His Tyr Ile Thr Pro Trp
                 85                  90                  95

Thr Phe Gly Gly Gly Thr Lys Leu Glu Ile Lys
            100                 105
```

<210> SEQ ID NO 30
<211> LENGTH: 321
<212> TYPE: DNA
<213> ORGANISM: Artificial Sequence
<220> FEATURE:
<223> OTHER INFORMATION: Polynucleotide Encoding Humanized Anti-DR5 mAb
       2 Light Chain Variable Region Variant 5

<400> SEQUENCE: 30

```
gatattcaga tgacccagag tccctcattt ctgtccgcct ccgtcggtga ccgcgtgact    60
attacttgtc gggcttctca ggatgtcaac accgccgtgg cttggtacca gcagaagccc   120
ggtaaagcac ctaagctgct gatctattgg gccagcactc ggcacaccgg agtcccagat   180
aggttctctg gcagtggatc agggacagac tttacccctg acaattagctc cctgcagccc   240 gaggatatcg ctacttacta ttgtcagcag cactacatca ctccttggac cttcggcggg   300
ggcacaaaac tggaaatcaa a                                             321
```

<210> SEQ ID NO 31
<211> LENGTH: 119
<212> TYPE: PRT
<213> ORGANISM: Artificial Sequence
<220> FEATURE:
<223> OTHER INFORMATION: Humanized Anti-DR5 mAb 2 Heavy Chain Variable
      Region Variant 2

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Ile Leu His Trp Val Arg Gln Ala Pro Gly Gln Gly Leu Glu Trp Met
        35                  40                  45

Gly Trp Phe Tyr Pro Gly Asn Asn Ile Lys Tyr Asn Glu Lys Phe
    50                  55                  60

Lys Asp Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Glu Gln Gly Pro Gly Tyr Phe Asp Tyr Trp Gly Gln Gly
            100                 105                 110

Thr Leu Val Thr Val Ser Ser
        115
```

<210> SEQ ID NO 32
<211> LENGTH: 357
<212> TYPE: DNA
<213> ORGANISM: Artificial Sequence
<220> FEATURE:
<223> OTHER INFORMATION: Polynucleotide Encoding Humanized Anti-DR5 mAb
      2 Heavy Chain Variable Region Variant 2

<400> SEQUENCE: 32

```
caggtccagc tggtgcagag tggggcagag gtgaaaaagc cagggcatc agtgaaagtg    60 tcttgtaaag catcaggtta tacatttact gagtacatcc tgcactgggt gcgacaggca   120
ccaggacagg gactggaatg gatggggtgg ttctaccctg caacaacaa cattaagtac   180 aacgagaagt ttaaagaccg ggtgaccatc acagcggata gtctaccag tacagtctat   240 atggagctga gctccctgag aagcgaagac accgccgtct actattgcgc tcgccacgaa   300
cagggtccag gttactttga ttattggggg cagggaactc tggtcacagt cagctcc     357
```

<210> SEQ ID NO 33
<211> LENGTH: 8
<212> TYPE: PRT
<213> ORGANISM: Artificial Sequence
<220> FEATURE:
<223> OTHER INFORMATION: Linker 1

```
<400> SEQUENCE: 33

Gly Gly Gly Ser Gly Gly Gly Gly
1               5

<210> SEQ ID NO 34
<211> LENGTH: 6
<212> TYPE: PRT
<213> ORGANISM: Artificial Sequence
<220> FEATURE:
<223> OTHER INFORMATION: Cysteine-Containing Domain ("Linker 2")

<400> SEQUENCE: 34

Gly Gly Cys Gly Gly Gly
1               5

<210> SEQ ID NO 35
<211> LENGTH: 7
<212> TYPE: PRT
<213> ORGANISM: Artificial Sequence
<220> FEATURE:
<223> OTHER INFORMATION: Variant of Cysteine-Containing Portion of Human
      IgG Hinge Domain

<400> SEQUENCE: 35

Gly Val Glu Pro Lys Ser Cys
1               5

<210> SEQ ID NO 36
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Cysteine-Containing Portion of Human IgG Hinge
      Domain

<400> SEQUENCE: 36

Val Glu Pro Lys Ser Cys
1               5

<210> SEQ ID NO 37
<211> LENGTH: 7
<212> TYPE: PRT
<213> ORGANISM: Artificial Sequence
<220> FEATURE:
<223> OTHER INFORMATION: Variant of Cysteine-Containing Portion of Human
      CL Domain

<400> SEQUENCE: 37

Gly Phe Asn Arg Gly Glu Cys
1               5

<210> SEQ ID NO 38
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Cysteine-Containing Portion of Human CL Domain

<400> SEQUENCE: 38

Phe Asn Arg Gly Glu Cys
1               5

<210> SEQ ID NO 39
```

```
<211> LENGTH: 28
<212> TYPE: PRT
<213> ORGANISM: Artificial Sequence
<220> FEATURE:
<223> OTHER INFORMATION: E-Coil Heterodimer-Promoting Domain

<400> SEQUENCE: 39

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 40
<211> LENGTH: 28
<212> TYPE: PRT
<213> ORGANISM: Artificial Sequence
<220> FEATURE:
<223> OTHER INFORMATION: K-Coil Heterodimer-Promoting Domain

<400> SEQUENCE: 40

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 41
<211> LENGTH: 28
<212> TYPE: PRT
<213> ORGANISM: Artificial Sequence
<220> FEATURE:
<223> OTHER INFORMATION: Cysteine-Containing E-Coil Heterodimer-
      Promoting Domain

<400> SEQUENCE: 41

Glu Val Ala Ala Cys Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 42
<211> LENGTH: 28
<212> TYPE: PRT
<213> ORGANISM: Artificial Sequence
<220> FEATURE:
<223> OTHER INFORMATION: Cysteine-Containing K-Coil Heterodimer-
      Promoting Domain

<400> SEQUENCE: 42

Lys Val Ala Ala Cys Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 43
<211> LENGTH: 46
<212> TYPE: PRT
<213> ORGANISM: Streptococcus dysgalactiae
<220> FEATURE:
<221> NAME/KEY: MISC_FEATURE
<222> LOCATION: (1)..(46)
<223> OTHER INFORMATION: Albumin-Binding Domain 3 (ABD3) of Protein G of
      Streptococcus

<400> SEQUENCE: 43

Leu Ala Glu Ala Lys Val Leu Ala Asn Arg Glu Leu Asp Lys Tyr Gly
1               5                   10                  15
```

```
Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45

<210> SEQ ID NO 44
<211> LENGTH: 46
<212> TYPE: PRT
<213> ORGANISM: Artificial Sequence
<220> FEATURE:
<223> OTHER INFORMATION: Variant Deimmunized Albumin-Binding Domain 3
      (ABD3) of Protein G of Streptococcus Strain G148

<400> SEQUENCE: 44

Leu Ala Glu Ala Lys Val Leu Ala Asn Arg Glu Leu Asp Lys Tyr Gly
1               5                   10                  15

Val Ser Asp Tyr Tyr Lys Asn Ala Ala Asn Ala Lys Thr Val Glu
            20                  25                  30

Gly Val Lys Ala Leu Ile Ala Glu Ile Leu Ala Ala Leu Pro
        35                  40                  45

<210> SEQ ID NO 45
<211> LENGTH: 46
<212> TYPE: PRT
<213> ORGANISM: Artificial Sequence
<220> FEATURE:
<223> OTHER INFORMATION: Variant Deimmunized Albumin-Binding Domain 3
      (ABD3) of Protein G of Streptococcus Strain G148

<400> SEQUENCE: 45

Leu Ala Glu Ala Lys Val Leu Ala Asn Arg Glu Leu Asp Lys Tyr Gly
1               5                   10                  15

Val Ser Asp Tyr Tyr Lys Asn Leu Ile Ser Asn Ala Lys Ser Val Glu
            20                  25                  30

Gly Val Lys Ala Leu Ile Ala Glu Ile Leu Ala Ala Leu Pro
        35                  40                  45

<210> SEQ ID NO 46
<211> LENGTH: 4
<212> TYPE: PRT
<213> ORGANISM: Artificial Sequence
<220> FEATURE:
<223> OTHER INFORMATION: Peptide Linker

<400> SEQUENCE: 46

Gly Gly Gly Ser
1

<210> SEQ ID NO 47
<211> LENGTH: 5
<212> TYPE: PRT
<213> ORGANISM: Artificial Sequence
<220> FEATURE:
<223> OTHER INFORMATION: Peptide Linker

<400> SEQUENCE: 47

Ala Ser Thr Lys Gly
1               5

<210> SEQ ID NO 48
<211> LENGTH: 10
<212> TYPE: PRT
<213> ORGANISM: Artificial Sequence
<220> FEATURE:
```

```
<223> OTHER INFORMATION: Cysteine-Containing Peptide Linker ("Linker 3")

<400> SEQUENCE: 48

Asp Lys Thr His Thr Cys Pro Pro Cys Pro
1               5                   10

<210> SEQ ID NO 49
<211> LENGTH: 6
<212> TYPE: PRT
<213> ORGANISM: Artificial Sequence
<220> FEATURE:
<223> OTHER INFORMATION: Peptide Linker ("Linker 3')

<400> SEQUENCE: 49

Leu Glu Pro Lys Ser Ser
1               5

<210> SEQ ID NO 50
<211> LENGTH: 8
<212> TYPE: PRT
<213> ORGANISM: Artificial Sequence
<220> FEATURE:
<223> OTHER INFORMATION: Peptide Linker ("Linker 3')

<400> SEQUENCE: 50

Ala Pro Ser Ser Ser Pro Met Glu
1               5

<210> SEQ ID NO 51
<211> LENGTH: 16
<212> TYPE: PRT
<213> ORGANISM: Artificial Sequence
<220> FEATURE:
<223> OTHER INFORMATION: Alternative Cysteine-Containing Linker Peptide
      ("Linker 3")

<400> SEQUENCE: 51

Leu Glu Pro Lys Ser Ser Asp Lys Thr His Thr Cys Pro Pro Cys Pro
1               5                   10                  15

<210> SEQ ID NO 52
<211> LENGTH: 217
<212> TYPE: PRT
<213> ORGANISM: Artificial Sequence
<220> FEATURE:
<223> OTHER INFORMATION: "Knob-Bearing" CH2-CH3 Domain

<400> SEQUENCE: 52

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
```

```
            115                 120                 125
Thr Lys Asn Gln Val Ser Leu Trp Cys Leu Val Lys Gly Phe Tyr Pro
        130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Asp Lys Ser Arg Trp Gln Gln Gly Asn Val
            180                 185                 190
Phe Ser Cys Ser Val Met His Glu Ala Leu His Asn His Tyr Thr Gln
        195                 200                 205
Lys Ser Leu Ser Leu Ser Pro Gly Lys
    210                 215

<210> SEQ ID NO 53
<211> LENGTH: 217
<212> TYPE: PRT
<213> ORGANISM: Artificial Sequence
<220> FEATURE:
<223> OTHER INFORMATION: Hole-Bearing" CH2-CH3 Domain

<400> SEQUENCE: 53

Ala Pro Glu Ala Ala Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Arg Glu Glu Met
        115                 120                 125
Thr Lys Asn Gln Val Ser Leu Ser Cys Ala Val Lys Gly Phe Tyr Pro
    130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Val Ser Lys Leu Thr Val Asp Lys Ser Arg Trp Gln Gln Gly Asn Val
            180                 185                 190
Phe Ser Cys Ser Val Met His Glu Ala Leu His Asn Arg Tyr Thr Gln
        195                 200                 205
Lys Ser Leu Ser Leu Ser Pro Gly Lys
    210                 215

<210> SEQ ID NO 54
<211> LENGTH: 108
<212> TYPE: PRT
<213> ORGANISM: Homo sapiens
<220> FEATURE:
<221> NAME/KEY: MISC_FEATURE
```

```
<222> LOCATION: (1)..(108)
<223> OTHER INFORMATION: drozitumab anti-DR5 Antibody Light Chain
      Variable Region

<400> SEQUENCE: 54

Ser Glu Leu Thr Gln Asp Pro Ala Val Ser Val Ala Leu Gly Gln Thr
1               5                   10                  15

Val Arg Ile Thr Cys Ser Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Ala Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Ala Asp Ser Ser Gly Asn His Val
                85                  90                  95

Val Phe Gly Gly Gly Thr Lys Leu Thr Val Leu Gly
            100                 105

<210> SEQ ID NO 55
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: drozitumab anti-DR5 Antibody Light Chain
      Variable Region CDRL1

<400> SEQUENCE: 55

Ser Gly Asp Ser Leu Arg Ser Tyr Tyr Ala Ser
1               5                   10

<210> SEQ ID NO 56
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: drozitumab anti-DR5 Antibody Light Chain
      Variable Region CDRL2

<400> SEQUENCE: 56

Gly Ala Asn Asn Arg Pro Ser
1               5

<210> SEQ ID NO 57
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: drozitumab anti-DR5 Antibody Light Chain
      Variable Region CDRL3

<400> SEQUENCE: 57

Asn Ser Ala Asp Ser Ser Gly Asn His Val Val
1               5                   10

<210> SEQ ID NO 58
<211> LENGTH: 121
<212> TYPE: PRT
```

```
<213> ORGANISM: Homo sapiens
<220> FEATURE:
<221> NAME/KEY: MISC_FEATURE
<222> LOCATION: (1)..(121)
<223> OTHER INFORMATION: drozitumab anti-DR5 Antibody Heavy Chain
      Variable Region

<400> SEQUENCE: 58

Glu Val Gln Leu Val Gln Ser Gly Gly Gly Val Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Asn Trp Gln Gly Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Tyr Trp Gly
            100                 105                 110

Lys Gly Thr Thr Val Thr Val Ser Ser
        115                 120

<210> SEQ ID NO 59
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: drozitumab anti-DR5 Antibody Heavy Chain
      Variable Region CDRH1

<400> SEQUENCE: 59

Gly Phe Thr Phe Asp Asp Tyr Ala Met Ser
1               5                   10

<210> SEQ ID NO 60
<211> LENGTH: 16
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: drozitumab anti-DR5 Antibody Heavy Chain
      Variable Region CDRH2

<400> SEQUENCE: 60

Ile Asn Trp Gln Gly Gly Ser Thr Gly Tyr Ala Asp Ser Val Lys Gly
1               5                   10                  15

<210> SEQ ID NO 61
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: drozitumab anti-DR5 Antibody Heavy Chain
      Variable Region CDRH3

<400> SEQUENCE: 61

Ile Leu Gly Ala Gly Arg Gly Trp Tyr Phe Asp Tyr
```

<210> SEQ ID NO 62
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: conatumumab anti-DR5 Antibody Light Chain
      Variable Region

<400> SEQUENCE: 62

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Ile Ser Arg Ser
            20                  25                  30

Tyr Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Pro
                85                  90                  95

Trp Thr Phe Gly Gln Gly Thr Lys Val Glu Ile Lys
            100                 105

<210> SEQ ID NO 63
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: conatumumab anti-DR5 Antibody Light Chain
      Variable Region CDRL1

<400> SEQUENCE: 63

Arg Ala Ser Gln Gly Ile Ser Arg Ser Tyr Leu Ala
1               5                   10

<210> SEQ ID NO 64
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: conatumumab anti-DR5 Antibody Light Chain
      Variable Region CDRL2

<400> SEQUENCE: 64

Gly Ala Ser Ser Arg Ala Thr
1               5

<210> SEQ ID NO 65
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: conatumumab anti-DR5 Antibody Light Chain
      Variable Region CDRL3

```
<400> SEQUENCE: 65

Gln Gln Phe Gly Ser Ser Pro Trp Thr
1               5

<210> SEQ ID NO 66
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: conatumumab anti-DR5 Antibody Heavy Chain
      Variable Region

<400> SEQUENCE: 66

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Asp Tyr Phe Trp Ser Trp Ile Arg Gln Leu Pro Gly Lys Gly Leu Glu
            35                  40                  45

Trp Ile Gly His Ile His Asn Ser Gly Thr Thr Tyr Tyr Asn Pro Ser
    50                  55                  60

Leu Lys Ser Arg Val Thr Ile Ser Val Asp Thr Ser Lys Lys Gln Phe
65                  70                  75                  80

Ser Leu Arg Leu Ser Ser Val Thr Ala Ala Asp Thr Ala Val Tyr Tyr
                85                  90                  95

Cys Ala Arg Asp Arg Gly Gly Asp Tyr Tyr Tyr Gly Met Asp Val Trp
            100                 105                 110

Gly Gln Gly Thr Thr Val Thr Val Ser Ser
        115                 120

<210> SEQ ID NO 67
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: conatumumab anti-DR5 Antibody Heavy Chain
      Variable Region CDRH1

<400> SEQUENCE: 67

Gly Gly Ser Ile Ser Ser Gly Asp Tyr Phe Trp Ser
1               5                   10

<210> SEQ ID NO 68
<211> LENGTH: 16
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: conatumumab anti-DR5 Antibody Heavy Chain
      Variable Region CDRH2

<400> SEQUENCE: 68

His Ile His Asn Ser Gly Thr Thr Tyr Tyr Asn Pro Ser Leu Lys Ser
1               5                   10                  15

<210> SEQ ID NO 69
<211> LENGTH: 12
<212> TYPE: PRT
<213> ORGANISM: Homo sapiens
```

-continued

```
<220> FEATURE:
<221> NAME/KEY: MISC_FEATURE
<222> LOCATION: (1)..(12)
<223> OTHER INFORMATION: conatumumab anti-DR5 Antibody Heavy Chain
      Variable Region CDRH3

<400> SEQUENCE: 69

Asp Arg Gly Gly Asp Tyr Tyr Tyr Gly Met Asp Val
1               5                   10

<210> SEQ ID NO 70
<211> LENGTH: 106
<212> TYPE: PRT
<213> ORGANISM: Artificial Sequence
<220> FEATURE:
<223> OTHER INFORMATION: tigatumumab humanized anti-DR5 Antibody Light
      Chain Variable Region

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Arg Thr
                85                  90                  95

Phe Gly Gln Gly Thr Lys Val Glu Ile Lys
            100                 105

<210> SEQ ID NO 71
<211> LENGTH: 11
<212> TYPE: PRT
<213> ORGANISM: Artificial Sequence
<220> FEATURE:
<223> OTHER INFORMATION: tigatumumab humanized anti-DR5 Antibody Light
      Chain Variable Region CDRL1

<400> SEQUENCE: 71

Lys Ala Ser Gln Asp Val Gly Thr Ala Val Ala
1               5                   10

<210> SEQ ID NO 72
<211> LENGTH: 7
<212> TYPE: PRT
<213> ORGANISM: Artificial Sequence
<220> FEATURE:
<223> OTHER INFORMATION: tigatumumab humanized anti-DR5 Antibody Light
      Chain Variable Region CDRL2

<400> SEQUENCE: 72

Trp Ala Ser Thr Arg His Thr
1               5

<210> SEQ ID NO 73
<211> LENGTH: 8
<212> TYPE: PRT
<213> ORGANISM: Artificial Sequence
<220> FEATURE:
<223> OTHER INFORMATION: tigatumumab humanized anti-DR5 Antibody Light
      Chain Variable Region CDRL3
```

<400> SEQUENCE: 73

Gln Gln Tyr Ser Ser Tyr Arg Thr
1               5

<210> SEQ ID NO 74
<211> LENGTH: 119
<212> TYPE: PRT
<213> ORGANISM: Artificial Sequence
<220> FEATURE:
<223> OTHER INFORMATION: tigatumumab humanized anti-DR5 Antibody Heavy
      Chain Variable Region

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Asp Ser Met Ile Thr Thr Asp Tyr Trp Gly Gln Gly
            100                 105                 110

Thr Leu Val Thr Val Ser Ser
        115

<210> SEQ ID NO 75
<211> LENGTH: 10
<212> TYPE: PRT
<213> ORGANISM: Artificial Sequence
<220> FEATURE:
<223> OTHER INFORMATION: tigatumumab humanized anti-DR5 Antibody Heavy
      Chain Variable Region CDRH1

<400> SEQUENCE: 75

Gly Phe Thr Phe Ser Ser Tyr Val Met Ser
1               5                   10

<210> SEQ ID NO 76
<211> LENGTH: 17
<212> TYPE: PRT
<213> ORGANISM: Artificial Sequence
<220> FEATURE:
<223> OTHER INFORMATION: tigatumumab humanized anti-DR5 Antibody Heavy
      Chain Variable Region CDRH3

<400> SEQUENCE: 76

Thr Ile Ser Ser Gly Gly Ser Tyr Thr Tyr Tyr Pro Asp Ser Val Lys
1               5                   10                  15

Gly

<210> SEQ ID NO 77
<211> LENGTH: 10
<212> TYPE: PRT
<213> ORGANISM: Artificial Sequence
<220> FEATURE:
<223> OTHER INFORMATION: tigatumumab humanized anti-DR5 Antibody Heavy
      Chain Variable Region CDRH3

<400> SEQUENCE: 77

Arg Gly Asp Ser Met Ile Thr Thr Asp Tyr
1               5                   10

<210> SEQ ID NO 78
<211> LENGTH: 109
<212> TYPE: PRT
<213> ORGANISM: Mus musculus
<220> FEATURE:
<221> NAME/KEY: MISC_FEATURE
<222> LOCATION: (1)..(109)
<223> OTHER INFORMATION: LBY135-1 anti-DR5 Antibody Light Chain Variable
      Region

<400> SEQUENCE: 78

Asp Ile Ala Met Thr Gln Ser His Lys Phe Met Ser Thr Leu Val Gly
1               5                   10                  15

Asp Arg Val Ser Ile Thr Cys Lys Ala Ser Gln Asp Val Asn Thr Ala
                20                  25                  30

Ile Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Tyr Gly
50                  55                  60

Ser Gly Ser Gly Thr Asp Tyr Thr Leu Thr Ile Ser Ser Met Glu Ala
65                  70                  75                  80

Glu Asp Ala Ala Thr Tyr Tyr Cys Gln Gln Trp Ser Ser Asn Pro Leu
                85                  90                  95

Thr Phe Gly Ala Gly Thr Lys Leu Glu Leu Lys Arg Ala
            100                 105

<210> SEQ ID NO 79
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: LBY135-1 anti-DR5 Antibody Light Chain Variable
      Region CDRL1

<400> SEQUENCE: 79

Gln Asp Val Asn Thr Ala Ile Ala
1               5

<210> SEQ ID NO 80
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: LBY135-1 anti-DR5 Antibody Light Chain Variable
      Region CDRL2

<400> SEQUENCE: 80

Trp Ala Ser Thr Arg His Thr
1               5

<210> SEQ ID NO 81
<211> LENGTH: 9
<212> TYPE: PRT
<213> ORGANISM: Mus musculus
<220> FEATURE:
<221> NAME/KEY: MISC_FEATURE

```
<222> LOCATION: (1)..(9)
<223> OTHER INFORMATION: LBY135-1 anti-DR5 Antibody Light Chain Variable
      Region CDRL3

<400> SEQUENCE: 81

Gln Gln Trp Ser Ser Asn Pro Leu Thr
1               5

<210> SEQ ID NO 82
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: LBY135-1 anti-DR5 Antibody Heavy Chain Variable
      Region

<400> SEQUENCE: 82

Lys Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asp Tyr
            20                  25                  30

Thr Ile His Trp Val Lys Gln Arg Ser Gly Gln Gly Leu Glu Trp Ile
        35                  40                  45

Gly Trp Phe Tyr Pro Gly Gly Gly Tyr Ile Lys Tyr Asn Glu Lys Phe
    50                  55                  60

Lys Asp Arg Ala Thr Leu Thr Ala Asp Lys Ser Ser Asn Thr Val Tyr
65                  70                  75                  80

Met Glu Leu Ser Arg Leu Thr Ser Glu Gly Ser Ala Val Tyr Phe Cys
                85                  90                  95

Ala Arg His Glu Glu Gly Ile Tyr Phe Asp Tyr Trp Gly Gln Gly Thr
            100                 105                 110

Thr Leu Thr Val Ser Ser
        115

<210> SEQ ID NO 83
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: LBY135-1 anti-DR5 Antibody Heavy Chain Variable
      Region CDRH1

<400> SEQUENCE: 83

Gly Tyr Thr Phe Thr Asp Tyr Thr Ile His
1               5                   10

<210> SEQ ID NO 84
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: LBY135-1 anti-DR5 Antibody Heavy Chain Variable
      Region CDRH2

<400> SEQUENCE: 84

Trp Phe Tyr Pro Gly Gly Gly Tyr Ile Lys Tyr Asn Glu Lys Phe Lys
1               5                   10                  15

Asp
```

```
<210> SEQ ID NO 85
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: LBY135-1 anti-DR5 Antibody Heavy Chain Variable
      Region CDRH3

<400> SEQUENCE: 85

His Glu Glu Gly Ile Tyr Phe Asp Tyr
1               5

<210> SEQ ID NO 86
<211> LENGTH: 104
<212> TYPE: PRT
<213> ORGANISM: Mus musculus
<220> FEATURE:
<221> NAME/KEY: MISC_FEATURE
<222> LOCATION: (1)..(104)
<223> OTHER INFORMATION: LBY135-2 anti-DR5 Antibody Light Chain Variable
      Region

<400> SEQUENCE: 86

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Ile Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Phe
                85                  90                  95

Thr Phe Gly Ser Gly Thr Lys Leu
            100

<210> SEQ ID NO 87
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: LBY135-2 anti-DR5 Antibody Light Chain Variable
      Region CDRL1

<400> SEQUENCE: 87

Lys Ala Ser Gln Asp Val Asn Thr Ala Ile Ala
1               5                   10

<210> SEQ ID NO 88
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: LBY135-2 anti-DR5 Antibody Light Chain Variable
      Region CDRL2

<400> SEQUENCE: 88
```

```
<210> SEQ ID NO 89
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: LBY135-2 anti-DR5 Antibody Light Chain Variable
      Region CDRL3

<400> SEQUENCE: 89
```

Trp Ala Ser Thr Arg His Thr
1               5

Gln Gln His Tyr Thr Thr Pro Phe Thr
1               5

```
<210> SEQ ID NO 90
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: LBY135-2 anti-DR5 Antibody Heavy Chain Variable
      Region

<400> SEQUENCE: 90
```

Lys Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asp Tyr
            20                  25                  30

Thr Ile His Trp Val Lys Gln Arg Ser Gly Gln Gly Leu Glu Trp Ile
        35                  40                  45

Gly Trp Phe Tyr Pro Gly Gly Gly Tyr Ile Lys Tyr Asn Glu Lys Phe
    50                  55                  60

Lys Asp Arg Ala Thr Leu Thr Ala Asp Lys Ser Ser Asn Thr Val Tyr
65                  70                  75                  80

Met Glu Leu Ser Arg Leu Thr Ser Glu Asp Ser Ala Val Tyr Phe Cys
                85                  90                  95

Ala Arg His Glu Glu Gly Ile Tyr Phe Asp Tyr Trp Gly Gln Gly Thr
            100                 105                 110

Thr Leu Thr Val Ser Ser
        115

```
<210> SEQ ID NO 91
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: LBY135-2 anti-DR5 Antibody Heavy Chain Variable
      Region CDRH1

<400> SEQUENCE: 91
```

Gly Tyr Thr Phe Thr Asp Tyr Thr Ile His
1               5                   10

```
<210> SEQ ID NO 92
<211> LENGTH: 17
<212> TYPE: PRT
<213> ORGANISM: Mus musculus
<220> FEATURE:
```

-continued

```
<221> NAME/KEY: MISC_FEATURE
<222> LOCATION: (1)..(17)
<223> OTHER INFORMATION: LBY135-2 anti-DR5 Antibody Heavy Chain Variable
      Region CDRH2

<400> SEQUENCE: 92

Trp Phe Tyr Pro Gly Gly Gly Tyr Ile Lys Tyr Asn Glu Lys Phe Lys
1               5                   10                  15

Asp

<210> SEQ ID NO 93
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: LBY135-2 anti-DR5 Antibody Heavy Chain Variable
      Region CDRH3

<400> SEQUENCE: 93

His Glu Glu Gly Ile Tyr Phe Asp Tyr
1               5

<210> SEQ ID NO 94
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: KMTR2 anti-DR5 Antibody Light Chain Variable
      Region

<400> SEQUENCE: 94

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg
            100                 105

<210> SEQ ID NO 95
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: KMTR2 anti-DR5 Antibody Light Chain Variable
      Region CDRL1

<400> SEQUENCE: 95

Arg Ala Ser Gln Ser Val Ser Ser Tyr Leu Ala
1               5                   10
```

<210> SEQ ID NO 96
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: KMTR2 anti-DR5 Antibody Light Chain Variable
      Region CDRL2

<400> SEQUENCE: 96

Asp Ala Ser Asn Arg Ala Thr
1               5

<210> SEQ ID NO 97
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: KMTR2 anti-DR5 Antibody Light Chain Variable
      Region CDRL3

<400> SEQUENCE: 97

Gln Gln Arg Ser Asn Trp Pro Leu Thr
1               5

<210> SEQ ID NO 98
<211> LENGTH: 126
<212> TYPE: PRT
<213> ORGANISM: Homo sapiens
<220> FEATURE:
<221> NAME/KEY: MISC_FEATURE
<222> LOCATION: (1)..(126)
<223> OTHER INFORMATION: KMTR2 anti-DR5 Antibody Heavy Chain Variable
      Region

<400> SEQUENCE: 98

Gln Val Gln Leu Val Gln Ser Gly Ala Glu Met Lys Lys Pro Gly Ala
1               5                   10                  15

Ser Val Lys Val Ser Cys Lys Thr Ser Gly Tyr Thr Phe Thr Asn Tyr
                20                  25                  30

Lys Ile Asn Trp Val Arg Gln Ala Pro Gly Gln Gly Leu Glu Trp Met
            35                  40                  45

Gly Trp Met Asn Pro Asp Thr Asp Ser Thr Gly Tyr Pro Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Gly Ser Gly Ser Tyr Tyr Arg Asp Tyr Tyr Tyr Gly
            100                 105                 110

Met Asp Val Trp Gly Gln Gly Thr Thr Val Thr Val Ser Ser
        115                 120                 125

<210> SEQ ID NO 99
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: KMTR2 anti-DR5 Antibody Heavy Chain Variable
      Region CDRH1

```
<400> SEQUENCE: 99

Gly Tyr Thr Phe Thr Asn Tyr Lys Ile Asn
1               5                   10

<210> SEQ ID NO 100
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: KMTR2 anti-DR5 Antibody Heavy Chain Variable
      Region CDRH2

<400> SEQUENCE: 100

Trp Met Asn Pro Asp Thr Asp Ser Thr Gly Tyr Pro Gln Lys Phe Gln
1               5                   10                  15

Gly

<210> SEQ ID NO 101
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: KMTR2 anti-DR5 Antibody Heavy Chain Variable
      Region CDRH3

<400> SEQUENCE: 101

Ser Tyr Gly Ser Gly Ser Tyr Tyr Arg Asp Tyr Tyr Tyr Gly Met Asp
1               5                   10                  15

Val

<210> SEQ ID NO 102
<211> LENGTH: 217
<212> TYPE: PRT
<213> ORGANISM: Artificial Sequence
<220> FEATURE:
<223> OTHER INFORMATION: IgG1 Fc Region L234A/L235A Variant

<400> SEQUENCE: 102

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
```

145                 150                 155                 160

Tyr Lys Thr Thr Pro Pro Val Leu Asp Ser Asp Gly Ser Phe Phe Leu
                    165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215

<210> SEQ ID NO 103
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: Human Wild-Type IgG4 CH2-CH3 Domain

<400> SEQUENCE: 103

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 104
<211> LENGTH: 110
<212> TYPE: PRT
<213> ORGANISM: Artificial Sequence
<220> FEATURE:
<223> OTHER INFORMATION: Humanized Anti-CD3 "mAb 2" Light Chain Variable
      Domain

<400> SEQUENCE: 104

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 105
<211> LENGTH: 14
<212> TYPE: PRT
<213> ORGANISM: Artificial Sequence
<220> FEATURE:
<223> OTHER INFORMATION: Humanized Anti-CD3 "mAb 2" Light Chain Variable
      Domain CDRL1

<400> SEQUENCE: 105

Arg Ser Ser Thr Gly Ala Val Thr Thr Ser Asn Tyr Ala Asn
1               5                   10

<210> SEQ ID NO 106
<211> LENGTH: 7
<212> TYPE: PRT
<213> ORGANISM: Artificial Sequence
<220> FEATURE:
<223> OTHER INFORMATION: Humanized Anti-CD3 "mAb 2" Light Chain Variable
      Domain CDRL2

<400> SEQUENCE: 106

Gly Thr Asn Lys Arg Ala Pro
1               5

<210> SEQ ID NO 107
<211> LENGTH: 9
<212> TYPE: PRT
<213> ORGANISM: Artificial Sequence
<220> FEATURE:
<223> OTHER INFORMATION: Humanized Anti-CD3 "mAb 2" Light Chain Variable
      Domain CDRL3

<400> SEQUENCE: 107

Ala Leu Trp Tyr Ser Asn Leu Trp Val
1               5

<210> SEQ ID NO 108
<211> LENGTH: 125
<212> TYPE: PRT
<213> ORGANISM: Artificial Sequence
<220> FEATURE:
<223> OTHER INFORMATION: Humanized Anti-CD3 "mAb 2" Heavy Chain Variable
      Domain

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

```
Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                    100                 105                 110

Ala Tyr Trp Gly Gln Gly Thr Leu Val Thr Val Ser Ser
            115                 120                 125

<210> SEQ ID NO 109
<211> LENGTH: 5
<212> TYPE: PRT
<213> ORGANISM: Artificial Sequence
<220> FEATURE:
<223> OTHER INFORMATION: Humanized Anti-CD3 "mAb 2" Heavy Chain Variable
      Domain CDRH1

<400> SEQUENCE: 109

Thr Tyr Ala Met Asn
1               5

<210> SEQ ID NO 110
<211> LENGTH: 19
<212> TYPE: PRT
<213> ORGANISM: Artificial Sequence
<220> FEATURE:
<223> OTHER INFORMATION: Humanized Anti-CD3 "mAb 2" Heavy Chain Variable
      Domain CDRH2

<400> SEQUENCE: 110

Arg Ile Arg Ser Lys Tyr Asn Asn Tyr Ala Thr Tyr Tyr Ala Asp Ser
1               5                   10                  15

Val Lys Asp

<210> SEQ ID NO 111
<211> LENGTH: 14
<212> TYPE: PRT
<213> ORGANISM: Artificial Sequence
<220> FEATURE:
<223> OTHER INFORMATION: Humanized Anti-CD3 "mAb 2" Heavy Chain Variable
      Domain CDRH3

<400> SEQUENCE: 111

His Gly Asn Phe Gly Asn Ser Tyr Val Ser Trp Phe Ala Tyr
1               5                   10

<210> SEQ ID NO 112
<211> LENGTH: 125
<212> TYPE: PRT
<213> ORGANISM: Artificial Sequence
<220> FEATURE:
<223> OTHER INFORMATION: Humanized Anti-CD3 "mAb 2" Heavy Chain Variable
      Domain D65G Variant

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
                    100                 105                 110

Ala Tyr Trp Gly Gln Gly Thr Leu Val Thr Val Ser Ser
                115                 120                 125

<210> SEQ ID NO 113
<211> LENGTH: 19
<212> TYPE: PRT
<213> ORGANISM: Artificial Sequence
<220> FEATURE:
<223> OTHER INFORMATION: Humanized Anti-CD3 "mAb 2" Heavy Chain Variable
      Domain D65G Variant CDRH2

<400> SEQUENCE: 113

Arg Ile Arg Ser Lys Tyr Asn Asn Tyr Ala Thr Tyr Tyr Ala Asp Ser
1               5                   10                  15

Val Lys Gly

<210> SEQ ID NO 114
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: Fluorescein antibody 4-4-20 Light Chain
      Variable Domain

<400> SEQUENCE: 114

Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
                100                 105                 110

<210> SEQ ID NO 115
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: Fluorescein antibody 4-4-20 Heavy Chain
      Variable Domain

<400> SEQUENCE: 115

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser
        115

<210> SEQ ID NO 116
<211> LENGTH: 503
<212> TYPE: PRT
<213> ORGANISM: Artificial Sequence
<220> FEATURE:
<223> OTHER INFORMATION: First Polypeptide Chain of an Exemplary DR5 mAb
      1 x DR5 mAb 2 Fc diabody

<400> SEQUENCE: 116

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45

Lys Val Leu Ile Phe Leu Ser Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Gly Asp Ala Ala Thr Tyr Tyr Cys Gln His Ser Arg
                85                  90                  95

Asp Leu Pro Pro Thr Phe Gly Gly Gly Thr Lys Leu Glu Ile Lys Gly
            100                 105                 110

Gly Gly Ser Gly Gly Gly Gly Lys Val Gln Leu Gln Gln Ser Gly Ala
        115                 120                 125

Glu Leu Val Lys Pro Gly Ala Ser Val Lys Leu Ser Cys Lys Ala Ser
    130                 135                 140

Gly Tyr Thr Phe Thr Glu Tyr Ile Leu His Trp Val Lys Gln Lys Ser
145                 150                 155                 160

Gly Gln Gly Leu Glu Trp Ile Gly Trp Phe Tyr Pro Gly Asn Asn Asn
                165                 170                 175

Ile Lys Tyr Asn Glu Lys Phe Lys Asp Lys Ala Thr Leu Thr Ala Asp
            180                 185                 190

Lys Ser Ser Ser Thr Val Tyr Met Glu Leu Ser Arg Leu Thr Ser Glu
        195                 200                 205

Asp Ser Ala Val Tyr Phe Cys Ala Arg His Glu Gln Gly Pro Gly Tyr
    210                 215                 220

```
Phe Asp Tyr Trp Gly Gln Gly Thr Thr Leu Thr Val Ser Ser Ala Ser
225                 230                 235                 240

Thr Lys Gly Glu Val Ala Ala Cys Glu Lys Glu Val Ala Ala Leu Glu
            245                 250                 255

Lys Glu Val Ala Ala Leu Glu Lys Glu Val Ala Ala Leu Glu Lys Leu
        260                 265                 270

Glu Pro Lys Ser Ser Asp Lys Thr His Thr Cys Pro Pro Cys Pro Ala
    275                 280                 285

Pro Glu Leu Leu Gly Gly Pro Ser Val Phe Leu Phe Pro Pro Lys Pro
290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
            325                 330                 335

Asp Gly Val Glu Val His Asn Ala Lys Thr Lys Pro Arg Glu Glu Gln
        340                 345                 350

Tyr Asn Ser Thr Tyr Arg Val Val Ser Val Leu Thr Val Leu His Gln
    355                 360                 365

Asp Trp Leu Asn Gly Lys Glu Tyr Lys Cys Lys Val Ser Asn Lys Ala
370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
            405                 410                 415

Lys Asn Gln Val Ser Leu Thr Cys Leu Val Lys Gly Phe Tyr Pro Ser
        420                 425                 430

Asp Ile Ala Val Glu Trp Glu Ser Asn Gly Gln Pro Glu Asn Asn Tyr
    435                 440                 445

Lys Thr Thr Pro Pro Val Leu Asp Ser Asp Gly Ser Phe Phe Leu Tyr
450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
            485                 490                 495

Ser Leu Ser Leu Ser Pro Gly
            500
```

<210> SEQ ID NO 117
<211> LENGTH: 1509
<212> TYPE: DNA
<213> ORGANISM: Artificial Sequence
<220> FEATURE:
<223> OTHER INFORMATION: Polynucleotide Encoding First Polypeptide Chain
      of an Exemplary DR5 mAb 1 x DR5 mAb 2 Fc diabody

<400> SEQUENCE: 117
gacattgtgc tgacacagtc tcctgcttcc ttagctgtat ctctcgggca gagggccacc      60
atctcatgca gggccagcaa agtgtcagt tcctctggct atagttatat gcactggtac      120
caacagaaac caggacagcc acccaaagtc ctcatctttc tttcatccaa cctagattct      180
ggggtccctg ccaggttcag tggcagtggg tctgggacag acttcaccct caacatccat      240
cctgtggagg atgggatgc tgcaacctat tactgtcagc acagtaggga tcttcctccg      300
acgttcggtg gaggcaccaa gctggaaatc aaaggaggcg gatccggcgg cggaggcaag      360
gtccagctgc agcagtctgg agctgaactg gtgaaacccg ggcatcagt gaagctgtcc      420

```
tgcaaggctt ctgggtacac cttcactgag tatattttac actgggtaaa gcagaagtct    480
ggacagggtc ttgagtggat tgggtggttt tatcctggaa ataataatat aaagtacaat    540
gagaaattca aggacaaggc cacactgact gcggacaaat cctccagcac agtctatatg    600
gaacttagta gattgacatc tgaagactct gcggtctatt tctgtgcaag acacgaacaa    660
ggaccaggtt actttgacta ctggggccaa ggcaccactc tcacagtctc ctccgcctcc    720
accaagggcg aagtggccgc atgtgagaaa gaggttgctg cttttggaga aggaggtcgct   780 gcacttgaaa aggaggtcgc agccctggag aaactggagc ccaaatcttc tgacaaaact    840
cacacatgcc caccgtgccc agcacctgaa ctcctggggg gaccgtcagt cttcctcttc    900
cccccaaaac ccaaggacac cctcatgatc tcccggaccc ctgaggtcac atgcgtggtg    960
gtggacgtga gccacgaaga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggagtacaa gtgcaaggtc   1140
tccaacaaag ccctcccagc ccccatcgag aaaaccatct ccaaagccaa agggcagccc   1200
cgagaaccac aggtgtacac cctgcccccca tcccgggagg agatgaccaa gaaccaggtc   1260
agcctgacct gcctggtcaa aggcttctat cccagcgaca tcgccgtgga gtgggagagc   1320
aatgggcagc cggagaacaa ctacaagacc acgcctcccg tgctggactc cgacggctcc   1380
ttcttcctct acagcaagct caccgtggac aagagcaggt ggcagcaggg gaacgtcttc   1440
tcatgctccg tgatgcatga ggctctgcac aaccactaca cgcagaagag cctctccctg   1500
tctccgggt                                                           1509
```

<210> SEQ ID NO 118
<211> LENGTH: 269
<212> TYPE: PRT
<213> ORGANISM: Artificial Sequence
<220> FEATURE:
<223> OTHER INFORMATION: Second Polypeptide Chain of an Exemplary DR5
    mAb 1 x DR5 mAb 2 Fc diabody

<400> SEQUENCE: 118

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Lys Ser Val Gln Ala
65                  70                  75                  80

Glu Asp Leu Thr Leu Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
            100                 105                 110

Gly Gly Gly Glu Val Lys Phe Leu Glu Ser Gly Gly Gly Leu Val Gln
        115                 120                 125

Pro Gly Gly Ser Leu Lys Leu Ser Cys Val Ala Ser Gly Phe Asp Phe
    130                 135                 140

Ser Arg Tyr Trp Met Ser Trp Val Arg Gln Ala Pro Gly Lys Gly Leu
145                 150                 155                 160
```

Glu Trp Ile Gly Glu Ile Asn Pro Asp Ser Asn Thr Ile Asn Tyr Thr
            165                 170                 175

Pro Ser Leu Lys Asp Lys Phe Ile Ile Ser Arg Asp Asn Ala Lys Asn
            180                 185                 190

Thr Leu Tyr Leu Gln Met Thr Lys Val Arg Ser Glu Asp Thr Ala Leu
            195                 200                 205

Tyr Tyr Cys Thr Arg Arg Ala Tyr Tyr Gly Asn Pro Ala Trp Phe Ala
        210                 215                 220

Tyr Trp Gly Gln Gly Thr Leu Val Thr Val Ser Ala Ala Ser Thr Lys
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
            260                 265

<210> SEQ ID NO 119
<211> LENGTH: 807
<212> TYPE: DNA
<213> ORGANISM: Artificial Sequence
<220> FEATURE:
<223> OTHER INFORMATION: Polynucleotide Encoding Second Polypeptide
      Chain of an Exemplary DR5 mAb 1 x DR5 mAb 2 Fc diabody

<400> SEQUENCE: 119
gacattgtga tgacccagtc tcacaaattc atgtccactt cagtaggaga cagggtcagc      60
atcacctgca aggccagtca ggatgtgaat actgctgtag cctggtatca acaaaaacca     120
gggcaatctc ctaaactact gatttactgg gcatccaccc ggcacactgg agtccctgat     180
cgcttcacag gcagtggatc tgggacagat tatacactca ccatcaaaag tgtgcaggct     240
gaagacctga cactttatta ctgtcagcaa cactatatca ctccgtggac gttcggtgga     300
ggcaccaagc tggaaatcaa aggaggcgga tccggcggcg gaggcgaggt gaagtttctc     360
gagtctggag gtggcctggt gcagcctgga ggatccctga actctcctg tgtagcctca      420 ggattcgatt ttagtagata ctggatgagt tgggtccggc aggctccagg aaagggcta      480 gaatggattg agaaattaa tccagatagc aatacgataa actatacgcc atctctaaag     540
gataaattca tcatctccag agacaacgcc aaaaatacgc tgtatctgca aatgaccaaa     600
gtgagatctg aggacacagc cctttattat tgtacaagaa gggcctacta tggtaacccg     660
gcctggtttg cttactgggg ccaagggact ctggtcactg tctctgcagc ctccaccaag     720
ggcaaagtgg ccgcatgtaa ggagaaagtt gctgctttga agagaaggt cgccgcactt      780 aaggaaaagg tcgcagccct gaaagag                                         807

<210> SEQ ID NO 120
<211> LENGTH: 503
<212> TYPE: PRT
<213> ORGANISM: Artificial Sequence
<220> FEATURE:
<223> OTHER INFORMATION: First Polypeptide Chain of an Exemplary DR5 mAb
      1 x DR5 mAb 2 Fc diabody L234A/L235A

<400> SEQUENCE: 120

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro

```
            35                  40                  45
Lys Val Leu Ile Phe Leu Ser Ser Asn Leu Asp Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Asp Gly Asp Ala Ala Thr Tyr Tyr Cys Gln His Ser Arg
                 85                  90                  95

Asp Leu Pro Pro Thr Phe Gly Gly Gly Thr Lys Leu Glu Ile Lys Gly
                100                 105                 110

Gly Gly Ser Gly Gly Gly Gly Lys Val Gln Leu Gln Gln Ser Gly Ala
                115                 120                 125

Glu Leu Val Lys Pro Gly Ala Ser Val Lys Leu Ser Cys Lys Ala Ser
                130                 135                 140

Gly Tyr Thr Phe Thr Glu Tyr Ile Leu His Trp Val Lys Gln Lys Ser
145                 150                 155                 160

Gly Gln Gly Leu Glu Trp Ile Gly Trp Phe Tyr Pro Gly Asn Asn Asn
                165                 170                 175

Ile Lys Tyr Asn Glu Lys Phe Lys Asp Lys Ala Thr Leu Thr Ala Asp
                180                 185                 190

Lys Ser Ser Ser Thr Val Tyr Met Glu Leu Ser Arg Leu Thr Ser Glu
                195                 200                 205

Asp Ser Ala Val Tyr Phe Cys Ala Arg His Glu Gln Gly Pro Gly Tyr
                210                 215                 220

Phe Asp Tyr Trp Gly Gln Gly Thr Thr Leu Thr Val Ser Ser Ala Ser
225                 230                 235                 240

Thr Lys Gly Glu Val Ala Ala Cys Glu Lys Glu Val Ala Ala Leu Glu
                245                 250                 255

Lys Glu Val Ala Ala Leu Glu Lys Glu Val Ala Ala Leu Glu Lys Leu
                260                 265                 270

Glu Pro Lys Ser Ser Asp Lys Thr His Thr Cys Pro Pro Cys Pro Ala
                275                 280                 285

Pro Glu Ala Ala Gly Gly Pro Ser Val Phe Leu Phe Pro Pro Lys Pro
                290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
                340                 345                 350

Tyr Asn Ser Thr Tyr Arg Val Val Ser Val Leu Thr Val Leu His Gln
                355                 360                 365

Asp Trp Leu Asn Gly Lys Glu Tyr Lys Cys Lys Val Ser Asn Lys Ala
                370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                405                 410                 415

Lys Asn Gln Val Ser Leu Thr Cys Leu Val Lys Gly Phe Tyr Pro Ser
                420                 425                 430

Asp Ile Ala Val Glu Trp Glu Ser Asn Gly Gln Pro Glu Asn Asn Tyr
                435                 440                 445

Lys Thr Thr Pro Pro Val Leu Asp Ser Asp Gly Ser Phe Phe Leu Tyr
450                 455                 460
```

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
            485                 490                 495

Ser Leu Ser Leu Ser Pro Gly
            500

<210> SEQ ID NO 121
<211> LENGTH: 1509
<212> TYPE: DNA
<213> ORGANISM: Artificial Sequence
<220> FEATURE:
<223> OTHER INFORMATION: Polynucleotide Encoding First Polypeptide Chain
      of an Exemplary DR5 mAb 1 x DR5 mAb 2 Fc diabody L234A/L235A

<400> SEQUENCE: 121
gacattgtgc tgacacagtc tcctgcttcc ttagctgtat ctctcgggca gagggccacc      60
atctcatgca gggccagcaa aagtgtcagt tcctctggct atagttatat gcactggtac     120
caacagaaac aggacagcc acccaaagtc ctcatctttc tttcatccaa cctagattct     180
ggggtccctg ccaggttcag tggcagtggg tctgggacag acttcaccct caacatccat     240
cctgtggagg atgggatgc tgcaacctat tactgtcagc acagtaggga tcttcctccg     300
acgttcggtg gaggcaccaa gctggaaatc aaaggaggcg gatccggcgg cggaggcaag     360
gtccagctgc agcagtctgg agctgaactg gtgaaacccg gggcatcagt gaagctgtcc     420
tgcaaggctt ctgggtacac cttcactgag tatattttac actgggtaaa gcagaagtct     480
ggacagggtc ttgagtggat tgggtggttt tatcctggaa ataataatat aaagtacaat     540
gagaaattca aggacaaggc cacactgact gcggacaaat cctccagcac agtctatatg     600
gaacttagta gattgacatc tgaagactct gcggtctatt tctgtgcaag acacgaacaa     660
ggaccaggtt actttgacta ctggggccaa ggcaccactc tcacagtctc ctccgcctcc     720
accaagggcg aagtggccgc atgtgagaaa gaggttgctg ctttggagaa ggaggtcgct     780
gcacttgaaa aggaggtcgc agccctggag aaactggagc ccaaatcttc tgacaaaact     840
cacacatgcc caccgtgccc agcacctgaa ctcctgggg gaccgtcagt cttcctcttc     900
cccccaaaac ccaaggacac cctcatgatc tcccggaccc ctgaggtcac atgcgtggtg     960
gtggacgtga gccacgaaga ccctgaggtc aagttcaact ggtacgtgga cggcgtggag    1020
gtgcataatg ccaagacaaa gccgcgggag gagcagtaca acagcacgta ccgtgtggtc    1080
agcgtcctca ccgtcctgca ccaggactgg ctgaatggca aggagtacaa gtgcaaggtc    1140
tccaacaaag ccctcccagc ccccatcgag aaaaccatct ccaaagccaa agggcagccc    1200
cgagaaccac aggtgtacac cctgccccca tcccgggagg agatgaccaa gaaccaggtc    1260
agcctgacct gcctggtcaa aggcttctat cccagcgaca tcgccgtgga gtgggagagc    1320
aatgggcagc cggagaacaa ctacaagacc acgcctcccg tgctggactc cgacggctcc    1380
ttcttcctct acagcaagct caccgtggac aagagcaggt ggcagcaggg gaacgtcttc    1440
tcatgctccg tgatgcatga ggctctgcac aaccactaca cgcagaagag cctctccctg    1500
tctccgggt                                                            1509

<210> SEQ ID NO 122
<211> LENGTH: 501
<212> TYPE: PRT
<213> ORGANISM: Artificial Sequence
<220> FEATURE:

<223> OTHER INFORMATION: First Polypeptide Chain of an Exemplary DR5 mAb 2 x DR5 mAb 1 Fc diabody

<400> SEQUENCE: 122

```
Asp Ile Val Met Thr Gln Ser His Lys Phe Met Ser Thr Ser Val Gly
  1               5                  10                  15

Asp Arg Val Ser Ile Thr Cys Lys Ala Ser Gln Asp Val Asn Thr Ala
             20                  25                  30

Val Ala Trp Tyr Gln Gln Lys Pro Gly Gln Ser Pro Lys Leu Leu Ile
         35                  40                  45

Tyr Trp Ala Ser Thr Arg His Thr Gly Val Pro Asp Arg Phe Thr Gly
 50                  55                  60

Ser Gly Ser Gly Thr Asp Tyr Thr Leu Thr Ile Lys Ser Val Gln Ala
 65                  70                  75                  80

Glu Asp Leu Thr Leu Tyr Tyr Cys Gln Gln His Tyr Ile Thr Pro Trp
                 85                  90                  95

Thr Phe Gly Gly Gly Thr Lys Leu Glu Ile Lys Gly Gly Gly Ser Gly
                100                 105                 110

Gly Gly Gly Glu Val Lys Phe Leu Glu Ser Gly Gly Gly Leu Val Gln
            115                 120                 125

Pro Gly Gly Ser Leu Lys Leu Ser Cys Val Ala Ser Gly Phe Asp Phe
130                 135                 140

Ser Arg Tyr Trp Met Ser Trp Val Arg Gln Ala Pro Gly Lys Gly Leu
145                 150                 155                 160

Glu Trp Ile Gly Glu Ile Asn Pro Asp Ser Asn Thr Ile Asn Tyr Thr
                165                 170                 175

Pro Ser Leu Lys Asp Lys Phe Ile Ile Ser Arg Asp Asn Ala Lys Asn
                180                 185                 190

Thr Leu Tyr Leu Gln Met Thr Lys Val Arg Ser Glu Asp Thr Ala Leu
            195                 200                 205

Tyr Tyr Cys Thr Arg Arg Ala Tyr Tyr Gly Asn Pro Ala Trp Phe Ala
        210                 215                 220

Tyr Trp Gly Gln Gly Thr Leu Val Thr Val Ser Ala Ala Ser Thr Lys
225                 230                 235                 240

Gly Glu Val Ala Ala Cys Glu Lys Glu Val Ala Ala Leu Glu Lys Glu
                245                 250                 255

Val Ala Ala Leu Glu Lys Glu Val Ala Ala Leu Glu Lys Leu Glu Pro
            260                 265                 270

Lys Ser Ser Asp Lys Thr His Thr Cys Pro Pro Cys Pro Ala Pro Glu
        275                 280                 285

Leu Leu Gly Gly Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Lys Val Ser Asn Lys Ala Leu Pro
    370                 375                 380

Ala Pro Ile Glu Lys Thr Ile Ser Lys Ala Lys Gly Gln Pro Arg Glu
385                 390                 395                 400
```

```
Pro Gln Val Tyr Thr Leu Pro Pro Ser Arg Glu Glu Met Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly
                500

<210> SEQ ID NO 123
<211> LENGTH: 1503
<212> TYPE: DNA
<213> ORGANISM: Artificial Sequence
<220> FEATURE:
<223> OTHER INFORMATION: Polynucleotide Encoding First Polypeptide Chain
      of an Exemplary DR5 mAb 2 x DR5 mAb 1 Fc diabody

<400> SEQUENCE: 123
gacattgtga tgacccagtc tcacaaattc atgtccactt cagtaggaga cagggtcagc     60
atcacctgca aggccagtca ggatgtgaat actgctgtag cctggtatca acaaaaacca    120
gggcaatctc ctaaactact gatttactgg gcatccaccc ggcacactgg agtccctgat    180
cgcttcacag gcagtggatc tgggacagat tatacactca ccatcaaaag tgtgcaggct    240
gaagacctga cactttatta ctgtcagcaa cactatatca ctccgtggac gttcggtgga    300
ggcaccaagc tggaaatcaa aggaggcgga tccggcggcg gaggcgaggt gaagtttctc    360
gagtctggag gtggcctggt gcagcctgga ggatccctga actctcctg tgtagcctca    420 ggattcgatt ttagtagata ctggatgagt tgggtccggc aggctccagg aaagggcta    480 gaatggattg agaaaattaa tccagatagc aatacgataa actatacgcc atctctaaag    540
gataaattca tcatctccag agacaacgcc aaaaatacgc tgtatctgca aatgaccaaa    600
gtgagatctg aggacacagc cctttattat tgtacaagaa gggcctacta tggtaacccg    660
gcctggtttg cttactgggg ccaagggact ctggtcactg tctctgcagc ctccaccaag    720
ggcgaagtgg ccgcatgtga aaagaggtt gctgctttgg agaaggaggt cgctgcactt    780
gaaaaggagg tcgcagccct ggagaaactg agcccaaat cttctgacaa aactcacaca    840
tgcccaccgt gcccagcacc tgaactcctg ggggaccgt cagtcttcct cttcccccca    900
aaacccaagg acaccctcat gatctcccgg acccctgagg tcacatgcgt ggtggtggac    960
gtgagccacg aagaccctga ggtcaagttc aactggtacg tggacggcgt ggaggtgcat   1020
aatgccaaga caaagccgcg ggaggagcag tacaacagca cgtaccgtgt ggtcagcgtc   1080
ctcaccgtcc tgcaccagga ctggctgaat ggcaaggagt acaagtgcaa ggtctccaac   1140
aaagccctcc cagcccccat cgagaaaacc atctccaaag ccaagggca gccccgagaa   1200 ccacaggtgt acaccctgcc cccatcccgg gaggagatga ccaagaacca ggtcagcctg   1260
acctgcctgg tcaaaggctt ctatcccagc gacatcgccg tggagtggga gagcaatggg   1320
cagccggaga acaactacaa gaccacgcct cccgtgctgg actccgacgg ctccttcttc   1380
```
ctctacagca agctcaccgt ggacaagagc aggtggcagc agggaacgt cttctcatgc   1440 tccgtgatgc atgaggctct gcacaaccac tacacgcaga agagcctctc cctgtctccg   1500
ggt                                                                 1503

<210> SEQ ID NO 124
<211> LENGTH: 271
<212> TYPE: PRT
<213> ORGANISM: Artificial Sequence
<220> FEATURE:
<223> OTHER INFORMATION: Second Polypeptide Chain of an Exemplary DR5
      mAb 2 x DR5 mAb 1 Fc diabody

<400> SEQUENCE: 124

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45

Lys Val Leu Ile Phe Leu Ser Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Gly Asp Ala Ala Thr Tyr Tyr Cys Gln His Ser Arg
                85                  90                  95

Asp Leu Pro Pro Thr Phe Gly Gly Gly Thr Lys Leu Glu Ile Lys Gly
            100                 105                 110

Gly Gly Ser Gly Gly Gly Gly Lys Val Gln Leu Gln Gln Ser Gly Ala
        115                 120                 125

Glu Leu Val Lys Pro Gly Ala Ser Val Lys Leu Ser Cys Lys Ala Ser
    130                 135                 140

Gly Tyr Thr Phe Thr Glu Tyr Ile Leu His Trp Val Lys Gln Lys Ser
145                 150                 155                 160

Gly Gln Gly Leu Glu Trp Ile Gly Trp Phe Tyr Pro Gly Asn Asn Asn
                165                 170                 175

Ile Lys Tyr Asn Glu Lys Phe Lys Asp Lys Ala Thr Leu Thr Ala Asp
            180                 185                 190

Lys Ser Ser Ser Thr Val Tyr Met Glu Leu Ser Arg Leu Thr Ser Glu
        195                 200                 205

Asp Ser Ala Val Tyr Phe Cys Ala Arg His Glu Gln Gly Pro Gly Tyr
    210                 215                 220

Phe Asp Tyr Trp Gly Gln Gly Thr Thr Leu Thr Val Ser Ser Ala Ser
225                 230                 235                 240

Thr Lys Gly Lys Val Ala Ala Cys Lys Glu Lys Val Ala Ala Leu Lys
                245                 250                 255

Glu Lys Val Ala Ala Leu Lys Glu Lys Val Ala Ala Leu Lys Glu
            260                 265                 270

<210> SEQ ID NO 125
<211> LENGTH: 813
<212> TYPE: DNA
<213> ORGANISM: Artificial Sequence
<220> FEATURE:
<223> OTHER INFORMATION: Polynucleotide Encoding Second Polypeptide
      Chain of an Exemplary DR5 mAb 2 x DR5 mAb 1 Fc diabody

<400> SEQUENCE: 125

```
gacattgtgc tgacacagtc tcctgcttcc ttagctgtat ctctcgggca gagggccacc    60
atctcatgca gggccagcaa aagtgtcagt tcctctggct atagttatat gcactggtac   120
caacagaaac caggacagcc acccaaagtc ctcatctttc tttcatccaa cctagattct   180
ggggtccctg ccaggttcag tggcagtggg tctgggacag acttcaccct caacatccat   240
cctgtggagg atgggggatgc tgcaacctat tactgtcagc acagtaggga tcttcctccg   300
acgttcggtg gaggcaccaa gctggaaatc aaaggaggcg gatccggcgg cggaggcaag   360
gtccagctgc agcagtctgg agctgaactg gtgaacccg gggcatcagt gaagctgtcc   420
tgcaaggctt ctgggtacac cttcactgag tatattttac actgggtaaa gcagaagtct   480
ggacagggtc ttgagtggat tgggtggttt atcctggaa ataataatat aaagtacaat   540
gagaaattca aggacaaggc cacactgact gcggacaaat cctccagcac agtctatatg   600
gaacttagta gattgacatc tgaagactct gcggtctatt tctgtgcaag acacgaacaa   660
ggaccaggtt actttgacta ctggggccaa ggcaccactc tcacagtctc ctccgcctcc   720
accaagggca agtggccgc atgtaaggag aaagttgctg ctttgaaaga aaggtcgcc   780
gcacttaagg aaaaggtcgc agccctgaaa gag                                813
```

<210> SEQ ID NO 126
<211> LENGTH: 501
<212> TYPE: PRT
<213> ORGANISM: Artificial Sequence
<220> FEATURE:
<223> OTHER INFORMATION: First Polypeptide Chain of an Exemplary DR5 mAb
2 x DR5 mAb 1 Fc diabody L234A/L235A

<400> SEQUENCE: 126

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Lys Ser Val Gln Ala
65                  70                  75                  80

Glu Asp Leu Thr Leu Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
            100                 105                 110

Gly Gly Gly Glu Val Lys Phe Leu Glu Ser Gly Gly Gly Leu Val Gln
        115                 120                 125

Pro Gly Gly Ser Leu Lys Leu Ser Cys Val Ala Ser Gly Phe Asp Phe
    130                 135                 140

Ser Arg Tyr Trp Met Ser Trp Val Arg Gln Ala Pro Gly Lys Gly Leu
145                 150                 155                 160

Glu Trp Ile Gly Glu Ile Asn Pro Asp Ser Asn Thr Ile Asn Tyr Thr
                165                 170                 175

Pro Ser Leu Lys Asp Lys Phe Ile Ile Ser Arg Asp Asn Ala Lys Asn
            180                 185                 190

Thr Leu Tyr Leu Gln Met Thr Lys Val Arg Ser Glu Asp Thr Ala Leu
        195                 200                 205

Tyr Tyr Cys Thr Arg Arg Ala Tyr Tyr Gly Asn Pro Ala Trp Phe Ala
```

Tyr Trp Gly Gln Gly Thr Leu Val Thr Val Ser Ala Ala Ser Thr Lys
225                 230                 235                 240

Gly Glu Val Ala Ala Cys Glu Lys Glu Val Ala Ala Leu Glu Lys Glu
            245                 250                 255

Val Ala Ala Leu Glu Lys Glu Val Ala Ala Leu Glu Lys Leu Glu Pro
                260                 265                 270

Lys Ser Ser Asp Lys Thr His Thr Cys Pro Pro Cys Pro Ala Pro Glu
        275                 280                 285

Ala Ala Gly Gly Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
            325                 330                 335

Val Glu Val His Asn Ala Lys Thr Lys Pro Arg Glu Glu Gln Tyr Asn
                340                 345                 350

Ser Thr Tyr Arg Val Val Ser Val Leu Thr Val Leu His Gln Asp Trp
        355                 360                 365

Leu Asn Gly Lys Glu Tyr Lys Cys Lys Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Glu Glu Met Thr Lys Asn
            405                 410                 415

Gln Val Ser Leu Thr Cys Leu Val Lys Gly Phe Tyr Pro Ser Asp Ile
                420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
            485                 490                 495

Ser Leu Ser Pro Gly
            500

<210> SEQ ID NO 127
<211> LENGTH: 1503
<212> TYPE: DNA
<213> ORGANISM: Artificial Sequence
<220> FEATURE:
<223> OTHER INFORMATION: Polynucleotide Encoding First Polypeptide Chain
      of an Exemplary DR5 mAb 2 x DR5 mAb 1 Fc diabody L234A/L235A

<400> SEQUENCE: 127
gacattgtga tgacccagtc tcacaaattc atgtccactt cagtaggaga cagggtcagc     60
atcacctgca aggccagtca ggatgtgaat actgctgtag cctggtatca acaaaaacca    120
gggcaatctc ctaaaactac tgatttactg gcatccaccc ggcacactgg agtccctgat    180
cgcttcacag gcagtggatc tgggacagat tatacactca ccatcaaaag tgtgcaggct    240
gaagacctga cactttatta ctgtcagcaa cactatatcc ctccgtgcac gttcggtgga    300
ggcaccaagc tggaaatcaa aggaggcgga tccggcggcg gaggcgaggt gaagtttctc    360

```
gagtctggag gtggcctggt gcagcctgga ggatccctga aactctcctg tgtagcctca    420
ggattcgatt ttagtagata ctggatgagt tgggtccggc aggctccagg gaaagggcta    480
gaatggattg agaaattaa tccagatagc aatacgataa actatacgcc atctctaaag    540
gataaattca tcatctccag agacaacgcc aaaaatacgc tgtatctgca aatgaccaaa    600
gtgagatctg aggacacagc cctttattat tgtacaagaa gggcctacta tggtaacccg    660
gcctggtttg cttactgggg ccaagggact ctggtcactg tctctgcagc ctccaccaag    720
ggcgaagtgg ccgcatgtga aaagaggtt gctgctttgg agaaggaggt cgctgcactt    780
gaaaaggagg tcgcagccct ggagaaactg agcccaaat cttctgacaa aactcacaca    840
tgcccaccgt gcccagcacc tgaactcctg ggggaccgt cagtcttcct cttccccca    900 aaacccaagg acaccctcat gatctcccgg acccctgagg tcacatgcgt ggtggtggac    960
gtgagccacg aagaccctga ggtcaagttc aactggtacg tggacggcgt ggaggtgcat   1020
aatgccaaga caaagccgcg ggaggagcag tacaacagca cgtaccgtgt ggtcagcgtc   1080
ctcaccgtcc tgcaccagga ctggctgaat ggcaaggagt acaagtgcaa ggtctccaac   1140
aaagccctcc cagcccccat cgagaaaacc atctccaaag ccaaagggca gccccgagaa   1200
ccacaggtgt acaccctgcc cccatcccgg gaggagatga ccaagaacca ggtcagcctg   1260
acctgcctgg tcaaaggctt ctatcccagc gacatcgccg tggagtggga gagcaatggg   1320
cagccggaga caactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga gagcctctc cctgtctccg    1500 ggt                                                                 1503
```

<210> SEQ ID NO 128
<211> LENGTH: 505
<212> TYPE: PRT
<213> ORGANISM: Artificial Sequence
<220> FEATURE:
<223> OTHER INFORMATION: First Polypeptide Chain of an Exemplary DR5 mAb
      1 x DR5 mAb 1 Fc diabody

<400> SEQUENCE: 128

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45

Lys Val Leu Ile Phe Leu Ser Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Gly Asp Ala Ala Thr Tyr Tyr Cys Gln His Ser Arg
                85                  90                  95

Asp Leu Pro Pro Thr Phe Gly Gly Gly Thr Lys Leu Glu Ile Lys Gly
            100                 105                 110

Gly Gly Ser Gly Gly Gly Gly Glu Val Lys Phe Leu Glu Ser Gly Gly
        115                 120                 125

Gly Leu Val Gln Pro Gly Gly Ser Leu Lys Leu Ser Cys Val Ala Ser
    130                 135                 140

Gly Phe Asp Phe Ser Arg Tyr Trp Met Ser Trp Val Arg Gln Ala Pro
```

145                 150                 155                 160
        Gly Lys Gly Leu Glu Trp Ile Gly Glu Ile Asn Pro Asp Ser Asn Thr
                        165                 170                 175

Ile Asn Tyr Thr Pro Ser Leu Lys Asp Lys Phe Ile Ile Ser Arg Asp
                        180                 185                 190

Asn Ala Lys Asn Thr Leu Tyr Leu Gln Met Thr Lys Val Arg Ser Glu
                        195                 200                 205

Asp Thr Ala Leu Tyr Tyr Cys Thr Arg Arg Ala Tyr Tyr Gly Asn Pro
            210                 215                 220

Ala Trp Phe Ala Tyr Trp Gly Gln Gly Thr Leu Val Thr Val Ser Ala
        225                 230                 235                 240

Ala Ser Thr Lys Gly Glu Val Ala Ala Cys Glu Lys Glu Val Ala Ala
                        245                 250                 255

Leu Glu Lys Glu Val Ala Ala Leu Glu Lys Glu Val Ala Ala Leu Glu
                        260                 265                 270

Lys Leu Glu Pro Lys Ser Ser Asp Lys Thr His Thr Cys Pro Pro Cys
                275                 280                 285

Pro Ala Pro Glu Leu Leu Gly Gly Pro Ser Val Phe Leu Phe Pro Pro
                290                 295                 300

Lys Pro Lys Asp Thr Leu Met Ile Ser Arg Thr Pro Glu Val Thr Cys
        305                 310                 315                 320

Val Val Val Asp Val Ser His Glu Asp Pro Glu Val Lys Phe Asn Trp
                        325                 330                 335

Tyr Val Asp Gly Val Glu Val His Asn Ala Lys Thr Lys Pro Arg Glu
                        340                 345                 350

Glu Gln Tyr Asn Ser Thr Tyr Arg Val Val Ser Val Leu Thr Val Leu
                        355                 360                 365

His Gln Asp Trp Leu Asn Gly Lys Glu Tyr Lys Cys Lys Val Ser Asn
                370                 375                 380

Lys Ala Leu Pro Ala Pro Ile Glu Lys Thr Ile Ser Lys Ala Lys Gly
        385                 390                 395                 400

Gln Pro Arg Glu Pro Gln Val Tyr Thr Leu Pro Pro Ser Arg Glu Glu
                        405                 410                 415

Met Thr Lys Asn Gln Val Ser Leu Thr Cys Leu Val Lys Gly Phe Tyr
                        420                 425                 430

Pro Ser Asp Ile Ala Val Glu Trp Glu Ser Asn Gly Gln Pro Glu Asn
                        435                 440                 445

Asn Tyr Lys Thr Thr Pro Pro Val Leu Asp Ser Asp Gly Ser Phe Phe
        450                 455                 460

Leu Tyr Ser Lys Leu Thr Val Asp Lys Ser Arg Trp Gln Gln Gly Asn
        465                 470                 475                 480

Val Phe Ser Cys Ser Val Met His Glu Ala Leu His Asn His Tyr Thr
                        485                 490                 495

Gln Lys Ser Leu Ser Leu Ser Pro Gly
                        500                 505

<210> SEQ ID NO 129
<211> LENGTH: 1515
<212> TYPE: DNA
<213> ORGANISM: Artificial Sequence
<220> FEATURE:
<223> OTHER INFORMATION: Polynucleotide Encoding First Polypeptide Chain
      of an Exemplary DR5 mAb 1 x DR5 mAb 1 Fc diabody

<400> SEQUENCE: 129

```
gacattgtgc tgacacagtc tcctgcttcc ttagctgtat ctctcgggca gagggccacc      60
atctcatgca gggccagcaa aagtgtcagt tcctctggct atagttatat gcactggtac     120
caacagaaac caggacagcc acccaaagtc ctcatctttc tttcatccaa cctagattct     180
ggggtccctg ccaggttcag tggcagtggg tctgggacag acttcaccct caacatccat     240
cctgtggagg atggggatgc tgcaacctat tactgtcagc acagtaggga tcttcctccg     300
acgttcggtg gaggcaccaa gctggaaatc aaaggaggcg gatccggcgg cggaggcgag     360
gtgaagtttc tcgagtctgg aggtggcctg gtgcagcctg gaggatccct gaaactctcc     420
tgtgtagcct caggattcga ttttagtaga tactggatga gttgggtccg gcaggctcca     480
gggaaagggc tagaatggat tggagaaatt aatccagata gcaatacgat aaactatacg     540
ccatctctaa aggataaatt catcatctcc agagacaacg ccaaaaatac gctgtatctg     600
caaatgacca aagtgagatc tgaggacaca gcccttgatt attgtacaag aagggcctac     660
tatggtaacc cggcctggtt tgcttactgg ggccaaggga ctctggtcac tgtctctgca     720
gcctccacca agggcgaagt ggccgcatgt gagaaagagg ttgctgcttt ggagaaggag     780
gtcgctgcac ttgaaaagga ggtcgcagcc ctggagaaac tggagcccaa atcttctgac     840
aaaactcaca catgcccacc gtgcccagca cctgaactcc tggggggacc gtcagtcttc     900
ctcttccccc caaaacccaa ggacaccctc atgatctccc ggacccctga ggtcacatgc     960
gtggtggtgg acgtgagcca cgaagaccct gaggtcaagt tcaactggta cgtggacggc    1020
gtggaggtgc ataatgccaa gacaaagccg cgggaggagc agtacaacag cacgtaccgt    1080
gtggtcagcg tcctcaccgt cctgcaccag gactggctga atggcaagga gtacaagtgc    1140
aaggtctcca acaaagccct cccagccccc atcgagaaaa ccatctccaa agccaaaggg    1200
cagccccgag aaccacaggt gtacaccctg cccccatccc gggaggagat gaccaagaac    1260
caggtcagcc tgacctgcct ggtcaaaggc ttctatccca gcgacatcgc cgtggagtgg    1320
gagagcaatg ggcagccgga gaacaactac aagaccacgc ctcccgtgct ggactccgac    1380
ggctccttct tcctctacag caagctcacc gtggacaaga gcaggtggca gcaggggaac    1440
gtcttctcat gctccgtgat gcatgaggct ctgcacaacc actacacgca gaagagcctc    1500
tccctgtctc cgggt                                                     1515
```

<210> SEQ ID NO 130
<211> LENGTH: 273
<212> TYPE: PRT
<213> ORGANISM: Artificial Sequence
<220> FEATURE:
<223> OTHER INFORMATION: Second Polypeptide Chain of an Exemplary DR5
       mAb 1 x DR5 mAb 1 Fc diabody

<400> SEQUENCE: 130

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45

Lys Val Leu Ile Phe Leu Ser Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Gly Asp Ala Ala Thr Tyr Tyr Cys Gln His Ser Arg
```

```
                 85                  90                  95
Asp Leu Pro Pro Thr Phe Gly Gly Thr Lys Leu Glu Ile Lys Gly
                100                 105                 110
Gly Gly Ser Gly Gly Gly Gly Glu Val Lys Phe Leu Glu Ser Gly
                115                 120                 125
Gly Leu Val Gln Pro Gly Gly Ser Leu Lys Leu Ser Cys Val Ala Ser
    130                 135                 140
Gly Phe Asp Phe Ser Arg Tyr Trp Met Ser Trp Val Arg Gln Ala Pro
145                 150                 155                 160
Gly Lys Gly Leu Glu Trp Ile Gly Glu Ile Asn Pro Asp Ser Asn Thr
                165                 170                 175
Ile Asn Tyr Thr Pro Ser Leu Lys Asp Lys Phe Ile Ile Ser Arg Asp
                180                 185                 190
Asn Ala Lys Asn Thr Leu Tyr Leu Gln Met Thr Lys Val Arg Ser Glu
                195                 200                 205
Asp Thr Ala Leu Tyr Tyr Cys Thr Arg Arg Ala Tyr Tyr Gly Asn Pro
    210                 215                 220
Ala Trp Phe Ala Tyr Trp Gly Gln Gly Thr Leu Val Thr Val Ser Ala
225                 230                 235                 240
Ala Ser Thr Lys Gly Lys Val Ala Ala Cys Lys Glu Lys Val Ala Ala
                245                 250                 255
Leu Lys Glu Lys Val Ala Ala Leu Lys Glu Lys Val Ala Ala Leu Lys
                260                 265                 270
Glu
```

<210> SEQ ID NO 131
<211> LENGTH: 819
<212> TYPE: DNA
<213> ORGANISM: Artificial Sequence
<220> FEATURE:
<223> OTHER INFORMATION: Polynucleotide Encoding Second Polypeptide
      Chain of an Exemplary DR5 mAb 1 x DR5 mAb 1 Fc diabody

<400> SEQUENCE: 131

```
gacattgtgc tgacacagtc tcctgcttcc ttagctgtat ctctcgggca gagggccacc    60
atctcatgca gggccagcaa agtgtcagt tcctctggct atagttatat gcactggtac    120
caacagaaac aggacagcc acccaaagtc ctcatctttc tttcatccaa cctagattct    180
ggggtccctg ccaggttcag tggcagtggg tctgggacag acttcaccct caacatccat    240
cctgtggagg atggggatgc tgcaacctat tactgtcagc acagtaggga tcttcctccg    300
acgttcggtg gaggcaccaa gctggaaatc aaaggaggcg gatccggcgg cggaggcgag    360
gtgaagtttc tcgagtctgg aggtggcctg gtgcagcctg gaggatccct gaaactctcc    420
tgtgtagcct caggattcga ttttagtaga tactggatga gttgggtccg gcaggctcca    480
gggaaagggc tagaatggat tggagaaatt aatccagata gcaatacgat aaactatacg    540
ccatctctaa aggataaatt catcatctcc agagacaacg ccaaaaatac gctgtatctg    600
caaatgacca agtgagatc tgaggacaca gcccttatt attgtacaag aagggcctac    660
tatggtaacc cggcctggtt tgcttactgg ggccaaggga ctctggtcac tgtctctgca    720
gcctccacca agggcaaagt ggccgcatgt aaggagaaag ttgctgcttt gaaagagaag    780
gtcgccgcac ttaaggaaaa ggtcgcagcc ctgaaagag                           819
```

<210> SEQ ID NO 132
<211> LENGTH: 505

```
<212> TYPE: PRT
<213> ORGANISM: Artificial Sequence
<220> FEATURE:
<223> OTHER INFORMATION: First Polypeptide Chain of an Exemplary DR5 mAb
      1 x DR5 mAb 1 Fc diabody L234A/L235A

<400> SEQUENCE: 132
```

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45

Lys Val Leu Ile Phe Leu Ser Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Gly Asp Ala Ala Thr Tyr Tyr Cys Gln His Ser Arg
                85                  90                  95

Asp Leu Pro Pro Thr Phe Gly Gly Gly Thr Lys Leu Glu Ile Lys Gly
            100                 105                 110

Gly Gly Ser Gly Gly Gly Gly Glu Val Lys Phe Leu Glu Ser Gly Gly
        115                 120                 125

Gly Leu Val Gln Pro Gly Gly Ser Leu Lys Leu Ser Cys Val Ala Ser
130                 135                 140

Gly Phe Asp Phe Ser Arg Tyr Trp Met Ser Trp Val Arg Gln Ala Pro
145                 150                 155                 160

Gly Lys Gly Leu Glu Trp Ile Gly Glu Ile Asn Pro Asp Ser Asn Thr
                165                 170                 175

Ile Asn Tyr Thr Pro Ser Leu Lys Asp Lys Phe Ile Ile Ser Arg Asp
            180                 185                 190

Asn Ala Lys Asn Thr Leu Tyr Leu Gln Met Thr Lys Val Arg Ser Glu
        195                 200                 205

Asp Thr Ala Leu Tyr Tyr Cys Thr Arg Arg Ala Tyr Tyr Gly Asn Pro
210                 215                 220

Ala Trp Phe Ala Tyr Trp Gly Gln Gly Thr Leu Val Thr Val Ser Ala
225                 230                 235                 240

Ala Ser Thr Lys Gly Glu Val Ala Ala Cys Glu Lys Glu Val Ala Ala
                245                 250                 255

Leu Glu Lys Glu Val Ala Ala Leu Glu Lys Glu Val Ala Ala Leu Glu
            260                 265                 270

Lys Leu Glu Pro Lys Ser Ser Asp Lys Thr His Thr Cys Pro Pro Cys
        275                 280                 285

Pro Ala Pro Glu Ala Ala Gly Gly Pro Ser Val Phe Leu Phe Pro Pro
290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
370                 375                 380

```
Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Glu Glu
            405                 410                 415

Met Thr Lys Asn Gln Val Ser Leu Thr Cys Leu Val Lys Gly Phe Tyr
        420                 425                 430

Pro Ser Asp Ile Ala Val Glu Trp Glu Ser Asn Gly Gln Pro Glu Asn
    435                 440                 445

Asn Tyr Lys Thr Thr Pro Pro Val Leu Asp Ser Asp Gly Ser Phe Phe
    450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly
                500                 505

<210> SEQ ID NO 133
<211> LENGTH: 1515
<212> TYPE: DNA
<213> ORGANISM: Artificial Sequence
<220> FEATURE:
<223> OTHER INFORMATION: Polynucleotide Encoding First Polypeptide Chain
      of an Exemplary DR5 mAb 1 x DR5 mAb 1 Fc diabody L234A/L235A

<400> SEQUENCE: 133
gacattgtgc tgacacagtc tcctgcttcc ttagctgtat ctctcgggca gagggccacc      60
atctcatgca gggccagcaa agtgtcagt tcctctggct atagttatat gcactggtac     120
caacagaaac caggacagcc acccaaagtc ctcatctttc tttcatccaa cctagattct     180
ggggtccctg ccaggttcag tggcagtggg tctgggacag acttcaccct caacatccat     240
cctgtggaga tggggatgc tgcaacctat tactgtcagc acagtaggga tcttcctccg     300
acgttcggtg aggcaccaa gctggaaatc aaaggaggcg gatccggcgg cggaggcgag     360
gtgaagtttc tcgagtctgg aggtggcctg gtgcagcctg gagatccct gaaactctcc     420 tgtgtagcct caggattcga ttttagtaga tactggatga gttgggtccg gcaggctcca     480
gggaaagggc tagaatggat tggagaaatt aatccagata gcaatacgat aaactatacg     540
ccatctctaa aggataaatt catcatctcc agagacaacg ccaaaaatac gctgtatctg     600
caaatgacca agtgagatc tgaggacaca gccctttatt attgtacaag aagggcctac     660
tatggtaacc cggcctggtt tgcttactgg ggccaaggga ctctggtcac tgtctctgca     720
gcctccacca agggcgaagt ggccgcatgt gagaaagagg ttgctgcttt ggagaaggag     780
gtcgctgcac ttgaaaagga ggtcgcagcc ctggagaaac tggagcccaa atcttctgac     840
aaaactcaca catgcccacc gtgcccagca cctgaagccg cggggggacc gtcagtcttc     900
ctcttccccc caaaacccaa ggacaccctc atgatctccc ggaccctga ggtcacatgc     960 gtggtggtgg acgtgagcca cgaagaccct gaggtcaagt tcaactggta cgtggacggc    1020
gtggaggtgc ataatgccaa gacaaagccg cgggaggagc agtacaacag cacgtaccgt    1080
gtggtcagcg tcctcaccgt cctgcaccag gactggctga atggcaagga gtacaagtgc    1140
aaggtctcca acaaagccct cccagccccc atcgagaaaa ccatctccaa agccaaaggg    1200
cagccccgag aaccacaggt gtacaccctg cccccatccc gggaggagat gaccaagaac    1260
caggtcagcc tgacctgcct ggtcaaaggc ttctatccca gcgacatcgc cgtggagtgg    1320
```

```
gagagcaatg ggcagccgga gaacaactac aagaccacgc ctcccgtgct ggactccgac      1380
ggctccttct tcctctacag caagctcacc gtggacaaga gcaggtggca gcagggggaac     1440 gtcttctcat gctccgtgat gcatgaggct ctgcacaacc actacacgca gaagagcctc     1500
tccctgtctc cgggt                                                      1515
```

<210> SEQ ID NO 134
<211> LENGTH: 499
<212> TYPE: PRT
<213> ORGANISM: Artificial Sequence
<220> FEATURE:
<223> OTHER INFORMATION: First Polypeptide Chain of an Exemplary DR5 mAb
      2 x DR5 mAb 2 Fc diabody

<400> SEQUENCE: 134

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Lys Ser Val Gln Ala
65                  70                  75                  80

Glu Asp Leu Thr Leu Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
            100                 105                 110

Gly Gly Gly Lys Val Gln Leu Gln Gln Ser Gly Ala Glu Leu Val Lys
        115                 120                 125

Pro Gly Ala Ser Val Lys Leu Ser Cys Lys Ala Ser Gly Tyr Thr Phe
    130                 135                 140

Thr Glu Tyr Ile Leu His Trp Val Lys Gln Lys Ser Gly Gln Gly Leu
145                 150                 155                 160

Glu Trp Ile Gly Trp Phe Tyr Pro Gly Asn Asn Ile Lys Tyr Asn
                165                 170                 175

Glu Lys Phe Lys Asp Lys Ala Thr Leu Thr Ala Asp Lys Ser Ser Ser
            180                 185                 190

Thr Val Tyr Met Glu Leu Ser Arg Leu Thr Ser Glu Asp Ser Ala Val
        195                 200                 205

Tyr Phe Cys Ala Arg His Glu Gln Gly Pro Gly Tyr Phe Asp Tyr Trp
    210                 215                 220

Gly Gln Gly Thr Thr Leu Thr Val Ser Ser Ala Ser Thr Lys Gly Glu
225                 230                 235                 240

Val Ala Ala Cys Glu Lys Glu Val Ala Ala Leu Glu Lys Glu Val Ala
                245                 250                 255

Ala Leu Glu Lys Glu Val Ala Ala Leu Glu Lys Leu Glu Pro Lys Ser
            260                 265                 270

Ser Asp Lys Thr His Thr Cys Pro Pro Cys Pro Ala Pro Glu Leu Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320
```

His Glu Asp Pro Glu Val Lys Phe Asn Trp Tyr Val Asp Gly Val Glu
            325                 330                 335
Val His Asn Ala Lys Thr Lys Pro Arg Glu Glu Gln Tyr Asn Ser Thr
        340                 345                 350
Tyr Arg Val Val Ser Val Leu Thr Val Leu His Gln Asp Trp Leu Asn
    355                 360                 365
Gly Lys Glu Tyr Lys Cys Lys Val Ser Asn Lys Ala Leu Pro Ala Pro
370                 375                 380
Ile Glu Lys Thr Ile Ser Lys Ala Lys Gly Gln Pro Arg Glu Pro Gln
385                 390                 395                 400
Val Tyr Thr Leu Pro Pro Ser Arg Glu Glu Met Thr Lys Asn Gln Val
            405                 410                 415
Ser Leu Thr Cys Leu Val Lys Gly Phe Tyr Pro Ser Asp Ile Ala Val
        420                 425                 430
Glu Trp Glu Ser Asn Gly Gln Pro Glu Asn Asn Tyr Lys Thr Thr Pro
    435                 440                 445
Pro Val Leu Asp Ser Asp Gly Ser Phe Phe Leu Tyr Ser Lys Leu Thr
    450                 455                 460
Val Asp Lys Ser Arg Trp Gln Gln Gly Asn Val Phe Ser Cys Ser Val
465                 470                 475                 480
Met His Glu Ala Leu His Asn His Tyr Thr Gln Lys Ser Leu Ser Leu
            485                 490                 495
Ser Pro Gly

<210> SEQ ID NO 135
<211> LENGTH: 1497
<212> TYPE: DNA
<213> ORGANISM: Artificial Sequence
<220> FEATURE:
<223> OTHER INFORMATION: Polynucleotide Encoding First Polypeptide Chain
      of an Exemplary DR5 mAb 2 x DR5 mAb 2 Fc diabody

<400> SEQUENCE: 135
gacattgtga tgacccagtc tcacaaattc atgtccactt cagtaggaga cagggtcagc    60
atcacctgca aggccagtca ggatgtgaat actgctgtag cctggtatca acaaaaacca   120
gggcaatctc ctaaactact gatttactgg gcatccaccc ggcacactgg agtccctgat   180
cgcttcacag gcagtggatc tgggacagat tatacactca ccatcaaaag tgtgcaggct   240
gaagacctga ctttattac tgtcagcaa cactatatca ctccgtggac gttcggtgga   300
ggcaccaagc tggaaatcaa aggaggcgga tccggcggcg gaggcaaggt ccagctgcag   360
cagtctggag ctgaactggt gaaacccggg gcatcagtga agctgtcctg caaggcttct   420
gggtacacct tcactgagta tattttacac tgggtaaagc agaagtctgg acagggtctt   480
gagtggattg gtggttttta tcctggaaat aataatataa agtacaatga gaaattcaag   540
gacaaggcca cactgactgc ggacaaatcc tccagcacag tctatatgga acttagtaga   600
ttgacatctg aagactctgc ggtctatttc tgtgcaagac acgaacaagg accaggttac   660
tttgactact ggggccaagg caccactctc acagtctcct ccgcctccac caagggcgaa   720
gtggccgcat gtgagaaaga ggttgctgct ttggagaagg aggtcgctgc acttgaaaag   780
gaggtcgcag ccctggagaa actggagccc aaatcttctg acaaaactca cacatgccca   840
ccgtgcccag cacctgaact cctggggga ccgtcagtct tcctcttccc cccaaaaccc   900
aaggacaccc tcatgatctc ccggaccct gaggtcacat gcgtggtggt ggacgtgagc   960

-continued

```
cacgaagacc ctgaggtcaa gttcaactgg tacgtggacg gcgtggaggt gcataatgcc    1020
aagacaaagc cgcgggagga gcagtacaac agcacgtacc gtgtggtcag cgtcctcacc    1080
gtcctgcacc aggactggct gaatggcaag gagtacaagt gcaaggtctc caacaaagcc    1140
ctcccagccc ccatcgagaa aaccatctcc aaagccaaag gcagccccg agaaccacag     1200 gtgtacaccc tgcccccatc ccgggaggag atgaccaaga accaggtcag cctgacctgc    1260
ctggtcaaag gcttctatcc cagcgacatc gccgtggagt gggagagcaa tgggcagccg    1320
gagaacaact acaagaccac gcctcccgtg ctggactccg acggctcctt cttcctctac    1380
agcaagctca ccgtggacaa gagcaggtgg cagcagggga acgtcttctc atgctccgtg    1440
atgcatgagg ctctgcacaa ccactacacg cagaagagcc tctccctgtc tccgggt       1497
```

<210> SEQ ID NO 136
<211> LENGTH: 267
<212> TYPE: PRT
<213> ORGANISM: Artificial Sequence
<220> FEATURE:
<223> OTHER INFORMATION: Second Polypeptide Chain of an Exemplary DR5
    mAb 2 x DR5 mAb 2 Fc diabody

<400> SEQUENCE: 136

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Lys Ser Val Gln Ala
65                  70                  75                  80

Glu Asp Leu Thr Leu Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
            100                 105                 110

Gly Gly Gly Lys Val Gln Leu Gln Gln Ser Gly Ala Glu Leu Val Lys
        115                 120                 125

Pro Gly Ala Ser Val Lys Leu Ser Cys Lys Ala Ser Gly Tyr Thr Phe
    130                 135                 140

Thr Glu Tyr Ile Leu His Trp Val Lys Gln Ser Gly Gln Gly Leu
145                 150                 155                 160

Glu Trp Ile Gly Trp Phe Tyr Pro Gly Asn Asn Asn Ile Lys Tyr Asn
                165                 170                 175

Glu Lys Phe Lys Asp Lys Ala Thr Leu Thr Ala Asp Lys Ser Ser
            180                 185                 190

Thr Val Tyr Met Glu Leu Ser Arg Leu Thr Ser Glu Asp Ser Ala Val
        195                 200                 205

Tyr Phe Cys Ala Arg His Glu Gln Gly Pro Gly Tyr Phe Asp Tyr Trp
    210                 215                 220

Gly Gln Gly Thr Thr Leu Thr Val Ser Ser Ala Ser Thr Lys Gly Lys
225                 230                 235                 240

Val Ala Ala Cys Lys Glu Lys Val Ala Ala Leu Lys Glu Lys Val Ala
                245                 250                 255

Ala Leu Lys Glu Lys Val Ala Ala Leu Lys Glu
            260                 265
```

<210> SEQ ID NO 137
<211> LENGTH: 801
<212> TYPE: DNA
<213> ORGANISM: Artificial Sequence
<220> FEATURE:
<223> OTHER INFORMATION: Polynucleotide Encoding Second Polypeptide
      Chain of an Exemplary DR5 mAb 2 x DR5 mAb 2 Fc diabody

<400> SEQUENCE: 137

```
gacattgtga tgacccagtc tcacaaattc atgtccactt cagtaggaga cagggtcagc      60
atcacctgca aggccagtca ggatgtgaat actgctgtag cctggtatca acaaaaacca     120
gggcaatctc ctaaactact gatttactgg gcatccaccc ggcacactgg agtccctgat     180
cgcttcacag gcagtggatc tgggacagat tatacactca ccatcaaaag tgtgcaggct     240
gaagacctga cactttatta ctgtcagcaa cactatatca ctccgtggac gttcggtgga     300
ggcaccaagc tggaaatcaa aggaggcgga tccggcggcg gaggcaaggt ccagctgcag     360
cagtctggag ctgaactggt gaaacccggg gcatcagtga agctgtcctg caaggcttct     420
gggtacacct tcactgagta tattttacac tgggtaaagc agaagtctgg acagggtctt     480
gagtggattg gtggttttta tcctggaaat aataatataa agtacaatga aaattcaag     540
gacaaggcca cactgactgc ggacaaatcc tccagcacag tctatatgga acttagtaga     600
ttgacatctg aagactctgc ggtctatttc tgtgcaagac acgaacaagg accaggttac     660
tttgactact ggggccaagg caccactctc acagtctcct ccgcctccac caagggcaaa     720
gtggccgcat gtaaggagaa agttgctgct ttgaaagaga aggtcgccgc acttaaggaa     780
aaggtcgcag ccctgaaaga g                                              801
```

<210> SEQ ID NO 138
<211> LENGTH: 499
<212> TYPE: PRT
<213> ORGANISM: Artificial Sequence
<220> FEATURE:
<223> OTHER INFORMATION: First Polypeptide Chain of an Exemplary DR5 mAb
      2 x DR5 mAb 2 Fc diabody L234A/L235A

<400> SEQUENCE: 138

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Lys Ser Val Gln Ala
65                  70                  75                  80

Glu Asp Leu Thr Leu Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
            100                 105                 110

Gly Gly Gly Lys Val Gln Leu Gln Gln Ser Gly Ala Glu Leu Val Lys
        115                 120                 125

Pro Gly Ala Ser Val Lys Leu Ser Cys Lys Ala Ser Gly Tyr Thr Phe
    130                 135                 140

Thr Glu Tyr Ile Leu His Trp Val Lys Gln Lys Ser Gly Gln Gly Leu
```

```
                      145                 150                 155                 160
Glu Trp Ile Gly Trp Phe Tyr Pro Gly Asn Asn Ile Lys Tyr Asn
                    165                 170                 175

Glu Lys Phe Lys Asp Lys Ala Thr Leu Thr Ala Asp Lys Ser Ser
                180                 185                 190

Thr Val Tyr Met Glu Leu Ser Arg Leu Thr Ser Glu Asp Ser Ala Val
                195                 200                 205

Tyr Phe Cys Ala Arg His Glu Gln Gly Pro Gly Tyr Phe Asp Tyr Trp
210                 215                 220

Gly Gln Gly Thr Thr Leu Thr Val Ser Ser Ala Ser Thr Lys Gly Glu
225                 230                 235                 240

Val Ala Ala Cys Glu Lys Val Ala Ala Leu Glu Lys Glu Val Ala
                245                 250                 255

Ala Leu Glu Lys Glu Val Ala Ala Leu Glu Lys Leu Glu Pro Lys Ser
                260                 265                 270

Ser Asp Lys Thr His Thr Cys Pro Pro Cys Pro Ala Pro Glu Ala Ala
                275                 280                 285

Gly Gly Pro Ser Val Phe Leu Phe Pro Pro Lys Pro Lys Asp Thr Leu
                290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
                340                 345                 350

Tyr Arg Val Val Ser Val Leu Thr Val Leu His Gln Asp Trp Leu Asn
                355                 360                 365

Gly Lys Glu Tyr Lys Cys Lys Val Ser Asn Lys Ala Leu Pro Ala Pro
                370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Glu Glu Met Thr Lys Asn Gln Val
                405                 410                 415

Ser Leu Thr Cys Leu Val Lys Gly Phe Tyr Pro Ser Asp Ile Ala Val
                420                 425                 430

Glu Trp Glu Ser Asn Gly Gln Pro Glu Asn Asn Tyr Lys Thr Thr Pro
                435                 440                 445

Pro Val Leu Asp Ser Asp Gly Ser Phe Phe Leu Tyr Ser Lys Leu Thr
450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly

<210> SEQ ID NO 139
<211> LENGTH: 1497
<212> TYPE: DNA
<213> ORGANISM: Artificial Sequence
<220> FEATURE:
<223> OTHER INFORMATION: Polynucleotide Encoding First Polypeptide Chain
      of an Exemplary DR5 mAb 2 x DR5 mAb 2 Fc diabody L234A/L235A

<400> SEQUENCE: 139
gacattgtga tgacccagtc tcacaaattc atgtccactt cagtaggaga cagggtcagc      60
```

```
atcacctgca aggccagtca ggatgtgaat actgctgtag cctggtatca acaaaaacca    120
gggcaatctc ctaaactact gatttactgg gcatccaccc ggcacactgg agtccctgat    180
cgcttcacag gcagtggatc tgggacagat tatacactca ccatcaaaag tgtgcaggct    240
gaagacctga cactttatta ctgtcagcaa cactatatca ctccgtggac gttcggtgga    300
ggcaccaagc tggaaatcaa aggaggcgga tccggcggcg aggcaaggt ccagctgcag    360 cagtctggag ctgaactggt gaaacccggg gcatcagtga agctgtcctg caaggcttct    420
gggtacacct tcactgagta tattttacac tgggtaaagc agaagtctgg acagggtctt    480
gagtggattg gtggttttta tcctggaaat aataatataa agtacaatga gaaattcaag    540
gacaaggcca cactgactgc ggacaaatcc tccagcacag tctatatgga acttagtaga    600
ttgacatctg aagactctgc ggtctatttc tgtgcaagac acgaacaagg accaggttac    660
tttgactact ggggccaagg caccactctc acagtctcct ccgcctccac caagggcgaa    720
gtggccgcat gtgagaaaga ggttgctgct ttggagaagg aggtcgctgc acttgaaaag    780
gaggtcgcag ccctggagaa actggagccc aaatcttctg acaaaactca cacatgccca    840
ccgtgcccag cacctgaagc gcgggggga ccgtcagtct tcctcttccc cccaaaaccc    900
aaggacaccc tcatgatctc ccggaccct gaggtcacat gcgtggtggt ggacgtgagc    960
cacgaagacc ctgaggtcaa gttcaactgg tacgtggacg gcgtggaggt gcataatgcc   1020
aagacaaagc cgcgggagga gcagtacaac agcacgtacc gtgtggtcag cgtcctcacc   1080
gtcctgcacc aggactggct gaatggcaag gagtacaagt gcaaggtctc caacaaagcc   1140
ctcccagccc ccatcgagaa aaccatctcc aaagccaaag gcagccccg agaaccacag   1200 gtgtacaccc tgcccccatc ccgggaggag atgaccaaga accaggtcag cctgacctgc   1260
ctggtcaaag gcttctatcc cagcgacatc gccgtggagt gggagagcaa tgggcagccg   1320
gagaacaact acaagaccac gcctcccgtg ctggactccg acggctcctt cttcctctac   1380
agcaagctca ccgtggacaa gagcaggtgg cagcagggga acgtcttctc atgctccgtg   1440
atgcatgagg ctctgcacaa ccactacacg cagaagagcc tctccctgtc tccgggt      1497
```

<210> SEQ ID NO 140
<211> LENGTH: 499
<212> TYPE: PRT
<213> ORGANISM: Artificial Sequence
<220> FEATURE:
<223> OTHER INFORMATION: First Polypeptide Chain of an Exemplary hDR5 mAb 2.2 x hDR5 mAb 2.2 Fc diabody

<400> SEQUENCE: 140

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
```

Gly Gly Gly Gln Val Gln Leu Val Gln Ser Gly Ala Glu Val Lys Lys
100                 105                 110
Pro Gly Ala Ser Val Lys Val Ser Cys Lys Ala Ser Gly Tyr Thr Phe
       115                 120                 125
Thr Glu Tyr Ile Leu His Trp Val Arg Gln Ala Pro Gly Gln Gly Leu
145                 150                 155                 160
Glu Trp Met Gly Trp Phe Tyr Pro Gly Asn Asn Asn Ile Lys Tyr Asn
                   165                 170                 175
Glu Lys Phe Lys Asp Arg Val Thr Ile Thr Ala Asp Lys Ser Thr Ser
               180                 185                 190
Thr Val Tyr Met Glu Leu Ser Ser Leu Arg Ser Glu Asp Thr Ala Val
           195                 200                 205
Tyr Tyr Cys Ala Arg His Glu Gln Gly Pro Gly Tyr Phe Asp Tyr Trp
       210                 215                 220
Gly Gln Gly Thr Leu Val Thr Val Ser Ser Ala Ser Thr Lys Gly Glu
225                 230                 235                 240
Val Ala Ala Cys Glu Lys Glu Val Ala Ala Leu Glu Lys Glu Val Ala
               245                 250                 255
Ala Leu Glu Lys Glu Val Ala Ala Leu Glu Lys Leu Glu Pro Lys Ser
           260                 265                 270
Ser Asp Lys Thr His Thr Cys Pro Pro Cys Pro Ala Pro Glu Leu Leu
       275                 280                 285
Gly Gly Pro Ser Val Phe Leu Phe Pro Pro Lys Pro Lys Asp Thr Leu
   290                 295                 300
Met Ile Ser Arg Thr Pro Glu Val Thr Cys Val Val Val Asp Val Ser
305                 310                 315                 320
His Glu Asp Pro Glu Val Lys Phe Asn Trp Tyr Val Asp Gly Val Glu
               325                 330                 335
Val His Asn Ala Lys Thr Lys Pro Arg Glu Glu Gln Tyr Asn Ser Thr
           340                 345                 350
Tyr Arg Val Val Ser Val Leu Thr Val Leu His Gln Asp Trp Leu Asn
       355                 360                 365
Gly Lys Glu Tyr Lys Cys Lys Val Ser Asn Lys Ala Leu Pro Ala Pro
   370                 375                 380
Ile Glu Lys Thr Ile Ser Lys Ala Lys Gly Gln Pro Arg Glu Pro Gln
385                 390                 395                 400
Val Tyr Thr Leu Pro Pro Ser Arg Glu Glu Met Thr Lys Asn Gln Val
               405                 410                 415
Ser Leu Thr Cys Leu Val Lys Gly Phe Tyr Pro Ser Asp Ile Ala Val
           420                 425                 430
Glu Trp Glu Ser Asn Gly Gln Pro Glu Asn Asn Tyr Lys Thr Thr Pro
       435                 440                 445
Pro Val Leu Asp Ser Asp Gly Ser Phe Phe Leu Tyr Ser Lys Leu Thr
   450                 455                 460
Val Asp Lys Ser Arg Trp Gln Gln Gly Asn Val Phe Ser Cys Ser Val
465                 470                 475                 480
Met His Glu Ala Leu His Asn His Tyr Thr Gln Lys Ser Leu Ser Leu
               485                 490                 495
Ser Pro Gly

<210> SEQ ID NO 141
<211> LENGTH: 1497

<212> TYPE: DNA
<213> ORGANISM: Artificial Sequence
<220> FEATURE:
<223> OTHER INFORMATION: Polynucleotide Encoding First Polypeptide Chain of an Exemplary hDR5 mAb 2.2 x hDR5 mAb 2.2 Fc diabody

<400> SEQUENCE: 141

```
gatattcaga tgacccagag tccctcattt ctgtccgcct ccgtcggtga ccgcgtgact      60
attacttgta aagcttctca ggatgtcaac accgccgtgg cttggtacca gcagaagccc     120
ggtaaagcac ctaagctgct gatctattgg gccagcactc ggcacaccgg agtcccatct     180
aggttctctg gcagtggatc agggacagac tttaccctga caattagctc cctgcagccc     240
gaggatgtgg ctacttacta ttgtcagcag cactacatca ctccttggac cttcggcggg     300
ggcacaaaac tggaaatcaa aggaggcgga tccggcggcg aggccaggt ccagctggtg      360
cagagtgggg cagaggtgaa aaagccaggg gcatcagtga aagtgtcttg taaagcatca     420
ggttatacat ttactgagta catcctgcac tgggtgcgac aggcaccagg acagggactg     480
gaatggatgg ggtggttcta ccctggcaac aacaacatta gtacaacga aagtttaaa      540
gaccgggtga ccatcacagc ggataagtct accagtacag tctatatgga gctgagctcc     600
ctgagaagcg aagacaccgc cgtctactat tgcgctcgcc acgaacaggg tccaggttac     660
tttgattatt gggggcaggg aactctggtc acagtcagct ccgcctccac caagggcgaa     720
gtggccgcat gtgagaaaga ggttgctgct ttggagaagg aggtcgctgc acttgaaaag     780
gaggtcgcag ccctggagaa actggagccc aaatcttctg acaaaactca cacatgccca     840
ccgtgcccag cacctgaact cctgggggga ccgtcagtct tcctcttccc cccaaaaccc     900
aaggacaccc tcatgatctc ccggaccct gaggtcacat gcgtggtggt ggacgtgagc     960
cacgaagacc ctgaggtcaa gttcaactgg tacgtgacg gcgtggaggt gcataatgcc    1020
aagacaaagc cgcgggagga gcagtacaac agcacgtacc gtgtggtcag cgtcctcacc    1080
gtcctgcacc aggactggct gaatggcaag gagtacaagt gcaaggtctc caacaaagcc    1140
ctcccagccc ccatcgagaa aaccatctcc aaagccaaag gcagccccg agaaccacag     1200
gtgtacaccc tgcccccatc ccgggaggag atgaccaaga accaggtcag cctgacctgc    1260
ctggtcaaag gcttctatcc cagcgacatc gccgtggagt gggagagcaa tgggcagccg    1320
gagaacaact acaagaccac gcctcccgtg ctggactccg acggctcctt cttcctctac    1380
agcaagctca ccgtggacaa gagcaggtgg cagcagggga acgtcttctc atgctccgtg    1440
atgcatgagg ctctgcacaa ccactacacg cagaagagcc tctccctgtc tccgggt      1497
```

<210> SEQ ID NO 142
<211> LENGTH: 267
<212> TYPE: PRT
<213> ORGANISM: Artificial Sequence
<220> FEATURE:
<223> OTHER INFORMATION: Second Polypeptide Chain of an Exemplary hDR5 mAb 2.2 x hDR5 mAb 2.2 Fc diabody

<400> SEQUENCE: 142

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
```

```
              50                  55                  60
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln His Tyr Ile Thr Pro Trp
                 85                  90                  95

Thr Phe Gly Gly Gly Thr Lys Leu Glu Ile Lys Gly Gly Gly Ser Gly
                100                 105                 110

Gly Gly Gly Gln Val Gln Leu Val Gln Ser Gly Ala Glu Val Lys Lys
            115                 120                 125

Pro Gly Ala Ser Val Lys Val Ser Cys Lys Ala Ser Gly Tyr Thr Phe
130                 135                 140

Thr Glu Tyr Ile Leu His Trp Val Arg Gln Ala Pro Gly Gln Gly Leu
145                 150                 155                 160

Glu Trp Met Gly Trp Phe Tyr Pro Gly Asn Asn Asn Ile Lys Tyr Asn
                165                 170                 175

Glu Lys Phe Lys Asp Arg Val Thr Ile Thr Ala Asp Lys Ser Thr Ser
            180                 185                 190

Thr Val Tyr Met Glu Leu Ser Ser Leu Arg Ser Glu Asp Thr Ala Val
        195                 200                 205

Tyr Tyr Cys Ala Arg His Glu Gln Gly Pro Gly Tyr Phe Asp Tyr Trp
    210                 215                 220

Gly Gln Gly Thr Leu Val Thr Val Ser Ser Ala Ser Thr Lys Gly Lys
225                 230                 235                 240

Val Ala Ala Cys Lys Glu Lys Val Ala Ala Leu Lys Glu Lys Val Ala
                245                 250                 255

Ala Leu Lys Glu Lys Val Ala Ala Leu Lys Glu
            260                 265

<210> SEQ ID NO 143
<211> LENGTH: 800
<212> TYPE: DNA
<213> ORGANISM: Artificial Sequence
<220> FEATURE:
<223> OTHER INFORMATION: Polynucleotide Encoding Second Polypeptide
      Chain of an Exemplary hDR5 mAb 2.2 x hDR5 mAb 2.2 Fc diabody

<400> SEQUENCE: 143
gatattcaga tgacccagag tccctcattt ctgtccgcct ccgtcggtga ccgcgtgact      60
attacttgta aagcttctca ggatgtcaac accgccgtgg cttggtacca gcagaagccc     120
ggtaaagcac ctaagctgct gatctattgg gccagcactc ggcacaccgg agtcccatct     180
aggttctctg gcagtggatc agggacagac tttacccctg caattagctc cctgcagccc     240
gaggatgtgg ctacttacta ttgtcagcag cactacatca ctccttggac cttcggcggg     300
ggcacaaaac tggaaatcaa aggaggcgga tccggcggcg gaggccaggt ccagctggtg     360
cagagtgggg cagaggtgaa aaagccaggg catcagtga agtgtcttg taaagcatca      420 ggttatacat ttactgagta catcctgcac tgggtgcgac aggcaccagg acagggactg     480
gaatggatgg ggtggttcta ccctggcaac aacaacatta gtacaacga agtttaaa       540 gaccgggtga ccatcacagc ggataagtct accgtacag tctatatgga gctgagctcc     600
ctgagaagcg aagacaccgc cgtctactat tgcgctcgcc acgaacaggg tccaggttac     660
tttgattatt gggggcaggg aactctggtc acagtcagct ccgcctccac caagggcaaa     720
gtggccgcat gtaaggagaa agttgctgct ttgaaagaga aggtcgccgc acttaaggaa     780
aaggtcgcag ccctgaaaga                                                800
```

<210> SEQ ID NO 144
<211> LENGTH: 499
<212> TYPE: PRT
<213> ORGANISM: Artificial Sequence
<220> FEATURE:
<223> OTHER INFORMATION: First Polypeptide Chain of an Exemplary hDR5 mAb 2.2 x hDR5 mAb 2.2 Fc diabody L234A/L235A

<400> SEQUENCE: 144

```
Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
130                 135                 140

Thr Glu Tyr Ile Leu His Trp Val Arg Gln Ala Pro Gly Gln Gly Leu
145                 150                 155                 160

Glu Trp Met Gly Trp Phe Tyr Pro Gly Asn Asn Asn Ile Lys Tyr Asn
                165                 170                 175

Glu Lys Phe Lys Asp Arg Val Thr Ile Thr Ala Asp Lys Ser Thr Ser
            180                 185                 190

Thr Val Tyr Met Glu Leu Ser Ser Leu Arg Ser Glu Asp Thr Ala Val
        195                 200                 205

Tyr Tyr Cys Ala Arg His Glu Gln Gly Pro Gly Tyr Phe Asp Tyr Trp
    210                 215                 220

Gly Gln Gly Thr Leu Val Thr Val Ser Ser Ala Ser Thr Lys Gly Glu
225                 230                 235                 240

Val Ala Ala Cys Glu Lys Glu Val Ala Ala Leu Glu Lys Glu Val Ala
                245                 250                 255

Ala Leu Glu Lys Glu Val Ala Ala Leu Glu Lys Leu Glu Pro Lys Ser
            260                 265                 270

Ser Asp Lys Thr His Thr Cys Pro Pro Cys Pro Ala Pro Glu Ala Ala
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
```

```
                355                 360                 365
Gly Lys Glu Tyr Lys Cys Lys Val Ser Asn Lys Ala Leu Pro Ala Pro
            370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Glu Glu Met Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
                435                 440                 445

Pro Val Leu Asp Ser Asp Gly Ser Phe Phe Leu Tyr Ser Lys Leu Thr
            450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly

<210> SEQ ID NO 145
<211> LENGTH: 1497
<212> TYPE: DNA
<213> ORGANISM: Artificial Sequence
<220> FEATURE:
<223> OTHER INFORMATION: Polynucleotide Encoding First Polypeptide Chain
      of an Exemplary hDR5 mAb 2.2 x hDR5 mAb 2.2 Fc diabody L234A/L235A

<400> SEQUENCE: 145
gatattcaga tgacccagag tccctcattt ctgtccgcct ccgtcggtga ccgcgtgact      60
attacttgta aagcttctca ggatgtcaac accgccgtgg cttggtacca gcagaagccc    120
ggtaaagcac ctaagctgct gatctattgg ccagcactc ggcacaccgg agtcccatct     180
aggttctctg gcagtggatc agggacagac tttaccctga caattagctc cctgcagccc    240
gaggatgtgg ctactacta ttgtcagcag cactacatca ctccttggac cttcggcggg     300
ggcacaaaac tggaaatcaa aggaggcgga tccggcggcg gaggccaggt ccagctggtg    360
cagagtgggg cagaggtgaa aaagccaggg gcatcagtga agtgtcttg taaagcatca     420 ggttatacat ttactgagta catcctgcac tgggtgcgac aggcaccagg acagggactg    480
gaatggatgg ggtggttcta ccctggcaac aacaacatta gtacaacga agtttaaa      540 gaccgggtga ccatcacagc ggataagtct accagtacag tctatatgga gctgagctcc    600
ctgagaagcg aagacaccgc cgtctactat tgcgctcgcc acgaacaggg tccaggttac    660
tttgattatt gggggcaggg aactctggtc acagtcagct ccgcctccac caagggcgaa    720
gtggccgcat gtgagaaaga ggttgctgct ttggagaagg aggtcgctgc acttgaaaag    780
gaggtcgcag ccctggagaa actggagccc aaatcttctg acaaaactca cacatgccca    840
ccgtgcccag cacctgaagc cgcgggggga ccgtcagtct tcctcttccc cccaaaaccc    900
aaggacaccc tcatgatctc ccggaccct gaggtcacat gcgtggtggt ggacgtgagc     960
cacgaagacc ctgaggtcaa gttcaactgg tacgtggacg gcgtggaggt gcataatgcc   1020
aagacaaagc cgcgggagga gcagtacaac agcacgtacc gtgtggtcag cgtcctcacc   1080
gtcctgcacc aggactggct gaatggcaag gagtacaagt gcaaggtctc caacaaagcc   1140
ctcccagccc ccatcgagaa aaccatctcc aaagccaaag gcagcccccg agaaccacag   1200
```

```
gtgtacaccc tgccccatc ccgggaggag atgaccaaga accaggtcag cctgacctgc    1260
ctggtcaaag gcttctatcc cagcgacatc gccgtggagt gggagagcaa tgggcagccg    1320
gagaacaact acaagaccac gcctcccgtg ctggactccg acggctcctt cttcctctac    1380
agcaagctca ccgtggacaa gagcaggtgg cagcagggga acgtcttctc atgctccgtg    1440
atgcatgagg ctctgcacaa ccactacacg cagaagagcc tctccctgtc tccgggt      1497
```

<210> SEQ ID NO 146
<211> LENGTH: 499
<212> TYPE: PRT
<213> ORGANISM: Artificial Sequence
<220> FEATURE:
<223> OTHER INFORMATION: First Polypeptide Chain of an Exemplary hDR5
    mAb 2.3 x hDR5 mAb 2.3 Fc diabody

<400> SEQUENCE: 146

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Glu Tyr Ile Leu His Trp Val Arg Gln Ala Pro Gly Gln Gly Leu
145                 150                 155                 160

Glu Trp Met Gly Trp Phe Tyr Pro Gly Asn Asn Asn Ile Lys Tyr Asn
                165                 170                 175

Glu Lys Phe Lys Asp Arg Val Thr Ile Thr Ala Asp Lys Ser Thr Ser
            180                 185                 190

Thr Val Tyr Met Glu Leu Ser Ser Leu Arg Ser Glu Asp Thr Ala Val
        195                 200                 205

Tyr Tyr Cys Ala Arg His Glu Gln Gly Pro Gly Tyr Phe Asp Tyr Trp
    210                 215                 220

Gly Gln Gly Thr Leu Val Thr Val Ser Ser Ala Ser Thr Lys Gly Glu
225                 230                 235                 240

Val Ala Ala Cys Glu Lys Glu Val Ala Ala Leu Glu Lys Glu Val Ala
                245                 250                 255

Ala Leu Glu Lys Glu Val Ala Ala Leu Glu Lys Leu Glu Pro Lys Ser
            260                 265                 270

Ser Asp Lys Thr His Thr Cys Pro Pro Cys Pro Ala Pro Glu Leu Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
```

```
His Glu Asp Pro Glu Val Lys Phe Asn Trp Tyr Val Asp Gly Val Glu
            325                 330                 335
Val His Asn Ala Lys Thr Lys Pro Arg Glu Glu Gln Tyr Asn Ser Thr
            340                 345                 350
Tyr Arg Val Val Ser Val Leu Thr Val Leu His Gln Asp Trp Leu Asn
            355                 360                 365
Gly Lys Glu Tyr Lys Cys Lys Val Ser Asn Lys Ala Leu Pro Ala Pro
    370                 375                 380
Ile Glu Lys Thr Ile Ser Lys Ala Lys Gly Gln Pro Arg Glu Pro Gln
385                 390                 395                 400
Val Tyr Thr Leu Pro Pro Ser Arg Glu Glu Met Thr Lys Asn Gln Val
                405                 410                 415
Ser Leu Thr Cys Leu Val Lys Gly Phe Tyr Pro Ser Asp Ile Ala Val
            420                 425                 430
Glu Trp Glu Ser Asn Gly Gln Pro Glu Asn Asn Tyr Lys Thr Thr Pro
        435                 440                 445
Pro Val Leu Asp Ser Asp Gly Ser Phe Phe Leu Tyr Ser Lys Leu Thr
    450                 455                 460
Val Asp Lys Ser Arg Trp Gln Gln Gly Asn Val Phe Ser Cys Ser Val
465                 470                 475                 480
Met His Glu Ala Leu His Asn His Tyr Thr Gln Lys Ser Leu Ser Leu
                485                 490                 495
Ser Pro Gly

<210> SEQ ID NO 147
<211> LENGTH: 1497
<212> TYPE: DNA
<213> ORGANISM: Artificial Sequence
<220> FEATURE:
<223> OTHER INFORMATION: Polynucleotide Encoding First Polypeptide Chain
      of an Exemplary hDR5 mAb 2.3 x hDR5 mAb 2.3 Fc diabody

<400> SEQUENCE: 147
gatattcaga tgacccagag tccctcattt ctgtccgcct ccgtcggtga ccgcgtgact      60
attacttgtc gggcttctca ggatgtcaac accgccgtgg cttggtacca gcagaagccc     120
ggtaaagcac ctaagctgct gatctattgg gccagcactc ggcacaccgg agtcccagat     180
aggttctctg gcagtggatc agggacagac tttaccctga caattagctc cctgcagccc     240
gaggatgtgg ctacttacta ttgtcagcag cactacatca ctccttggac cttcggcggg     300
ggcacaaaac tggaaatcaa aggaggcgga tccggcggcg gaggccaggt ccagctggtg     360
cagagtgggg gagaggtgaa aaagccaggg gcatcagtga agtgtcttg taaagcatca     420
ggttatacat ttactgagta catcctgcac tgggtgcgac aggcaccagg acagggactg     480
gaatggatgg gtggttcta ccctggcaac aacaacatta gtacaacga gaagtttaaa      540
gaccgggtga ccatcacagc ggataagtct accagtacag tctatatgga gctgagctcc     600
ctgagaagcg aagacaccgc cgtctactat tgcgctcgcc acgaacaggg tccaggttac     660
tttgattatt gggggcaggg aactctggtc acagtcagct ccgcctccac caagggcgaa     720
gtggccgcat gtgagaaaga ggttgctgct ttggagaagg aggtcgctgc acttgaaaag     780
gaggtcgcag ccctggagaa actggagccc aaatcttctg acaaaactca cacatgccca     840
ccgtgcccag cacctgaact cctgggggga ccgtcagtct tcctcttccc cccaaaaccc     900
aaggacaccc tcatgatctc ccggacccct gaggtcacat gcgtggtggt ggacgtgagc     960
```

```
cacgaagacc ctgaggtcaa gttcaactgg tacgtggacg gcgtggaggt gcataatgcc    1020
aagacaaagc cgcgggagga gcagtacaac agcacgtacc gtgtggtcag cgtcctcacc    1080
gtcctgcacc aggactggct gaatggcaag gagtacaagt gcaaggtctc caacaaagcc    1140
ctcccagccc ccatcgagaa aaccatctcc aaagccaaag gcagccccg agaaccacag    1200 gtgtacaccc tgcccccatc ccgggaggag atgaccaaga accaggtcag cctgacctgc    1260
ctggtcaaag gcttctatcc cagcgacatc gccgtggagt gggagagcaa tgggcagccg    1320
gagaacaact acaagaccac gcctcccgtg ctggactccg acggctcctt cttcctctac    1380
agcaagctca ccgtggacaa gagcaggtgg cagcagggga cgtcttctc atgctccgtg    1440 atgcatgagg ctctgcacaa ccactacacg cagaagagcc tctccctgtc tccgggt      1497
```

<210> SEQ ID NO 148
<211> LENGTH: 267
<212> TYPE: PRT
<213> ORGANISM: Artificial Sequence
<220> FEATURE:
<223> OTHER INFORMATION: Second Polypeptide Chain of an Exemplary hDR5
      mAb 2.3 x hDR5 mAb 2.3 Fc diabody

<400> SEQUENCE: 148

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Glu Tyr Ile Leu His Trp Val Arg Gln Ala Pro Gly Gln Gly Leu
145                 150                 155                 160

Glu Trp Met Gly Trp Phe Tyr Pro Gly Asn Asn Asn Ile Lys Tyr Asn
                165                 170                 175

Glu Lys Phe Lys Asp Arg Val Thr Ile Thr Ala Asp Lys Ser Thr Ser
            180                 185                 190

Thr Val Tyr Met Glu Leu Ser Ser Leu Arg Ser Glu Asp Thr Ala Val
        195                 200                 205

Tyr Tyr Cys Ala Arg His Glu Gln Gly Pro Gly Tyr Phe Asp Tyr Trp
    210                 215                 220

Gly Gln Gly Thr Leu Val Thr Val Ser Ser Ala Ser Thr Lys Gly Lys
225                 230                 235                 240

Val Ala Ala Cys Lys Glu Lys Val Ala Ala Leu Lys Glu Lys Val Ala
                245                 250                 255

Ala Leu Lys Glu Lys Val Ala Ala Leu Lys Glu
```

```
                260                 265
```

<210> SEQ ID NO 149
<211> LENGTH: 801
<212> TYPE: DNA
<213> ORGANISM: Artificial Sequence
<220> FEATURE:
<223> OTHER INFORMATION: Polynucleotide Encoding Second Polypeptide
      Chain of an Exemplary hDR5 mAb 2.3 x hDR5 mAb 2.3 Fc diabody

<400> SEQUENCE: 149

```
gatattcaga tgacccagag tccctcattt ctgtccgcct ccgtcggtga ccgcgtgact    60
attacttgtc gggcttctca ggatgtcaac accgccgtgg cttggtacca gcagaagccc   120
ggtaaagcac ctaagctgct gatctattgg gccagcactc ggcacaccgg agtcccagat   180
aggttctctg gcagtggatc agggacagac tttacccctg caattagctc cctgcagccc   240
gaggatgtgg ctacttacta ttgtcagcag cactacatca ctccttggac cttcggcggg   300
ggcacaaaac tggaaatcaa aggaggcgga tccggcggcg gaggccaggt ccagctggtg   360
cagagtgggg cagaggtgaa aaagccaggg gcatcagtga agtgtcttg taaagcatca   420 ggttatacat ttactgagta catcctgcac tgggtgcgac aggcaccagg acagggactg   480
gaatggatgg ggtggttcta ccctggcaac aacaacatta gtacaacga agtttaaa     540 gaccgggtga ccatcacagc ggataagtct accagtacag tctatatgga gctgagctcc   600
ctgagaagcg aagacaccgc cgtctactat tgcgctcgcc acgaacaggg tccaggttac   660
tttgattatt gggggcaggg aactctggtc acagtcagct ccgcctccac caagggcaaa   720
gtggccgcat gtaaggagaa agttgctgct ttgaaagaga aggtcgccgc acttaaggaa   780
aaggtcgcag ccctgaaaga g                                             801
```

<210> SEQ ID NO 150
<211> LENGTH: 499
<212> TYPE: PRT
<213> ORGANISM: Artificial Sequence
<220> FEATURE:
<223> OTHER INFORMATION: First Polypeptide Chain of an Exemplary hDR5
      mAb 2.3 x hDR5 mAb 2.3 Fc diabody L234A/L235A

<400> SEQUENCE: 150

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140
```

Thr Glu Tyr Ile Leu His Trp Val Arg Gln Ala Pro Gly Gln Gly Leu
145                 150                 155                 160

Glu Trp Met Gly Trp Phe Tyr Pro Gly Asn Asn Asn Ile Lys Tyr Asn
            165                 170                 175

Glu Lys Phe Lys Asp Arg Val Thr Ile Thr Ala Asp Lys Ser Thr Ser
            180                 185                 190

Thr Val Tyr Met Glu Leu Ser Ser Leu Arg Ser Glu Asp Thr Ala Val
            195                 200                 205

Tyr Tyr Cys Ala Arg His Glu Gln Gly Pro Gly Tyr Phe Asp Tyr Trp
210                 215                 220

Gly Gln Gly Thr Leu Val Thr Val Ser Ala Ser Thr Lys Gly Glu
225                 230                 235                 240

Val Ala Ala Cys Glu Lys Glu Val Ala Ala Leu Glu Lys Glu Val Ala
            245                 250                 255

Ala Leu Glu Lys Glu Val Ala Ala Leu Glu Lys Leu Glu Pro Lys Ser
            260                 265                 270

Ser Asp Lys Thr His Thr Cys Pro Pro Cys Pro Ala Pro Glu Ala Ala
            275                 280                 285

Gly Gly Pro Ser Val Phe Leu Phe Pro Pro Lys Pro Lys Asp Thr Leu
290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
            355                 360                 365

Gly Lys Glu Tyr Lys Cys Lys Val Ser Asn Lys Ala Leu Pro Ala Pro
370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Glu Glu Met Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
            435                 440                 445

Pro Val Leu Asp Ser Asp Gly Ser Phe Phe Leu Tyr Ser Lys Leu Thr
            450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly

<210> SEQ ID NO 151
<211> LENGTH: 1497
<212> TYPE: DNA
<213> ORGANISM: Artificial Sequence
<220> FEATURE:
<223> OTHER INFORMATION: Polynucleotide Encoding First Polypeptide Chain
      of an Exemplary hDR5 mAb 2.3 x hDR5 mAb 2.3 Fc diabody L234A/L235A

<400> SEQUENCE: 151

```
gatattcaga tgacccagag tccctcattt ctgtccgcct ccgtcggtga ccgcgtgact    60
attacttgtc gggcttctca ggatgtcaac accgccgtgg cttggtacca gcagaagccc   120
ggtaaagcac ctaagctgct gatctattgg gccagcactc ggcacaccgg agtcccagat   180
aggttctctg gcagtggatc agggacagac tttaccctga caattagctc cctgcagccc   240
gaggatgtgg ctacttacta ttgtcagcag cactacatca ctccttggac cttcggcggg   300
ggcacaaaac tggaaatcaa aggaggcgga tccggcggcg gaggccaggt ccagctggtg   360
cagagtgggg cagaggtgaa aaagccaggg gcatcagtga aagtgtcttg taaagcatca   420
ggttatacat ttactgagta catcctgcac tgggtgcgac aggcaccagg acagggactg   480
gaatggatgg ggtggttcta ccctggcaac aacaacatta gtacaacga aagtttaaa    540
gaccgggtga ccatcacagc ggataagtct accagtacag tctatatgga gctgagctcc   600
ctgagaagcg aagacaccgc cgtctactat tgcgctcgcc acgaacaggg tccaggttac   660
tttgattatt gggggcaggg aactctggtc acagtcagct ccgcctccac caagggcgaa   720
gtggccgcat gtgagaaaga ggttgctgct ttggagaagg aggtcgctgc acttgaaaag   780
gaggtcgcag ccctggagaa actggagccc aaatcttctg acaaaactca cacatgccca   840
ccgtgcccag cacctgaagc cgcgggggga ccgtcagtct tcctcttccc cccaaaaccc   900
aaggacaccc tcatgatctc ccggacccct gaggtcacat gcgtggtggt ggacgtgagc   960
cacgaagacc ctgaggtcaa gttcaactgg tacgtggacg gcgtggaggt gcataatgcc  1020
aagacaaagc cgcgggagga gcagtacaac agcacgtacc gtgtggtcag cgtcctcacc  1080
gtcctgcacc aggactggct gaatggcaag gagtacaagt gcaaggtctc caacaaagcc  1140
ctcccagccc ccatcgagaa aaccatctcc aaagccaaag gcagccccg agaaccacag   1200
gtgtacaccc tgcccccatc ccgggaggag atgaccaaga accaggtcag cctgacctgc  1260
ctggtcaaag gcttctatcc cagcgacatc gccgtggagt gggagagcaa tgggcagccg  1320
gagaacaact acaagaccac gcctcccgtg ctggactccg acggctcctt cttcctctac  1380
agcaagctca ccgtggacaa gagcaggtgg cagcagggga acgtcttctc atgctccgtg  1440
atgcatgagg ctctgcacaa ccactacacg cagaagagcc tctccctgtc tccgggt     1497
```

<210> SEQ ID NO 152
<211> LENGTH: 499
<212> TYPE: PRT
<213> ORGANISM: Artificial Sequence
<220> FEATURE:
<223> OTHER INFORMATION: First Polypeptide Chain of an Exemplary hDR5
      mAb 2.4 x hDR5 mAb 2.4 Fc diabody

<400> SEQUENCE: 152

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln His Tyr Ile Thr Pro Trp
                85                  90                  95
```

```
Thr Phe Gly Gly Gly Thr Lys Leu Glu Ile Lys Gly Gly Ser Gly
                100                 105                 110
Gly Gly Gly Gln Val Gln Leu Val Gln Ser Gly Ala Glu Val Lys Lys
        115                 120                 125
Pro Gly Ala Ser Val Lys Val Ser Cys Lys Ala Ser Gly Tyr Thr Phe
    130                 135                 140
Thr Glu Tyr Ile Leu His Trp Val Arg Gln Ala Pro Gly Gln Gly Leu
145                 150                 155                 160
Glu Trp Met Gly Trp Phe Tyr Pro Gly Asn Asn Asn Ile Lys Tyr Asn
                165                 170                 175
Glu Lys Phe Lys Asp Arg Val Thr Ile Thr Ala Asp Lys Ser Thr Ser
            180                 185                 190
Thr Val Tyr Met Glu Leu Ser Ser Leu Arg Ser Glu Asp Thr Ala Val
        195                 200                 205
Tyr Tyr Cys Ala Arg His Glu Gln Gly Pro Gly Tyr Phe Asp Tyr Trp
    210                 215                 220
Gly Gln Gly Thr Leu Val Thr Val Ser Ser Ala Ser Thr Lys Gly Glu
225                 230                 235                 240
Val Ala Ala Cys Glu Lys Glu Val Ala Ala Leu Glu Lys Glu Val Ala
                245                 250                 255
Ala Leu Glu Lys Glu Val Ala Ala Leu Glu Lys Leu Glu Pro Lys Ser
            260                 265                 270
Ser Asp Lys Thr His Thr Cys Pro Pro Cys Pro Ala Pro Glu Leu Leu
        275                 280                 285
Gly Gly Pro Ser Val Phe Leu Phe Pro Pro Lys Pro Lys Asp Thr Leu
    290                 295                 300
Met Ile Ser Arg Thr Pro Glu Val Thr Cys Val Val Val Asp Val Ser
305                 310                 315                 320
His Glu Asp Pro Glu Val Lys Phe Asn Trp Tyr Val Asp Gly Val Glu
                325                 330                 335
Val His Asn Ala Lys Thr Lys Pro Arg Glu Glu Gln Tyr Asn Ser Thr
            340                 345                 350
Tyr Arg Val Val Ser Val Leu Thr Val Leu His Gln Asp Trp Leu Asn
        355                 360                 365
Gly Lys Glu Tyr Lys Cys Lys Val Ser Asn Lys Ala Leu Pro Ala Pro
    370                 375                 380
Ile Glu Lys Thr Ile Ser Lys Ala Lys Gly Gln Pro Arg Glu Pro Gln
385                 390                 395                 400
Val Tyr Thr Leu Pro Pro Ser Arg Glu Glu Met Thr Lys Asn Gln Val
                405                 410                 415
Ser Leu Thr Cys Leu Val Lys Gly Phe Tyr Pro Ser Asp Ile Ala Val
            420                 425                 430
Glu Trp Glu Ser Asn Gly Gln Pro Glu Asn Asn Tyr Lys Thr Thr Pro
        435                 440                 445
Pro Val Leu Asp Ser Asp Gly Ser Phe Phe Leu Tyr Ser Lys Leu Thr
    450                 455                 460
Val Asp Lys Ser Arg Trp Gln Gln Gly Asn Val Phe Ser Cys Ser Val
465                 470                 475                 480
Met His Glu Ala Leu His Asn His Tyr Thr Gln Lys Ser Leu Ser Leu
                485                 490                 495
Ser Pro Gly

<210> SEQ ID NO 153
```

<211> LENGTH: 1397
<212> TYPE: DNA
<213> ORGANISM: Artificial Sequence
<220> FEATURE:
<223> OTHER INFORMATION: Polynucleotide Encoding First Polypeptide Chain
of an Exemplary hDR5 mAb 2.4 x hDR5 mAb 2.4 Fc diabody

<400> SEQUENCE: 153

```
cttggtacca gcagaagccc ggtaaagcac ctaagctgct gatctattgg gccagcactc      60
ggcacaccgg agtcccatct aggttctctg gcagtggatc agggacagac tttaccctga     120
caattagctc cctgcagcca gaggatatcg ctacatacta ttgtcagcag cactacatca     180
ctccttggac cttcggcggg ggcacaaaac tggaaatcaa aggaggcgga tccggcggcg     240
gaggccaggt ccagctggtg cagagtgggg cagaggtgaa aaagccaggg gcatcagtga     300
aagtgtcttg taaagcatca ggttatacat ttactgagta catcctgcac tgggtgcgac     360
aggcaccagg acagggactg gaatggatgg ggtggttcta ccctggcaac aacaacatta     420
agtacaacga agtttaaa gaccgggtga ccatcacagc ggataagtct accagtacag     480
tctatatgga gctgagctcc ctgagaagcg aagacaccgc cgtctactat tgcgctcgcc     540
acgaacaggg tccaggttac tttgattatt gggggcaggg aactctggtc acagtcagct     600
ccgcctccac caagggcgaa gtggccgcat gtgagaaaga ggttgctgct ttggagaagg     660
aggtcgctgc acttgaaaag gaggtcgcag ccctggagaa actggagccc aaatcttctg     720
acaaaactca cacatgccca ccgtgcccag cacctgaact cctgggggga ccgtcagtct     780
tcctcttccc cccaaaaccc aaggacaccc tcatgatctc ccggacccct gaggtcacat     840
gcgtggtggt ggacgtgagc cacgaagacc ctgaggtcaa gttcaactgg tacgtggacg     900
gcgtggaggt gcataatgcc aagacaaagc cgcgggagga gcagtacaac agcacgtacc     960
gtgtggtcag cgtcctcacc gtcctgcacc aggactggct gaatggcaag gagtacaagt    1020
gcaaggtctc caacaaagcc ctcccagccc ccatcgagaa aaccatctcc aaagccaaag    1080
ggcagccccg agaaccacag gtgtacaccc tgcccccatc ccgggaggag atgaccaaga    1140
accaggtcag cctgacctgc ctggtcaaag gcttctatcc cagcgacatc gccgtggagt    1200
gggagagcaa tgggcagccg gagaacaact acaagaccac gcctcccgtg ctggactccg    1260
acggctcctt cttcctctac agcaagctca ccgtggacaa gagcaggtgg cagcagggga    1320
acgtcttctc atgctccgtg atgcatgagg ctctgcacaa ccactacacg cagaagagcc    1380
tctccctgtc tccgggt                                                   1397
```

<210> SEQ ID NO 154
<211> LENGTH: 267
<212> TYPE: PRT
<213> ORGANISM: Artificial Sequence
<220> FEATURE:
<223> OTHER INFORMATION: Second Polypeptide Chain of an Exemplary hDR5
mAb 2.4 x hDR5 mAb 2.4 Fc diabody

<400> SEQUENCE: 154

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln Gln His Tyr Ile Thr Pro Trp
                 85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Glu Tyr Ile Leu His Trp Val Arg Gln Ala Pro Gly Gln Gly Leu
145                 150                 155                 160

Glu Trp Met Gly Trp Phe Tyr Pro Gly Asn Asn Asn Ile Lys Tyr Asn
                165                 170                 175

Glu Lys Phe Lys Asp Arg Val Thr Ile Thr Ala Asp Lys Ser Thr Ser
            180                 185                 190

Thr Val Tyr Met Glu Leu Ser Ser Leu Arg Ser Glu Asp Thr Ala Val
        195                 200                 205

Tyr Tyr Cys Ala Arg His Glu Gln Gly Pro Gly Tyr Phe Asp Tyr Trp
    210                 215                 220

Gly Gln Gly Thr Leu Val Thr Val Ser Ser Ala Ser Thr Lys Gly Lys
225                 230                 235                 240

Val Ala Ala Cys Lys Glu Lys Val Ala Ala Leu Lys Glu Lys Val Ala
                245                 250                 255

Ala Leu Lys Glu Lys Val Ala Ala Leu Lys Glu
            260                 265

<210> SEQ ID NO 155
<211> LENGTH: 801
<212> TYPE: DNA
<213> ORGANISM: Artificial Sequence
<220> FEATURE:
<223> OTHER INFORMATION: Polynucleotide Encoding Second Polypeptide
      Chain of an Exemplary hDR5 mAb 2.4 x hDR5 mAb 2.4 Fc diabody

<400> SEQUENCE: 155
gatattcaga tgacccagag tccctcattt ctgtccgcct ccgtcggtga ccgcgtgact     60
attacttgtc gggcttctca ggatgtcaac accgccgtgg cttggtacca gcagaagccc    120
ggtaaagcac ctaagctgct gatctattgg gccagcactc ggcacaccgg agtcccatct    180
aggttctctg gcagtggatc agggacagac tttaccctga caattagctc cctgcagcca    240
gaggatatcg ctacatacta ttgtcagcag cactacatca ctccttggac cttcggcggg    300
ggcacaaaac tggaaatcaa aggaggcgga tccggcggcg gaggccaggt ccagctggtg    360
cagagtgggg cagaggtgaa aaagccaggg gcatcagtga aagtgtcttg taaagcatca    420
ggttatacat ttactgagta catcctgcac tgggtgcgac aggcaccagg acagggactg    480
gaatggatgg ggtggttcta ccctggcaac aacaacatta gtacaacga gaagtttaaa    540
gaccgggtga ccatcacagc ggataagtct accagtacag tctatatgga gctgagctcc    600
ctgagaagcg aagacaccgc cgtctactat tgcgctcgcc acgaacaggg tccaggttac    660
tttgattatt gggggcaggg aactctggtc acagtcagct ccgcctccac caagggcaaa    720
gtggccgcat gtaaggagaa agttgctgct ttgaaagaga aggtcgccgc acttaaggaa    780
aaggtcgcag ccctgaaaga g                                               801
```

<210> SEQ ID NO 156
<211> LENGTH: 499
<212> TYPE: PRT
<213> ORGANISM: Artificial Sequence
<220> FEATURE:
<223> OTHER INFORMATION: First Polypeptide Chain of an Exemplary hDR5 mAb 2.4 x hDR5 mAb 2.4 Fc diabody L234A/L235A

<400> SEQUENCE: 156

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
130                 135                 140

Thr Glu Tyr Ile Leu His Trp Val Arg Gln Ala Pro Gly Gln Gly Leu
145                 150                 155                 160

Glu Trp Met Gly Trp Phe Tyr Pro Gly Asn Asn Asn Ile Lys Tyr Asn
                165                 170                 175

Glu Lys Phe Lys Asp Arg Val Thr Ile Thr Ala Asp Lys Ser Thr Ser
            180                 185                 190

Thr Val Tyr Met Glu Leu Ser Ser Leu Arg Ser Glu Asp Thr Ala Val
        195                 200                 205

Tyr Tyr Cys Ala Arg His Glu Gln Gly Pro Gly Tyr Phe Asp Tyr Trp
210                 215                 220

Gly Gln Gly Thr Leu Val Thr Val Ser Ser Ala Ser Thr Lys Gly Glu
225                 230                 235                 240

Val Ala Ala Cys Glu Lys Glu Val Ala Ala Leu Glu Lys Glu Val Ala
                245                 250                 255

Ala Leu Glu Lys Glu Val Ala Ala Leu Glu Lys Leu Glu Pro Lys Ser
            260                 265                 270

Ser Asp Lys Thr His Thr Cys Pro Pro Cys Pro Ala Pro Glu Ala Ala
        275                 280                 285

Gly Gly Pro Ser Val Phe Leu Phe Pro Pro Lys Pro Lys Asp Thr Leu
290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365
```

```
Gly Lys Glu Tyr Lys Cys Lys Val Ser Asn Lys Ala Leu Pro Ala Pro
            370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Glu Glu Met Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
            435                 440                 445

Pro Val Leu Asp Ser Asp Gly Ser Phe Phe Leu Tyr Ser Lys Leu Thr
        450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly

<210> SEQ ID NO 157
<211> LENGTH: 1497
<212> TYPE: DNA
<213> ORGANISM: Artificial Sequence
<220> FEATURE:
<223> OTHER INFORMATION: Polynucleotide Encoding First Polypeptide Chain
      of an Exemplary hDR5 mAb 2.4 x hDR5 mAb 2.4 Fc diabody L234A/L235A

<400> SEQUENCE: 157
gatattcaga tgacccagag tccctcattt ctgtccgcct ccgtcggtga ccgcgtgact     60
attacttgtc gggcttctca ggatgtcaac accgccgtgg cttggtacca gcagaagccc    120
ggtaaagcac ctaagctgct gatctattgg gccagcactc ggcacaccgg agtcccatct    180
aggttctctg gcagtggatc agggacagac tttaccctga caattagctc cctgcagcca    240
gaggatatcg ctacatacta ttgtcagcag cactacatca ctccttggac cttcggcggg    300
ggcacaaaac tggaaatcaa aggaggcgga tccggcggcg gaggccaggt ccagctggtg    360
cagagtgggg cagaggtgaa aaagccaggg gcatcagtga agtgtcttg taaagcatca    420 ggttatacat ttactgagta catcctgcac tgggtgcgac aggcaccagg acagggactg    480
gaatggatgg ggtggttcta ccctggcaac aacaacatta gtacaacga agtttaaa     540 gaccgggtga ccatcacagc ggataagtct accgtacag tctatatgga gctgagctcc    600
ctgagaagcg aagacaccgc cgtctactat tgcgctcgcc acgaacaggg tccaggttac    660
tttgattatt gggggcaggg aactctggtc acagtcagct ccgcctccac caagggcgaa    720
gtggccgcat gtgagaaaga ggttgctgct ttggagaagg aggtcgctgc acttgaaaag    780
gaggtcgcag ccctggagaa actggagccc aaatcttctg acaaaactca cacatgccca    840
ccgtgcccag cacctgaagc cgcggggga cgtcagtct cctcttccc cccaaaaccc    900 aaggacaccc tcatgatctc ccggaccct gaggtcacat gcgtggtggt ggacgtgagc    960
cacgaagacc ctgaggtcaa gttcaactgg tacgtggacg gcgtggaggt gcataatgcc   1020
aagacaaagc cgcgggagga gcagtacaac agcacgtacc gtgtggtcag cgtcctcacc   1080
gtcctgcacc aggactggct gaatggcaag gagtacaagt gcaaggtctc caacaaagcc   1140
ctcccagccc ccatcgagaa aaccatctcc aaagccaaag gcagccccg agaaccacag   1200 gtgtacaccc tgcccccatc ccgggaggag atgaccaaga accaggtcag cctgacctgc   1260
```

```
ctggtcaaag gcttctatcc cagcgacatc gccgtggagt gggagagcaa tgggcagccg   1320
gagaacaact acaagaccac gcctcccgtg ctggactccg acggctcctt cttcctctac   1380
agcaagctca ccgtggacaa gagcaggtgg cagcagggga acgtcttctc atgctccgtg   1440
atgcatgagg ctctgcacaa ccactacacg cagaagagcc tctccctgtc tccgggt     1497
```

<210> SEQ ID NO 158
<211> LENGTH: 499
<212> TYPE: PRT
<213> ORGANISM: Artificial Sequence
<220> FEATURE:
<223> OTHER INFORMATION: First Polypeptide Chain of an Exemplary hDR5
      mAb 2.5 x hDR5 mAb 2.5 Fc diabody

<400> SEQUENCE: 158

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Glu Tyr Ile Leu His Trp Val Arg Gln Ala Pro Gly Gln Gly Leu
145                 150                 155                 160

Glu Trp Met Gly Trp Phe Tyr Pro Gly Asn Asn Ile Lys Tyr Asn
                165                 170                 175

Glu Lys Phe Lys Asp Arg Val Thr Ile Thr Ala Asp Lys Ser Thr Ser
            180                 185                 190

Thr Val Tyr Met Glu Leu Ser Ser Leu Arg Ser Glu Asp Thr Ala Val
        195                 200                 205

Tyr Tyr Cys Ala Arg His Glu Gln Gly Pro Gly Tyr Phe Asp Tyr Trp
    210                 215                 220

Gly Gln Gly Thr Leu Val Thr Val Ser Ser Ala Ser Thr Lys Gly Glu
225                 230                 235                 240

Val Ala Ala Cys Glu Lys Glu Val Ala Ala Leu Glu Lys Glu Val Ala
                245                 250                 255

Ala Leu Glu Lys Glu Val Ala Ala Leu Glu Lys Leu Glu Pro Lys Ser
            260                 265                 270

Ser Asp Lys Thr His Thr Cys Pro Pro Cys Pro Ala Pro Glu Leu Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320
```

```
His Glu Asp Pro Glu Val Lys Phe Asn Trp Tyr Val Asp Gly Val Glu
            325                 330                 335

Val His Asn Ala Lys Thr Lys Pro Arg Glu Glu Gln Tyr Asn Ser Thr
        340                 345                 350

Tyr Arg Val Val Ser Val Leu Thr Val Leu His Gln Asp Trp Leu Asn
    355                 360                 365

Gly Lys Glu Tyr Lys Cys Lys Val Ser Asn Lys Ala Leu Pro Ala Pro
370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Glu Glu Met Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly

<210> SEQ ID NO 159
<211> LENGTH: 1497
<212> TYPE: DNA
<213> ORGANISM: Artificial Sequence
<220> FEATURE:
<223> OTHER INFORMATION: Polynucleotide Encoding First Polypeptide Chain
      of an Exemplary hDR5 mAb 2.5 x hDR5 mAb 2.5 Fc diabody

<400> SEQUENCE: 159
gatattcaga tgacccagag tccctcattt ctgtccgcct ccgtcggtga ccgcgtgact      60
attacttgtc gggcttctca ggatgtcaac accgccgtgg cttggtacca gcagaagccc    120
ggtaaagcac ctaagctgct gatctattgg gccagcactc ggcacaccgg agtcccagat    180
aggttctctg gcagtggatc aggacagaca tttaccctga caattagctc cctgcagccc    240
gaggatatcg ctacttacta ttgtcagcag cactacatca ctccttggac cttcggcggg    300
ggcacaaaac tggaaatcaa aggaggcgga tccggcggcg gaggccaggt ccagctggtg    360
cagagtgggg cagaggtgaa aaagccaggg gcatcagtga agtgtcttg taaagcatca    420 ggttatacat ttactgagta catcctgcac tgggtgcgac aggcaccagg acagggactg    480
gaatggatgg ggtggttcta ccctggcaac aacaacatta gtacaacga agtttaaa      540 gaccgggtga ccatcacagc ggataagtct accagtacag tctatatgga gctgagctcc    600
ctgagaagcg aagacaccgc cgtctactat tgcgctcgcc acgaacaggg tccaggttac    660
tttgattatt gggggcaggg aactctggtc acagtcagct ccgcctccac caagggcgaa    720
gtggccgcat gtgagaaaga ggttgctgct ttggagaagg aggtcgctgc acttgaaaag    780
gaggtcgcag ccctggagaa actggagccc aaatcttctg acaaaactca cacatgccca    840
ccgtgcccag cacctgaact cctgggggga ccgtcagtct tcctcttccc cccaaaaccc    900
aaggacaccc tcatgatctc ccggacccct gaggtcacat gcgtggtggt ggacgtgagc    960
```

```
cacgaagacc ctgaggtcaa gttcaactgg tacgtggacg gcgtggaggt gcataatgcc    1020
aagacaaagc cgcgggagga gcagtacaac agcacgtacc gtgtggtcag cgtcctcacc    1080
gtcctgcacc aggactggct gaatggcaag gagtacaagt gcaaggtctc caacaaagcc    1140
ctcccagccc ccatcgagaa aaccatctcc aaagccaaag gcagccccg agaaccacag    1200 gtgtacaccc tgcccccatc ccgggaggag atgaccaaga accaggtcag cctgacctgc    1260
ctggtcaaag gcttctatcc cagcgacatc gccgtggagt gggagagcaa tgggcagccg    1320
gagaacaact acaagaccac gcctcccgtg ctggactccg acggctcctt cttcctctac    1380
agcaagctca ccgtggacaa gagcaggtgg cagcagggga acgtcttctc atgctccgtg    1440
atgcatgagg ctctgcacaa ccactacacg cagaagagcc tctccctgtc tccgggt     1497
```

<210> SEQ ID NO 160
<211> LENGTH: 267
<212> TYPE: PRT
<213> ORGANISM: Artificial Sequence
<220> FEATURE:
<223> OTHER INFORMATION: Second Polypeptide Chain of an Exemplary hDR5
    mAb 2.5 x hDR5 mAb 2.5 Fc diabody

<400> SEQUENCE: 160

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Glu Tyr Ile Leu His Trp Val Arg Gln Ala Pro Gly Gln Gly Leu
145                 150                 155                 160

Glu Trp Met Gly Trp Phe Tyr Pro Gly Asn Asn Asn Ile Lys Tyr Asn
                165                 170                 175

Glu Lys Phe Lys Asp Arg Val Thr Ile Thr Ala Asp Lys Ser Thr Ser
            180                 185                 190

Thr Val Tyr Met Glu Leu Ser Ser Leu Arg Ser Glu Asp Thr Ala Val
        195                 200                 205

Tyr Tyr Cys Ala Arg His Glu Gln Gly Pro Gly Tyr Phe Asp Tyr Trp
    210                 215                 220

Gly Gln Gly Thr Leu Val Thr Val Ser Ser Ala Ser Thr Lys Gly Lys
225                 230                 235                 240

Val Ala Ala Cys Lys Glu Lys Val Ala Ala Leu Lys Glu Lys Val Ala
                245                 250                 255

Ala Leu Lys Glu Lys Val Ala Ala Leu Lys Glu
            260                 265
```

<210> SEQ ID NO 161
<211> LENGTH: 801
<212> TYPE: DNA
<213> ORGANISM: Artificial Sequence
<220> FEATURE:
<223> OTHER INFORMATION: Polynucleotide Encoding Second Polypeptide
      Chain of an Exemplary hDR5 mAb 2.5 x hDR5 mAb 2.5 Fc diabody

<400> SEQUENCE: 161

```
gatattcaga tgacccagag tccctcattt ctgtccgcct ccgtcggtga ccgcgtgact    60
attacttgtc gggcttctca ggatgtcaac accgccgtgg cttggtacca gcagaagccc   120
ggtaaagcac ctaagctgct gatctattgg gccagcactc gcacaccgg agtcccagat    180
aggttctctg gcagtggatc agggacagac tttacccctga caattagctc cctgcagccc  240
gaggatatcg ctacttacta ttgtcagcag cactacatca ctccttggac cttcggcggg   300
ggcacaaaac tggaaatcaa aggaggcgga tccggcggcg gaggccaggt ccagctggtg   360
cagagtgggg cagaggtgaa aaagccaggg gcatcagtga agtgtcttg taaagcatca   420
ggttatacat ttactgagta catcctgcac tgggtgcgac aggcaccagg acagggactg   480
gaatggatgg ggtggttcta ccctggcaac aacaacatta gtacaacga agagtttaaa    540
gaccgggtga ccatcacagc ggataagtct accagtacag tctatatgga gctgagctcc   600
ctgagaagcg aagacaccgc cgtctactat tgcgctcgcc acgaacaggg tccaggttac   660
tttgattatt gggggcaggg aactctggtc acagtcagct ccgcctccac caagggcaaa   720
gtggccgcat gtaaggagaa agttgctgct ttgaaagaga aggtcgccgc acttaaggaa   780
aaggtcgcag ccctgaaaga g                                             801
```

<210> SEQ ID NO 162
<211> LENGTH: 499
<212> TYPE: PRT
<213> ORGANISM: Artificial Sequence
<220> FEATURE:
<223> OTHER INFORMATION: First Polypeptide Chain of an Exemplary hDR5
      mAb 2.5 x hDR5 mAb 2.5 Fc diabody L234A/L235A

<400> SEQUENCE: 162

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln His Tyr Ile Thr Pro Trp
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Glu Tyr Ile Leu His Trp Val Arg Gln Ala Pro Gly Gln Gly Leu
```

```
            145                 150                 155                 160
Glu Trp Met Gly Trp Phe Tyr Pro Gly Asn Asn Ile Lys Tyr Asn
                    165                 170                 175
Glu Lys Phe Lys Asp Arg Val Thr Ile Thr Ala Asp Lys Ser Thr Ser
                180                 185                 190
Thr Val Tyr Met Glu Leu Ser Ser Leu Arg Ser Glu Asp Thr Ala Val
                195                 200                 205
Tyr Tyr Cys Ala Arg His Glu Gln Gly Pro Gly Tyr Phe Asp Tyr Trp
            210                 215                 220
Gly Gln Gly Thr Leu Val Thr Val Ser Ala Ser Thr Lys Gly Glu
225                 230                 235                 240
Val Ala Ala Cys Glu Lys Val Ala Ala Leu Glu Lys Glu Val Ala
                245                 250                 255
Ala Leu Glu Lys Glu Val Ala Ala Leu Glu Lys Leu Glu Pro Lys Ser
                260                 265                 270
Ser Asp Lys Thr His Thr Cys Pro Pro Cys Pro Ala Pro Glu Ala Ala
                275                 280                 285
Gly Gly Pro Ser Val Phe Leu Phe Pro Pro Lys Pro Lys Asp Thr Leu
            290                 295                 300
Met Ile Ser Arg Thr Pro Glu Val Thr Cys Val Val Val Asp Val Ser
305                 310                 315                 320
His Glu Asp Pro Glu Val Lys Phe Asn Trp Tyr Val Asp Gly Val Glu
                325                 330                 335
Val His Asn Ala Lys Thr Lys Pro Arg Glu Glu Gln Tyr Asn Ser Thr
                340                 345                 350
Tyr Arg Val Val Ser Val Leu Thr Val Leu His Gln Asp Trp Leu Asn
                355                 360                 365
Gly Lys Glu Tyr Lys Cys Lys Val Ser Asn Lys Ala Leu Pro Ala Pro
            370                 375                 380
Ile Glu Lys Thr Ile Ser Lys Ala Lys Gly Gln Pro Arg Glu Pro Gln
385                 390                 395                 400
Val Tyr Thr Leu Pro Pro Ser Arg Glu Glu Met Thr Lys Asn Gln Val
                405                 410                 415
Ser Leu Thr Cys Leu Val Lys Gly Phe Tyr Pro Ser Asp Ile Ala Val
                420                 425                 430
Glu Trp Glu Ser Asn Gly Gln Pro Glu Asn Asn Tyr Lys Thr Thr Pro
            435                 440                 445
Pro Val Leu Asp Ser Asp Gly Ser Phe Phe Leu Tyr Ser Lys Leu Thr
            450                 455                 460
Val Asp Lys Ser Arg Trp Gln Gln Gly Asn Val Phe Ser Cys Ser Val
465                 470                 475                 480
Met His Glu Ala Leu His Asn His Tyr Thr Gln Lys Ser Leu Ser Leu
                485                 490                 495
Ser Pro Gly

<210> SEQ ID NO 163
<211> LENGTH: 1497
<212> TYPE: DNA
<213> ORGANISM: Artificial Sequence
<220> FEATURE:
<223> OTHER INFORMATION: Polynucleotide Encoding First Polypeptide Chain
      of an Exemplary hDR5 mAb 2.5 x hDR5 mAb 2.5 Fc diabody L234A/L235A

<400> SEQUENCE: 163
gatattcaga tgacccagag tccctcattt ctgtccgcct ccgtcggtga ccgcgtgact      60
```

```
attacttgtc gggcttctca ggatgtcaac accgccgtgg cttggtacca gcagaagccc    120
ggtaaagcac ctaagctgct gatctattgg gccagcactc ggcacaccgg agtcccagat    180
aggttctctg gcagtggatc agggacagac tttaccctga caattagctc cctgcagccc    240
gaggatatcg ctacttacta ttgtcagcag cactacatca ctccttggac cttcggcggg    300
ggcacaaaac tggaaatcaa aggaggcgga tccggcggcg gaggccaggt ccagctggtg    360
cagagtgggg cagaggtgaa aaagccaggg gcatcagtga agtgtcttg taaagcatca    420 ggttatacat ttactgagta catcctgcac tgggtgcgac aggcaccagg acagggactg    480
gaatggatgg ggtggttcta ccctggcaac aacaacatta gtacaacga aagtttaaa    540 gaccgggtga ccatcacagc ggataagtct accagtacag tctatatgga gctgagctcc    600
ctgagaagcg aagacaccgc cgtctactat tgcgctcgcc acgaacaggg tccaggttac    660
tttgattatt gggggcaggg aactctggtc acagtcagct ccgcctccac caagggcgaa    720
gtggccgcat gtgagaaaga ggttgctgct ttggagaagg aggtcgctgc acttgaaaag    780
gaggtcgcag ccctggagaa actggagccc aaatcttctg acaaaactca cacatgccca    840
ccgtgcccag cacctgaagc cgcggggga ccgtcagtct tcctcttccc cccaaaaccc    900
aaggacaccc tcatgatctc ccggaccct gaggtcacat gcgtggtggt ggacgtgagc    960
cacgaagacc ctgaggtcaa gttcaactgg tacgtggacg gcgtggaggt gcataatgcc    1020
aagacaaagc cgcgggagga gcagtacaac agcacgtacc gtgtggtcag cgtcctcacc    1080
gtcctgcacc aggactggct gaatggcaag gagtacaagt gcaaggtctc caacaaagcc    1140
ctcccagccc ccatcgagaa aaccatctcc aaagccaaag gcagccccg agaaccacag    1200 gtgtacaccc tgcccccatc ccgggaggag atgaccaaga accaggtcag cctgacctgc    1260
ctggtcaaag gcttctatcc cagcgacatc gccgtggagt gggagagcaa tgggcagccg    1320
gagaacaact acaagaccac gcctcccgtg ctggactccg acggctcctt cttcctctac    1380
agcaagctca ccgtggacaa gagcaggtgg cagcagggga acgtcttctc atgctccgtg    1440
atgcatgagg ctctgcacaa ccactacacg cagaagagcc tctccctgtc tccgggt     1497
```

<210> SEQ ID NO 164
<211> LENGTH: 216
<212> TYPE: PRT
<213> ORGANISM: Homo sapiens
<220> FEATURE:
<221> NAME/KEY: MISC_FEATURE
<222> LOCATION: (1)..(216)
<223> OTHER INFORMATION: Human Wild-Type IgG2 CH2-CH3 Domain

<400> SEQUENCE: 164

```
Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95
```

```
Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 165
<211> LENGTH: 11
<212> TYPE: PRT
<213> ORGANISM: Artificial Sequence
<220> FEATURE:
<223> OTHER INFORMATION: Humanized Anti-DR5 mAb 2 Light Chain Variable
      Region Variant 3, 4, 5 CDRL1

<400> SEQUENCE: 165

Arg Ala Ser Gln Asp Val Asn Thr Ala Val Ala
1               5                   10

<210> SEQ ID NO 166
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: OKT3 Anti-CD3 Antibody Light Chain Variable
      Domain

<400> SEQUENCE: 166

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105

<210> SEQ ID NO 167
<211> LENGTH: 192
<212> TYPE: PRT
<213> ORGANISM: Mus musculus
<220> FEATURE:
<221> NAME/KEY: MISC_FEATURE
```

```
<222> LOCATION: (1)..(192)
<223> OTHER INFORMATION: OKT3 Anti-CD3 Antibody Heavy Chain Variable
      Domain

<400> SEQUENCE: 167

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

<210> SEQ ID NO 168
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: Human Wild-Type IgG3 CH2-CH3 Domain

<400> SEQUENCE: 168

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
```

```
                  130                135                140
Ser Asp Ile Ala Val Glu Trp Glu Ser Ser Gly Gln Pro Glu Asn Asn
145                150                155                160

Tyr Asn Thr Thr Pro Pro Met Leu Asp Ser Asp Gly Ser Phe Phe Leu
                165                170                175

Tyr Ser Lys Leu Thr Val Asp Lys Ser Arg Trp Gln Gln Gly Asn Ile
            180                185                190

Phe Ser Cys Ser Val Met His Glu Ala Leu His Asn Arg Phe Thr Gln
            195                200                205

Lys Ser Leu Ser Leu Ser Pro Gly Lys
    210                215
```

MULTIVALENT MOLECULES COMPRISING DR5-BINDING DOMAINS

CROSS-REFERENCE TO RELATED APPLICATIONS

This application is a § 371 National Stage Application of PCT/US2015/033099 (filed May 29, 2015), which application claims priority to U.S. Patent Applications No. 62/149,139 (filed Apr. 17, 2015) and 62/107,871 (filed Jan. 26, 2015), each of which applications is herein incorporated by reference in its entirety.

REFERENCE TO SEQUENCE LISTING

This application includes one or more Sequence Listings pursuant to 37 C.F.R. 1.821 et seq., which are disclosed in computer-readable media (file name: 1301_0118PCT_Sequence_Listing_ST25.txt, created on 18 May 2015, and having a size of 215,084 bytes), which files is herein incorporated by reference in its entirety.

BACKGROUND OF THE INVENTION

Field of the Invention

The present invention is directed to multivalent DR5-Binding Molecules that comprise Binding Domain(s) of anti-DR5 antibodies, and particularly Binding Domain(s) of anti-human DR5 antibodies. The DR5-Binding Molecules of the present invention include bivalent and tetravalent molecules having two, three or four DR5-Binding Domains each capable of binding human DR5. In particular, the present invention is directed to multivalent DR5-Binding Molecules that comprise diabodies, and more particularly, diabodies that comprise a covalently bonded complex of two or more polypeptide chains. The invention particularly pertains to such multivalent DR5-Binding Molecules that comprise fragments of the anti-DR5 antibodies DR5 mAb 1 and/or DR5 mAb 2, and/or humanized and chimeric versions of such antibodies.

Description of Related Art

I. Death Receptor 5 ("DR5")

Healthy animals maintain a continuous immune surveillance against tumor cells. Through the interplay of various growth factors, cytokines and hormones, such animals can mediate the programmed death (apoptosis) of encountered damaged cells. Damaged cells that acquire resistance to this cell death process can and which acquire the ability to replicate in an uncontrolled fashion can become tumor cells and lead to cancer (Abdulghani, J. et al. (2010) "*TRAIL Receptor Signaling And Therapeutics*," Expert Opin. Ther. Targets 14(10):1091-1108; Andera, L. (2009) "*Signaling Activated By The Death Receptors Of The TNFR Family*," Biomed. Pap. Med. Fac. Univ. Palacky Olomouc Czech. Repub. 153(3):173-180; Carlo-Stella, C. et al. (2007) "*Targeting TRAIL Agonistic Receptors for Cancer Therapy*," Clin. Cancer 13(8):2313-2317; Chaudhari, B. R. et al. (2006) "*Following the TRAIL to Apoptosis*," Immunologic Res. 35(3):249-262).

Methods that are capable of selectively targeting the cell death pathways so as to spare normal cells while increasing the effectiveness of such pathways in killing cancer cells are of particular interest in cancer therapy. Members of the Tumor Necrosis Factor (TNF) superfamily including Fas ligand, TNF and the TNF-related apoptosis-inducing ligand (TRAIL) have been identified as targets for cancer biotherapy (Walczak, H. (2013) "*Death Receptor—Ligand Systems in Cancer, Cell Death, and Inflammation*," Cold Spring Harb. Perspect. Biol. 2013; 5:a008698; pp. 1-19; Falschlehner, C. et al. (2007) "*TRAIL Signalling: Decisions Between Life And Death*," Intl. J. Biochem. Cell Biol. 39:1462-1475; Abdulghani, J. et al. (2010) "*TRAIL Receptor Signaling And Therapeutics*," Expert Opin. Ther. Targets 14(10):1091-1108). TRAIL is a cytokine that is expressed by effector lymphocytes. TRAIL is expressed on the surface of immune effector cells such as natural killer cells, macrophages, dendritic cells and cytotoxic T cells in response to cytokines, particularly interferon-gamma that possesses a response element in the TRAIL gene promoter (Allen, J. E. et al. (2012) "*Regulation Of The Human TRAIL Gene*," Cancer Biol. Ther. 13(12):1143-1151). Its expression level is extremely low in freshly-isolated lymphocytes, and only a small fraction of natural killer (NK) cells express detectable TRAIL. TRAIL is believed to play a role in regulating the innate immune response involving the interferons, boosting host responses to tumor cells and changing the tumor microenvironment to enhance antigen presentation and promote tissue infiltration by NK cells and other immune system cells.

One important distinction between TRAIL-induced apoptosis and apoptosis induced by conventional chemotherapy and radiotherapy is that the latter is largely dependent on cellular damage recognition by, for example, the p53 tumor suppressor protein (Dimberg, L. Y. et al. (2013) "*On The TRAIL To Successful Cancer Therapy? Predicting And Counteracting Resistance Against TRAIL-Based Therapeutics*," Oncogene 32:1341-1350). The dependence on p53 to elicit an apoptotic response poses a problem in cancer therapy, as loss of p53 occurs in more than half of all cancers cells because of inactivating mutations (Hollstein, M. et al. (1994) "*Database Of p53 Gene Somatic Mutations In Human Tumors And Cell Lines*," Nucleic Acids Res. 22:3551-3555).

TRAIL is a type II protein with 281 amino acid residues and has homology with TNF-α and FasL (CD95L) (Chaudhari, B. R. et al. (2006) "*Following the TRAIL to Apoptosis*," Immunologic Res. 35(3):249-262). TRAIL consists of an extracellular TNF-like Domain, an extracellular stalk, a transmembrane helix, and a Cytoplasmic Domain. TRAIL binds to two different types of receptors: death receptors (DR) that trigger TRAIL-induced apoptosis and decoy receptors inhibit this pathway. To date, two human death receptors specific for TRAIL have been recognized: TRAIL-R1 (also known as DR4) and TRAIL-R2 (also known as DR5). Additionally, three putative decoy receptors have been identified: TRAIL-R3 (DcR1), TRAIL-R4 (DcR2) and osteoprotegerin (Chaudhari, B. R. et al. (2006) "*Following the TRAIL to Apoptosis*," Immunologic Res. 35(3):249-262; Carlo-Stella, C. et al. (2007) "*Targeting TRAIL Agonistic Receptors for Cancer Therapy*," Clin. Cancer 13(8):2313-2317; Allen, J. E. et al. (2012) "Regulation Of The Human TRAIL Gene," Cancer Biol. Ther. 13(12):1143-1151). TRAIL-R1 (DR4) is expressed at very low levels in most human tissues including the spleen, thymus, liver, peripheral blood leukocytes, activated T cells, small intestine and some tumor cell lines. In contrast, TRAIL-R2 (DR5) is ubiquitously distributed both in normal and tumor cell lines but is more abundant in spleen, peripheral blood leukocytes, activated lymphocytes and hepatocytes (Abdulghani, J. et al. (2010) "*TRAIL Receptor Signaling And Therapeutics*," Expert Opin. Ther. Targets 14(10):1091-1108).

DR4 and DR5 are single-pass type-I membrane proteins and are encoded by two genes located on chromosome 8p. DR4 and DR5 each contain extracellular regions that comprise Cysteine-Rich Domains (CRDs), a Transmembrane Domain, and a Death Domain located within the cytoplasmic portion of the receptors. Two splice variants of DR5 have been identified, long DR5 (DR5(L)) and short DR5 (DR5(S)). These variants differ in a stretch of 29 amino acids located between the receptors' CRDs and their Transmembrane Domain. DR4 and DR5 are able to transduce an apoptosis signal following TRAIL binding (van Roosmalen, I. A. M. et al. (2014) "*Two Death-Inducing Human TRAIL Receptors To Target In Cancer: Similar Or Distinct Regulation And Function?*," Biochem. Pharamcol. 91:447-456).

When TRAIL binds to DR4 or DR5, the receptors homotrimerize, enabling the receptor's Death Domain to recruit the adaptor protein Fas-Associated Death Domain and the inactive, uncleaved form of caspase 8 (pro-caspase 8) or the uncleaved form of caspase 10 (pro-caspase 10). The receptors, Fas-associated protein with Death Domain, and pro-caspase 8 or pro-caspase 10 together form the Death-Inducing Signaling Complex, (DISC). At the DISC, pro-caspase 8 is activated, in a process that is dependent on both dimerization and cleavage. Activated caspase 8 then cleaves downstream substrates ultimately resulting in the cleavage and activation of effector caspase 3. Activation of caspase 3 initiates a cascade of molecular activation events that ultimately leads to the production of death substrates (Schneider-Brachert, W. et al. (2013) "*Membrane Trafficking of Death Receptors: Implications on Signalling*," Int. J. Mol. Sci. 14:14475-14503; Falschlehner, C. et al. (2009) "*TRAIL and Other TRAIL Receptor Agonists as Novel Cancer Therapeutics*," In: THERAPEUTIC TARGETS OF THE TNF SUPERFAMILY (Grewal, I. S., Ed.) Landes Bioscience and Springer Science+Business Media, NY; pp. 195-206; Falschlehner, C. et al. (2007) "*TRAIL Signalling: Decisions Between Life And Death*," Intl. J. Biochem. Cell Biol. 39:1462-1475; Guicciardi, M. E. et al. (2009) "*Life And Death By Death Receptors*," FASEB J. 23:1625-1637; Kischkel, F. C. et al. (2000) "*Apo2L/TRAIL-Dependent Recruitment of Endogenous FADD and Caspase-8 to Death Receptors 4 and 5*," Immunity 12:611-620; Dimberg, L. Y. et al. (2013) "*On The TRAIL To Successful Cancer Therapy? Predicting And Counteracting Resistance Against TRAIL-Based Therapeutics*," Oncogene 32:1341-1350; Buchsbaum, D. J. et al. (2007) "*TRAIL-Receptor-Antibodies as a Potential Cancer Treatment*," Future Oncol. 3(4):405-409; Buchsbaum, D. J. et al. (2006) "*TRAIL Receptor-Targeted Therapy*," Future Oncol. 2(4):493-508; Andera, L. (2009) "*Signaling Activated By The Death Receptors Of The TNFR Family*," Biomed. Pap. Med. Fac. Univ. Palacky Olomouc Czech. Repub. 153(3):173-180; Chan, F. K.-M. (2007) "*Three is Better Than One: Pre-Ligand Receptor Assembly in the Regulation of TNF Receptor Signaling*," Cytokine 37(2): 101-107). The three decoy receptors either act as decoys or transduce antiapoptotic signals (Carlo-Stella, C. et al. (2007) "*Targeting TRAIL Agonistic Receptors for Cancer Therapy*," Clin, Cancer 13(8):2313-2317; Mahmood, Z. et al. (2010) "*Death Receptors: Targets For Cancer Therapy*," Exper. Cell. Res. 316:887-899; Oikonomou, E. et al. (2013) "*The TRAIL Of Oncogenes To Apoptosis*," Intl. J Union Biochem. Molec. Biol. 39(4):343-354).

In addition to such an "extrinsic" pathway, TRAIL may mediate cell death via an "intrinsic" pathway (Carlo-Stella, C. et al. (2007) "*Targeting TRAIL Agonistic Receptors for Cancer Therapy*," Clin, Cancer 13(8):2313-2317; Buchsbaum, D. J. et al. (2006) "*TRAIL Receptor-Targeted Therapy*," Future Oncol. 2(4):493-508; Buchsbaum, D. J. et al. (2007) "*TRAIL-Receptor-Antibodies as a Potential Cancer Treatment*," Future Oncol. 3(4):405-409). The intrinsic pathway is mediated by the cleavage activation of the pro-apoptotic protein Bid, which then binds with other pro-apoptotic proteins to form a complex that mediates the release of cytochrome c from mitochondria. Such release triggers a cascade of caspase release and activation leading to cell death (Kandasamy, K. et al. (2003) "*Involvement Of Proapoptotic Molecules Bax And Bak In Tumor Necrosis Factor-Related Apoptosis-Inducing Ligand (TRAIL)-Induced Mitochondrial Disruption And Apoptosis: Differential Regulation Of Cytochrome C And Smac/DIABLO Release*," Cancer Res. 63:1712-1721; Rudner, J. et al. (2005) "*Type I And Type II Reactions In TRAIL-Induced Apoptosis—Results From Dose-Response Studies*," Oncogene 24:130-140).

The molecular pathways are, however, complex. Depending on the cell type, the relative strength and duration of the ligand signal, and either the presence, absence or activation state of the intracellular proteins that signal downstream of TRAIL receptors, treatment with TRAIL may stimulate either apoptosis or in rare instances cell proliferation (Abdulghani, J. et al. (2010) "*TRAIL Receptor Signaling And Therapeutics*," Expert Opin. Ther. Targets 14(10):1091-1108; Andera, L. (2009) "*Signaling Activated By The Death Receptors Of The TNFR Family*," Biomed. Pap. Med. Fac. Univ. Palacky Olomouc Czech. Repub. 153(3):173-180). Moreover, certain cancers have a DR preference (i.e., DR4 or DR5) for inducing apoptosis, whereas other tumor types do not (van Roosmalen, I. A. M. et al. (2014) "*Two Death-Inducing Human TRAIL Receptors To Target In Cancer: Similar Or Distinct Regulation And Function?*," Biochem. Pharamcol. 91:447-456).

II. Therapeutic Uses of TRAIL Proteins and Anti-DR Antibodies

Because TRAIL is highly selective in its ability to recognize and kill damaged cells, while sparing normal cells, soluble recombinant TRAIL has been stated to have potential utility in the treatment of cancer (e.g., colorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer and rectal cancer (see, Micheau, O. et al. (2013) "*Death Receptors As Targets In Cancer*," Br. J. Pharmacol. 169:1723-1744); Falschlehner, C. et al. (2009) "*TRAIL and Other TRAIL Receptor Agonists as Novel Cancer Therapeutics*," In: THERAPEUTIC TARGETS OF THE TNF SUPERFAMILY (Grewal, I. S., Ed.) Landes Bioscience and Springer Science+Business Media, NY; pp. 195-206; Buchsbaum, D. J. et al. (2006) "*TRAIL Receptor-Targeted Therapy*," Future Oncol. 2(4):493-508; Wajant, H. et al. (2013) "*Engineering Death Receptor Ligands For Cancer Therapy*," Canc. Lett. 332:163-174; Buchsbaum, D. J. et al. (2007) "*TRAIL-Receptor-Antibodies as a Potential Cancer Treatment*," Future Oncol. 3(4):405-409; Abdulghani, J. et al. (2010) ("*TRAIL Receptor Signaling And Therapeutics*," Expert Opin. Ther. Targets 14(10):1091-1108; Finnberg, N. et al. (2008) "*TRAIL Death Receptors As Tumor Suppressors And Drug Targets*," Cell Cycle 7(11): 1525-1528; Hellwig, C. T. et al. (2012) "*TRAIL Signaling and Synergy Mechanisms Used in TRAIL-Based Combination Therapies*," Molec. Cancer Ther. 11(1):3-13; Henson, E. S. et al. (2008) "*The Role Of TRAIL Death Receptors In The Treatment Of Hematological Malignancies*," Leukemia & Lymphoma 49(1):27-35; Huang, Y. et al. (2007) "*TRAIL Death Receptors And Cancer Therapeutics*," Toxicol. Appl.

Pharmacol. 224:284-289; Humphreys, R. C. et al. (2008) "Trail Receptors: Targets for Cancer Therapy," In: PROGRAMMED CELL DEATH IN CANCER PROGRESSION AND THERAPY Khosravi-Far, R. and White, E. (Eds.) Springer, NY; pp. 127-158; Koschny, R. et al. (2007) "The Promise Of TRAIL—Potential And Risks Of A Novel Anticancer Therapy," J. Molec. Med. 85:923-935; Kruyt, F. A. E. (2008) "TRAIL and Cancer Therapy," Cancer Lett. 263:14-25; Kuijlen, J. M. A. et al. (2010) "Review: On TRAIL For Malignant Glioma Therapy?," Neuropathol. Appl. Neurobiol. 36:168-182; Mellier, G. et al. (2010) ("TRAILing Death in Cancer," Molec. Aspects Med. 31:93-112; Rahman, M. et al. (2009) "The TRAIL To Targeted Therapy Of Breast Cancer," Adv. Cancer Res. 103:43-73; Voelkel-Johnson, C. (2011) "TRAIL-Mediated Signaling In Prostate, Bladder And Renal Cancer," Nat. Rev. Urol. 8:417-427).

Anti-DR4 and anti-DR5 monoclonal antibodies that might be capable of mimicking the signaling of TRAIL have been proposed as providing greater selectivity (Buchsbaum, D. J. et al. (2006) "TRAIL Receptor-Targeted Therapy," Future Oncol. 2:493-508; Kelley, S. K. et al. (2004) "Targeting Death Receptors In Cancer With Apo2L/TRAIL," Curr. Opin. Pharmacol. 4:333-339; Papenfuss, K. et al. (2008) "Death Receptors As Targets For Anti-Cancer Therapy," J. Cell. Mol. Med. 12:2566-2585; de Bruyn, M. et al. (2013) "Antibody-Based Fusion Proteins To Target Death Receptors In Cancer," Cancer Lett. 332:175-183).

Three Phase II clinical studies of mapatumumab, an anti-DR4 agonist antibody (Human Genome Sciences) have been reported to show a therapeutic effect in patients suffering from non-Hodgkin's lymphoma (NHL), colorectal cancer (CRC) and non-small cell lung cancer (NSCLC) (Greco, F. A. et al. (2008) "Phase 2 Study Of Mapatumumab, A Fully Human Agonistic Monoclonal Antibody Which Targets And Activates The TRAIL Receptor-1, In Patients With Advanced Non-Small Cell Lung Cancer," Lung Cancer 61:82-90; Trarbach, T. et al. (2010) "Phase II Trial Of Mapatumumab, A Fully Human Agonistic Monoclonal Antibody That Targets And Activates The Tumour Necrosis Factor Apoptosis-Inducing Ligand Receptor-1 (TRAIL-R1), In Patients With Refractory Colorectal Cancer," Br. J. Cancer 102:506-512; Falschlehner, C. et al. (2009) "TRAIL and Other TRAIL Receptor Agonists as Novel Cancer Therapeutics," In: THERAPEUTIC TARGETS OF THE TNF SUPERFAMILY (Grewal, I. S., Ed.) Landes Bioscience and Springer Science+Business Media, NY; pp. 195-206). TRA-8/CS-1008, a humanized anti-DR5 antibody (Daiichi Sankyo (Tokyo, Japan)) is reported to have exhibited high antitumor activity against astrocytoma and leukemia cells in vitro and engrafted breast cancer cells in vivo (Buchsbaum, D. J. et al. (2003) "Antitumor Efficacy Of TRA-8 Anti-DR5 Monoclonal Antibody Alone Or In Combination With Chemotherapy And/Or Radiation Therapy In A Human Breast Cancer Model," Clin. Cancer Res. 9:3731-3741; Ichikawa, K. et al. (2001) "Tumoricidal Activity Of A Novel Anti-Human DR5 Monoclonal Antibody Without Hepatocyte Cytotoxicity," Nat. Med. 7:954-960; Saleh, M. N. et al. (2008) "A Phase I Study Of CS-1008 (Humanized Monoclonal Antibody Targeting Death Receptor 5 Or DR5), Administered Weekly To Patients With Advanced Solid Tumors Or Lymphomas," 2008 ASCO Annual Meeting Proceedings, J. Clin. Oncol. 26(20S): Abstract 3537). mDRA-6 (IgG1-k), a murine antihuman anti-DR5 monoclonal antibody (Henan University) has been reported to be able to induce the apoptosis of Jurkat cells via the TRAIL extrinsic pathway (Du, Y.-W. et al. (2011) "A Novel Agonistic Anti-Human Death Receptor 5 Monoclonal Antibody With Tumoricidal Activity Induces Caspase-And Mitochondrial-Dependent Apoptosis In Human Leukemia Jurkat Cells," Cancer Biother. Radiopharmaceut. 26(2):143-152). The chimeric DR-5-targeting antibody LBY135 (Novartis) has been reported to have induced apoptosis in 50% of a panel of 40 human colon cancer cell lines with an IC50 of 10 nM or less and to have verified in vivo antitumor activity in human colorectal xenograft models in mice (Li, J. et al. (2008) "LBY135, A Novel Anti-DR5 Agonistic Antibody Induces Tumor Cell-Specific Cytotoxic Activity In Human Colon Tumor Cell Lines And Xenografts," Drug Dev. Res. 69:69-82; Sharma, S. et al. (2008) "Phase I Trial Of LBY135, A Monoclonal Antibody Agonist To DR5, Alone And In Combination With Capecitabine In Advanced Solid Tumors," 2008 ASCO Annual Meeting Proceedings. J. Clin. Oncol. 26(15S):3538). Additional anti-DR antibodies in clinical development include: ApomAb (Camidge, D. et al. (2007) "A Phase I Safety And Pharmacokinetic Study Of Apomab, A Human DR5 Agonist Antibody, In Patients With Advanced Cancer," 2007 ASCO Annual Meeting Proceedings (Post-Meeting Edition), J. Clin. Oncol. 25(18S):3582; Johnstone, R. W. et al. (2008) "The TRAIL Apoptotic Pathway In Cancer Onset, Progression And Therapy," Nat. Rev. Cancer 8:782-798); AMG655 (LoRusso, P. et al. (2007) "First-In-Human Study Of AMG 655, A Pro-Apoptotic TRAIL Receptor-2 Agonist, In Adult Patients With Advanced Solid Tumors," 2007 ASCO Annual Meeting Proceedings Part I. J. Clin. Oncol. 25(18S): 3534); conatumumab (Bajaj, M. et al. (2011) "Conatumumab: A Novel Monoclonal Antibody Against Death Receptor 5 For The Treatment Of Advanced Malignancies In Adults," Expert Opin. Biol. Ther. 11(11):1519-1524); lexatumumab, an anti-DR5 agonist antibody (Human Genome Sciences) (Plummer, R. et al. (2007) "Phase 1 And Pharmacokinetic Study Of LEXATUMUMAB In Patients With Advanced Cancers," Clin. Cancer Res. 13:6187-6194); drozitumab (Kang, Z. et al. (2011) "Drozitumab, A Human Antibody To Death Receptor 5, Has Potent Antitumor Activity Against Rhabdomyosarcoma With The Expression Of Caspase-8 Predictive Of Response," Clin. Cancer Res. 17(10):3181-3192; Zinonos, I. et al. (2014) "Doxorubicin Overcomes Resistance to Drozitumab by Antagonizing Inhibitor of Apoptosis Proteins (IAPs)," Anticancer Res. 34(12):7007-7020; Xiang, H. et al. (2013) "Death Receptor 5 Agonistic Antibody PRO95780: Preclinical Pharmacokinetics And Concentration-Effect Relationship Support Clinical Dose And Regimen Selection," Cancer Chemother. Pharmacol. 72(2):405-415; Stern, H. M. et al. (2010) "Development Of Immunohistochemistry Assays To Assess GALNT14 And FUT3/6 In Clinical Trials Of Dulanermin And Drozitumab," Clin. Cancer Res. 16(5):1587-1596) and KMTR2 (Nagane, M. et al. (2010) "Predominant Antitumor Effects By Fully Human Anti-TRAIL-Receptor 2 (DR5) Monoclonal Antibodies In Human Glioma Cells In Vitro And In Vivo," Neuro. Oncol. 12(7):687-700; Motoki, K. et al. (2005) "Enhanced Apoptosis And Tumor Regression Induced By A Direct Agonist Antibody To Tumor Necrosis Factor-Related Apoptosis-Inducing Ligand Receptor 2," Clin. Cancer Res. 11(8):3126-3135).

The use of anti-DR antibodies is reviewed in: Falschlehner, C. et al. (2009) ("TRAIL and Other TRAIL Receptor Agonists as Novel Cancer Therapeutics," In: THERAPEUTIC TARGETS OF THE TNF SUPERFAMILY (Grewal, I. S., Ed.) Landes Bioscience and Springer Science+Business Media, NY; pp. 195-206); Hellwig, C. T. et al. (2012) ("TRAIL Signaling and Synergy Mechanisms Used in TRAIL-Based Combination Therapies," Molec. Cancer Ther. 11(1):3-13); Huang, Y. et al. (2007) ("TRAIL Death Receptors And Cancer Therapeutics," Toxicol. Appl. Pharmacol. 224:284-289); Humphreys, R. C. et al. (2008) ("*Trail Receptors: Targets for Cancer Therapy*," In: PROGRAMMED CELL DEATH IN CANCER PROGRESSION AND THERAPY Khosravi-Far, R. and White, E. (Eds.) Springer, NY; pp. 127-158); Kruyt, F. A. E. (2008) ("*TRAIL and Cancer Therapy*," Cancer Lett. 263:14-25); Mellier, G. et al. (2010) ("*TRAILing Death in Cancer*," Molec. Aspects Med. 31:93-112); Oldenhuis, C. N. A. M. et al. (2008) ("*Targeting TRAIL Death Receptors*," Curr. Opin. Pharmacol. 8:433-439); Papenfuss, K. et al. (2008) ("*Death Receptors As Targets For Anti-Cancer Therapy*," J. Cell. Mol. Med. 12(6B):2566-2585); Micheau, O. et al. (2013) ("*Death Receptors As Targets In Cancer*," Br. J. Pharmacol. 169:1723-1744; and in van Roosmalen, I. A. M. et al. (2014) ("*Two Death-Inducing Human TRAIL Receptors To Target In Cancer: Similar Or Distinct Regulation And Function?,*" Biochem. Pharamcol. 91:447-456).

Present data suggests that such agents are well-tolerated and have plasma half-lives of less than 12 days, however, the potential application of this therapy is limited by the fact that some primary cancer cells are resistant to TRAIL apoptosis, even after combination treatment with chemotherapy (Buchsbaum, D. J. et al. (2007) "*TRAIL-Receptor-Antibodies as a Potential Cancer Treatment*," Future Oncol. 3(4):405-409; see also, Dimberg, L. Y. et al. (2013) "*On The TRAIL To Successful Cancer Therapy? Predicting And Counteracting Resistance Against TRAIL-Based Therapeutics*," Oncogene 32:1341-1350; Falschlehner, C. et al. (2009) "*TRAIL and Other TRAIL Receptor Agonists as Novel Cancer Therapeutics*," In: THERAPEUTIC TARGETS OF THE TNF SUPERFAMILY (Grewal, I. S., Ed.) Landes Bioscience and Springer Science+ Business Media, NY; pp. 195-206; Maksimovic-Ivanic, D. et al. (2012) "*Resistance To TRAIL And How To Surmount It*," Immunol. Res. 52:157-168).

Despite the promise of such antibody therapy, studies have shown that some anti-DR monoclonal antibodies have not exhibited sufficient selectivity for clinical use. This may reflect the fact that only one specific isoform of TRAIL among the nine reported variants exhibit such selectivity (Allen, J. E. et al. (2012) "*Regulation Of The Human TRAIL Gene*," Cancer Biol. Ther. 13(12):1143-1151). Induction of apoptosis in normal human cells, such as hepatocytes or keratinocytes by some rTRAIL and anti-DR monoclonal antibodies have been observed in vitro (Jo, M. et al. (2000) "*Apoptosis Induced In Normal Human Hepatocytes By Tumor Necrosis Factor-Related Apoptosis-Inducing Ligand*," Nat. Med. 6:564-567; Lawrence, D, et al. (2001) "*Differential Hepatocyte Toxicity Of Recombinant Apo2L/ TRAIL Versions*," Nat. Med. 7:383-385; Mori, E. et al. (2004) "*Human Normal Hepatocytes Are Susceptible To Apoptosis Signal Mediated By Both TRAIL-R1 And TRAIL-R2*," Cell. Death Differ. 11:203-207; Qin, J. et al. (2001) "*Avoiding Premature Apoptosis Of Normal Epidermal Cells*," Nat. Med. 7:385-386). Hepatotoxicity with increased serum alanine aminotransferase, aspartate aminotransferase and bilirubin was reported in a few patients when treated with higher doses (20 mg per kg) of lexatumummab anti-DR5 agonist antibody from Human Genome Sciences) (Plummer, R. et al. (2007) "*Phase I And Pharmacokinetic Study Of LEXATUMUMAB In Patients With Advanced Cancers*," Clin. Cancer Res. 13:6187-6194).

Anti-DR antibodies are disclosed in U.S. Pat. Nos. 8,790, 663; 8,715,668; 8,703,712; 8,461,311; 8,409,570; 8,372, 396; 8,329,180; 8,173,128; 8,097,704; 8,067,001; 8,030, 023; 8,029,783; 7,981,421; 7,897,730; 7,893,216; 7,704,502 and 7,476,383; in United States Patent Publications No. 2014/0370019; 2014/0308288; 2014/0105898; 2014/ 0004120; 2014/0010812; 2013/0324433; 2013/0280282; 2013/0243780; 2013/0064838; 2012/0184718; 2012/ 0087922; 2012/0070432; 2011/0070248; 2010/0080806; 2009/0317384; 2009/0317396; 2009/0208483; 2009/ 0175854 and 2009/0136503; in European Patent Publications No. EP 2021370; EP 1790663; EP 2059533; EP 1506285; EP 1576179; EP 2636736; EP 2684896; EP 2636736; EP 2569336; EP 2046836; EP 2480230; EP 2368910; EP 2350641; EP 2292794; EP 2287285; EP 2292794 and EP 2021370; and in WIPO Patent Publications No. WO 2014/159562; WO 2014/161845; WO 2014/ 050779; WO 2014/035474; WO 2014/009358; WO 2013/ 163229 and WO 2013/148877.

Bispecific antibody molecules, having an scFv Domain capable of binding to a tumor antigen and a soluble TRAIL (sTRAIL) or Fas (CD95) Ligand (FasL) Domain capable of binding to a death receptor or to Fas, have also been proposed (see, Wajant, H. et al. (2013) "*Engineering Death Receptor Ligands For Cancer Therapy*," Canc. Lett. 332: 163-174). Such genetic fusion of a tumor-selective antibody fragment to sTRAIL and sFasL yielded highly selective anticancer therapeutics with favorable anticancer features. However, the employed fusion proteins were twice the size of non-targeted soluble ligands. Thus, the approach appears to be limited by the relative difficulty of the fusion protein diffusing through multiple cellular in order to penetrate into solid tumors (de Bruyn, M. et al. (2013) "*Antibody-Based Fusion Proteins To Target Death Receptors In Cancer*," Cancer Lett. 332:175-183). Bispecific antibody molecules capable of binding to DR5 are disclosed in United States Patent Publications No. 2014/0370019; 2014/0308288; 2013/0243780; 2012/0184718 and 2009/0175854; in European Patent Publication Nos. EP 1790663; EP 2059533; EP 2684896 and EP 2350641; and in WIPO Publications No. WO 2014/159562; WO 2014/161845; WO 2014/050779; WO 2014/009358 and WO 2013/148877.

In addition to its potential in the treatment of cancer, TRAIL has been proposed as a potential therapeutic for the treatment of bacterial pathogens (Benedict, C. A. et al. (2012) "*TRAIL: Not Just For Tumors Anymore?,*" J. Exp. Med. 209(11):1903-1906). TRAIL may also have a role in the structural changes in asthmatic airways because it is expressed by various inflammatory cells including eosinophils (Chaudhari, B. R. et al. (2006) "*Following the TRAIL to Apoptosis*," Immunologic Res. 35(3):249-262). One drawback of the use of soluble TRAIL preparations has been its relatively short in vivo half-life (approximately 30 minutes; Walczak, H. et al. (1999) "*Tumoricidal Activity Of Tumor Necrosis Factor-Related Apoptosis-Inducing Ligand In Vivo*," Nat. Med. 5:157-163). Additionally, soluble recombinant TRAIL is capable of binding to TRAIL receptors (thus promoting cancer treatment) and to TRAIL decoy receptors (thus putatively providing no therapeutic benefit). TRAIL may also have a role in cardiovascular disease (Martin-Ventura, J. L. et al. (2007) "TRAIL and Vascular Injury," Frontiers in Bioscience 12:3656-3667) and in inflammation (Walczak, H. (2013) "*Death Receptor—Ligand Systems in Cancer, Cell Death, and Inflammation*," Cold Spring Harb. Perspect. Biol. 2013; 5:a008698; pp. 1-19).

Whereas clinical trials using TRAIL therapies have shown low toxicity in patients, disappointingly small therapeutic effects have been observed when TRAIL agonists are used as a monotherapy (Dimberg, L. Y. et al. (2013) "*On The TRAIL To Successful Cancer Therapy? Predicting And Counteracting Resistance Against TRAIL-Based Therapeutics*," Oncogene 32:1341-1350). This conclusion reflects the observation that a substantial proportion of damaged cells that have evolved into tumor cells are found to be TRAIL-resistant. Such experiences have led to the conclusion that TRAIL therapy may be very beneficial, but only for a small subset of patients (Dimberg, L. Y. et al. (2013) "*On The TRAIL To Successful Cancer Therapy? Predicting And Counteracting Resistance Against TRAIL-Based Therapeutics*," Oncogene 32:1341-1350).

Multiple mechanisms of TRAIL resistance have been identified (Maksimovic-Ivanic, D. et al. (2012) "*Resistance To TRAIL And How To Surmount It*," Immunol. Res. 52:157-168; Dimberg, L. Y. et al. (2013) "*On The TRAIL To Successful Cancer Therapy? Predicting And Counteracting Resistance Against TRAIL-Based Therapeutics*," Oncogene 32:1341-1350; Thorburn, A. et al. (2008) "*TRAIL Receptor-Targeted Therapeutics: Resistance Mechanisms And Strategies To Avoid Them*," Drug Resist. Updat. 11(1-2):17-24; Whiteside, T. L. (2007) "*The Role of Death Receptor Ligands in Shaping Tumor Microenvironment*," Immunol. Investig. 36:25-46). Among the hypothesized explanations are the possibility of decreased expression of certain caspases (e.g., caspase 8) by TRAIL-resistant tumor cells, or the increased expression of caspase inhibitors (e.g., XIAP, cIAP) by such cells, or the increased expression of inhibitors of apoptosis (e.g., Bcl-2, Mcl-1, etc.) by such cells (Abdulghani, J. et al. (2010) "*TRAIL Receptor Signaling And Therapeutics*," Expert Opin. Ther. Targets 14(10):1091-1108; Buchsbaum, D. J. et al. (2006) "*TRAIL Receptor-Targeted Therapy*," Future Oncol. 2(4):493-508). Alternatively, TRAIL resistance may reflect the presence of defects in the TRAIL receptors of the tumor cells, or increased expression of inhibitors that are very selective for death receptors such as FLIP or the decoy receptors TRAIL-R3 and TRAIL-R4. See, Abdulghani, J. et al. (2010) ("*TRAIL Receptor Signaling And Therapeutics*," Expert Opin. Ther. Targets 14(10):1091-1108). In light of such resistance, TRAIL-based therapeutics have typically been proposed only as agents to be provided in concert with other chemotherapeutic agents (Buchsbaum, D. J. et al. (2006) "*TRAIL Receptor-Targeted Therapy*," Future Oncol. 2(4):493-508).

Thus, despite all prior advances, a need remains for anti-DR5 antibodies and molecules comprising DR5-binding domains that could provide improved therapeutic value to patients suffering from cancer or other diseases and conditions. The present invention is directed to this and other goals.

SUMMARY OF THE INVENTION

The present invention is directed to multivalent DR5-Binding Molecules that comprise Binding Domain(s) of anti-DR5 antibodies, and particularly Binding Domain(s) of anti-human DR5 antibodies. The DR5-Binding Molecules of the present invention include bivalent and tetravalent molecules having two, three or four DR5-Binding Domains each capable of binding human DR5. In particular, the present invention is directed to multivalent DR5-Binding Molecules that comprise diabodies, and more particularly, diabodies that comprise a covalently bonded complex of two or more polypeptide chains. The invention particularly pertains to such multivalent DR5-Binding Molecules that comprise fragments of the anti-DR5 antibodies DR5 mAb 1 and/or DR5 mAb 2, and/or humanized and chimeric versions of such antibodies.

In detail, the invention provides a multivalent DR5-Binding Molecule that is a bispecific binding molecule, capable of simultaneously binding to two different epitopes of human Death Receptor 5 (DR5), wherein the multivalent DR5-Binding Molecule comprises four antigen-binding domains each capable of binding human DR5. The invention also provides a multivalent DR5-Binding Molecule that is a monospecific binding molecule, capable of binding to an epitope of human DR5, wherein the multivalent DR5-Binding Molecule comprises four antigen-binding domains each capable of binding human DR5. The invention particularly concerns the embodiment of all such multivalent DR5-Binding Molecules capable of simultaneously binding to two, three, or four human DR5 polypeptides.

The invention further concerns the embodiments of such multivalent DR5-Binding Molecules, wherein the multivalent DR5-Binding Molecule is an Fc Region-containing diabody, the diabody being a covalently bonded complex that comprises two pairs of polypeptides, wherein each pair comprises a first polypeptide chain and a second polypeptide chain.

The invention further concerns the embodiments of such multivalent DR5-Binding Molecules, wherein:

(A) the first polypeptide chain comprises, in the N-terminal to C-terminal direction:
  (i) a variable light chain (VL) Domain of a monoclonal antibody capable of binding to a first DR5 epitope (VL1);
  (ii) a first peptide linker (Linker 1);
  (iii) a variable heavy chain (VH) Domain of a monoclonal capable of binding to a second DR5 epitope (VH2);
  (iv) a second peptide linker (Linker 2);
  (v) a Heterodimer-Promoting Domain comprising a E-coil Domain or a K-coil Domain;
  (vi) a third peptide linker (Linker 3); and
  (vii) a polypeptide portion of an IgG Fc Region having CH2 and CH3 domains of an IgG immunoglobulin Fc Region; and (B) the second polypeptide chain comprises, in the N-terminal to C-terminal direction:
  (i) a VL Domain of a monoclonal antibody capable of binding to the second DR5 epitope (VL2);
  (ii) a first peptide linker (Linker 1);
  (iii) a VH Domain of a monoclonal capable of binding to the first DR5 epitope (VH1);
  (iv) a second peptide linker (Linker 2); and
  (v) a Heterodimer-Promoting Domain comprising a E-coil Domain or a K-coil Domain, wherein the Heterodimer-Promoting Domain of the first polypeptide chain and the Heterodimer-Promoting Domain of the second polypeptide chain are not both E-coil Domains or both K-coil Domains;

and wherein:
(a) the VL1 Domain of the first polypeptide chain and the VH1 Domain of the second polypeptide chain form an Antigen-Binding Domain capable of specific binding to a first epitope of DR5;
(b) the VH2 Domain of the first polypeptide chain and the VL1 Domain of the second polypeptide chain form an Antigen-Binding Domain capable of specific binding to a second epitope of DR5; and
(c) the CH2-CH3 portions of the pair of first polypeptide chains form an IgG Fc Region.

The invention further concerns the embodiments of such multivalent DR5-Binding Molecules, wherein:
  (i) the Linker 1 has the amino acid sequence of SEQ ID NO:33,
  (ii) the Linker 1 has the amino acid sequence of SEQ ID NO:47, (iii) the E-coil Domain has the amino acid sequence of SEQ ID NO: SEQ ID NO:41,
(iv) the K-coil Domain has the amino acid sequence of SEQ ID NO:42,
(v) the Linker 3 has the amino acid sequence of SEQ ID NO:51, and
(vi) the CH2-CH3 domain has the amino acid sequence of SEQ ID NO:1 or SEQ ID NO:102, wherein the C-terminal residue is optionally included.

The invention further concerns the embodiments of all such multivalent DR5-Binding Molecules, wherein the Fc Region comprises one or more amino acid modifications that reduce the affinity of the variant Fc Region for an FcγR or stabilizes the Fc Region. The invention further concerns the embodiments of all such DR5-Binding Molecule, wherein the modifications comprise the substitution of L234A; L235A; or L234A and L235A.

The invention particularly concerns the embodiments of such multivalent DR5-Binding Molecules, wherein the VL1 comprises a $CDR_L1$ Domain, a $CDR_L2$ Domain, and a $CDR_L3$ Domain, and the VH1 comprises a $CDR_H1$ Domain, a $CDR_H2$ Domain and a $CDR_H3$ Domain, wherein:
  (i) the $CDR_L1$ Domain, $CDR_L2$ Domain, and $CDR_L3$ Domain are the Light Chain CDRs of DR5 mAb 1, and respectively have the amino acid sequences: SEQ ID NO:4, SEQ ID NO:5, and SEQ ID NO:6, and the $CDR_H1$ Domain, $CDR_H2$ Domain, and $CDR_H3$ Domain are the Heavy Chain CDRs of DR5 mAb 1, and respectively have the amino acid sequences: SEQ ID NO:9, SEQ ID NO:10, and SEQ ID NO:11; or
  (ii) the $CDR_L1$ Domain, $CDR_L2$ Domain, and $CDR_L3$ Domain are the Light Chain CDRs of DR5 mAb 2, and, respectively have the amino acid sequences: SEQ ID NO:14, SEQ ID NO:15, and SEQ ID NO:16, and the $CDR_H1$ Domain, $CDR_H2$ Domain, and $CDR_H3$ Domain are the Heavy Chain CDRs of DR5 mAb 2, and respectively have the amino acid sequences: SEQ ID NO:19, SEQ ID NO:20, and SEQ ID NO:21; or
  (iii) the $CDR_L1$ Domain, $CDR_L2$ Domain, and $CDR_L3$ Domain are the Light Chain CDRs of hDR5 mAb 2 VL-3, and, respectively have the amino acid sequences: SEQ ID NO:162, SEQ ID NO:15, and SEQ ID NO:16, and the $CDR_H1$ Domain, $CDR_H2$ Domain, and $CDR_H3$ Domain are the Heavy Chain CDRs of hDR5 mAb 2 VH-3, and respectively have the amino acid sequences: SEQ ID NO:19, SEQ ID NO:20, and SEQ ID NO:21; or
  (iv) the $CDR_L1$ Domain, $CDR_L2$ Domain, and $CDR_L3$ Domain are the Light Chain CDRs of DR5 mAb 2, and, respectively have the amino acid sequences: SEQ ID NO:55, SEQ ID NO:56, and SEQ ID NO:57, and the $CDR_H1$ Domain, $CDR_H2$ Domain, and $CDR_H3$ Domain are the Heavy Chain CDRs of DR5 mAb 2, and respectively have the amino acid sequences: SEQ ID NO:59, SEQ ID NO:60, and SEQ ID NO:61; or
  (v) the $CDR_L1$ Domain, $CDR_L2$ Domain, and $CDR_L3$ Domain are the Light Chain CDRs of DR5 mAb 2, and, respectively have the amino acid sequences: SEQ ID NO:63, SEQ ID NO:64, and SEQ ID NO:65, and the $CDR_H1$ Domain, $CDR_H2$ Domain, and $CDR_H3$ Domain are the Heavy Chain CDRs of DR5 mAb 2, and respectively have the amino acid sequences: SEQ ID NO:67, SEQ ID NO:68, and SEQ ID NO:69; or
  (vi) the $CDR_L1$ Domain, $CDR_L2$ Domain, and $CDR_L3$ Domain are the Light Chain CDRs of DR5 mAb 2, and, respectively have the amino acid sequences: SEQ ID NO:71, SEQ ID NO:72, and SEQ ID NO:73, and the $CDR_H1$ Domain, $CDR_H2$ Domain, and $CDR_H3$ Domain are the Heavy Chain CDRs of DR5 mAb 2, and respectively have the amino acid sequences: SEQ ID NO:75, SEQ ID NO:76, and SEQ ID NO:77; or
  (vii) the $CDR_L1$ Domain, $CDR_L2$ Domain, and $CDR_L3$ Domain are the Light Chain CDRs of DR5 mAb 2, and, respectively have the amino acid sequences: SEQ ID NO:79, SEQ ID NO:80, and SEQ ID NO:81, and the $CDR_H1$ Domain, $CDR_H2$ Domain, and $CDR_H3$ Domain are the Heavy Chain CDRs of DR5 mAb 2, and respectively have the amino acid sequences: SEQ ID NO:83, SEQ ID NO:84, and SEQ ID NO:85; or
  (viii) the $CDR_L1$ Domain, $CDR_L2$ Domain, and $CDR_L3$ Domain are the Light Chain CDRs of DR5 mAb 2, and, respectively have the amino acid sequences: SEQ ID NO:87, SEQ ID NO:88, and SEQ ID NO:89, and the $CDR_H1$ Domain, $CDR_H2$ Domain, and $CDR_H3$ Domain are the Heavy Chain CDRs of DR5 mAb 2, and respectively have the amino acid sequences: SEQ ID NO:91, SEQ ID NO:92, and SEQ ID NO:93; or
  (ix) the $CDR_L1$ Domain, $CDR_L2$ Domain, and $CDR_L3$ Domain are the Light Chain CDRs of DR5 mAb 2, and, respectively have the amino acid sequences: SEQ ID NO:95, SEQ ID NO:96, and SEQ ID NO:97, and the $CDR_H1$ Domain, $CDR_H2$ Domain, and $CDR_H3$ Domain are the Heavy Chain CDRs of DR5 mAb 2, and respectively have the amino acid sequences: SEQ ID NO:99, SEQ ID NO:100, and SEQ ID NO:101.

The invention particularly concerns the embodiments of such multivalent DR5-Binding Molecules, wherein the VL2 comprises a $CDR_L1$ Domain, a $CDR_L2$ Domain, and a $CDR_L3$ Domain, and the VH2 comprises a $CDR_H1$ Domain, a $CDR_H2$ Domain and a $CDR_H3$ Domain, wherein:
  (i) the $CDR_L1$ Domain, $CDR_L2$ Domain, and $CDR_L3$ Domain are the Light Chain CDRs of DR5 mAb 1, and respectively have the amino acid sequences: SEQ ID NO:4, SEQ ID NO:5, and SEQ ID NO:6, and the $CDR_H1$ Domain, $CDR_H2$ Domain, and $CDR_H3$ Domain are the Heavy Chain CDRs of DR5 mAb 1, and respectively have the amino acid sequences: SEQ ID NO:9, SEQ ID NO:10, and SEQ ID NO:11; or
  (ii) the $CDR_L1$ Domain, $CDR_L2$ Domain, and $CDR_L3$ Domain are the Light Chain CDRs of DR5 mAb 2, and, respectively have the amino acid sequences: SEQ ID NO:14, SEQ ID NO:15, and SEQ ID NO:16, and the $CDR_H1$ Domain, $CDR_H2$ Domain, and $CDR_H3$ Domain are the Heavy Chain CDRs of DR5 mAb 2, and respectively have the amino acid sequences: SEQ ID NO:19, SEQ ID NO:20, and SEQ ID NO:21; or
  (iii) the $CDR_L1$ Domain, $CDR_L2$ Domain, and $CDR_L3$ Domain are the Light Chain CDRs of DR5 mAb 2, and, respectively have the amino acid sequences: SEQ ID NO:162, SEQ ID NO:15, and SEQ ID NO:16, and the $CDR_H1$ Domain, $CDR_H2$ Domain, and $CDR_H3$ Domain are the Heavy Chain CDRs of DR5 mAb 2, and respectively have the amino acid sequences: SEQ ID NO:19, SEQ ID NO:20, and SEQ ID NO:21; or
  (iv) the $CDR_L1$ Domain, $CDR_L2$ Domain, and $CDR_L3$ Domain are the Light Chain CDRs of DR5 mAb 2, and, respectively have the amino acid sequences: SEQ ID NO:55, SEQ ID NO:56, and SEQ ID NO:57, and the $CDR_H1$ Domain, $CDR_H2$ Domain, and $CDR_H3$ Domain are the Heavy Chain CDRs of DR5 mAb 2, and respectively have the amino acid sequences: SEQ ID NO:59, SEQ ID NO:60, and SEQ ID NO:61; or
  (v) the $CDR_L1$ Domain, $CDR_L2$ Domain, and $CDR_L3$ Domain are the Light Chain CDRs of DR5 mAb 2, and, respectively have the amino acid sequences: SEQ ID NO:63, SEQ ID NO:64, and SEQ ID NO:65, and the $CDR_H1$ Domain, $CDR_H2$ Domain, and $CDR_H3$ Domain are the Heavy Chain CDRs of DR5 mAb 2, and respectively have the amino acid sequences: SEQ ID NO:67, SEQ ID NO:68, and SEQ ID NO:69; or (vi) the $CDR_L1$ Domain, $CDR_L2$ Domain, and $CDR_L3$ Domain are the Light Chain CDRs of DR5 mAb 2, and, respectively have the amino acid sequences: SEQ ID NO:71, SEQ ID NO:72, and SEQ ID NO:73, and the $CDR_H1$ Domain, $CDR_H2$ Domain, and $CDR_H3$ Domain are the Heavy Chain CDRs of DR5 mAb 2, and respectively have the amino acid sequences: SEQ ID NO:75, SEQ ID NO:76, and SEQ ID NO:77; or (vii) the $CDR_L1$ Domain, $CDR_L2$ Domain, and $CDR_L3$ Domain are the Light Chain CDRs of DR5 mAb 2, and, respectively have the amino acid sequences: SEQ ID NO:79, SEQ ID NO:80, and SEQ ID NO:81, and the $CDR_H1$ Domain, $CDR_H2$ Domain, and $CDR_H3$ Domain are the Heavy Chain CDRs of DR5 mAb 2, and respectively have the amino acid sequences: SEQ ID NO:83, SEQ ID NO:84, and SEQ ID NO:85; or (viii) the $CDR_L1$ Domain, $CDR_L2$ Domain, and $CDR_L3$ Domain are the Light Chain CDRs of DR5 mAb 2, and, respectively have the amino acid sequences: SEQ ID NO:87, SEQ ID NO:88, and SEQ ID NO:89, and the $CDR_H1$ Domain, $CDR_H2$ Domain, and $CDR_H3$ Domain are the Heavy Chain CDRs of DR5 mAb 2, and respectively have the amino acid sequences: SEQ ID NO:91, SEQ ID NO:92, and SEQ ID NO:93; or (ix) the $CDR_L1$ Domain, $CDR_L2$ Domain, and $CDR_L3$ Domain are the Light Chain CDRs of DR5 mAb 2, and, respectively have the amino acid sequences: SEQ ID NO:95, SEQ ID NO:96, and SEQ ID NO:97, and the $CDR_H1$ Domain, $CDR_H2$ Domain, and $CDR_H3$ Domain are the Heavy Chain CDRs of DR5 mAb 2, and respectively have the amino acid sequences: SEQ ID NO:99, SEQ ID NO:100, and SEQ ID NO:101.

The invention further concerns the embodiments of such multivalent DR5-Binding Molecules, wherein the VL1 and the VL2 comprise the same $CDR_L1$ Domain, $CDR_L2$ Domain, and $CDR_L3$ Domain, and wherein the VH1 and the VH2 comprise the same $CDR_H1$ Domain, $CDR_H2$ Domain and $CDR_H3$ Domain, and particularly concerns the embodiment of such multivalent DR5-Binding Molecules, wherein:

(i) the $CDR_L1$ Domain, $CDR_L2$ Domain, and $CDR_L3$ Domain are the Light Chain CDRs of DR5 mAb 1, and respectively have the amino acid sequences: SEQ ID NO:4, SEQ ID NO:5, and SEQ ID NO:6, and the $CDR_H1$ Domain, $CDR_H2$ Domain, and $CDR_H3$ Domain are the Heavy Chain CDRs of DR5 mAb 1, and respectively have the amino acid sequences: SEQ ID NO:9, SEQ ID NO:10, and SEQ ID NO:11; or (ii) the $CDR_L1$ Domain, $CDR_L2$ Domain, and $CDR_L3$ Domain are the Light Chain CDRs of DR5 mAb 2, and, respectively have the amino acid sequences: SEQ ID NO:14, SEQ ID NO:15, and SEQ ID NO:16, and the $CDR_H1$ Domain, $CDR_H2$ Domain, and $CDR_H3$ Domain are the Heavy Chain CDRs of DR5 mAb 2, and respectively have the amino acid sequences: SEQ ID NO:19, SEQ ID NO:20, and SEQ ID NO:21; or (iii) the $CDR_L1$ Domain, $CDR_L2$ Domain, and $CDR_L3$ Domain are the Light Chain CDRs of DR5 mAb 2, and, respectively have the amino acid sequences: SEQ ID NO:162, SEQ ID NO:15, and SEQ ID NO:16, and the $CDR_H1$ Domain, $CDR_H2$ Domain, and $CDR_H3$ Domain are the Heavy Chain CDRs of DR5 mAb 2, and respectively have the amino acid sequences: SEQ ID NO:19, SEQ ID NO:20, and SEQ ID NO:21.

The invention further concerns the embodiments of such multivalent DR5-Binding Molecules, wherein the VL1 and the VL2 do not comprise the same $CDR_L1$ Domain, $CDR_L2$ Domain, and $CDR_L3$ Domain, and wherein the VH1 and the VH2 do not comprise the same $CDR_H1$ Domain, $CDR_H2$ Domain and $CDR_H3$ Domain, and particularly concerns the embodiment of such multivalent DR5-Binding Molecules, wherein:

(i) the $CDR_L1$ Domain, $CDR_L2$ Domain, and $CDR_L3$ Domain of VL1 are the Light Chain CDRs of DR5 mAb 1, and respectively have the amino acid sequences: SEQ ID NO:4, SEQ ID NO:5, and SEQ ID NO:6, and the $CDR_H1$ Domain, $CDR_H2$ Domain, and $CDR_H3$ Domain of VH1 are the Heavy Chain CDRs of DR5 mAb 1, and respectively have the amino acid sequences: SEQ ID NO:9, SEQ ID NO:10, and SEQ ID NO:11; and the $CDR_L1$ Domain, $CDR_L2$ Domain, and $CDR_L3$ Domain of VL2 are the Light Chain CDRs of DR5 mAb 2, and, respectively have the amino acid sequences: SEQ ID NO:14, SEQ ID NO:15, and SEQ ID NO:16, and the $CDR_H1$ Domain, $CDR_H2$ Domain, and $CDR_H3$ Domain of VH2 are the Heavy Chain CDRs of DR5 mAb 2, and respectively have the amino acid sequences: SEQ ID NO:19, SEQ ID NO:20, and SEQ ID NO:21; or (ii) the $CDR_L1$ Domain, $CDR_L2$ Domain, and $CDR_L3$ Domain of VL1 are the Light Chain CDRs of DR5 mAb 2, and, respectively have the amino acid sequences: SEQ ID NO:14, SEQ ID NO:15, and SEQ ID NO:16, and the $CDR_H1$ Domain, $CDR_H2$ Domain, and $CDR_H3$ Domain of VH1 are the Heavy Chain CDRs of DR5 mAb 2, and respectively have the amino acid sequences: SEQ ID NO:19, SEQ ID NO:20, and SEQ ID NO:21; and the $CDR_L1$ Domain, $CDR_L2$ Domain, and $CDR_L3$ Domain of VL2 are the Light Chain CDRs of DR5 mAb 1, and respectively have the amino acid sequences: SEQ ID NO:4, SEQ ID NO:5, and SEQ ID NO:6, and the $CDR_H1$ Domain, $CDR_H2$ Domain, and $CDR_H3$ Domain of VH2 are the Heavy Chain CDRs of DR5 mAb 1, and respectively have the amino acid sequences: SEQ ID NO:9, SEQ ID NO:10, and SEQ ID NO:11.

The invention further concerns the embodiments of such multivalent DR5-Binding Molecules, wherein:

(A) (i) the VL1 has the amino acid sequence of SEQ ID NO:3, and the VH1 has the amino acid sequence of SEQ ID NO:8; or (ii) the VL1 has the amino acid sequence of SEQ ID NO:13, and the VH1 has the amino acid sequence of SEQ ID NO:18; or (iii) the VL1 has the amino acid sequence of SEQ ID NO:23, and the VH1 has the amino acid sequence of SEQ ID NO:31; or (iv) the VL1 has the amino acid sequence of SEQ ID NO:25, and the VH1 has the amino acid sequence of SEQ ID NO:31; or (vi) the VL1 has the amino acid sequence of SEQ ID NO:27, and the VH1 has the amino acid sequence of SEQ ID NO:31; or (vii) the VL1 has the amino acid sequence of SEQ ID NO:29, and the VH1 has the amino acid sequence of SEQ ID NO:31; or (viii) the VL1 has the amino acid sequence of SEQ ID NO:54, and the VH1 has the amino acid sequence of SEQ ID NO:58; or (ix) the VL1 has the amino acid sequence of SEQ ID NO:62, and the VH1 has the amino acid sequence of SEQ ID NO:66; or
(x) the VL1 has the amino acid sequence of SEQ ID NO:70, and the VH1 has the amino acid sequence of SEQ ID NO:74; or
(xi) the VL1 has the amino acid sequence of SEQ ID NO:78, and the VH1 has the amino acid sequence of SEQ ID NO:82; or
(xii) the VL1 has the amino acid sequence of SEQ ID NO:86, and the VH1 has the amino acid sequence of SEQ ID NO:90; or
(xiii) the VL1 has the amino acid sequence of SEQ ID NO:94, and the VH1 has the amino acid sequence of SEQ ID NO:98;
and wherein:
(B) (i) the VL2 has the amino acid sequence of SEQ ID NO:3, and the VH2 has the amino acid sequence of SEQ ID NO:8; or
(ii) the VL2 has the amino acid sequence of SEQ ID NO:13, and the VH2 has the amino acid sequence of SEQ ID NO:18; or
(iii) the VL2 has the amino acid sequence of SEQ ID NO:23, and the VH2 has the amino acid sequence of SEQ ID NO:31; or
(iv) the VL2 has the amino acid sequence of SEQ ID NO:25, and the VH2 has the amino acid sequence of SEQ ID NO:31; or
(vi) the VL2 has the amino acid sequence of SEQ ID NO:27, and the VH2 has the amino acid sequence of SEQ ID NO:31; or
(vii) the VL2 has the amino acid sequence of SEQ ID NO:29, and the VH2 has the amino acid sequence of SEQ ID NO:31; or
(viii) the VL2 has the amino acid sequence of SEQ ID NO:54, and the VH2 has the amino acid sequence of SEQ ID NO:58; or
(ix) the VL2 has the amino acid sequence of SEQ ID NO:62, and the VH2 has the amino acid sequence of SEQ ID NO:66; or
(x) the VL2 has the amino acid sequence of SEQ ID NO:70, and the VH1 has the amino acid sequence of SEQ ID NO:74; or
(xi) the VL2 has the amino acid sequence of SEQ ID NO:78, and the VH1 has the amino acid sequence of SEQ ID NO:82; or
(xii) the VL2 has the amino acid sequence of SEQ ID NO:86, and the VH1 has the amino acid sequence of SEQ ID NO:90; or
(xiii) the VL2 has the amino acid sequence of SEQ ID NO:94, and the VH2 has the amino acid sequence of SEQ ID NO:98.

The invention further concerns the embodiments of such multivalent DR5-Binding Molecules, wherein the VL1 and the VL2 have the same amino acid sequence, and wherein the VH1 and the VH2 have the same amino acid sequence.

The invention further concerns the embodiments of such multivalent DR5-Binding Molecules, wherein the VL1 and the VL2 do not have the same amino acid sequence, and wherein the VH1 and the VH2 do not have the same amino acid sequence.

The invention further concerns the embodiments of such multivalent DR5-Binding Molecules, wherein the multivalent DR5-Binding Molecule is an Fc Region-containing diabody, the diabody being a covalently bonded complex that comprises two pairs of polypeptides wherein:

(i) the first polypeptide chain has the amino acid sequence of SEQ ID NO:116 or SEQ ID NO:120, and the second polypeptide chain has the amino acid sequence of SEQ ID NO:118; or
(ii) the first polypeptide chain has the amino acid sequence of SEQ ID NO:122 or SEQ ID NO:126, and the second polypeptide chain has the amino acid sequence of SEQ ID NO:124; or
(iii) the first polypeptide chain has the amino acid sequence of SEQ ID NO:128 or SEQ ID NO:132, and the second polypeptide chain has the amino acid sequence of SEQ ID NO:130; or
(iv) the first polypeptide chain has the amino acid sequence of SEQ ID NO:134 or SEQ ID NO:138, and the second polypeptide chain has the amino acid sequence of SEQ ID NO:136; or
(v) the first polypeptide chain has the amino acid sequence of SEQ ID NO:140 or SEQ ID NO:144, and the second polypeptide chain has the amino acid sequence of SEQ ID NO:142; or
(vi) the first polypeptide chain has the amino acid sequence of SEQ ID NO:146 or SEQ ID NO:150, and the second polypeptide chain has the amino acid sequence of SEQ ID NO:148; or
(vii) the first polypeptide chain has the amino acid sequence of SEQ ID NO:152 or SEQ ID NO:156, and the second polypeptide chain has the amino acid sequence of SEQ ID NO:154; or
(vi) the first polypeptide chain has the amino acid sequence of SEQ ID NO:158 or SEQ ID NO:162, and the second polypeptide chain has the amino acid sequence of SEQ ID NO:160.

The invention further concerns compositions comprising any of the above described multivalent DR5-Binding Molecules and an excipient. The invention further concerns such compositions further comprising a histone deacetylase inhibitor.

The invention further concerns methods of promoting cell death comprising exposing a cell to any of the above described multivalent DR5-Binding Molecules. In particular, where the cell is a tumor cell. The invention further concerns such methods of promoting cell death further comprising exposing the cell to a histone deacetylase inhibitor.

The invention further concerns the embodiments in which any of the above-described multivalent DR5-Binding Molecules is used in the treatment of cancer. The invention further concerns the embodiments in which any of the above-described multivalent DR5-binding molecules is used in combination with a histone deacetylase inhibitor in the treatment of cancer.

The invention further concerns the embodiments in which any of the above-described multivalent DR5-Binding Molecules is detectably labeled and is used in the diagnosis or prognosis of cancer.

The invention particularly concerns such use of any of the above described multivalent DR5-Binding Molecules in the treatment or diagnosis or prognosis of cancer, wherein the cancer is characterized by the presence of a cancer cell selected from the group consisting of a cell of: an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

The invention particularly concerns such use of any of the above described multivalent DR5-Binding Molecules in the treatment or diagnosis or prognosis of cancer, wherein the cancer is acolorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer or a rectal cancer.

The invention particularly concerns such use of any of the above described multivalent DR5-Binding Molecules in the treatment or diagnosis or prognosis of cancer, wherein the cancer is acute myeloid leukemia (AML), chronic myelogenous leukemia (CML), acute B lymphoblastic leukemia (B-ALL), chronic lymphocytic leukemia (CLL), hairy cell leukemia (HCL), blastic plasmacytoid dendritic cell neoplasm (BPDCN), non-Hodgkin's lymphomas (NHL), including mantel cell leukemia (MCL), and small lymphocytic lymphoma (SLL), Hodgkin's lymphoma, systemic mastocytosis, or Burkitt's lymphoma.

BRIEF DESCRIPTION OF THE DRAWINGS

FIG. 4B shown and Fe-containing diabody which contains E-coil and K-coil Heterodimer-Promoting Domains comprising a cysteine residue and a linker (with an optional cysteine residue).

Figure 7A:
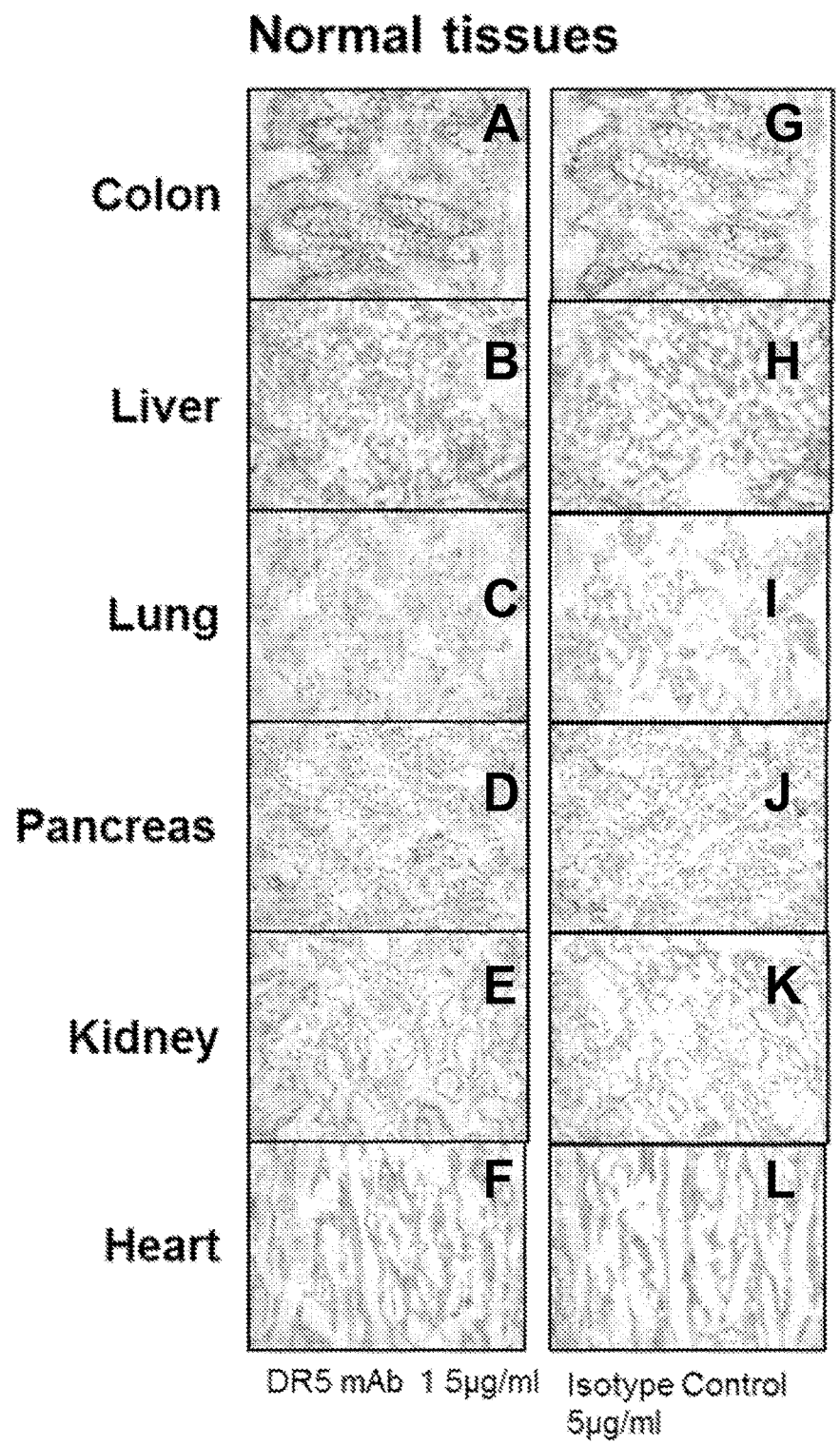
Figure 7B:
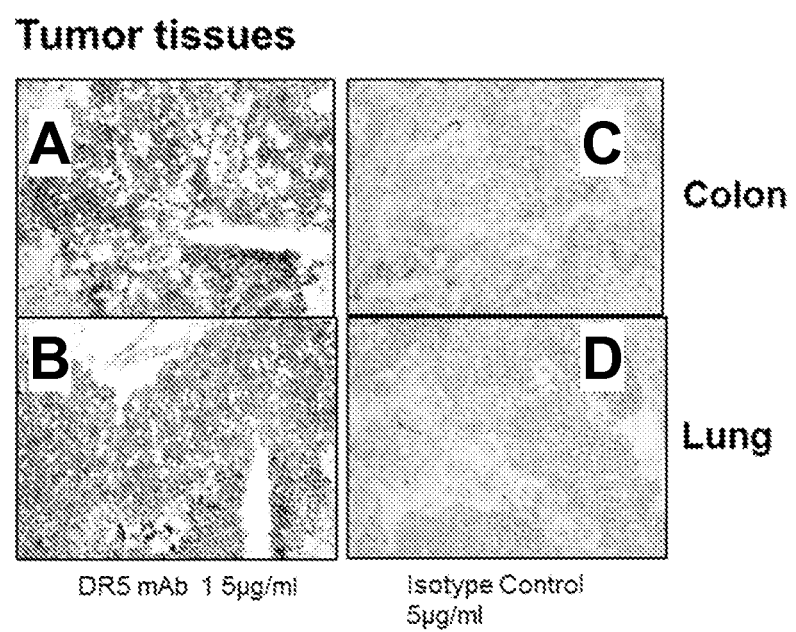

FIGS. 7A-7B show the ability of DR5 mAb 1 to differentially bind to tumor cells. FIG. 7A shows histological stains of normal colon (Panels A and G), liver (Panels B and H), lung (Panels C and I), pancreas (Panels D and J), kidney (Panels E and K) and heart (Panels F and L) tissue. FIG. 7A, Panels A-F show the results of tissue incubated with labeled DR5 mAb 1 (5 μg/mL). FIG. 7A, Panels G-L show the results of tissue incubated with labeled isotype control mAb (5 μg/mL). FIG. 7B shows histological stains of tumorous colon (Panels A and C) and tumorous lung (Panels B and D). FIG. 7B, Panels A-B show the results of tissue incubated with labeled DR5 mAb 1 (5 μg/mL). FIG. 7B, Panels C-D show the results of tissue incubated with labeled isotype control mAb (5 μg/mL).

Figure 8A:
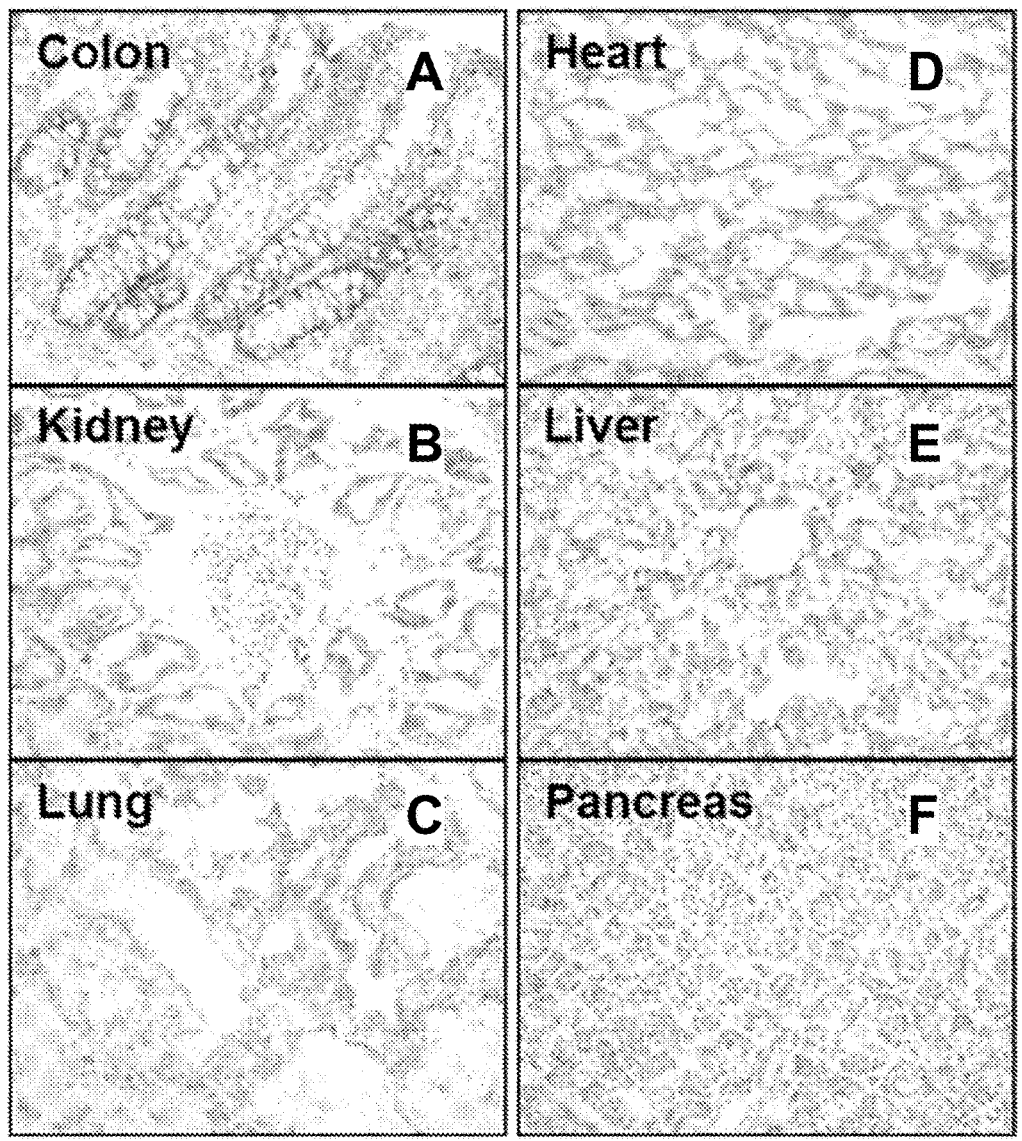
Figure 8B:
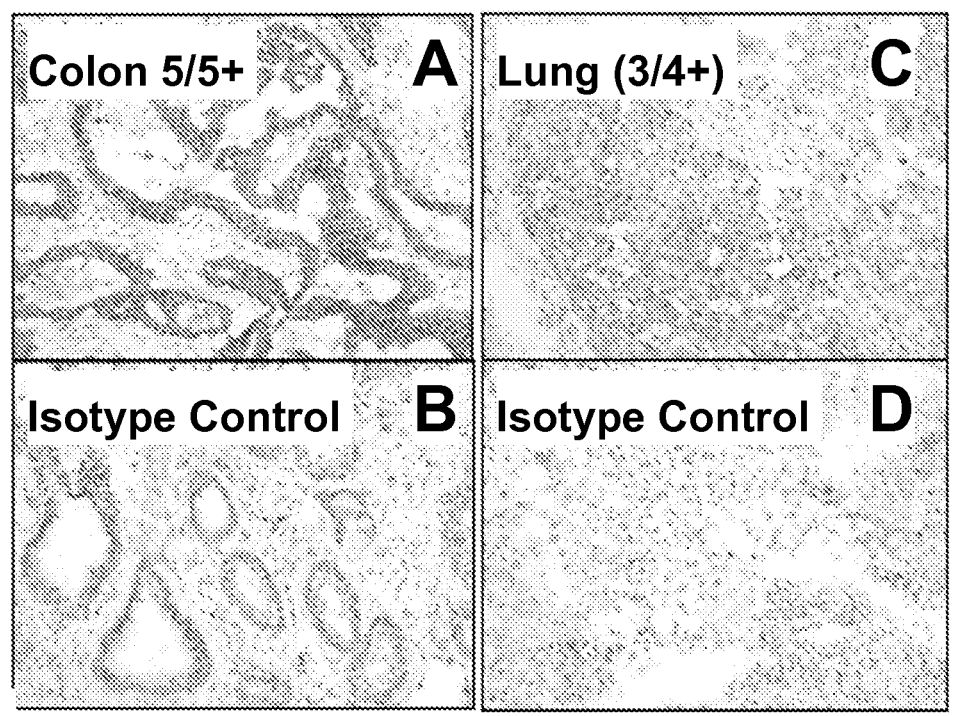

FIGS. 8A-8B show the ability of DR5 mAb 2 to differentially bind to tumor cells. FIG. 8A shows histological stains of normal colon (Panel A), kidney (Panel B), lung (Panel C), heart (Panel D), liver (Panel E) and pancreas (Panel F) tissue incubated with labeled DR5 mAb 2 (5 μg/mL). FIG. 8B shows histological stains of tumorous colon (Panels A and B) and tumorous lung (Panels C and D). FIG. 8B, Panels A and C show the results of tissue incubated with labeled DR5 mAb 2 (5 μg/mL). FIG. 8B, Panels B and D show the results of tissue incubated with labeled isotype control mAb (5 μg/mL).

Figure 9A:
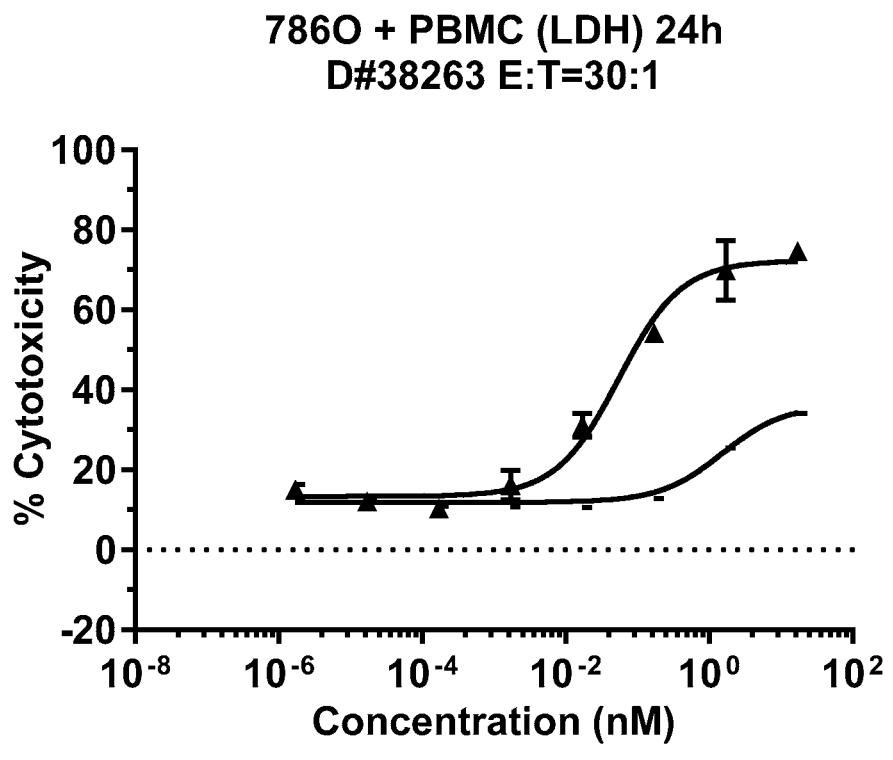
Figure 9B:
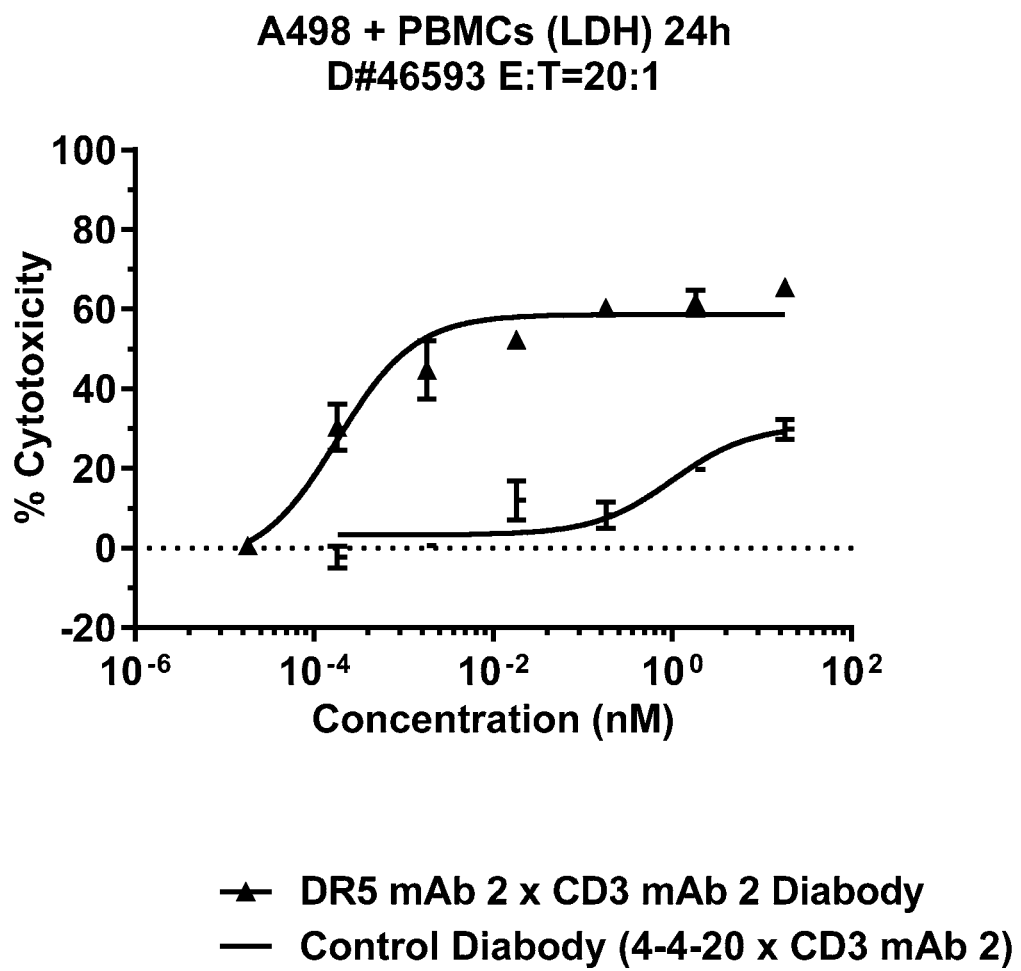
Figure 9C:
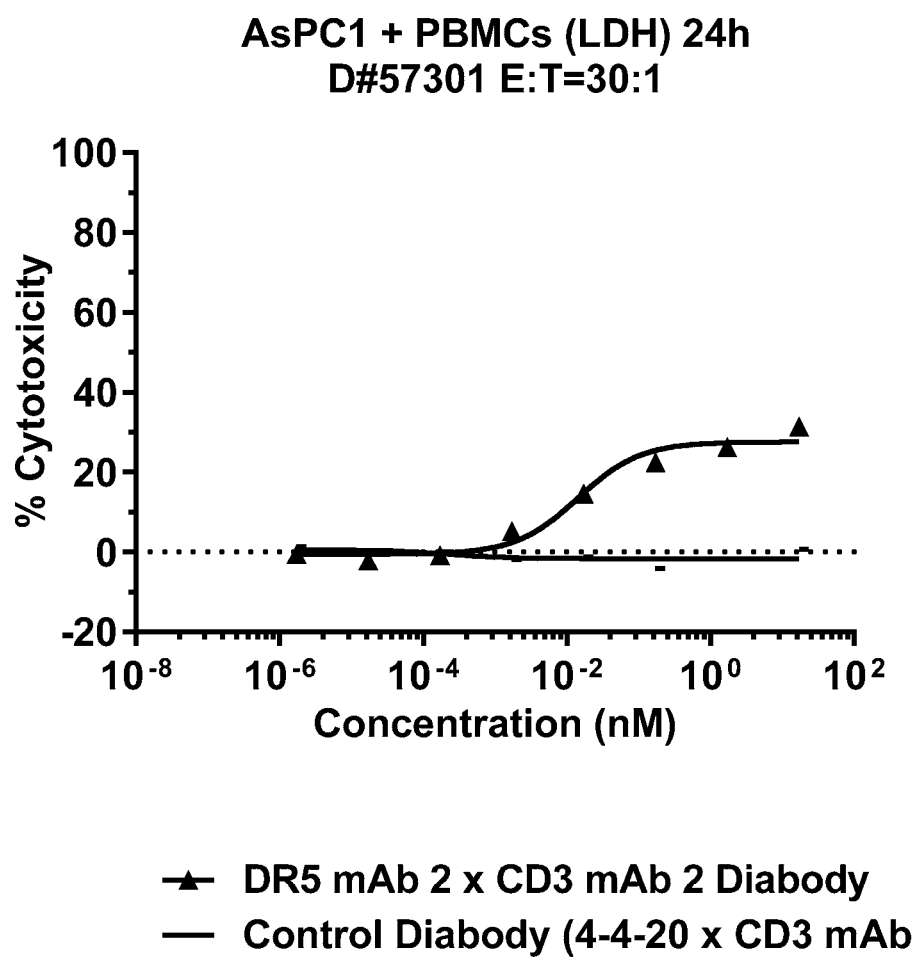
Figure 9D:
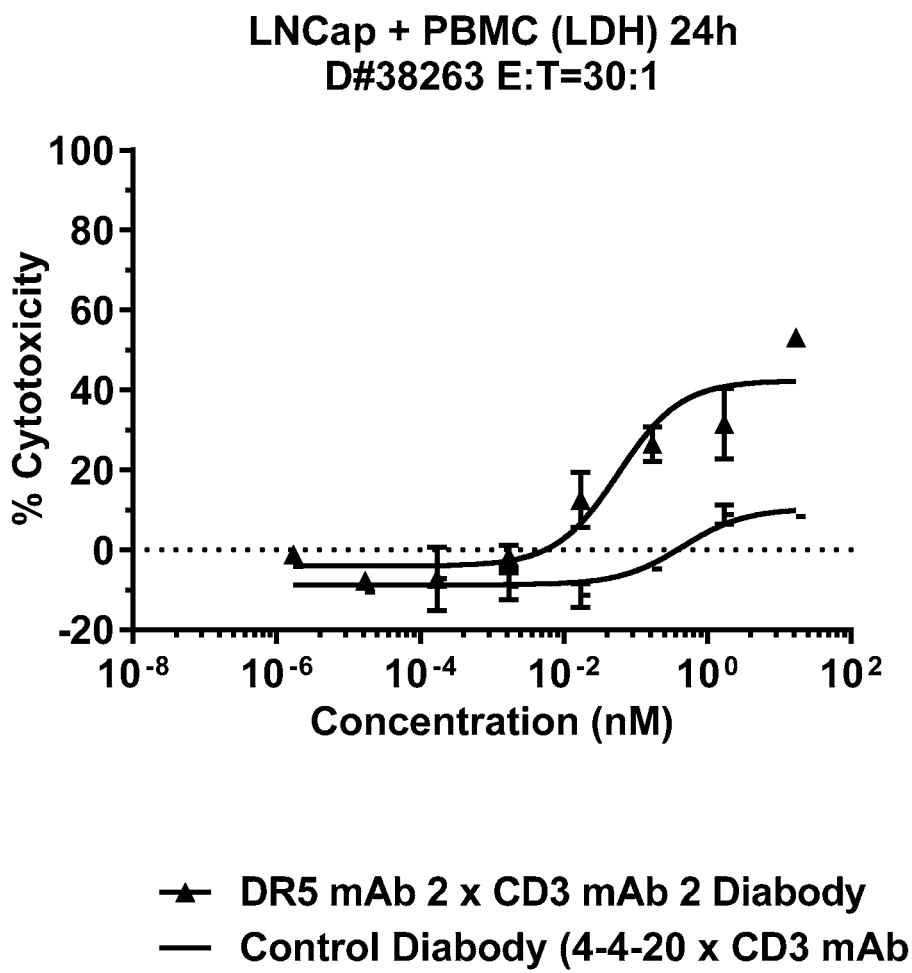
Figure 9E:
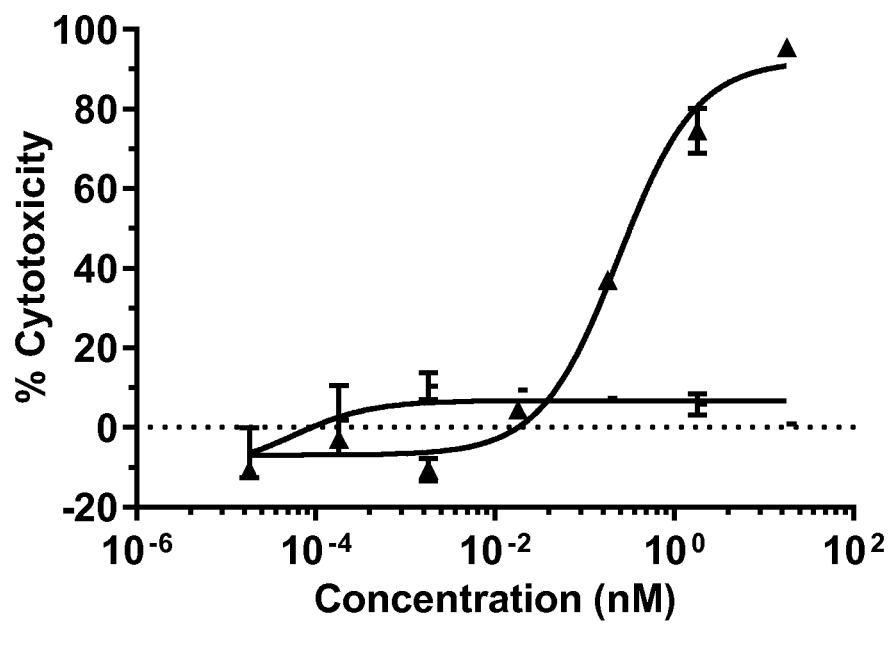
Figure 9F:
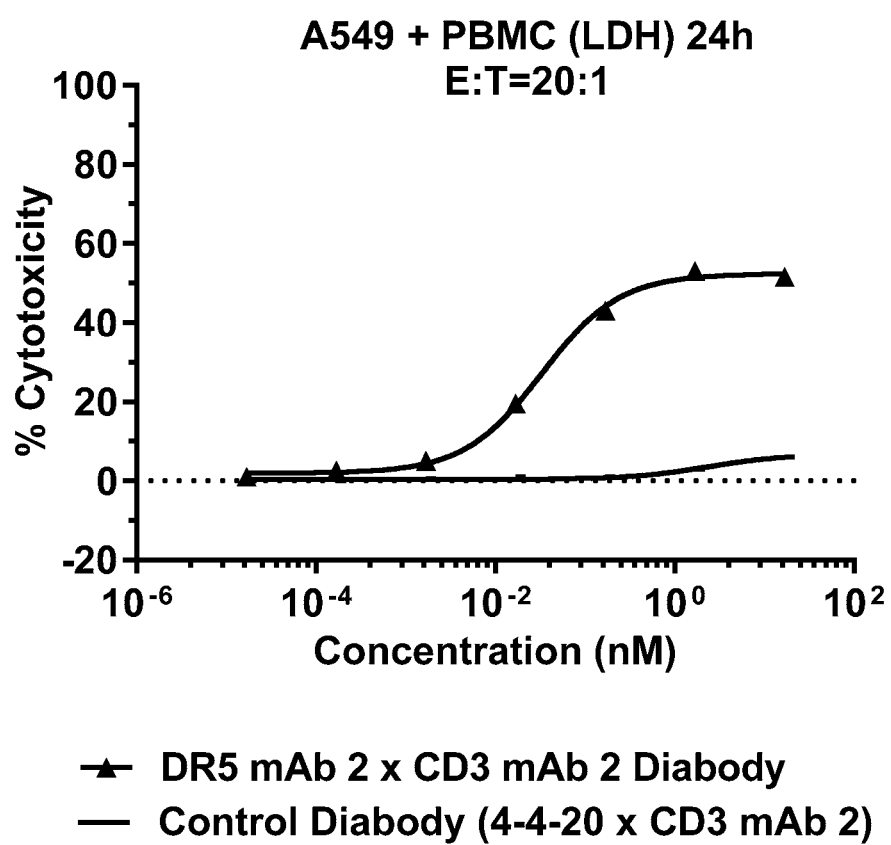
Figure 9G:
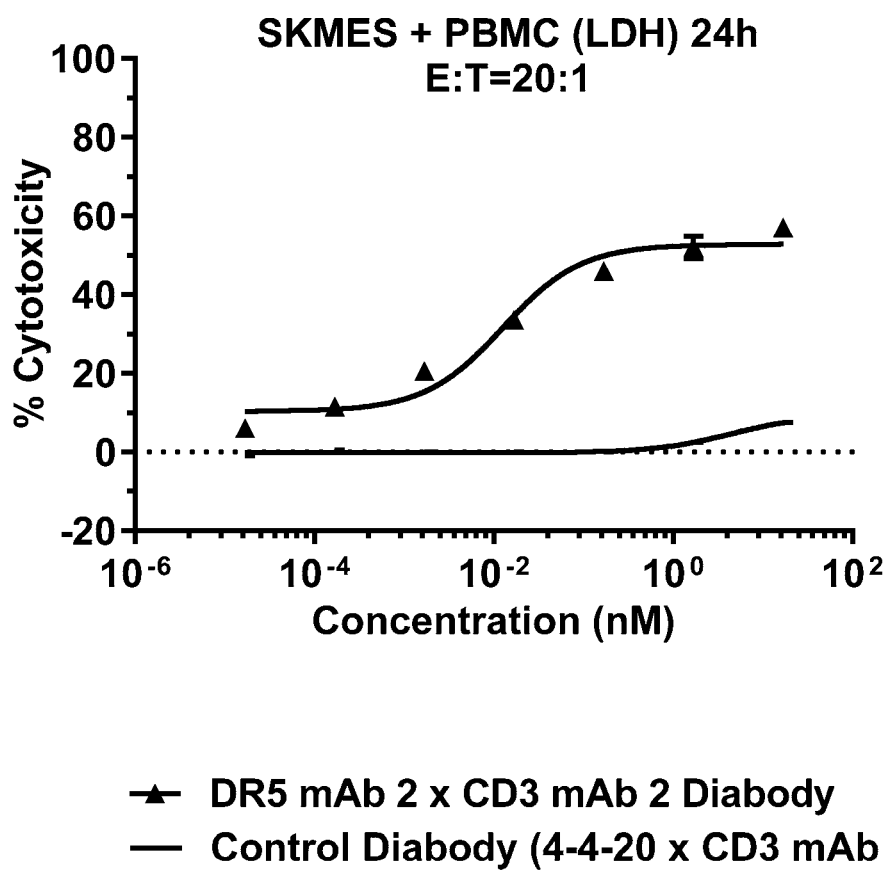
Figure 9H:
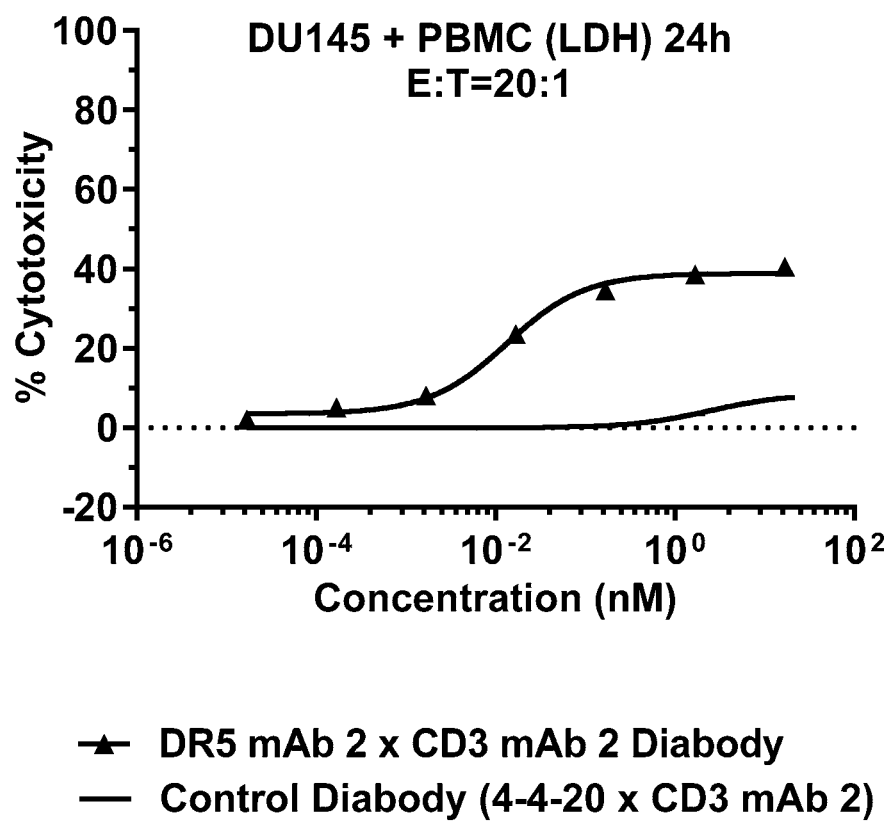
Figure 9I:
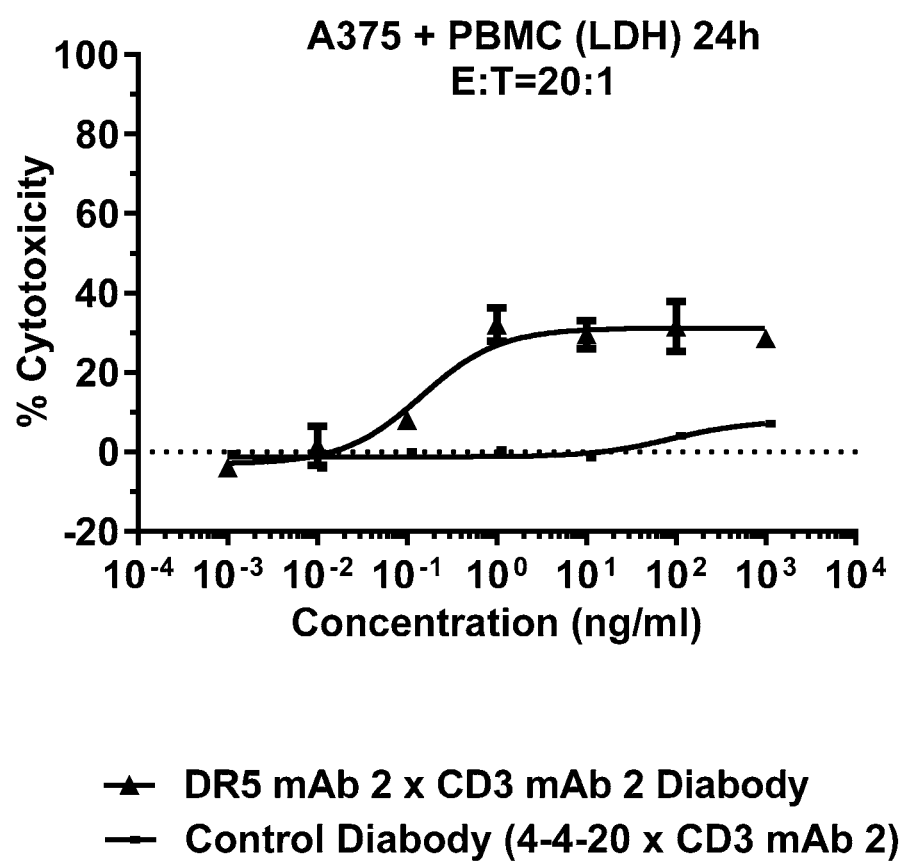
Figure 9J:
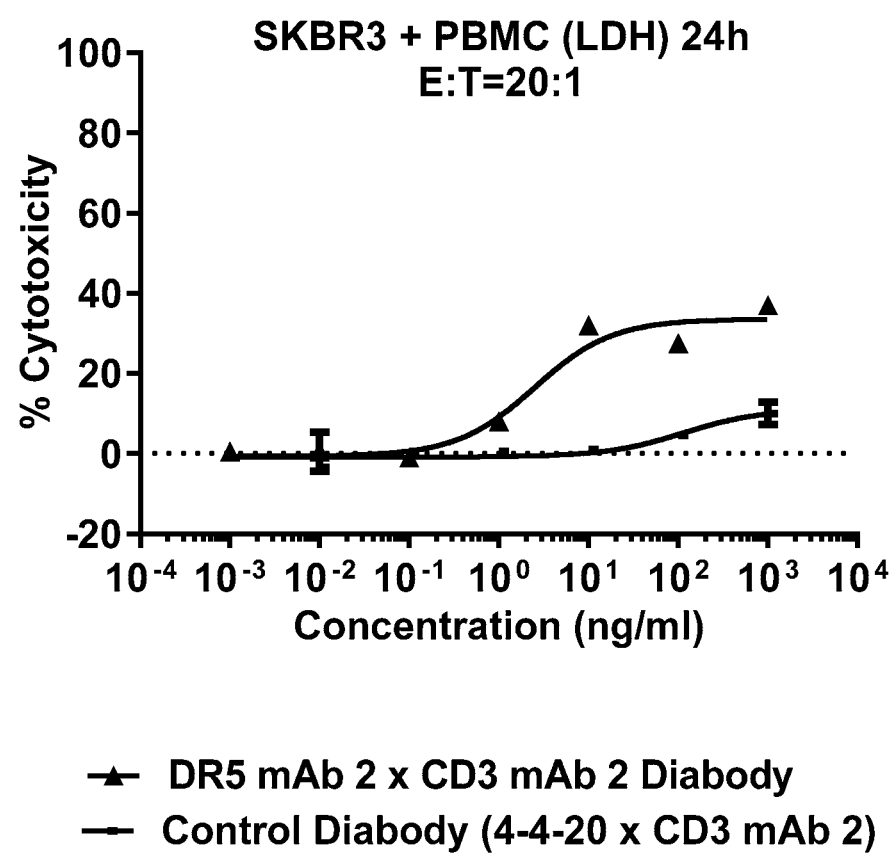
Figure 9K:
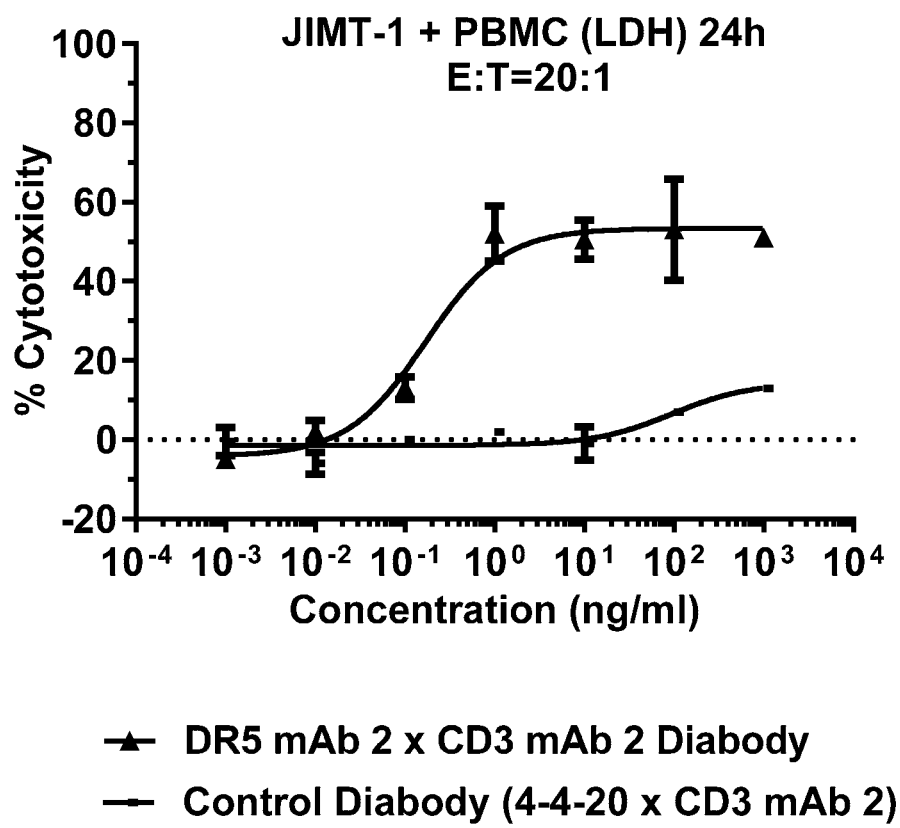

FIGS. 9A-9K show the ability of the DR5 mAb 2×CD3 mAb 2 diabody to mediate the cytotoxicity of 7860 renal cell adenocarcinoma cells (FIG. 9A), A498 kidney carcinoma cells (FIG. 9B), AsPC1 pancreatic adenocarcinoma cells (FIG. 9C), LNCap androgen-sensitive human prostate adenocarcinoma cells (FIG. 9D), SW48 colorectal adenocarcinoma cells (FIG. 9E), A549 adenocarcinomic human alveolar basal epithelial cells (FIG. 9F), SKMES human lung cancer cells (FIG. 9G), DU145 human prostate cancer cells (FIG. 9H), A375 human malignant melanoma cells (FIG. 9I), SKBR3 human HER2-overexpressing breast carcinoma cells (FIG. 9J) and JIMT human breast carcinoma cells (FIG. 9K). Such target cells were incubated in the presence of peripheral blood mononuclear cells (PBMC) for 24 hours at an effector to target cell ratio of 20:1 or 30:1. The percentage cytotoxicity of the target cells was determined by measuring the release of lactate dehydrogenase (LDH) into the media by damaged cells.

Figure 10A:
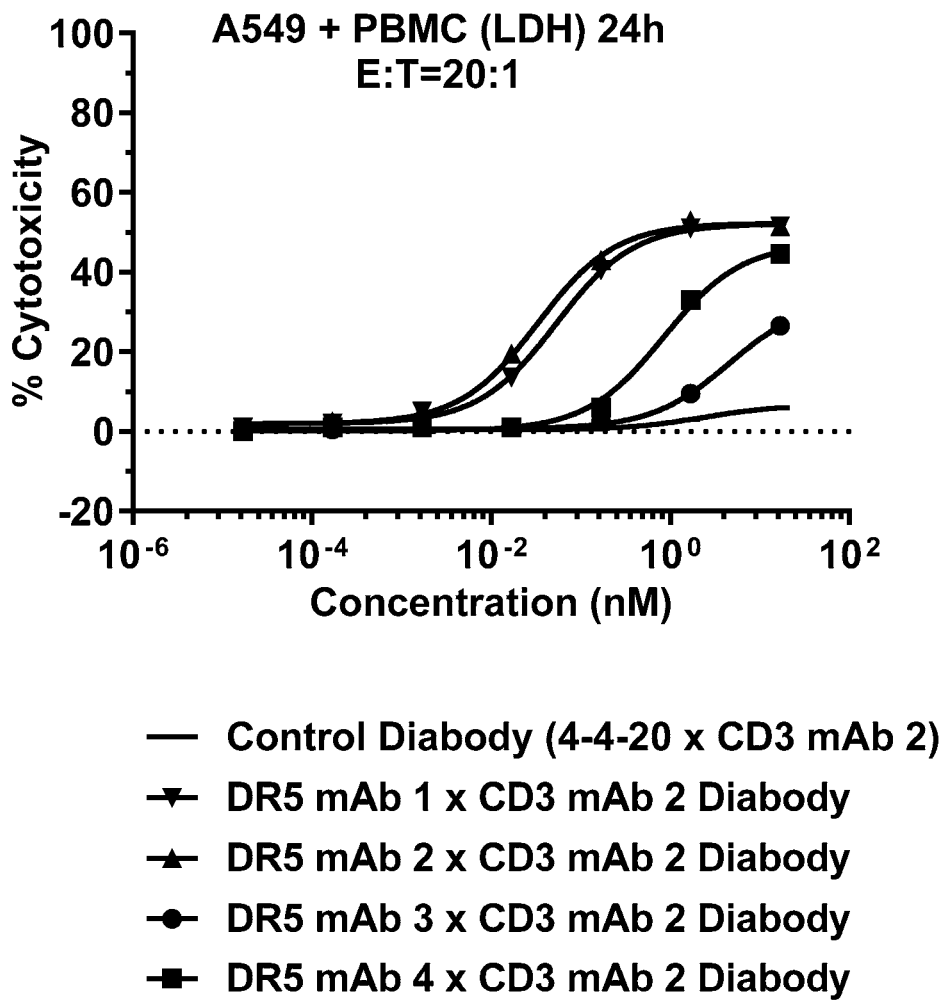
Figure 10B:
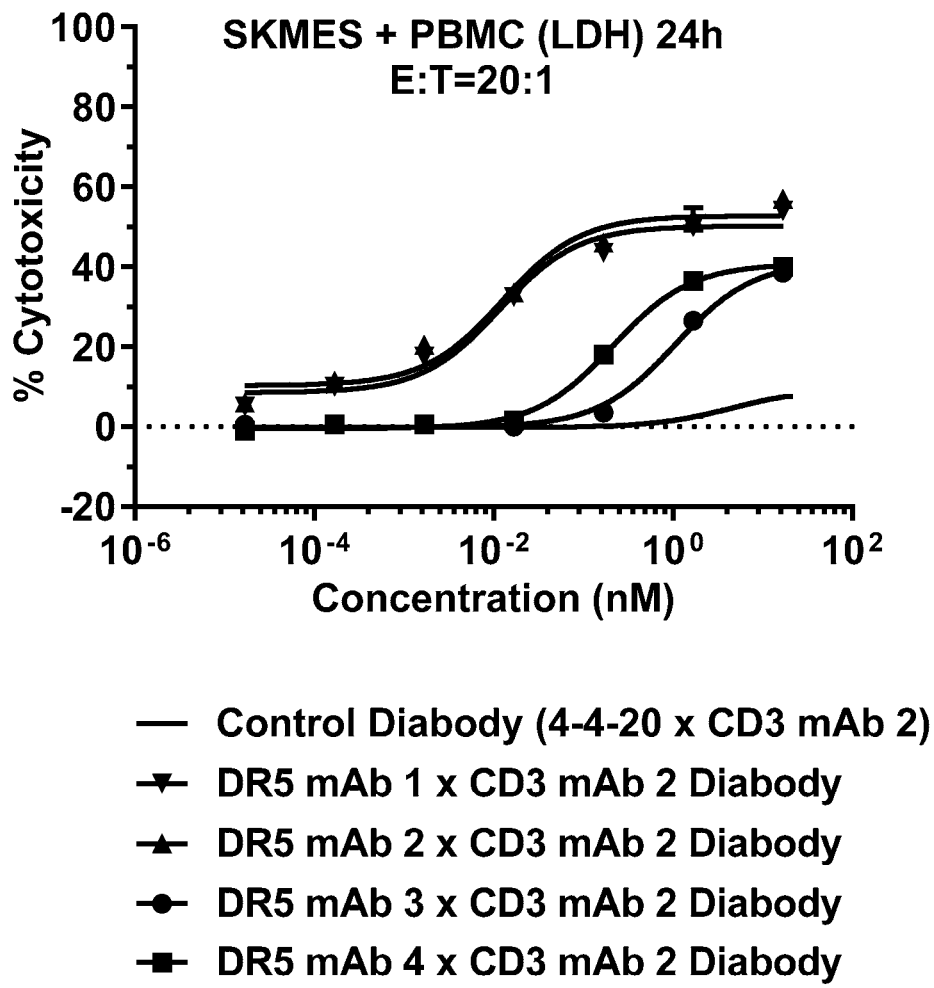
Figure 10C:
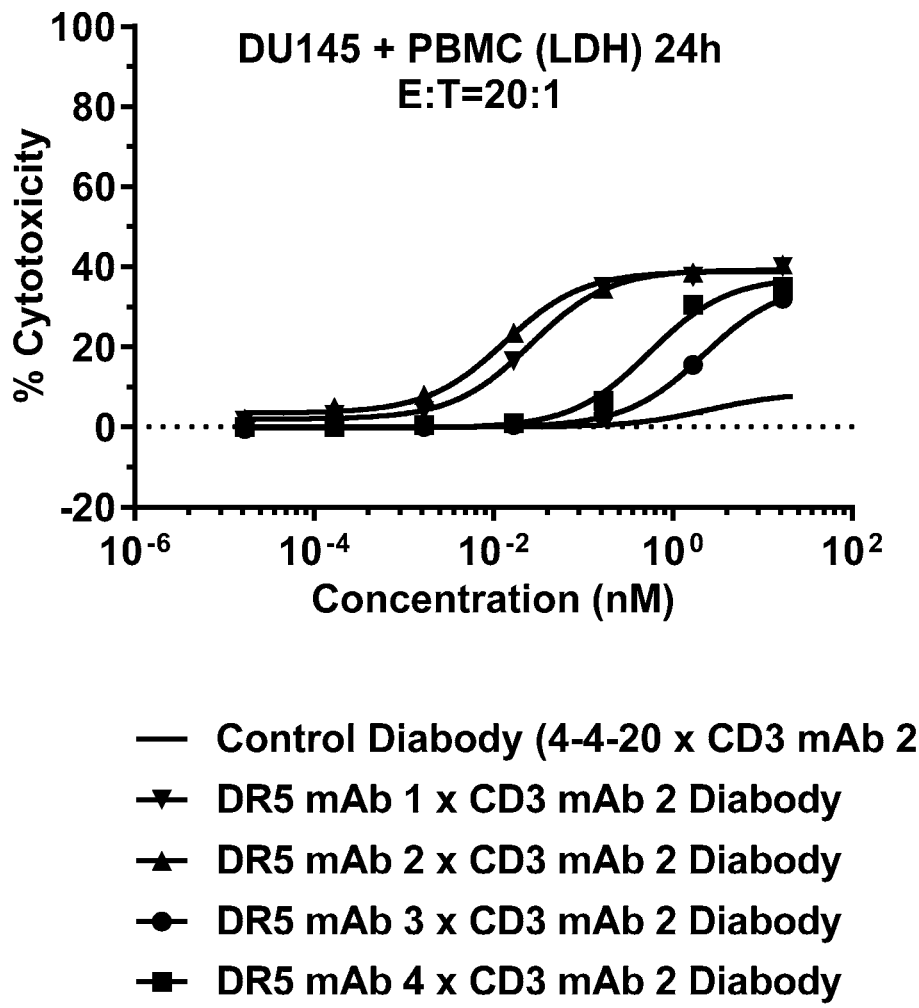
Figure 10D:
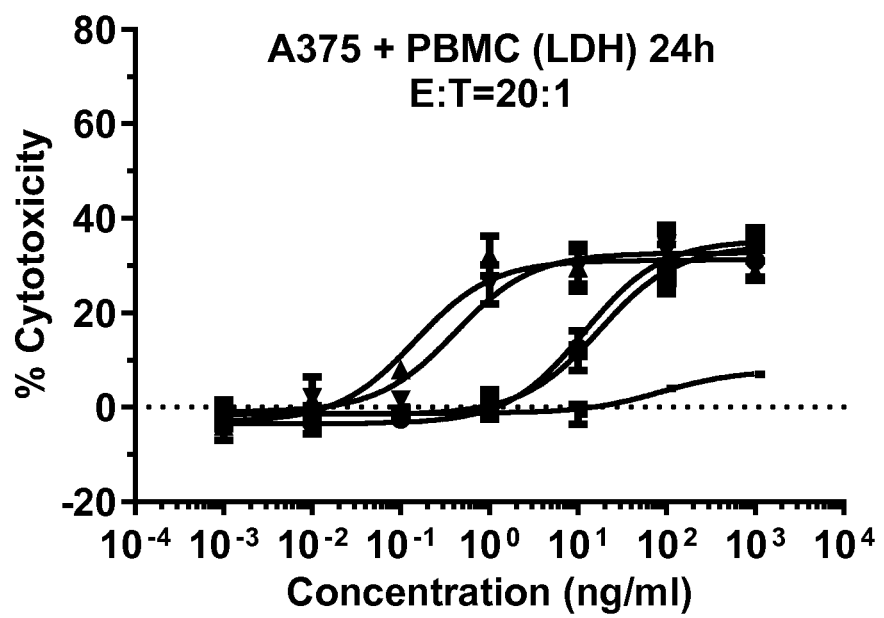
Figure 10E:
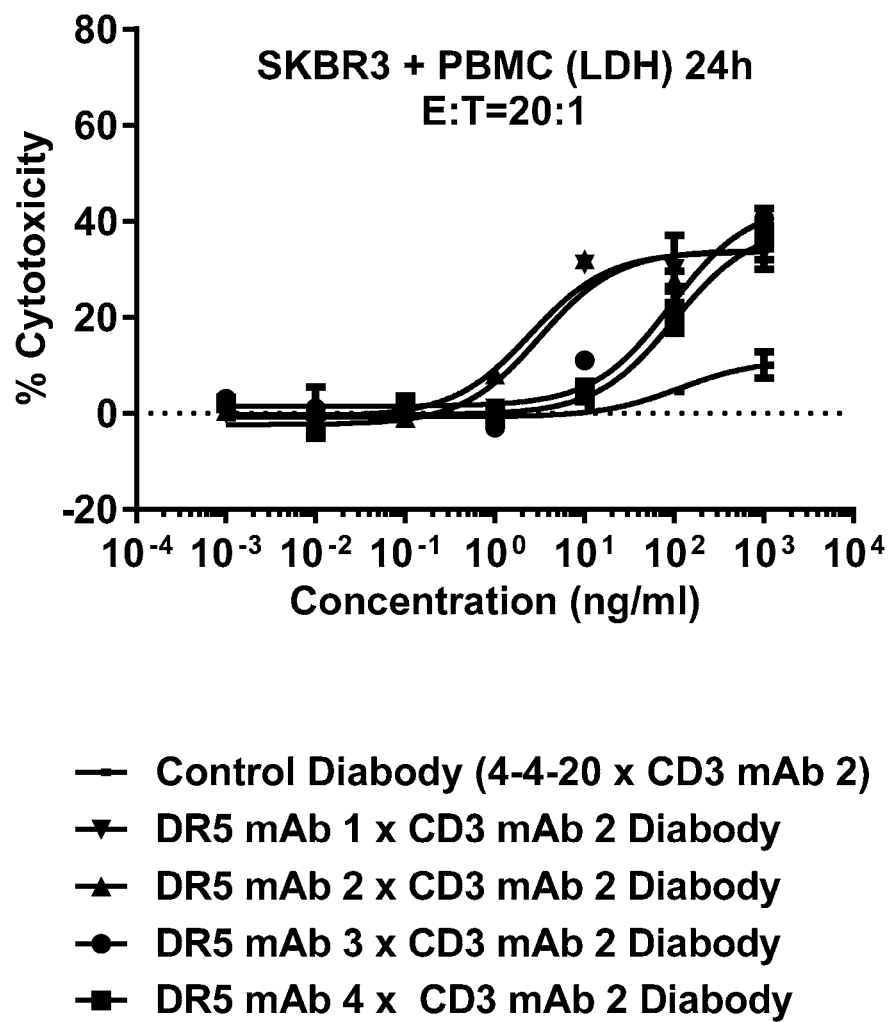
Figure 10F:
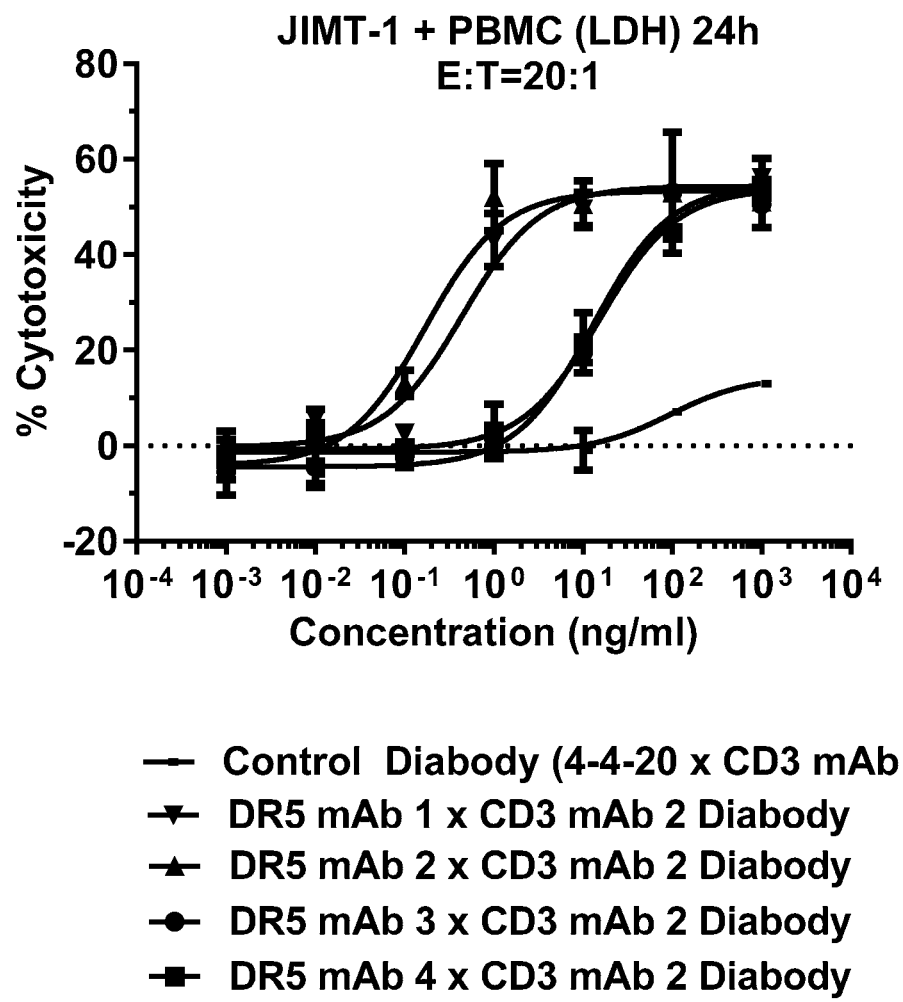

FIGS. 10A-10F show the unexpected superiority of DR5 mAb 1 and DR5 mAb 2. Superiority was assessed by comparing the ability of DR5×CD3 diabodies having the VL and VH Domains of DR5 mAb 1, DR5 mAb 2, DR5 mAb 3, or DR5 mAb 4, to mediate the cytotoxicity of tumor cells. The employed target tumor cells were: A549 adenocarcinomic human alveolar basal epithelial cells (FIG. 10A), SKMES human lung cancer cells (FIG. 10B), DU145 human prostate cancer cells (FIG. 10C), A375 human malignant melanoma cells (FIG. 10D), and SKBR3 human HER2-overexpressing breast carcinoma cells (FIG. 10E) and JIMT human breast carcinoma cells (FIG. 10F).

Figure 11:
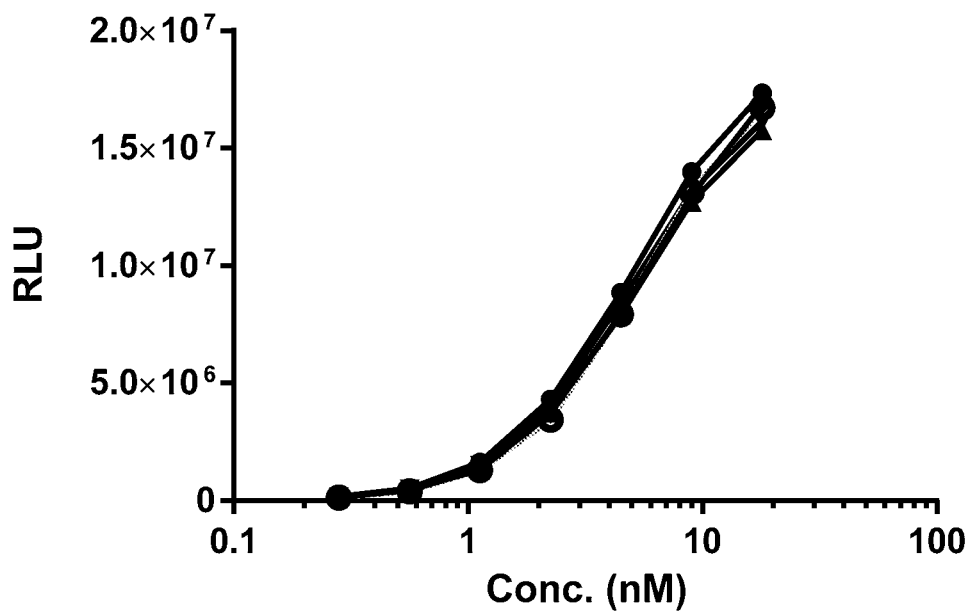

FIG. 11 shows the ability of DR5 mAb 2×CD3 mAb 2 diabody and its humanized derivatives: hDR5 mAb 2 (2.2)× CD3 mAb 2, hDR5 mAb 2 (2.3)×CD3 mAb 2, hDR5 mAb 2 (2.4)×CD3 mAb 2, or hDR5 mAb 2 (2.5)×CD3 mAb 2 to simultaneously bind to DR5 and to CD3.

Figure 12:
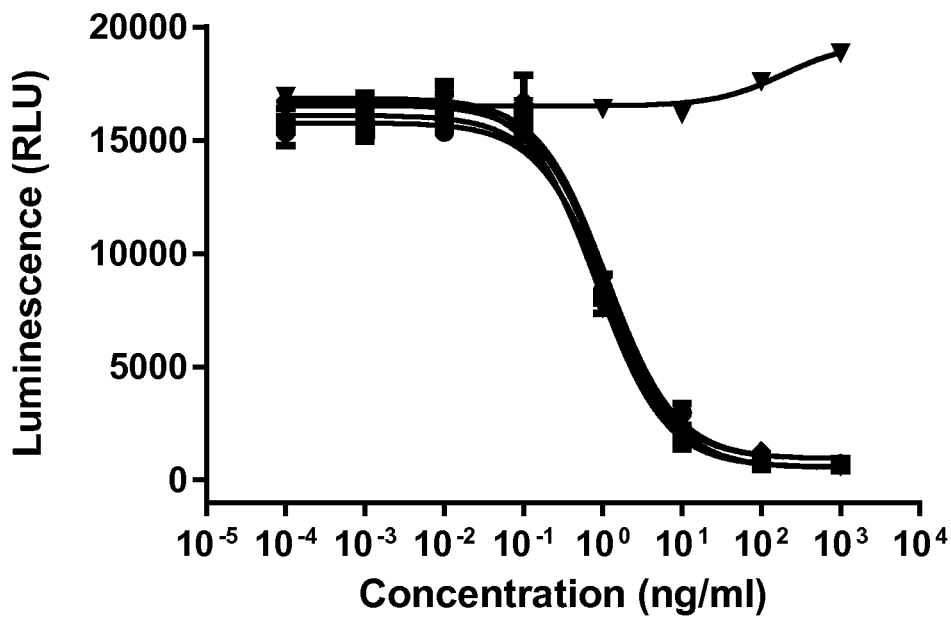

FIG. 12 shows the ability of DR5 mAb 2×CD3 mAb 2 diabody and its humanized derivatives: hDR5 mAb 2 (2.2)× CD3 mAb 2, hDR5 mAb 2 (2.3)×CD3 mAb 2, hDR5 mAb 2 (2.4)×CD3 mAb 2, or hDR5 mAb 2 (2.5)×CD3 mAb 2 to mediate the cytotoxicity of Colo205 colorectal carcinoma cells.

Figure 13:
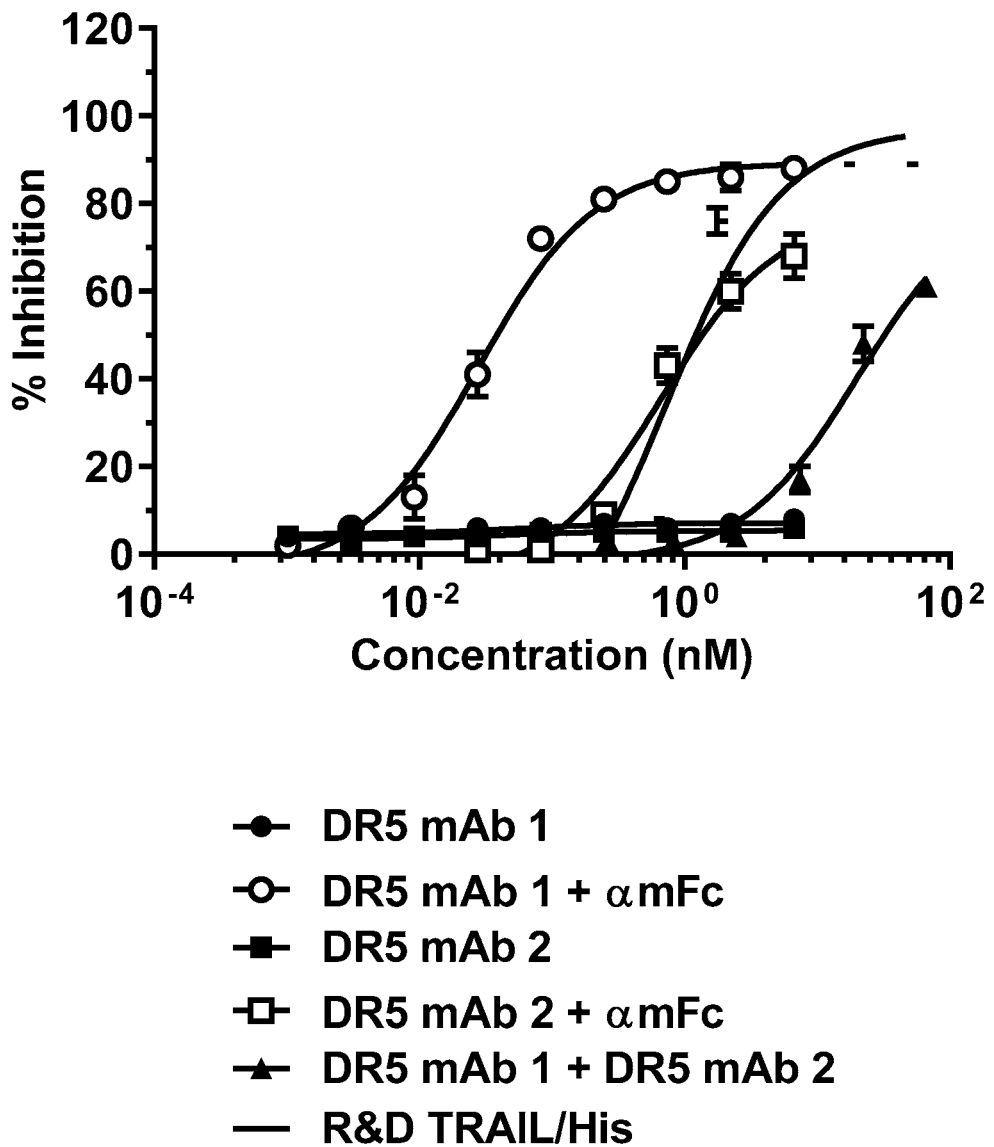

FIG. 13 shows the growth inhibition curves of COLO205 cells treated with DR5 mAb 1, DR5 mAb 2, cross-linked DR5 mAb 1, cross-linked DR5 mAb 2, or the combination of DR5 mAb 1 and DR5 mAb 2 without cross-linking. Cross-linked DR5 mAb 1, cross-linked DR5 mAb 2, and the combination of DR5 mAb 1 and DR5 mAb 2 without cross-linking are able to inhibit the growth of COLO205 cells.

Figure 14A:
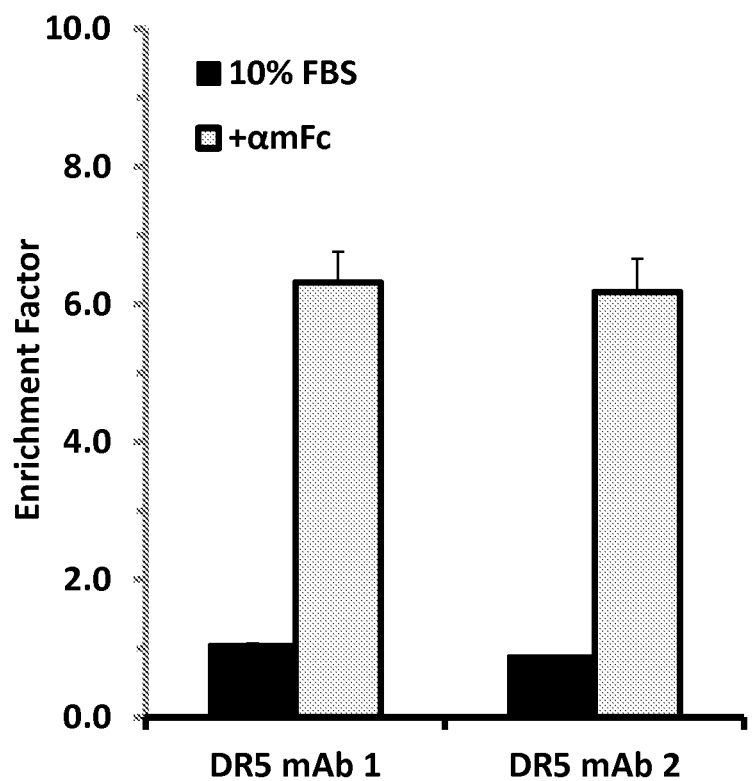
Figure 14B:
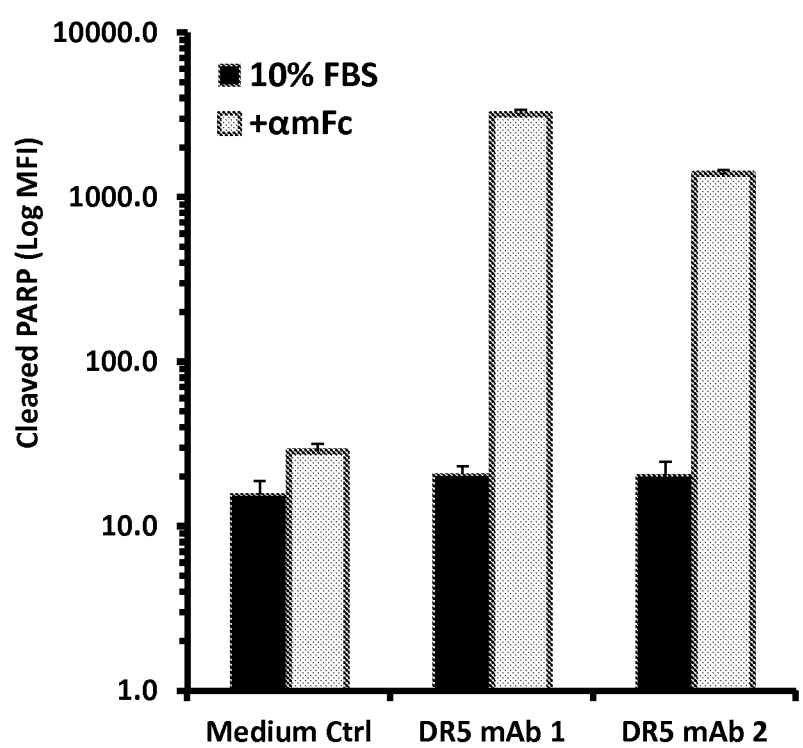
Figure 14C:
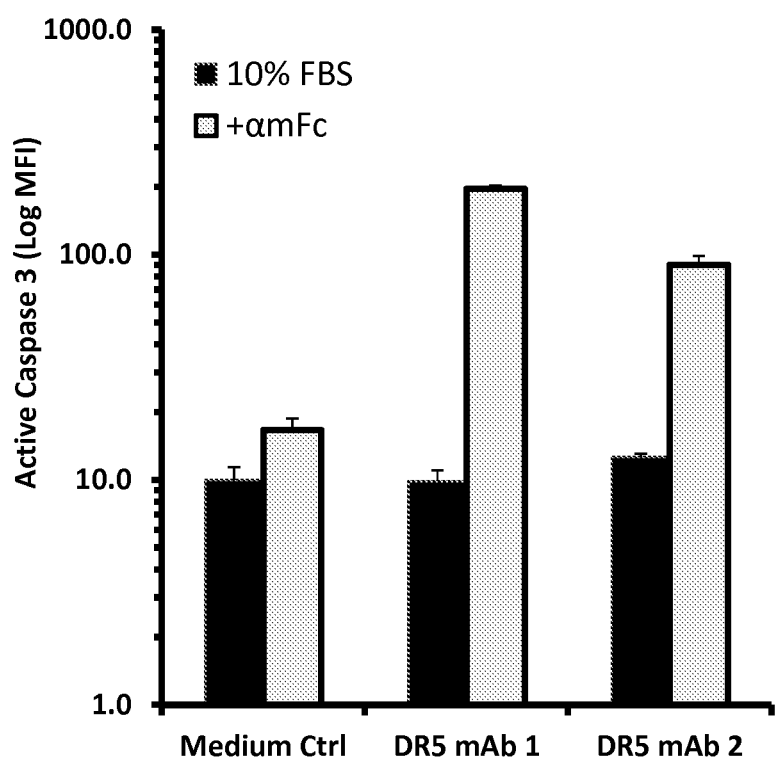

FIG. 14A-14C show that both cross-linked DR5 mAb 1 and cross-linked DR5 mAb 2 induce apoptosis as measured by increased production of nucleosomes (FIG. 14A), increased cleaved PARP (FIG. 14B), and increased active caspase 3 (FIG. 14C).

Figure 15A:
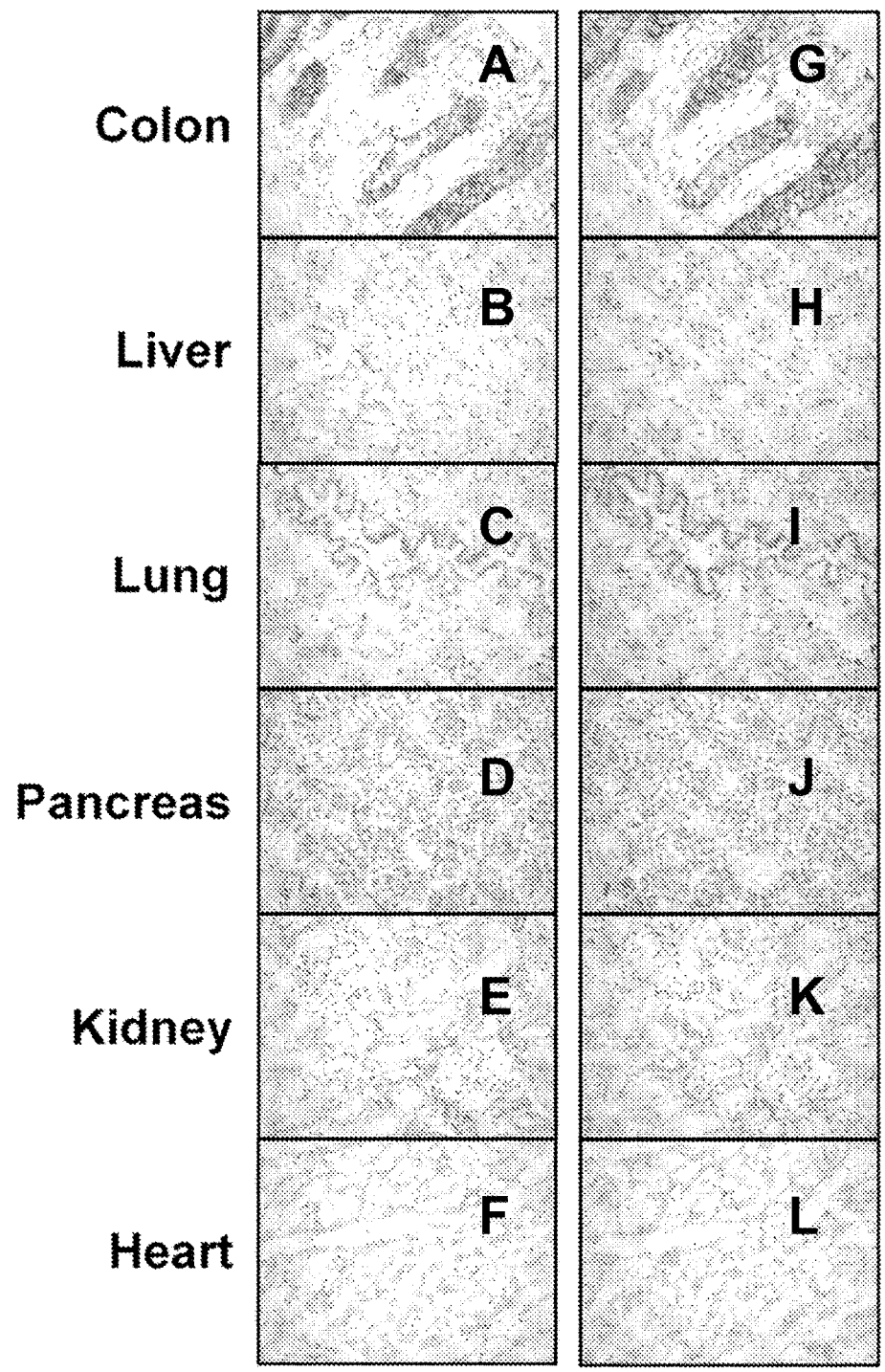
Figure 15B:
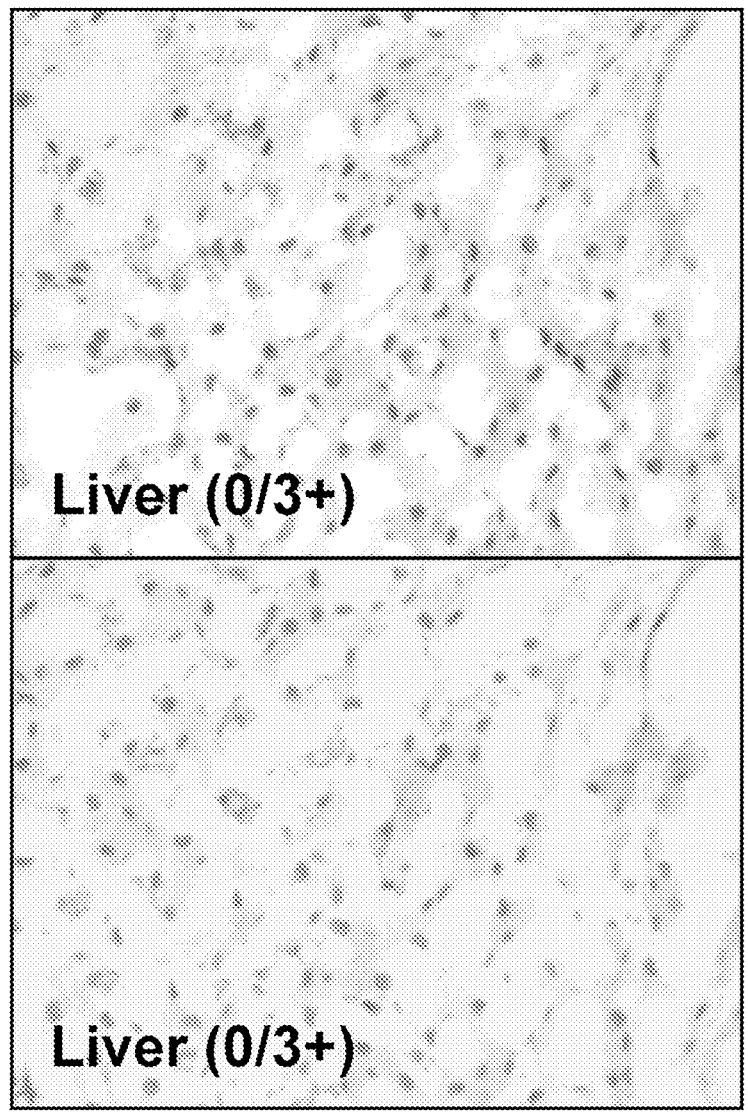

FIG. 15A-15B show that a representative tetravalent DR5-Binding Molecule (a bispecific E-coil/K-coil-Fc Region-containing diabody tetravalent for DR5 designated "DR5 mAb 2×DR5 mAb 1 Fc diabody") does not bind normal tissues. FIG. 15A shows histological stains of normal colon (Panels A and G), liver (Panels B and H), lung (Panels C and I), pancreas (Panels D and J), kidney (Panels E and K) and heart (Panels F and L) tissue. FIG. 15A, Panels A-F show the results of tissue incubated with labeled with the tetravalent DR5-Binding Molecule (DR5 mAb 2×DR5 mAb 1 Fc diabody at 0.625 μg/mL). FIG. 15A, Panels G-L show the results of tissue incubated with labeled a control diabody (4-4-20×CD3 mAb 2 at 0.625 μg/mL). FIG. 15B shows representative histological stains of additional normal liver samples. FIG. 15B, Top Panel shows the results of tissue incubated with a labeled tetravalent DR5-Binding Molecule (DR5 mAb 2×DR5 mAb 1 Fc diabody at 0.625 μg/mL). FIG. 15B, Bottom Panel show the results of tissue incubated with labeled control diabody (4-4-20×CD3 mAb 2 at 0.625 μg/mL).

Figure 16:
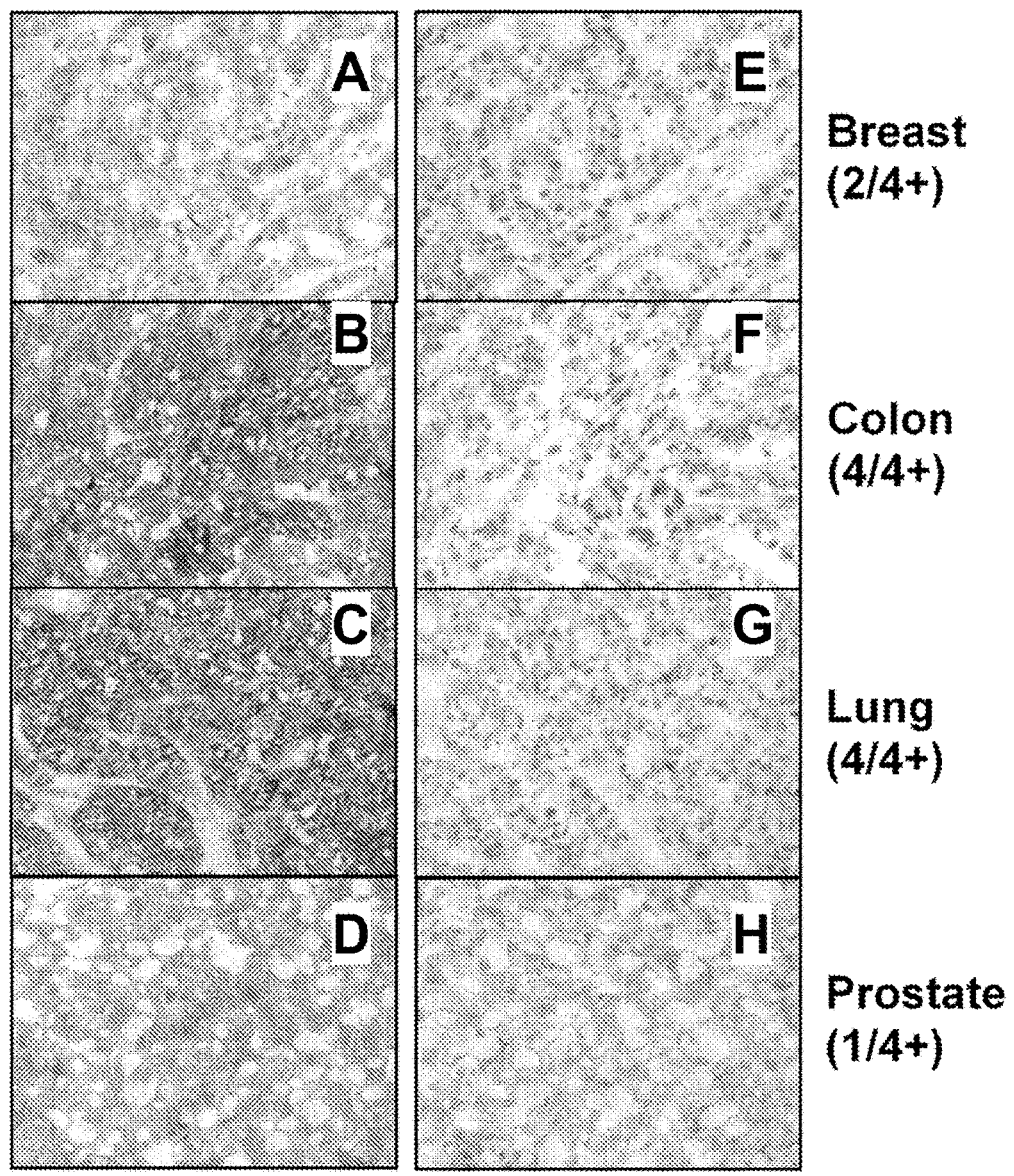

FIG. 16 show that a representative tetravalent DR5-Binding Molecule (a bispecific E-coil/K-coil-Fc Region-containing diabody tetravalent for DR5) strongly binds tumorous tissues. FIG. 16 shows histological stains of tumorous breast (Panels A and E), tumorous colon (Panels B and F), tumorous lung (Panels C and G), and tumorous prostate tissue (Panels D and H). FIG. 16, Panels A-D show the results of tissue incubated with a labeled tetravalent DR5-Binding Molecule (DR5 mAb 2×DR5 mAb 2 Fc diabody at 0.625 μg/mL). FIG. 16, Panels E-H show the results of tissue incubated with labeled control diabody (4-4-20×CD3 mAb 2 at 0.625 μg/mL).

Figure 17A:
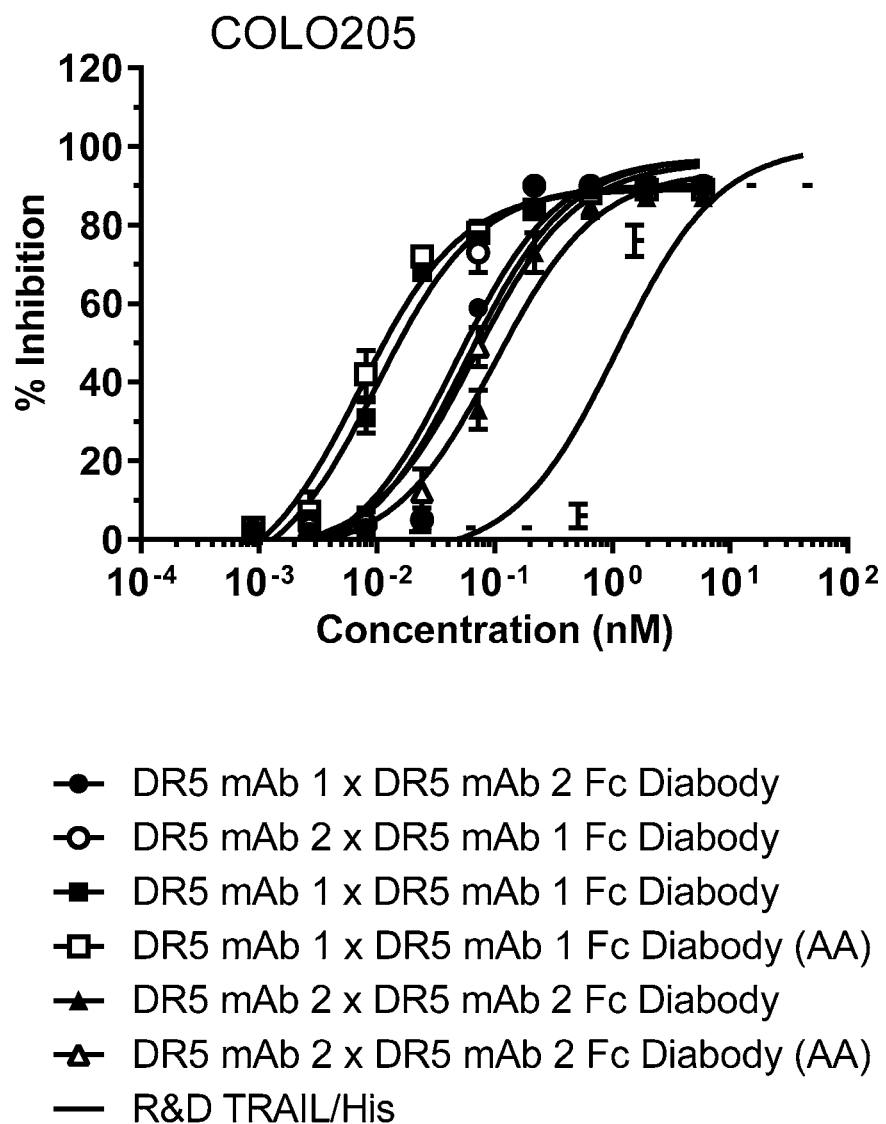
Figure 17B:
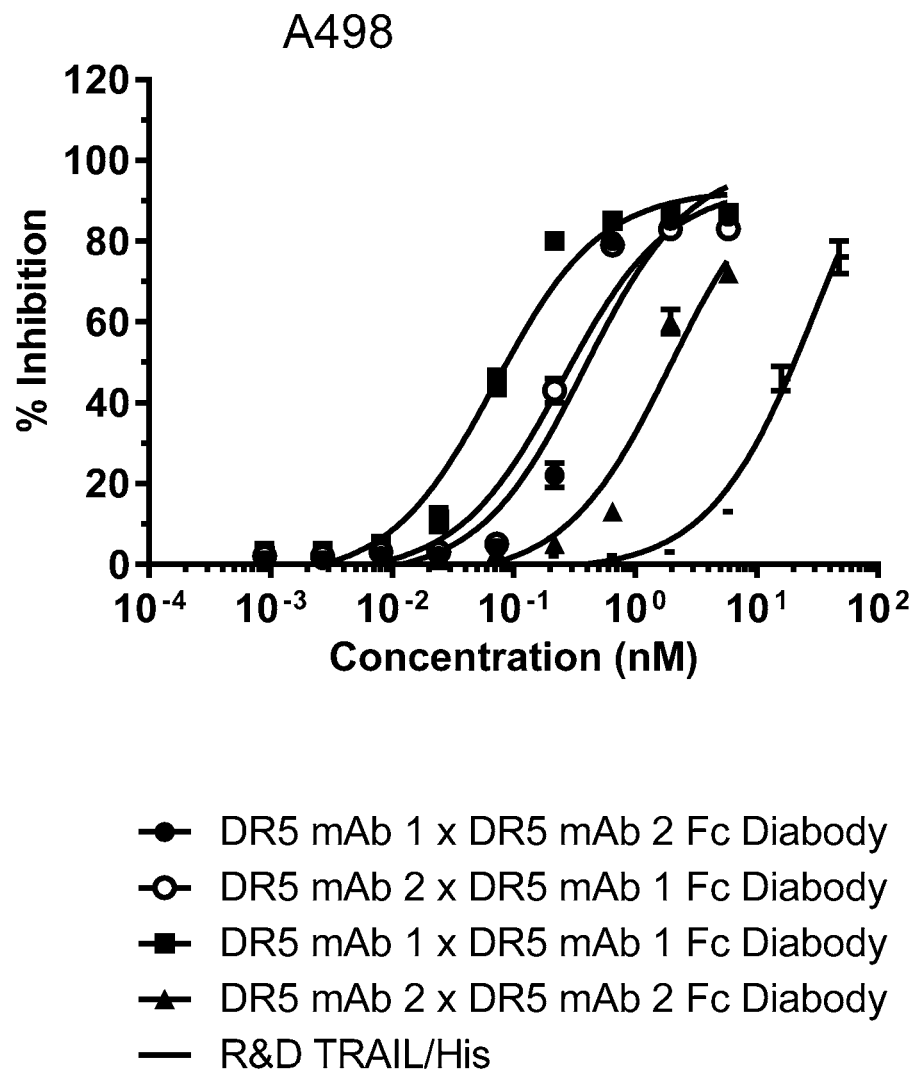
Figure 17C:
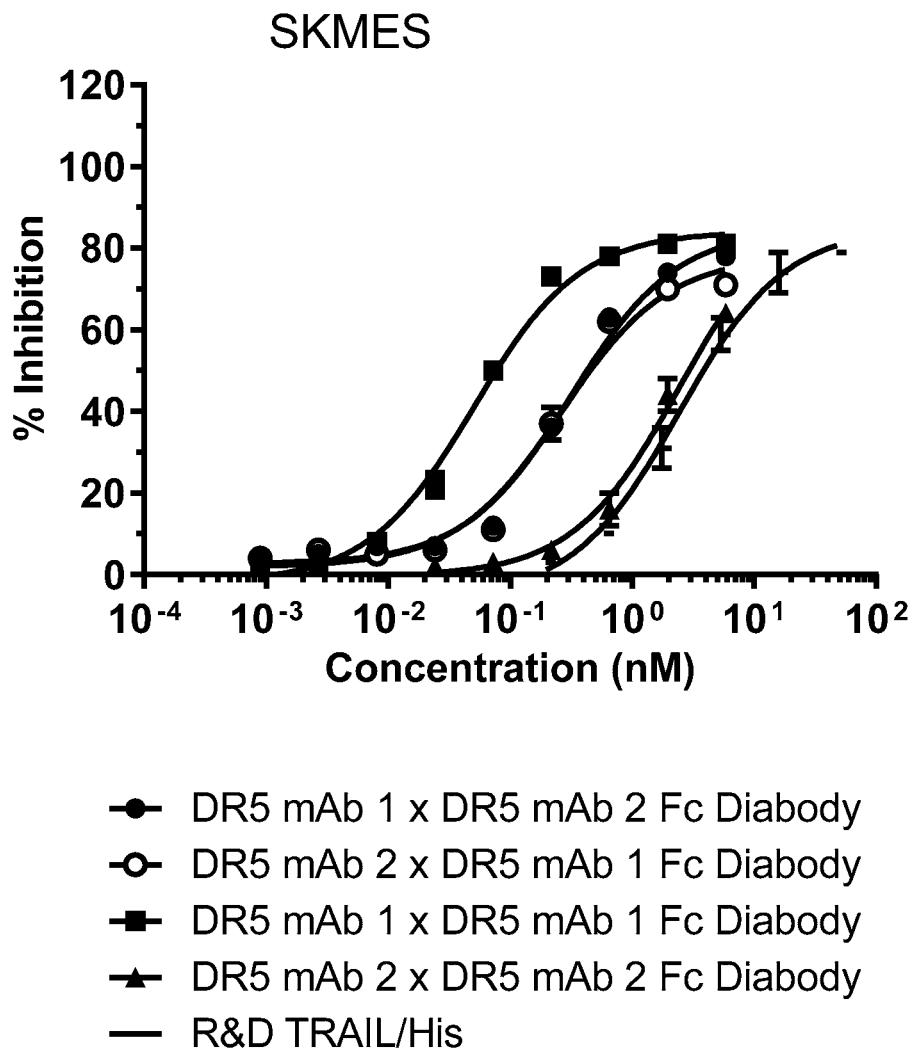

FIG. 17A-17C shows the growth inhibition curves of COLO205 (FIG. 17A), A498 (FIG. 17B) and SKMES (FIG. 17C) cells treated with six different representative tetravalent DR5-Binding Molecules (monospecific or bispecific E-coil/K-coil-Fc Region-containing diabodies tetravalent for DR5) including two comprising Fc Region variants with reduce binding to FcγRs and reduced effector function activity. All the tetravalent DR5-Binding Molecules have potent cytotoxicity in these cells and were more potent than the TRAIL-His positive control.

Figure 18:
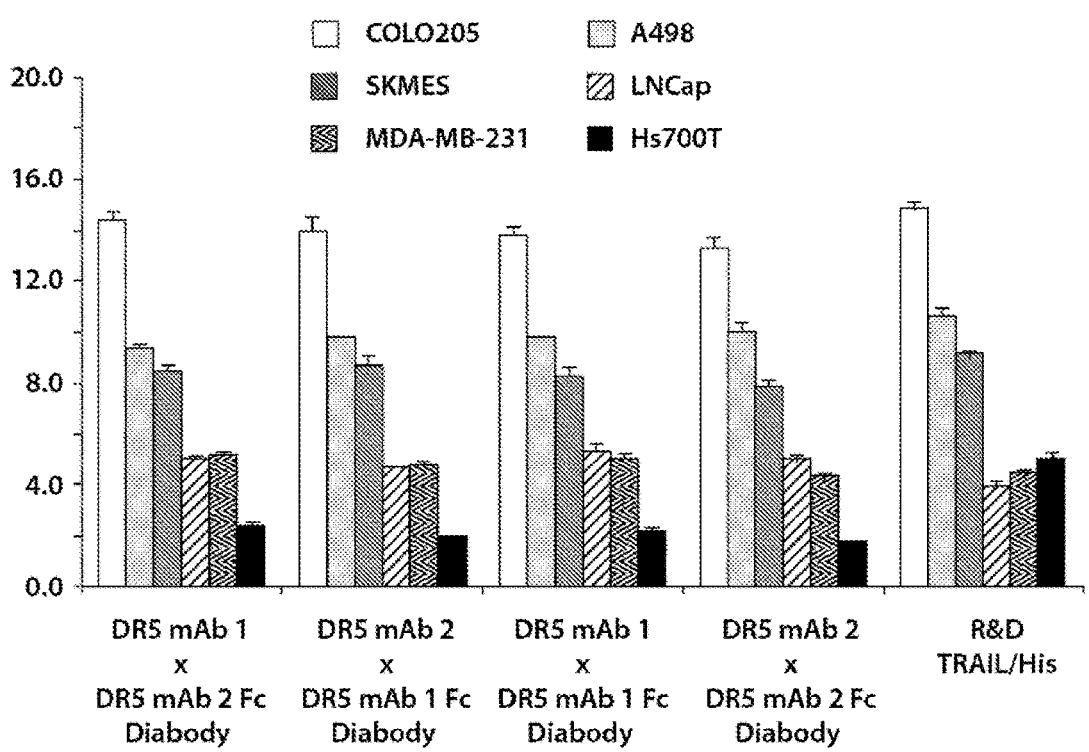

FIG. 18 shows that representative tetravalent DR5-Binding Molecules (monospecific or bispecific E-coil/K-coil-Fc Region-containing diabodies tetravalent for DR5) induce apoptosis as measured by increased production of nucleosomes.

Figure 19:
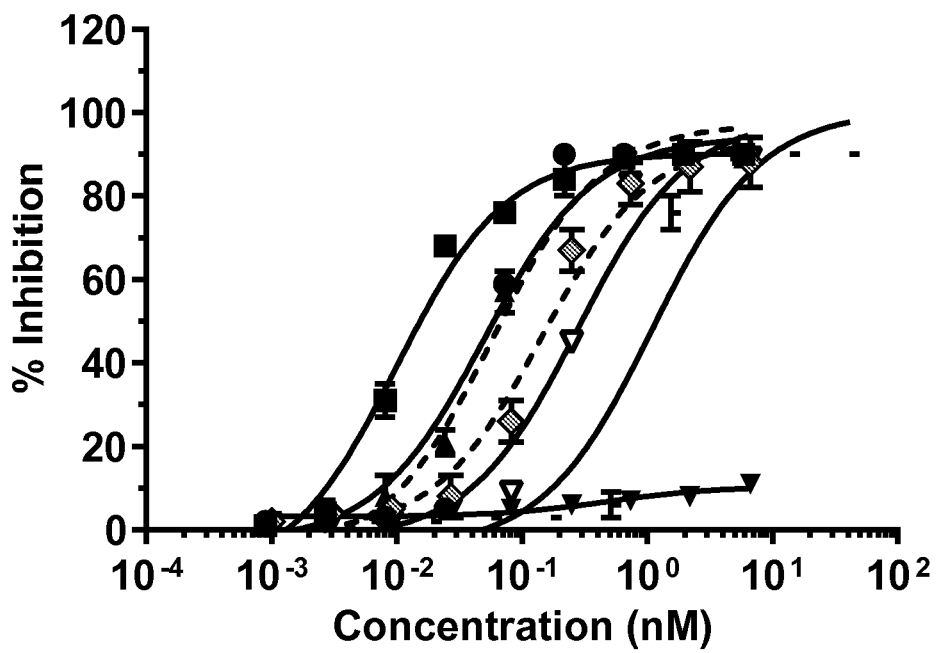

FIG. 19 shows the growth inhibition curves of COLO205 cells treated with different DR5-Binding Molecules including three different representative tetravalent DR5-Binding Molecules (monospecific or bispecific E-coil/K-coil-Fc Region-containing diabodies tetravalent for DR5); and two different anti-DR5 antibodies (DR5 mAb 8 (KMTR2); and DR5 mAb 4 (conatumumab) with and without cross-linking) Each DR5-Binding Molecule tested comprised an Fc Region variant with reduce binding to FcγRs and reduced effector function activity. The cytotoxic activity of the tetravalent DR5-Binding Molecules is independent of cross-linking and more potent than the anti-DR5 antibodies DR5 mAb 4 and DR5 mAb 8.

Figure 20:
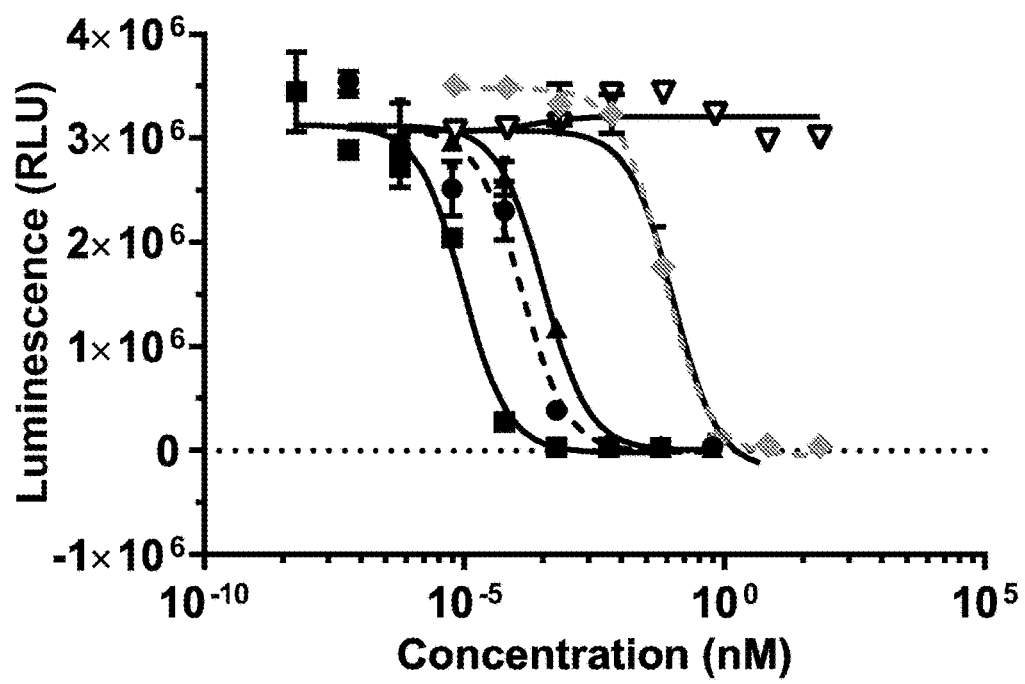

FIG. 20 shows the cytotoxicity activity of several different DR5-Binding Molecules including three different representative tetravalent DR5-Binding Molecules (monospecific or bispecific E-coil/K-coil-Fc Region-containing diabodies tetravalent for DR5); and two different anti-DR5 antibodies (DR5 mAb 8 (KMTR2), and DR5 mAb 4 (conatumumab)) on cancer stem cell-like (CSLC) RECA0201 cells. Each DR5-Binding Molecule tested comprised an Fc Region variant with reduced binding to FcγRs and reduced effector function activity. All the tetravalent DR5-Binding Molecules have potent cytotoxicity in these cells and were more potent than the anti-DR5 antibodies DR5 mAb 4 and DR5 mAb 8.

Figure 21:
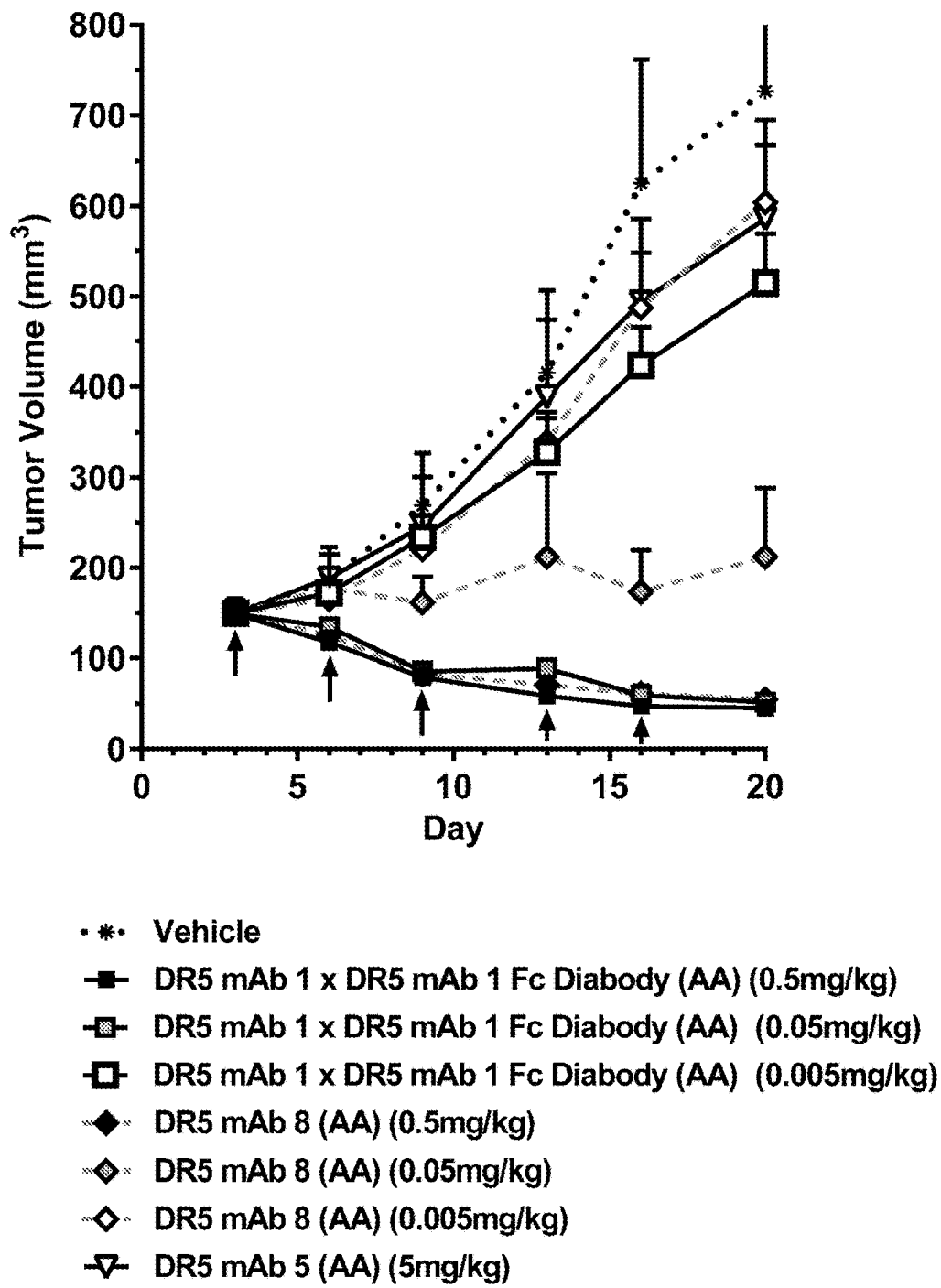

FIG. 21 shows the change in tumor volume over time in mice implanted with COLO205 cells. Female hCD16A FOX N1 mice (n=7/group) were implanted subcutaneously (SC) with COLO205 cells Day 0. The mice were then treated twice a week with a representative tetravalent DR5-Binding Molecule (monospecific tetravalent DR5 mAb 1×DR5 mAb 1 Fc diabody (AA) at 0.5, 0.05, 0.005 mg/kg); two different DR5 antibodies (DR5 mAb 4 (AA) at 5 mg/kg; DR5 mAb 8 (AA) at 0.5, 0.05, 0.005 mg/kg), or vehicle. Tumor volume is shown as a group mean±SEM.

DETAILED DESCRIPTION OF THE INVENTION

The present invention is directed to multivalent DR5-Binding Molecules that comprise Binding Domain(s) of anti-DR5 antibodies, and particularly Binding Domain(s) of anti-human DR5 antibodies. The DR5-Binding Molecules of the present invention include bivalent and tetravalent molecules having two, three or four DR5-Binding Domains each capable of binding human DR5. In particular, the present invention is directed to multivalent DR5-Binding Molecules that comprise diabodies, and more particularly, diabodies that comprise a covalently bonded complex of two or more polypeptide chains. The invention particularly pertains to such multivalent DR5-Binding Molecules that comprise fragments of the anti-DR5 antibodies DR5 mAb 1 and/or DR5 mAb 2, and/or humanized and chimeric versions of such antibodies.

I. ANTIBODIES AND THEIR BINDING DOMAINS

The antibodies of the present invention are immunoglobulin molecules capable of specific binding to a target, such as a carbohydrate, polynucleotide, lipid, polypeptide, etc., through at least one antigen recognition site, located in the Variable Region of the immunoglobulin molecule. As used herein, the terms "antibody" and "antibodies" refer to monoclonal antibodies, multispecific antibodies, human antibodies, humanized antibodies, synthetic antibodies, chimeric antibodies, polyclonal antibodies, camelized antibodies, single-chain Fvs (scFv), single-chain antibodies, Fab fragments, F(ab') fragments, disulfide-linked bispecific Fvs (sdFv), intrabodies, and and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. In addition to their known uses in diagnostics, antibodies have been shown to be useful as therapeutic agents. The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases*," Singapore Med. J. 50(7):663-666). Nearly 200 antibody-based drugs have been approved for use or are under development.

The term "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single epitope (or antigenic site). The term "monoclonal antibody" encompasses not only intact monoclonal antibodies and full-length monoclonal antibodies, but also fragments thereof (such as Fab, Fab', F(ab')2 Fv), single-chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi (see, e.g., Jennings, V. M. (1995) "*Review of Selected Adjuvants Used in Antibody Production*," ILAR J. 37(3):119-125). In general, cells should be kept intact and preferably viable when used as immunogens. Intact cells may allow antigens to be better detected than ruptured cells by the immunized animal Use of denaturing or harsh adjuvants, e.g., Freud's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the multispecific (e.g., bispecific, trispecific and tetraspecific) molecules of the invention as well as an affinity optimized antibody, a chimeric antibody, a humanized antibody, or a caninized antibody, to improve the affinity, or other characteristics of the antibody. The general principle in humanizing an antibody involves retaining the basic sequence of the antigen-binding portion of the antibody, while swapping the non-human remainder of the antibody with human antibody sequences.

Natural antibodies (such as IgG antibodies) are composed of two Light Chains complexed with two Heavy Chains. Each light chain contains a Variable Domain (VL) and a Constant Domain (CL). Each heavy chain contains a Variable Domain (VH), and three Constant Domains (CH1, CH2 and CH3), and a Hinge Domain located between the CH1 and CH2 Domains. The basic structural unit of naturally occurring immunoglobulins (e.g., IgG) is thus a tetramer having two light chains and two heavy chains, usually expressed as a glycoprotein of about 150,000 Da. The amino-terminal ("N") portion of each chain includes a Variable Domain of about 100 to 110 or more amino acids primarily responsible for antigen recognition. The carboxy-terminal ("C") portion of each chain defines a constant region, with light chains having a single constant domain and heavy chains usually having three constant domains and a hinge region. Thus, the structure of the light chains of an IgG molecule is n-VL-CL-c and the structure of the IgG heavy chains is n-VH-CH1-H-CH2-CH3-c (where H is the hinge region, and n and c represent, respectively, the N-terminus and the C-terminus of the polypeptide). The Variable Domains of an IgG molecule consist of the complementarity determining regions (CDR), which contain the residues in contact with epitope, and non-CDR segments, referred to as framework segments (FR), which in general maintain the structure and determine the positioning of the CDR loops so as to permit such contacting (although certain framework residues may also contact antigen). Thus, the VL and VH Domains have the structure n-FR1-CDR1-FR2-CDR2-FR3-CDR3-FR4-c. Polypeptides that are (or may serve as) the first, second and third CDR of an antibody Light Chain are herein respectively designated $CDR_L1$ Domain, $CDR_L2$ Domain, and $CDR_L3$ Domain. Similarly, polypeptides that are (or may serve as) the first, second and third CDR of an antibody Heavy Chain are herein respectively designated $CDR_H1$ Domain, $CDR_H2$ Domain, and $CDR_H3$ Domain. Thus, the terms $CDR_L1$ Domain, $CDR_L2$ Domain, $CDR_L3$ Domain, $CDR_H3$ Domain, $CDR_H2$ Domain, and $CDR_H3$ Domain are directed to polypeptides that when incorporated into a protein cause that protein to be able to bind to an specific epitope regardless of whether such protein is an antibody having light and heavy chains or a diabody or a single-chain binding molecule (e.g., an scFv, a BiTe, etc.), or is another type of protein.

The invention also encompasses multivalent DR5-Binding Molecules comprising single-chain Variable Domain fragments ("scFv") of the anti-DR5 antibodies of this invention. Single-chain Variable Domain fragments are made by linking Light and/or Heavy chain Variable Domain by using a short linking peptide. Bird et al. (1988) ("*Single-Chain Antigen-Binding Proteins*," Science 242:423-426) describes example of linking peptides which bridge approximately 3.5 nm between the carboxy terminus of one Variable Domain and the amino terminus of the other Variable Domain. Linkers of other sequences have been designed and used (Bird et al. (1988) "*Single-Chain Antigen-Binding Proteins*," Science 242:423-426). Linkers can in turn be modified for additional functions, such as attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The invention also particularly encompasses multivalent DR5-Binding Molecules comprising humanized variants of the anti-DR5 antibodies of the invention. The term "humanized" antibody refers to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin.

The anti-human DR5 antibodies of the present invention include humanized, chimeric or caninized derivatives of antibodies DR5 mAb 1 or DR5 mAb 2. The polynucleotide sequence of the variable domains of such antibodies may be used for genetic manipulation to generate such derivatives and to improve the affinity, or other characteristics of such antibodies. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; and 6,331,415.

The antigen-binding site may comprise either complete variable domains fused onto constant domains or only the complementarity determining regions (CDRs) grafted onto appropriate framework regions in the Variable Domains. Antigen-binding sites may be wild-type or modified by one or more amino acid substitutions. This eliminates the constant region as an immunogen in human individuals, but the possibility of an immune response to the foreign Variable Domains remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the Variable Domains as well so as to reshape them as closely as possible to human form. It is known that the Variable Domains of both heavy and light chains contain three complementarity determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the Variable Domains can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy,*" Nature 332:323-327; Verhoeyen, M. et al. (1988) "*Reshaping Human Antibodies: Grafting An Antilysozyme Activity,*" Science 239:1534-1536; Kettleborough, C. A. et al. (1991) "*Humanization Of A Mouse Monoclonal Antibody By CDR-Grafting: The Importance Of Framework Residues On Loop Conformation,*" Protein Engineering 4:773-3783; Maeda, H. et al. (1991) "*Construction Of Reshaped Human Antibodies With HIV-Neutralizing Activity,*" Human Antibodies Hybridoma 2:124-134; Gorman, S. D. et al. (1991) "*Reshaping A Therapeutic CD4 Antibody,*" Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo,*" Bio/Technology 9:266-271; Co, M. S. et al. (1991) "*Humanized Antibodies For Antiviral Therapy,*" Proc. Natl. Acad. Sci. (U.S.A.) 88:2869-2873; Carter, P. et al. (1992) "*Humanization Of An Anti-p185her2 Antibody For Human Cancer Therapy,*" Proc. Natl. Acad. Sci. (U.S.A.) 89:4285-4289; and Co, M. S. et al. (1992) "*Chimeric And Humanized Antibodies With Specificity For The CD33 Antigen,*" J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which are altered with respect to the original antibody, which differ in sequence relative to the original antibody.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains (see, for example, Winter et al. (1991) "*Man-made Antibodies,*" Nature 349: 293-299; Lobuglio et al. (1989) "*Mouse/Human Chimeric Monoclonal Antibody In Man: Kinetics And Immune Response,*" Proc. Natl. Acad. Sci. (U.S.A.) 86:4220-4224 (1989), Shaw et al. (1987) "*Characterization Of A Mouse/Human Chimeric Monoclonal Antibody* (17-1*A*) *To A Colon Cancer Tumor-Associated Antigen,*" J. Immunol. 138:4534-4538, and Brown et al. (1987) "*Tumor-Specific Genetically Engineered Murine/Human Chimeric Monoclonal Antibody,*" Cancer Res. 47:3577-3583). Other references describe rodent CDRs grafted into a human supporting framework region (FR) prior to fusion with an appropriate human antibody constant domain (see, for example, Riechmann, L. et al. (1988) "*Reshaping Human Antibodies for Therapy,*" Nature 332:323-327; Verhoeyen, M. et al. (1988) "*Reshaping Human Antibodies: Grafting An Antilysozyme Activity,*" Science 239:1534-1536; and Jones et al. (1986) "*Replacing The Complementarity-Determining Regions In A Human Antibody With Those From A Mouse,*" Nature 321: 522-525). Another reference describes rodent CDRs supported by recombinantly veneered rodent framework regions. See, for example, European Patent Publication No. 519,596. These "humanized" molecules are designed to minimize unwanted immunological response toward rodent anti-human antibody molecules, which limits the duration and effectiveness of therapeutic applications of those moieties in human recipients. Other methods of humanizing antibodies that may also be utilized are disclosed by Daugherty et al. (1991) "*Polymerase Chain Reaction Facilitates The Cloning, CDR-Grafting, And Rapid Expression Of A Murine Monoclonal Antibody Directed Against The CD*18 *Component Of Leukocyte Integrins,*" Nucl. Acids Res. 19:2471-2476 and in U.S. Pat. Nos. 6,180,377; 6,054,297; 5,997,867; and 5,866,692.

II. FCγ RECEPTORS (FCγRS)

The CH2 and CH3 Domains of the two heavy chains interact to form the Fc Region, which is a domain that is recognized by cellular Fc Receptors (FcγRs). As used herein, the term "Fc Region" is used to define a C-terminal region of an IgG heavy chain. The amino acid sequence of the CH2-CH3 Domain of an exemplary human IgG1 is (SEQ ID NO:1):

```
      231       240            250            260            270            280
    APELLGGPSV       FLFPPKPKDT     LMISRTPEVT     CVVVDVSHED     PEVKFNWYVD 290            300            310            320            330
    GVEVHNAKTK       PREEQYNSTY     RVVSVLTVLH     QDWLNGKEYK     CKVSNKALPA 340            350            360            370            380
    PIEKTISKAK       GQPREPQVYT     LPPSREEMTK     NQVSLTCLVK     GFYPSDIAVE 390            400            910            420            430
    WESNGQPENN       YKTTPPVLDS     DGSFFLYSKL     TVDKSRWQQG     NVFSCSVMHE 440            447
    ALHNHYTQKS       LSLSPGK
```

The amino acid sequence of the CH2-CH3 domain of an exemplary human IgG2 is (SEQ ID NO:164):

```
      231       240            250            260            270            280
    APPVA-GPSV       FLFPPKPKDT     LMISRTPEVT     CVVVDVSHED     PEVQFNWYVD 290            300            310            320            330
    GVEVHNAKTK       PREEQFNSTF     RVVSVLTVVH     QDWLNGKEYK     CKVSNKGLPA 340            350            360            370            380
    PIEKTISKTK       GQPREPQVYT     LPPSREEMTK     NQVSLTCLVK     GFYPSDISVE
```

```
        390           400           910           420           430
WESNGQPENN    YKTTPPMLDS    DGSFFLYSKL    TVDKSRWQQG    NVFSCSVMHE 440           447
ALHNHYTQKS    LSLSPGK
```

The amino acid sequence of the CH2-CH3 Domain of an exemplary human IgG3 is (SEQ ID NO:168):

```
231           240           250           260           270           280
APELLGGPSV    FLFPPKPKDT    LMISRTPEVT    CVVVDVSHED    PEVQFKWYVD 290           300           310           320           330
GVEVHNAKTK    PREEQYNSTF    RVVSVLTVLH    QDWLNGKEYK    CKVSNKALPA 340           350           360           370           380
PIEKTISKTK    GQPREPQVYT    LPPSREEMTK    NQVSLTCLVK    GFYPSDIAVE 390           400           910           420           430
WESSGQPENN    YNTTPPMLDS    DGSFFLYSKL    TVDKSRWQQG    NIFSCSVMHE 440           447
ALHNRFTQKS    LSLSPGK
```

The amino acid sequence of the CH2-CH3 domain of an exemplary human IgG4 is (SEQ ID NO:103):

```
231           240           250           260           270           280
APEFLGGPSV    FLFPPKPKDT    LMISRTPEVT    CVVVDVSQED    PEVQFNWYVD 290           300           310           320           330
GVEVHNAKTK    PREEQFNSTY    RVVSVLTVLH    QDWLNGKEYK    CKVSNKGLPS 340           350           360           370           380
SIEKTISKAK    GQPREPQVYT    LPPSQEEMTK    NQVSLTCLVK    GFYPSDIAVE 390           400           910           420           430
WESNGQPENN    YKTTPPVLDS    DGSFFLYSRL    TVDKSRWQEG    NVFSCSVMHE 440           447
ALHNHYTQKS    LSLSLGK
```

Throughout the present specification, the numbering of the residues in an IgG heavy chain is that of the EU index as in Kabat et al., *Sequences of Proteins of Immunological Interest*, 5$^{th}$ Ed. Public Health Service, NH1, MD (1991), expressly incorporated herein by references. The "EU index as in Kabat" refers to the numbering of the human IgG1 EU antibody. Amino acids from the Variable Domains of the mature heavy and light chains of immunoglobulins are designated by the position of an amino acid in the chain. Kabat described numerous amino acid sequences for antibodies, identified an amino acid consensus sequence for each subgroup, and assigned a residue number to each amino acid. Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain.

Polymorphisms have been observed at a number of different positions within antibody constant regions (e.g., Fc positions, including but not limited to positions 270, 272, 312, 315, 356, and 358 as numbered by the EU index as set forth in Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc, et al., "*The Human IgG Subclasses: Molecular Analysis Of Structure, Function And Regulation*," Pergamon, Oxford, pp. 43-78 (1990); Lefranc, G. et al., 1979, Hum. Genet. 50:199-211). It is specifically contemplated that the antibodies of the present invention may incorporate any allotype, isoallotype, or haplotype of any immunoglobulin gene, and are not limited to the allotype, isoallotype or haplotype of the sequences provided herein. Furthermore, in some expression systems the C-terminal amino acid residue (bolded above) of the CH3 Domain may be post-translationally removed. Accordingly, the C-terminal residue of the CH3 Domain is an optional amino acid residue in the Multivalent DR5-Binding Molecules of the invention. Exemplary Multivalent DR5-Binding Molecules lacking the C-terminal residue of SEQ ID NO:1 are provided below. Also specifically encompassed by the instant invention are such constructs comprising the C-terminal residue.

Activating and inhibitory signals are transduced through the Fc Receptors (FcγRs) following their ligation to an Fc Region. These diametrically opposing functions result from structural differences among the different receptor isoforms.

Two distinct domains within the cytoplasmic signaling domains of the receptor called immunoreceptor tyrosine-based activation motifs (ITAMs) or immunoreceptor tyrosine-based inhibitory motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, whereas ITIM-containing complexes only include FcγRIIB. Human neutrophils express the FcγRIIA gene. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., $PI_3K$). Cellular activation leads to release of proinflammatory mediators. The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When co-ligated along with an activating FcγR, the ITIM in FcγRIIB becomes phosphorylated and attracts the SH2 domain of the inositol polyphosphate 5'-phosphatase (SHIP), which hydrolyzes phosphoinositol messengers released as a consequence of ITAM-containing FcγR-mediated tyrosine kinase activation, consequently preventing the influx of intracellular $Ca^{++}$. Thus, cross-linking of FcγRIIB dampens the activating response to FcγR ligation and inhibits cellular responsiveness. B cell activation, B cell proliferation and antibody secretion is thus aborted.

III. MULTIVALENT ANTIBODIES, MULTIVALENT DIABODIES AND DART® DIABODIES

The ability of an antibody to bind an epitope of an antigen depends upon the presence and amino acid sequence of the antibody's VL and VH Domains. Interaction of an antibody light chain and an antibody heavy chain and, in particular, interaction of its VL and VH Domains forms one of the two epitope-binding sites of a natural antibody. Natural antibodies are capable of binding to only one epitope species (i.e., they are monospecific), although they can bind multiple copies of that species (i.e., exhibiting bivalency or multivalency).

The binding domains of the present invention bind to epitopes in an "immunospecific" manner. As used herein, an antibody, diabody or other epitope binding molecule is said to "immunospecifically" bind a region of another molecule (i.e., an epitope) if it reacts or associates more frequently, more rapidly, with greater duration and/or with greater affinity with that epitope relative to alternative epitopes. For example, an antibody that immunospecifically binds to a viral epitope is an antibody that binds this viral epitope with greater affinity, avidity, more readily, and/or with greater duration than it immunospecifically binds to other viral epitopes or non-viral epitopes. It is also understood by reading this definition that, for example, an antibody (or moiety or epitope) that immunospecifically binds to a first target may or may not specifically or preferentially bind to a second target. As such, "specific binding" does not necessarily require (although it can include) exclusive binding. Generally, but not necessarily, reference to binding means "specific" binding. Two molecules are said to be capable of binding to one another in a "physiospecific" manner, if such binding exhibits the specificity with which receptors bind to their respective ligands.

The functionality of antibodies can be enhanced by generating multispecific antibody-based molecules that can simultaneously bind two separate and distinct antigens (or different epitopes of the same antigen) and/or by generating antibody-based molecule having higher valency (i.e., more than two binding sites) for the same epitope and/or antigen.

In order to provide molecules having greater capability than natural antibodies, a wide variety of recombinant bispecific antibody formats have been developed (see, e.g., PCT Publication Nos. WO 2008/003116, WO 2009/132876, WO 2008/003103, WO 2007/146968, WO 2009/018386, WO 2012/009544, WO 2013/070565), most of which use linker peptides either to fuse a further binding protein (e.g., an scFv, VL, VH, etc.) to, or within the antibody core (IgA, IgD, IgE, IgG or IgM, or to fuse multiple antibody binding portions e.g., two Fab fragments or scFvs. Alternative formats use linker peptides to fuse a binding protein (e.g., an scFv, VL, VH, etc.) to an a dimerization domain such as the CH2-CH3 Domain or alternative polypeptides (WO 2005/070966, WO 2006/107786A WO 2006/107617A, WO 2007/046893). Typically, such approaches involve compromises and trade-offs. For example, PCT Publications Nos. WO 2013/174873, WO 2011/133886 and WO 2010/136172 disclose that the use of linkers may cause problems in therapeutic settings, and teaches a trispecific antibody in which the CL and CH1 Domains are switched from their respective natural positions and the VL and VH Domains have been diversified (WO 2008/027236; WO 2010/108127) to allow them to bind to more than one antigen. Thus, the molecules disclosed in these documents trade binding specificity for the ability to bind additional antigen species. PCT Publications Nos. WO 2013/163427 and WO 2013/119903 disclose modifying the CH2 Domain to contain a fusion protein adduct comprising a binding domain. The document notes that the CH2 Domain likely plays only a minimal role in mediating effector function. PCT Publications Nos. WO 2010/028797, WO2010028796 and WO 2010/028795 disclose recombinant antibodies whose Fc Regions have been replaced with additional VL and VH Domains, so as to form trivalent binding molecules. PCT Publications Nos. WO 2003/025018 and WO2003012069 disclose recombinant diabodies whose individual chains contain scFv Domains. PCT Publications No. WO 2013/006544 discloses multivalent Fab molecules that are synthesized as a single polypeptide chain and then subjected to proteolysis to yield heterodimeric structures. Thus, the molecules disclosed in these documents trade all or some of the capability of mediating effector function for the ability to bind additional antigen species. PCT Publications Nos. WO 2014/022540, WO 2013/003652, WO 2012/162583, WO 2012/156430, WO 2011/086091, WO 2008/024188, WO 2007/024715, WO 2007/075270, WO 1998/002463, WO 1992/022583 and WO 1991/003493 disclose adding additional binding domains or functional groups to an antibody or an antibody portion (e.g., adding a diabody to the antibody's light chain, or adding additional VL and VH Domains to the antibody's light and heavy chains, or adding a heterologous fusion protein or chaining multiple Fab Domains to one another). Thus, the molecules disclosed in these documents trade native antibody structure for the ability to bind additional antigen species.

The art has additionally noted the capability to produce diabodies that differ from such natural antibodies in being capable of binding two or more different epitope species (i.e., exhibiting bispecificity or multispecificity in addition to bivalency or multivalency) (see, e.g., Holliger et al. (1993) "'*Diabodies*': *Small Bivalent And Bispecific Antibody Fragments*," Proc. Natl. Acad. Sci. (U.S.A.) 90:6444-6448; US 2004/0058400 (Hollinger et al.); US 2004/0220388 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672; WO 02/02781 (Mertens et al.); Olafsen, T. et al. (2004) "*Covalent Disulfide-Linked Anti-CEA Diabody Allows Site-Specific Conjugation And Radiolabeling For Tumor Targeting Applications*," Protein Eng. Des. Sel. 17(1):21-27; Wu, A. et al. (2001) "*Multimerization Of A Chimeric Anti-CD20 Single Chain Fv-Fv Fusion Protein Is Mediated Through Variable Domain Exchange*," Protein Engineering 14(2):1025-1033; Asano et al. (2004) "*A Diabody For Cancer Immunotherapy And Its Functional Enhancement By Fusion Of Human Fc Domain*," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8):583-588; Baeuerle, P. A. et al. (2009) "*Bispecific T-Cell Engaging Antibodies For Cancer Therapy*," Cancer Res. 69(12):4941-4944).

The design of a diabody is based on the antibody derivative known as a single-chain Variable Domain fragment (scFv). Such molecules are made by linking Light and/or Heavy chain Variable Domain by using a short linking peptide. Bird et al. (1988) ("*Single-Chain Antigen-Binding Proteins*," Science 242:423-426) describes example of linking peptides which bridge approximately 3.5 nm between the carboxy terminus of one Variable Domain and the amino terminus of the other Variable Domain. Linkers of other sequences have been designed and used (Bird et al. (1988) "*Single-Chain Antigen-Binding Proteins*," Science 242:423-426). Linkers can in turn be modified for additional functions, such as attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The provision of non-monospecific diabodies provides significant advantages over antibodies, including but not limited to, the capacity to co-ligate and co-localize cells that express different epitopes and the capacity to form inter- and/or intra molecular interactions by binding different epitopes of the same antigen. Bivalent diabodies thus have wide-ranging applications including therapy and immunodiagnosis. Bispecificity allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the field of tumor imaging (Fitzgerald et al. (1997) "*Improved Tumour Targeting By Disulphide Stabilized Diabodies Expressed In Pichia pastoris*," Protein Eng. 10:1221). Of particular importance is the co-ligating of differing cells, for example, the cross-linking of cytotoxic T cells to tumor cells (Staerz et al. (1985) "*Hybrid Antibodies Can Target Sites For Attack By T Cells*," Nature 314:628-631, and Holliger et al. (1996) "*Specific Killing Of Lymphoma Cells By Cytotoxic T-Cells Mediated By A Bispecific Diabody*," Protein Eng. 9:299-305; Marvin et al. (2005) "Recombinant Approaches To IgG-Like Bispecific Antibodies," Acta Pharmacol. Sin. 26:649-658).

However, the above advantages come at a salient cost. The formation of such non-monospecific diabodies requires the successful assembly of two or more distinct and different polypeptides (i.e., such formation requires that the diabodies be formed through the heterodimerization of different polypeptide chain species). This fact is in contrast to monospecific diabodies, which are formed through the homodimerization of identical polypeptide chains. Because at least two dissimilar polypeptides (i.e., two polypeptide species) must be provided in order to form a non-monospecific diabody, and because homodimerization of such polypeptides leads to inactive molecules (Takemura, S. et al. (2000) "*Construction Of A Diabody (Small Recombinant Bispecific Antibody) Using A Refolding System*," Protein Eng. 13(8): 583-588), the production of such polypeptides must be accomplished in such a way as to prevent covalent bonding between polypeptides of the same species (i.e., so as to prevent homodimerization) (Takemura, S. et al. (2000) "*Construction Of A Diabody (Small Recombinant Bispecific Antibody) Using A Refolding System*," Protein Eng. 13(8): 583-588). The art has therefore taught the non-covalent association of such polypeptides (see, e.g., Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27; Asano et al. (2004) "*A Diabody For Cancer Immunotherapy And Its Functional Enhancement By Fusion Of Human Fc Domain*," Abstract 3P-683, J. Biochem. 76(8): 992; Takemura, S. et al. (2000) "*Construction Of A Diabody (Small Recombinant Bispecific Antibody) Using A Refolding System*," Protein Eng. 13(8):583-588; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

However, the art has recognized that bispecific diabodies composed of non-covalently associated polypeptides are unstable and readily dissociate into non-functional monomers (see, e.g., Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

In the face of this challenge, the art has succeeded in developing stable, covalently bonded heterodimeric non-monospecific diabodies, termed DART® (Dual Affinity Re-Targeting Reagents) diabodies; see, e.g., United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538; and Moore, P. A. et al. (2011) "*Application Of Dual Affinity Retargeting Molecules To Achieve Optimal Redirected T-Cell Killing Of B-Cell Lymphoma*," Blood 117(17):4542-4551; Veri, M. C. et al. (2010) "*Therapeutic Control Of B Cell Activation Via Recruitment Of Fcgamma*

Receptor IIb (CD32B) Inhibitory Function With A Novel Bispecific Antibody Scaffold," Arthritis Rheum. 62(7):1933-1943; Johnson, S. et al. (2010) "*Effector Cell Recruitment With Novel Fv-Based Dual-Affinity Re-Targeting Protein Leads To Potent Tumor Cytolysis And in vivo B-Cell Depletion*," J. Mol. Biol. 399(3):436-449). Such diabodies comprise two or more covalently complexed polypeptides and involve engineering one or more cysteine residues into each of the employed polypeptide species that permit disulfide bonds to form and thereby covalently bond two polypeptide chains. For example, the addition of a cysteine residue to the c-terminus of such constructs has been shown to allow disulfide bonding between the polypeptide chains, stabilizing the resulting heterodimer without interfering with the binding characteristics of the bivalent molecule.

Figure 1:
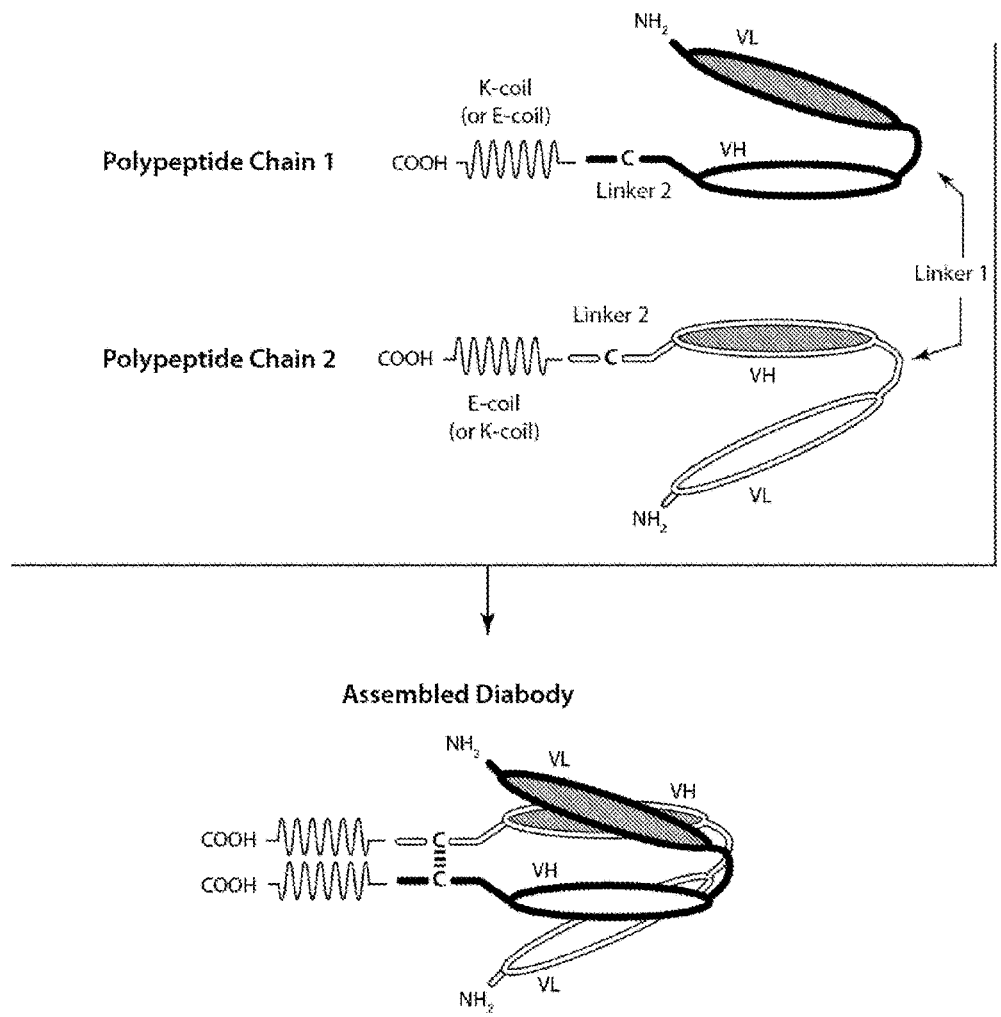
FIG. 1 provides a schematic of a representative covalently bonded diabody molecule having two epitope binding sites composed of two polypeptide chains, each having an E-coil or K-coil Heterodimer-Promoting Domain. VL and VH Domains that recognize the same epitope are shown using the same shading. In certain embodiments, the epitopes are different epitopes of the same antigen resulting in a bispecific molecule that is monovalent for each epitope, but is bivalent with respect to the antigen (e.g., DR5). In certain embodiments the epitopes are the same epitope (e.g., the same VL Domain CDRs and VH Domain CDRs are used on each chain) resulting in a monospecific molecule that is bivalent.

Each of the two polypeptides of the simplest bispecific DART® diabody comprises three Domains. The first polypeptide comprises (in the N-terminal to C-terminal direction): (i) a First Domain that comprises a binding region of a Light Chain Variable Domain of a first immunoglobulin (VL1), (ii) a Second Domain that comprises a binding region of a Heavy Chain Variable Domain of a second immunoglobulin (VH2), and (iii) a Third Domain that contains a cysteine residue (or a cysteine-containing domain) and a Heterodimer-Promoting Domain that serves to promote heterodimerization with the second polypeptide of the diabody and to covalently bond the diabody's first and second polypeptides to one another. The second polypeptide contains (in the N-terminal to C-terminal direction): (i) a First Domain that comprises a binding region of a Light Chain Variable Domain of the second immunoglobulin (VL2), (ii) a Second Domain that comprises a binding region of a Heavy Chain Variable Domain of the first immunoglobulin (VH1), and (iii) a Third Domain that contains a cysteine residue (or a cysteine-containing domain) and, a complementary Heterodimerization-Promoting Domain that complexes with the Heterodimerization-Promoting Domain of the first polypeptide chain in order to promote heterodimerization with the first polypeptidechain. The cysteine residue (or cysteine-containing domain) of the third domain of the second polypeptide serves to promote the covalent bonding of the second polypeptide chain to the first polypeptide chain of the diabodydiabody. Such molecules are stable, potent and have the ability to simultaneously bind two or more different antigens or two different epitopes on the same antigen. In one embodiment, the Third Domains of the first and second polypeptides each contain a cysteine residue, which serves to bind the polypeptides together via a disulfide bond. FIG. 1 provides a schematic of such a diabody, which utilizes E-coil/K-coil heterodimerization domains and a cysteine containing linker for covalent bonding. As provided in FIGS. 2-4, one or both of the polypeptides may additionally possesses the sequence of a CH2-CH3 Domain, such that complexing between the two diabody polypeptides forms an Fc Region that is capable of binding to the Fc receptor of cells (such as B lymphocytes, dendritic cells, natural killer cells, macrophages, neutrophils, eosinophils, basophils and mast cells). As provided in more detail below, the CH2 and/or CH3 Domains of such polypeptide chains need not be identical in sequence, and advantageously are modified to foster complexing between the two polypeptide chains.

Figure 3:
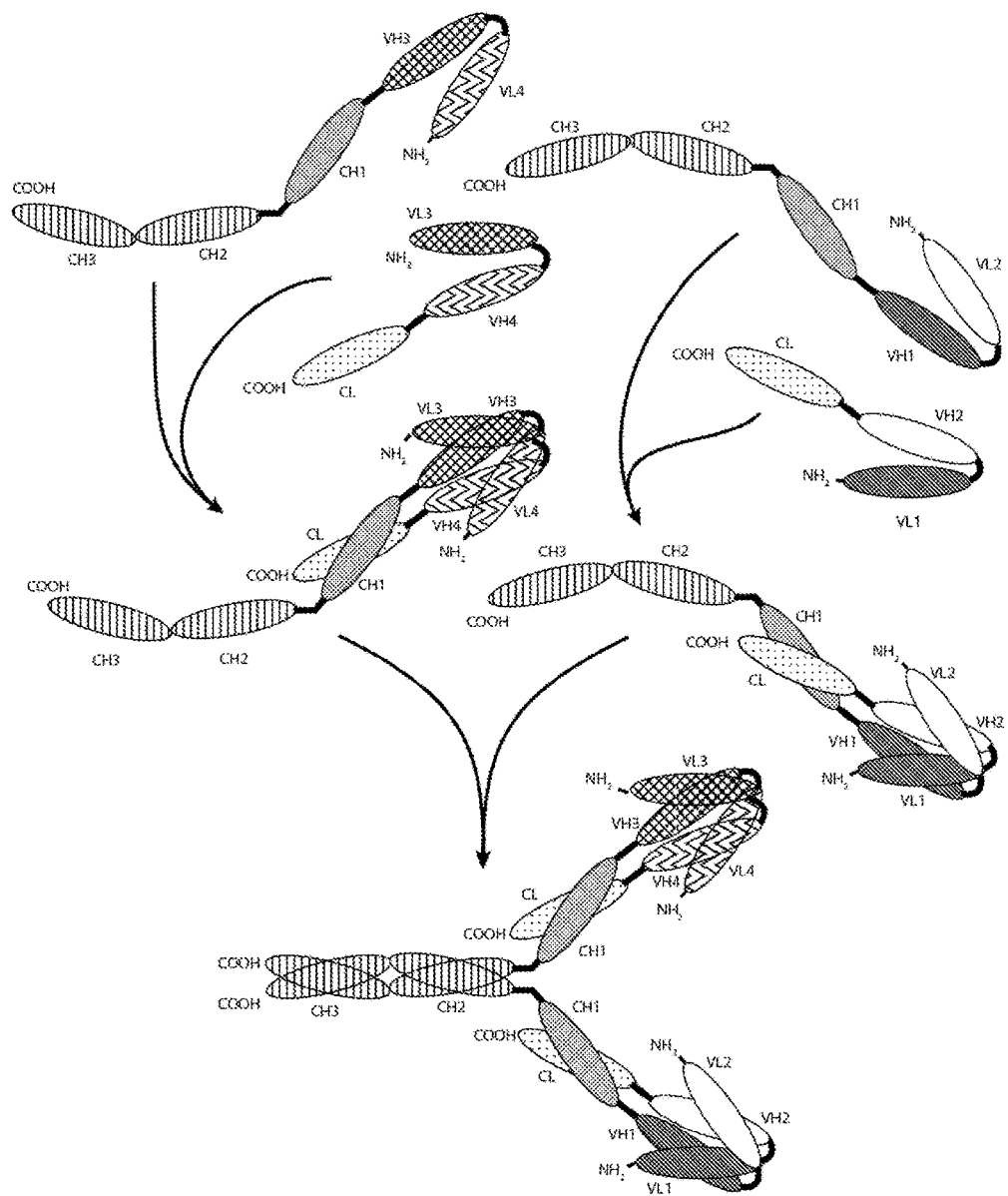
FIG. 3 provides a schematic showing a representative tetravalent diabody molecule composed of two pairs of polypeptide chains (i.e., four polypeptide chains in all). One polypeptide of each pair possesses a CH2 and CH3 Domain, such that the associated chains form an Fc Region that comprises all or part of a naturally occurring Fc Region. VL and VH Domains that recognize the same epitope are shown using the same shading. The two pairs of polypeptide chains may be same. In such embodiments wherein the VL and VH Domains recognize different epitopes (as shown), the resulting molecule is bispecific and bivalent with respect to each bound epitope. In such embodiments wherein the VL and VH Domains recognize the same epitope (e.g., the same VL Domain CDRs and the same VH Domain CDRs are used on both chains) the resulting molecule is monospecific and tetravalent with respect to a single epitope. Alternatively, the two pairs of polypeptides may be different. In such embodiments wherein the VL and VH Domains of each pair of polypeptides recognize different epitopes (as shown), the resulting molecule is tetraspecific and monovalent with respect to each bound epitope. In embodiments wherein the epitopes are all epitopes of the same antigen, the resulting molecule is tetravalent with respect to the antigen (e.g., DR5). In certain embodiments the epitopes are the same epitope (e.g., the same 3 $CDR_{LS}$ and the same 3 $CDR_{HS}$ domains are used on each chain), the resulting molecule is monospecific and tetravalent.
Figure 4A:
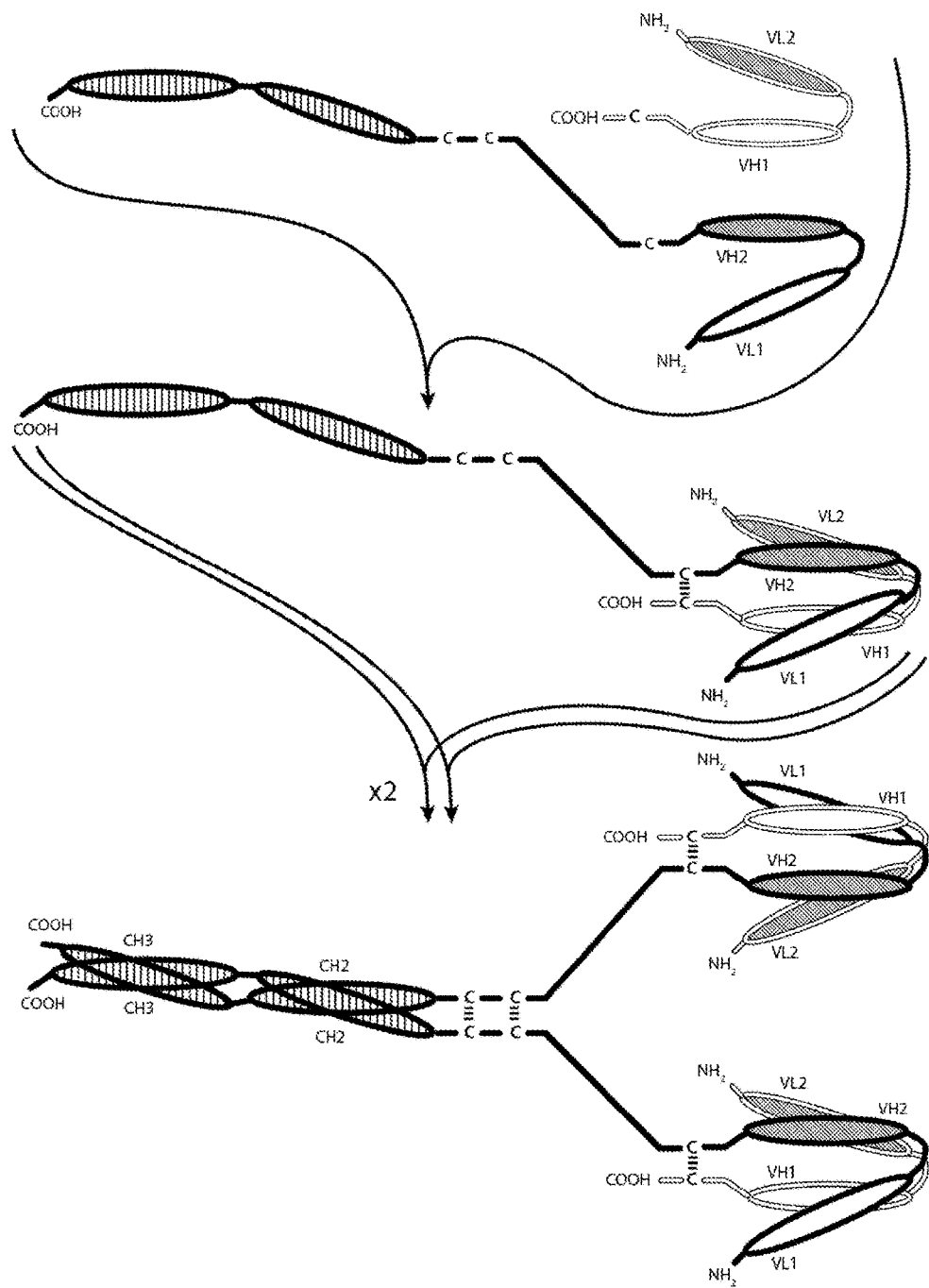
FIGS. 4A and 4B provide schematics of alternative tetravalent diabody molecules that are also composed of two pairs of polypeptide chains (i.e., four polypeptide chains in all). One polypeptide of each pair possesses a CH2 and CH3 Domain, such that the associated chains form an Fc Region that comprises all or part of a naturally occurring Fc Region. VL and VH Domains that recognize the same epitope are shown using the same shading. The two pairs of polypeptide chains may be the same. In such embodiments, wherein the VL and VH Domains recognize different epitopes (as shown) the resulting molecule is bispecific and bivalent with respect to each bound epitope. In such embodiments, wherein the VL and VH Domains recognize the same epitope (e.g., the same VL Domain CDRs and the same VH Domain CDRs are used on both chains) the resulting molecule is monospecific and tetravalent with respect to a single epitope. Alternatively, the two pairs of polypeptides may be different. In such embodiments, wherein the VL and VH Domains recognize different epitopes, the resulting molecule is tetraspecific and monovalent with respect to each bound epitope. In embodiments wherein the epitopes are all epitopes of the same antigen, the resulting molecule is tetravalent with respect to the antigen (e.g., DR5). The diabody portion of the construct in FIG. 4A shows an Fe-containing diabody which contains a peptide Heterodimer-Promoting Domain comprising a cysteine residue.
Figure 4B:
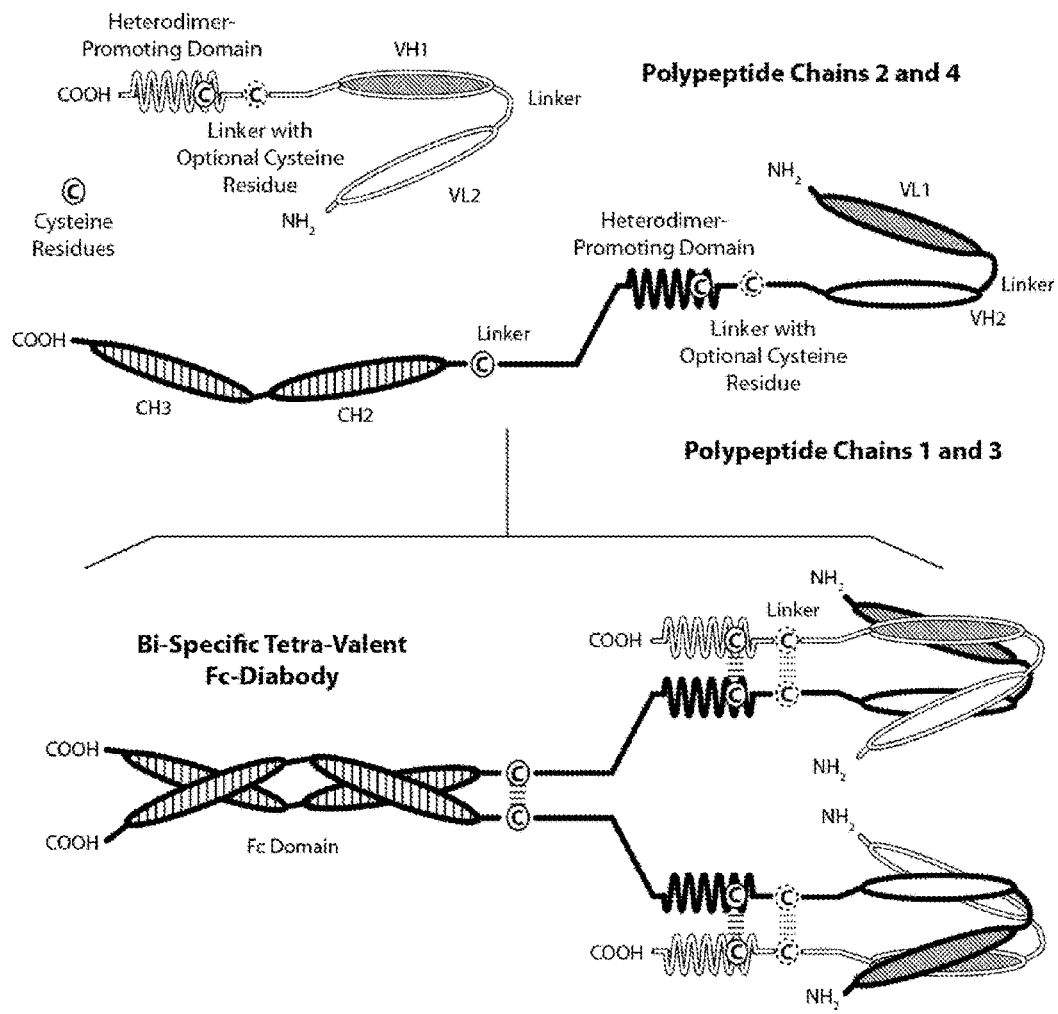

Many variations of such molecules have been described (see, e.g., United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538). These Fc Region-containing DART® diabodies may comprise two pairs of polypeptide chains. The first polypeptide comprises (in the N-terminal to C-terminal direction): (i) a First Domain that comprises a binding region of a Light Chain Variable Domain of a first immunoglobulin (VL1), (ii) a Second Domain that comprises a binding region of a Heavy Chain Variable Domain of a second immunoglobulin (VH2), (iii) a Third Domain that contains a cysteine residue (or a cysteine containing domain) and a Heterodimerization-Promoting Domain that serves to promote heterodimerization with the second polypeptide of the diabody and to covalently bond the diabody's first and second polypeptides to one another, and (iv) a CH2-CH3 Domain. The second polypeptide contains (in the N-terminal to C-terminal direction): (i) a First Domain that comprises a binding region of a Light Chain Variable Domain of the second immunoglobulin (VL2), (ii) a Second Domain that comprises a binding region of a Heavy Chain Variable Domain of the first immunoglobulin (VH1), and (iii) a Third Domain that contains a cysteine residue (or a cysteine containing domain) and a Heterodimerization-Promoting Domain capable of interacting with the Third Domain of the first polypeptide chain in order to promote heterodimerization and covalent bonding between the two polypeptide chains. Here two first polypeptides complex with each other to form an Fc Region. FIGS. 3 and 4A-4B provide schematics of three variations of such diabodies utilizing different heterodimer-promoting domains. Other Fc Region-containing DART® diabodies may comprise three polypeptide chains. The first polypeptide of such DART® diabodies contains three Domains: (i) a VL1-containing Domain, (ii) a VH2-containing Domain and (iii) a Domain containing a CH2-CH3 sequence. The second polypeptide of such DART® diabodies contains: (i) a VL2-containing Domain, (ii) a VH1-containing Domain and (iii) a Domain that promotes heterodimerization and covalent bonding with the diabody's first polypeptide chain. The third polypeptide of such DART® diabodies comprises a CH2-CH3 sequence. Thus, the first and second polypeptide chains of such a diabody associate together to form a VL1/VH1 binding site that is capable of binding to the epitope, as well as a VL2NH2 binding site that is capable of binding to the second epitope. Such more complex diabodies also possess cysteine-containing domains which function to form a covalently bonded complex. Thus, the first and second polypeptides are bonded to one another through a disulfide bond involving cysteine residues in their respective third Domains. Notably, the first and third polypeptide chains complex with one another to form an Fc Region that is stabilized via a disulfide bond.

Alternative constructs are known in the art for applications where a tetravalent molecule is desirable but an Fc is not required including, but not limited to, tetravalent tandem antibodies, also referred to as "TandAbs" (see, e.g. United States Patent Publications Nos. 2005-0079170, 2007-0031436, 2010-0099853, 2011-020667 2013-0189263; European Patent Publication Nos. EP 1078004, EP 2371866, EP 2361936 and EP 1293514; PCT Publications Nos. WO 1999/057150, WO 2003/025018, and WO 2013/013700) which are formed by the homo-dimerization of two identical chains each possessing a VH1, VL2, VH2, and VL2 Domain.

IV. ANTI-HUMAN DR5-BINDING MOLECULES OF THE PRESENT INVENTION

The preferred multivalent DR5-Binding Molecules of the present invention are capable of binding to a continuous or discontinuous (e.g., conformational) portion (epitope) of human DR5. The DR5-Binding Molecules of the present invention will preferably also exhibit the ability to bind to the DR5 molecules of one or more non-human species, especially, murine, rodent, canine, and primate species. The amino acid sequence of human DR5 precursor (NCBI Sequence NP_003833.4) (SEQ ID NO:2) is:

```
MEQRGQNAPA ASGARKRHGP GPREARGARP GLRVPKTLVL
VVAAVLLLVS AESALITQQD LAPQQRVAPQ QKRSSPSEGL
CPPGHHISED GRDCISCKYG QDYSTHWNDL LFCLRCTRCD
SGEVELSPCT TTRNTVCQCE EGTFREEDSP EMCRKCRTGC
PRGMVKVGDC TPWSDIECVH KESGTKHSGE APAVEETVTS
SPGTPASPCS LSGIIIGVTV AAVVLIVAVF VCKSLLWKKV
LPYLKGICSG GGGDPERVDR SSQRPGAEDN VLNEIVSILQ
PTQVPEQEME VQEPAEPTGV NMLSPGESEH LLEPAEAERS
QRRRLLVPAN EGDPTETLRQ CFDDFADLVP FDSWEPLMRK
LGLMDNEIKV AKAEAAGHRD TLYTMLIKWV NKTGRDASVH
TLLDALETLG ERLAKQKIED HLLSSGKFMY LEGNADSAMS
```

Of the 440 amino acid residues of DR5 (SEQ ID NO:2), residues 1-55 are a signal sequence, residues 57-94 are a first Cysteine-Rich Domain (CRD), residues 97-137 are a second Cysteine-Rich Domain (CRD), residues 138-178 are a third Cysteine-Rich Domain (CRD), residues 211-231 are the Transmembrane Domain, and residues 232-440 are the Cytoplasmic Domain (containing the receptor's Death Domain).

The present invention includes multivalent DR5-Binding Molecules possessing at least two, and preferably, at least four DR5 binding sites. The DR5 binding sites may bind the same DR5 epitope or different DR5 epitopes. Accordingly, the multivalent DR5-Binding Molecules of the invention may be monospecific, binding just one epitope of DR5, or they may be multispecific, binding different epitopes of DR5.

Exemplary multivalent DR5-Binding Molecules of the present invention includes bispecific molecules (e.g., bispecific antibodies, non-monospecific diabodies, etc.) possessing at least one "First Binding Site" which binds a "First DR5 Epitope" and at least one "Second Binding Site" which binds a "Second DR5 Epitope." Such molecules are bispecific with respect to said first DR5 epitope and second DR5 epitope and are at least bivalent with respect to DR5. Bispecific multivalent DR5-Binding Molecules exhibiting a higher valency for DR5 may be generated by the addition of one or more additional First Binding Sites and/or Second Binding Sites. Exemplary multivalent DR5-Binding Molecules of the present invention also include multispecific molecules possessing at least three, or at least four, or more different binding sites each of which binds a different DR5 epitope. Such molecules are multispecific with respect to said DR5 epitopes and are multivalent with respect to DR5.

One exemplary bispecific multivalent DR5-Binding Molecule of the present invention possesses two First Binding Sites which bind a first DR5 epitope, and two Second Binding Sites which bind a second DR5 epitope. Such a DR5-Binding Molecule is bispecific with respect to said first and second DR5 epitopes and tetravalent with respect to DR5.

Preferably, the multispecific multivalent (e.g., bispecific, bivalent) DR5-Binding Molecules of the invention are capable of simultaneously binding to the different DR5 epitopes. Such binding may be intramolecular (i.e., to the different DR5 epitopes on a single DR5 polypeptide) and/or intermolecular (i.e., to the different DR5 epitopes on separate DR5 polypeptides).

Exemplary multivalent DR5-Binding Molecules of the present invention also includes monospecific molecules (e.g., bispecific antibodies, monospecific diabodies, etc.) possessing at least two, preferably at least four, binding sites which bind the same DR5 epitope. Such molecules are monospecific with respect to said DR5 epitope, and are at least bivalent, preferably tetravalent, with respect to DR5. It will be noted that where more than two binding sites that bind the same DR5 epitope are present, the multivalent DR5-Binding Molecule will remain monospecific with respect to the epitope but will exhibit a higher valency for DR5.

One exemplary monospecific multivalent DR5-Binding Molecule of the present invention possesses four binding sites which bind the same DR5 epitope, and is monospecific with respect to said DR5 epitope and tetravalent with respect to DR5.

Preferably, the monospecific multivalent (e.g., monospecific, bivalent) DR5-Binding Molecules of the invention are capable of simultaneously binding to the DR5 epitope. Such binding is intermolecular (i.e., to the same DR5 epitope on separate DR5 polypeptides).

The multivalent DR5-Binding Molecules of the present invention may possess the VL and/or VH Domains of one or more of the anti-DR5 antibodies disclosed herein. The preferred multivalent DR5-Binding Molecules of the present invention possess the VL and/or VH Domains of anti-human DR5 monoclonal antibodies "DR5 mAb 1" and/or "DR5 mAb 2," and/or "hDR5 mAb2," and more preferably possess 1, 2 or all 3 of the $CDR_{LS}$ of the VL Domain and/or 1, 2 or all 3 of the $CDR_{HS}$ of the VH Domain of such anti-human DR5 monoclonal antibodies. The amino acid sequences of particular anti-DR5-Binding Molecules, and polynucleotides encoding the same, are provided below. The present invention also encompasses minor variations of these sequences including, for example amino acid substitutions of the C-terminal and/or N-terminal amino acid residues which may be introduced to facilitate subcloning.

A. The Anti-Human DR5 Antibody DR5 mAb 1

The amino acid sequence of the VL Domain of DR5 mAb 1 (SEQ ID NO:3) is shown below ($CDR_L$ residues are shown underlined):

DIVLTQSPAS LAVSLGQRAT ISCRASKSVS SSGYSYMHWY
QQKPGQPPKV LIFLSSNLDS GVPARFSGSG SGTDFILNIH
PVEDGDAATY YCQHSRDLPP TFGGGTKLEI K $CDR_L1$ of DR5 mAb 1: (SEQ ID NO: 4)
RASKSVSSSGYSYMH

$CDR_L2$ of DR5 mAb 1: (SEQ ID NO: 5)
LSSNLDS

$CDR_L3$ of DR5 mAb 1: (SEQ ID NO: 6)
QHSRDLPPT

The VL Domain of DR5 mAb 1 is preferably encoded by a polynucleotide (SEQ ID NO:7) having the sequence shown below (polynucleotides encoding the CDR$_L$ residues are shown in underline):

```
gacattgtgc tgacacagtc tcctgcttcc ttagctgtat ctctcgggca gagggccacc atctcatgca gggccagcaa aagtgtcagt tcctctggct atagttatat gcactggtac caacagaaac caggacagcc acccaaagtc ctcatctttc tttcatccaa cctagattct ggggtccctg ccaggttcag tggcagtggg tctgggacag acttcaccct caacatccat cctgtggagg atggggatgc tgcaacctat tactgtcagc acagtaggga tcttcctccg acgttcggtg gaggcaccaa gctggaaatc aaa
```

The amino acid sequence of the VH Domain of DR5 mAb 1 (SEQ ID NO:8) is shown below (CDR$_H$ residues are shown underlined), the C-terminal amino acid may be substituted with alanine to facilitate subcloning of this VH Domain:

```
EVKFLESGGG LVQPGGSLKL SCVASGFDFS RYWMSWVRQA

PGKGLEWIGE INPDSNTINY TPSLKDKFII SRDNAKNTLY

LQMTKVRSED TALYYCTRRA YYGNPAWFAY WGQGTLVTVSS
```

CDR$_H$1 of DR5 mAb 1:
(SEQ ID NO: 9)
GFDFSRYWMS

CDR$_H$2 of DR5 mAb 1:
(SEQ ID NO: 10)
EINPDSNTINYTPSLKD

CDR$_H$3 of DR5 mAb 1:
(SEQ ID NO: 11)
RAYYGNPAWFAY

The VH Domain of DR5 mAb 1 is preferably encoded by a polynucleotide (SEQ ID NO:12) having the sequence shown below (polynucleotides encoding the CDR$_H$ residues are shown in underline):

```
gaggtgaagt tctcgagtc tggaggtggc ctggtgcagc ctggaggatc cctgaaactc tcctgtgtag cctcaggatt cgatttagt agatactgga tgagttgggt ccggcaggct ccagggaaag ggctagaatg gattggagaa attaatccag atagcaatac gataaactat acgccatctc taaaggataa attcatcatc tccagacaa acgccaaaaa tacgctgtat ctgcaaatga ccaaagtgag atctgaggac acagcccttt attattgtac aagaagggcc tactatggta acccggcctg gtttgcttac tggggccaag ggactctggt cactgtctct tcc
```

B. The Anti-Human DR5 Antibody DR5 mAb 2

1. Murine Anti-Human Antibody DR5 mAb 2

The amino acid sequence of the VL Domain of DR5 mAb 2 (SEQ ID NO:13) is shown below (CDR$_L$ residues are shown underlined):

```
DIVMTQSHKF MSTSVGDRVS ITCKASQDVN TAVAWYQQKP

GQSPKLLIYW ASTRHTGVPD RFTGSGSGTD YTLTIKSVQA

EDLTLYYCQQ HYITPWTFGG GTKLEIK
```

CDR$_L$1 of DR5 mAb 2:
(SEQ ID NO: 14)
KASQDVNTAVA

CDR$_L$2 of DR5 mAb 2:
(SEQ ID NO: 15)
WASTRHT

CDR$_L$3 of DR5 mAb 2:
(SEQ ID NO: 16)
QQHYITPWT

The VL Domain of DR5 mAb 2 is preferably encoded by a polynucleotide (SEQ ID NO:17) having the sequence shown below (polynucleotides encoding the CDR$_L$ residues are shown in underline):

```
gacattgtga tgacccagtc tcacaaattc atgtccactt cagtaggaga cagggtcagc atcacctgca aggccagtca ggatgtgaat actgctgtag cctggtatca acaaaaacca gggcaatctc ctaaactact gatttactgg gcatccaccc ggcacactgg agtccctgat cgcttcacag gcagtggatc tgggacagat tatacactca ccatcaaaag tgtgcaggct gaagacctga cactttatta ctgtcagcaa cactatatca ctccgtggac gttcggtgga ggcaccaagc tggaaatcaaa
```

The amino acid sequence of the VH Domain of DR5 mAb 2 (SEQ ID NO:18) is shown below (CDR$_H$ residues are shown underlined):

```
KVQLQQSGAE LVKPGASVKL SCKASGYTFT EYILHWVKQK

SGQGLEWIGW FYPGNNNIKY NEKFKDKATL TADKSSSIVY

MELSRLTSED SAVYFCARHE QGPGYFDYWG QGTTLTVSS
```

CDR$_H$1 of DR5 mAb 2:
(SEQ ID NO: 19)
GYTFTEYILH

CDR$_H$2 of DR5 mAb 2:
(SEQ ID NO: 20)
WFYPGNNNIKYNEKFKD

CDR$_H$3 of DR5 mAb 2:
(SEQ ID NO: 21)
HEQGPGYFDY

The VH Domain of DR5 mAb 2 is preferably encoded by a polynucleotide (SEQ ID NO:22) having the sequence shown below (polynucleotides encoding the CDR$_H$ residues are shown in underline):

```
aaggtccagc tgcagcagtc tggagctgaa ctggtgaaac ccggggcatc agtgaagctg tcctgcaagg cttctgggta caccttcact gagtatattt tacactgggt aaagcagaag tctggacagg gtcttgagtg gattgggtgg ttttatcctg gaaataataa tataaagtac aatgagaaat tcaaggacaa ggccacactg actgcggaca aatcctccag cacagtctat atggaactta gtagattgac atctgaagac tctgcggtct atttctgtgc aagacacgaa caaggaccag gttactttga ctactggggc caaggcacca ctctcacagt ctcctcc
```

2. Humanization of the Anti-Human DR5 Antibody DR5 mAb 2 to Form "hDR5 mAb 2"

The above-described murine anti-human DR5 antibody DR5 mAb 2 was humanized in order to demonstrate the capability of humanizing an anti-human DR5 antibody so as to decrease its antigenicity upon administration to a human recipient. The humanization yielded four humanized VL Domains designated herein as "hDR5 mAb 2 VL-2," "hDR5 mAb 2 VL-3," "hDR5 mAb 2 VL-4," and "hDR5 mAb 2 VL-5," and one humanized VH Domain, designated herein as "hDR5 mAb 2 VH-2." Any of the humanized VL Domains may be paired with the humanized VH Domain. Accordingly, any antibody comprising one of the humanized VL Domains paired with the humanized VH Domain is referred to generically as "hDR5 mAb 2," and particular combinations of humanized VL/VH Domains are referred to by reference to the VL Domain.

The amino acid sequence of the VL Domain of hDR5 mAb 2 VL-2 (SEQ ID NO:23) is shown below (CDR$_L$ residues are shown underlined):

```
DIQMTQSPSF LSASVGDRVT ITCKASQDVN TAVAWYQQKP

GKAPKLLIYW ASTRHTGVPS RFSGSGSGTD FTLTISSLQP

EDVATYYCQQ HYITPWTFGG GTKLEIK
``` hDR5 mAb 2 VL-2 is preferably encoded by a polynucleotide (SEQ ID NO:24) having the sequence shown below:

```
gatattcaga tgacccagag tccctcattt ctgtccgcct ccgtcggtga ccgcgtgact attacttgta aagcttctca ggatgtcaac accgccgtgg cttggtacca gcagaagccc ggtaaagcac ctaagctgct gatctattgg gccagcactc ggcacaccgg agtcccatct aggttctctg gcagtggatc agggacagac tttaccctga caattagctc cctgcagccc gaggatgtgg ctacttacta ttgtcagcag cactacatca ctccttggac cttcggcggg ggcacaaaac tggaaatcaa a
```

The amino acid sequence of the VL Domain of hDR5 mAb 2 VL-3 (SEQ ID NO:25) is shown below (CDR$_L$ residues are shown underlined):

```
DIQMTQSPSF LSASVGDRVT ITCRASQDVN TAVAWYQQKP

GKAPKLLIYW ASTRHTGVPD RFSGSGSGTD FTLTISSLQP

EDVATYYCQQ HYITPWTFGG GTKLEIK
``` hDR5 mAb 2 VL-3 is preferably encoded by a polynucleotide (SEQ ID NO:26) having the sequence shown below:

```
gatattcaga tgacccagag tccctcattt ctgtccgcct ccgtcggtga ccgcgtgact attacttgtc gggcttctca ggatgtcaac accgccgtgg cttggtacca gcagaagccc ggtaaagcac ctaagctgct gatctattgg gccagcactc ggcacaccgg agtcccagat aggttctctg gcagtggatc agggacagac tttaccctga caattagctc cctgcagccc gaggatgtgg ctacttacta ttgtcagcag cactacatca ctccttggac cttcggcggg ggcacaaaac tggaaatcaa a
```

The amino acid sequence of the VL Domain of hDR5 mAb 2 VL-4 (SEQ ID NO:27) is shown below (CDR$_L$ residues are shown underlined):

```
DIQMTQSPSF LSASVGDRVT ITCRASQDVN TAVAWYQQKP

GKAPKLLIYW ASTRHTGVPS RFSGSGSGTD FTLTISSLQP

EDIATYYCQQ HYITPWTFGG GTKLEIK
``` hDR5 mAb 2 VL-4 is preferably encoded by a polynucleotide (SEQ ID NO:28) having the sequence shown below:

```
gatattcaga tgacccagag tccctcattt ctgtccgcct ccgtcggtga ccgcgtgact attacttgtc gggcttctca ggatgtcaac accgccgtgg cttggtacca gcagaagccc ggtaaagcac ctaagctgct gatctattgg gccagcactc ggcacaccgg agtcccatct aggttctctg gcagtggatc agggacagac tttaccctga caattagctc cctgcagcca gaggatatcg ctacatacta ttgtcagcag cactacatca ctccttggac cttcggcggg ggcacaaaac tggaaatcaa a
```

The amino acid sequence of the VL Domain of hDR5 mAb 2 VL-5 (SEQ ID NO:29) is shown below (CDR$_L$ residues are shown underlined):

```
DIQMTQSPSF LSASVGDRVT ITCRASQDVN TAVAWYQQKP

GKAPKLLIYW ASTRHTGVPD RFSGSGSGTD FTLTISSLQP

EDIATYYCQQ HYITPWTFGG GTKLEIK
``` hDR5 mAb 2 VL-5 is preferably encoded by a polynucleotide (SEQ ID NO:30) having the sequence shown below:

```
gatattcaga tgacccagag tccctcattt ctgtccgcct ccgtcggtga ccgcgtgact attacttgtc gggcttctca ggatgtcaac accgccgtgg cttggtacca gcagaagccc ggtaaagcac ctaagctgct gatctattgg gccagcactc ggcacaccgg agtcccagat aggttctctg gcagtggatc agggacagac tttaccctga caattagctc cctgcagccc gaggatatcg ctacttacta ttgtcagcag cactacatca ctccttggac cttcggcggg ggcacaaaac tggaaatcaa a
```

The CDR$_L$1 of the VL Domain of hDR5 mAb 2 VL-3, hDR5 mAb 2 VL-4 and hDR5 mAb VL-5 has the amino acid sequence (SEQ ID NO: 165)
RASQDVNTAVA.

The amino acid sequence of the VH Domain of hDR5 mAb 2 VH-2 (SEQ ID NO:31) is shown below (CDR$_H$ residues are shown underlined):

```
QVQLVQSGAE VKKPGASVKV SCKASGYTFT EYILHWVRQA

PGQGLEWMGW FYPGNNNIKY NEKFKDRVTI TADKSTSTVY

MELSSLRSED TAVYYCARHE QGPGYFDYWG QGTLVTVSS
``` hDR5 mAb 2 VH-2 is preferably encoded by a polynucleotide (SEQ ID NO:32) having the sequence shown below:

```
caggtccagc tggtgcagag tggggcagag gtgaaaaagc caggggcatc agtgaaagtg tcttgtaaag catcaggtta tacatttact gagtacatcc tgcactgggt gcgacaggca ccaggacagg gactggaatg gatggggtgg ttctaccctg gcaacaacaa cattaagtac aacgagaagt ttaaagaccg ggtgaccatc acagcggata gtctaccag tacagtctat atggagctga gctccctgag aagcgaagac accgccgtct actattgcgc tcgccacgaa cagggtccag gttactttga ttattggggg cagggaactc tggtcacagt cagctcc
```

C. Additional Anti-Human DR5 Antibodies

In addition to the novel anti-human DR5 antibodies DR5 mAb 1 and DR5 mAb 2, a number of additional anti-human DR5 antibodies are known in the art including: drozitumab (designated herein as "DR5 mAb 3"), conatumumab (designated herein as "DR5 mAb 4"), tigatumumab (designated herein as "DR5 mAb 5"), LBY135-1 (designated herein as "DR5 mAb 6"), LBY135-2 (designated herein as "DR5 mAb 7") and KMTR2 (designated herein as "DR5 mAb 8"). It is specifically contemplated that the multivalent DR5-Binding Molecules of the instant invention may comprise the CDRs of the VL and/or VH Domains from one or more of DR5 mAb 1, DR5 mAb 2, hDR5 mAb2, DR5 mAb 3, DR5 mAb 4, DR5 mAb 5, DR5 mAb 6, DR5 mAb 7, and DR5 mAb 8. Alternatively, or optionally, the multivalent DR5-Binding Molecules of the instant invention may comprise at least one antigen-binding portion from one or more of DR5 mAb 1, DR5 mAb 2, hDR5 mAb2, DR5 mAb 3, DR5 mAb 4, DR5 mAb 5, DR5 mAb 6, DR5 mAb 7, and DR5 mAb 8. In one embodiment, the multivalent DR5-Binding Molecules of the instant invention comprise at least one antigen-binding portion from DR5 mAb 1 and/or DR5 mAb 2.

1. Drozitumab ("DR5 mAb 3")

The amino acid sequence of the VL Domain of drozitumab ("DR5 mAb 3") (SEQ ID NO:54) is shown below (CDR$_L$ residues are shown underlined):

```
SELTQDPAVS VALGQTVRIT CSGDSLRSYY ASWYQQKPG
QAPVLVIYGA NNRPSGIPDR FSGSSSGNTA SLTITGAQAE
DEADYYCNSA DSSGNHVVFG GGTKLTVLG
```

CDR$_L$1 of DR5 mAb 3:
(SEQ ID NO: 55)
SGDSLRSYYAS

CDR$_L$2 of DR5 mAb 3:
(SEQ ID NO: 56)
GANNRPS

CDR$_L$3 of DR5 mAb 3:
(SEQ ID NO: 57)
NSADSSGNHVV

The amino acid sequence of the VH Domain of drozitumab ("DR5 mAb 3") (SEQ ID NO:58) is shown below (CDR$_H$ residues are shown underlined):

```
EVQLVQSGGG VERPGGSLRL SCAASGFTFD DYAMSWVRQA
PGKGLEWVSG INWQGGSTGY ADSVKGRVTI SRDNAKNSLY
LQMNSLRAED TAVYYCAKIL GAGRGWYFDY WGKGTTVTVS
S
```

CDR$_H$1 of DR5 mAb 3:
(SEQ ID NO: 59)
GFTFDDYAMS

CDR$_H$2 of DR5 mAb 3:
(SEQ ID NO: 60)
INWQGGSTGYADSVKG

CDR$_H$3 of DR5 mAb 3:
(SEQ ID NO: 61)
ILGAGRGWYFDY

2. Conatumumab ("DR5 mAb 4")

The amino acid sequence of the VL Domain of conatumumab ("DR5 mAb 4") (SEQ ID NO:62) is shown below (CDR$_L$ residues are shown underlined):

```
EIVLTQSPGT LSLSPGERAT LSCRASQGIS RSYLAWYQQK
PGQAPSLLIY GASSRATGIP DRFSGSGSGT DFTLTISRLE
PEDFAVYYCQ QFGSSPWTFG QGTKVEIK
```

CDR$_L$1 of DR5 mAb 4:
(SEQ ID NO: 63)
RASQGISRSYLA

CDR$_L$2 of DR5 mAb 4:
(SEQ ID NO: 64)
GASSRAT

CDR$_L$3 of DR5 mAb 4:
(SEQ ID NO: 65)
QQFGSSPWT

The amino acid sequence of the VH Domain of conatumumab ("DR5 mAb 4") (SEQ ID NO:66) is shown below (CDR$_H$ residues are shown underlined):

```
QVQLQESGPG LVKPSQTLSL TCTVSGGSIS SGDYFWSWIR
QLPGKGLEWI GHIHNSGTTY YNPSLKSRVT ISVDTSKKQF
SLRLSSVTAA DTAVYYCARD RGGDYYYGMD VWGQGTTVTV
SS

CDR_H1 of DR5 mAb 4:
                                   (SEQ ID NO: 67)
GGSISSGDYFWS

CDR_H2 of DR5 mAb 4:
                                   (SEQ ID NO: 68)
HIHNSGTTYYNPSLKS

CDR_H3 of DR5 mAb 4:
                                   (SEQ ID NO: 69)
DRGGDYYYGMDV
```

3. Tigatumumab ("DR5 mAb 5")

The amino acid sequence of the VL Domain of tigatumumab ("DR5 mAb 5") (SEQ ID NO:70) is shown below (CDR_L residues are shown underlined):

```
DIQMTQSPSS LSASVGDRVT ITCKASQDVG TAVAWYQQKP

GKAPKLLIYW ASTRHTGVPS RFSGSGSGTD FTLTISSLQP

EDFATYYCQQ YSSYRTFGQG TKVEIK

CDR_L1 of DR5 mAb 5:
                                   (SEQ ID NO: 71)
KASQDVGTAVA

CDR_L2 of DR5 mAb 5:
                                   (SEQ ID NO: 72)
WASTRHT

CDR_L3 of DR5 mAb 5:
                                   (SEQ ID NO: 73)
QQYSSYRT
```

The amino acid sequence of the VH Domain of tigatumumab ("DR5 mAb 5") (SEQ ID NO:74) is shown below (CDR_H residues are shown underlined):

```
EBVQLVESGGG LVQPGGSLRL SCAASGFTFS SYVMSWVRQA

PGKGLEWVAT ISSGGSYTYY PDSVKGRFTI SRDNAKNTLY

LQMNSLRAED TAVYYCARRG DSMITTDYWG QGTLVTVSS

CDR_H1 of DR5 mAb 5:
                                   (SEQ ID NO: 75)
GFTFSSYVMS

CDR_H2 of DR5 mAb 5:
                                   (SEQ ID NO: 76)
TISSGGSYTYYPDSVKG

CDR_H3 of DR5 mAb 5:
                                   (SEQ ID NO: 77)
RGDSMITTDY
```

4. LBY135-1 ("DR5 mAb 6")

The amino acid sequence of the VL Domain of LBY135-1 ("DR5 mAb 6") (SEQ ID NO:78) is shown below (CDR_L residues are shown underlined):

```
DIAMTQSHKF MSTLVGDRVS ITCKASQDVN TAIAWYQQKP

GQSPKLLIYW ASTRHTGVPD RFYGSGSGTD YTLTISSMEA

EDAATYYCQQ WSSNPLTFGA GTKLELKRA

CDR_L1 of DR5 mAb 6:
                                   (SEQ ID NO: 79)
QDVNTAIA

CDR_L2 of DR5 mAb 6:
                                   (SEQ ID NO: 80)
WASTRHT

CDR_L3 of DR5 mAb 6:
                                   (SEQ ID NO: 81)
QQWSSNPLT
```

The amino acid sequence of the VH Domain of LBY135-1 ("DR5 mAb 6") (SEQ ID NO:82) is shown below (CDR_H residues are shown underlined):

```
KVQLQQSGAE LVKPGASVKL SCKASGYTFT DYTIHWVKQR

SGQGLEWIGW FYPGGGYIKY NEKFKDRATL TADKSSNTVY

MELSRLTSEG SAVYFCARHE EGIYFDYWGQ GTTLTVSS

CDR_H1 of DR5 mAb 6:
                                   (SEQ ID NO: 83)
GYTFTDYTIH

CDR_H2 of DR5 mAb 6:
                                   (SEQ ID NO: 84)
WFYPGGGYIKYNEKFKD

CDR_H3 of DR5 mAb 6:
                                   (SEQ ID NO: 85)
HEEGIYFDY
```

5. LBY135-2 ("DR5 mAb 7")

The amino acid sequence of the VL Domain of LBY135-2 ("DR5 mAb 7") (SEQ ID NO:86) is shown below (CDR_L residues are shown underlined):

```
DIVMTQSHKF MSTSVGDRVS ITCKASQDVN TAIAWYQQKP

GQSPKLLIYW ASTRHTGVPD RFTGSGSGTD YTLTISSVQA

EDLALYYCQQ HYTTPFTFGS GTKL

CDR_L1 of DR5 mAb 7:
                                   (SEQ ID NO: 87)
KASQDVNTAIA

CDR_L2 of DR5 mAb 7:
                                   (SEQ ID NO: 88)
WASTRHT

CDR_L3 of DR5 mAb 7:
                                   (SEQ ID NO: 89)
QQHYTTPFT
```

The amino acid sequence of the VH Domain of LBY135-2 ("DR5 mAb 7") (SEQ ID NO:90) is shown below (CDR_H residues are shown underlined):

```
KVQLQQSGAE LVKPGASVKL SCKASGYTFT DYTIHWVKQR

SGQGLEWIGW FYPGGGYIKY NEKFKDRATL TADKSSNTVY

MELSRLTSED SAVYFCARHE EGIYFDYWGQ GTTLTVSS

CDR_H1 of DR5 mAb 7:
                                   (SEQ ID NO: 91)
GYTFTDYTIH

CDR_H2 of DR5 mAb 7:
                                   (SEQ ID NO: 92)
WFYPGGGYIKYNEKFKD
```

-continued

CDR$_H$3 of DR5 mAb 7:

(SEQ ID NO: 93)

HEEGIYFDY

6. KMTR2 ("DR5 mAb 8")

The amino acid sequence of the VL Domain of KMTR2 ("DR5 mAb 8") (SEQ ID NO:94) is shown below (CDR$_L$ residues are shown underlined):

```
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ RSNWPLTFGG GTKVEIKR
```

CDR$_L$1 of DR5 mAb 8:

(SEQ ID NO: 95)

RASQSVSSYLA

CDR$_L$2 of DR5 mAb 8:

(SEQ ID NO: 96)

DASNRAT

CDR$_L$3 of DR5 mAb 8:

(SEQ ID NO: 97)

QQRSNWPLT

The amino acid sequence of the VH Domain of KMTR2 ("DR5 mAb 8") (SEQ ID NO:98) is shown below (CDR$_H$ residues are shown underlined):

```
QVQLVQSGAE MKKPGASVKV SCKTSGYTFT NYKINWVRQA

PGQGLEWMGW MNPDTDSTGY PQKFQGRVTM TRNTSISTAY

MELSSLRSED TAVYYCARSY GSGSYYRDYY YGMDVWGQGT

TVTVSS
```

CDR$_H$1 of DR5 mAb 8:

(SEQ ID NO: 99)

GYTFTNYKIN

CDR$_H$2 of DR5 mAb 8:

(SEQ ID NO: 100)

WMNPDTDSTGYPQKFQG

CDR$_H$3 of DR5 mAb 8:

(SEQ ID NO: 101)

SYGSGSYYRDYYYGMDV

D. Multivalent DR5-Binding Molecules Having an Engineered Fc Region

In traditional immune function, the interaction of antibody-antigen complexes with cells of the immune system results in a wide array of responses, ranging from effector functions such as antibody dependent cytotoxicity, mast cell degranulation, and phagocytosis to immunomodulatory signals such as regulating lymphocyte proliferation and antibody secretion. All of these interactions are initiated through the binding of the Fc Region of antibodies or immune complexes to specialized cell surface receptors on hematopoietic cells. The diversity of cellular responses triggered by antibodies and immune complexes results from the structural heterogeneity of the three Fc receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors; FcγRIIB (CD32B) is an inhibiting (i.e., immune system dampening) receptor. The amino acid sequence of an exemplary IgG1 Fc Region (SEQ ID NO:1) is presented above.

Modification of the Fc Region normally leads to an altered phenotype, for example altered serum half-life, altered stability, altered susceptibility to cellular enzymes or altered effector function. It may be desirable to modify the antibody of the invention with respect to effector function, so as to enhance the effectiveness of the antibody in treating cancer, for example. Reduction or elimination of effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor specific B cells with low levels of FcγRIIB (e.g., non-Hodgkins lymphoma, CLL, and Burkitt's lymphoma). In said embodiments, molecules of the invention with conferred or altered effector function activity are useful for the treatment and/or prevention of a disease, disorder or infection where an enhanced efficacy of effector function activity is desired.

In certain embodiments, the multivalent DR5-Binding Molecules of the present invention comprise an Fc Region that possesses one or more modifications (e.g., substitutions, deletions, or insertions) to the sequence of amino acids of a wild-type Fc Region (SEQ ID NO:1), which reduce the affinity and avidity of the Fc Region and, thus, the molecule of the invention, for one or more FcγR receptors. In other embodiments, the multivalent DR5-Binding Molecules of the invention comprise an Fc Region that possesses one or more modifications to the amino acids of the wild-type Fc Region, which increase the affinity and avidity of the Fc Region and, thus, the molecule of the invention, for one or more FcγR receptors. In other embodiments, the multivalent DR5-Binding Molecules comprise a variant Fc Region wherein said variant confers or mediates increased ADCC activity and/or an increased binding to FcγRIIA, relative to a molecule comprising no Fc Region or comprising a wild-type Fc Region. In alternate embodiments, the molecules comprise a variant Fc Region wherein said variant confers or mediates decreased ADCC activity (or other effector function) and/or an increased binding to FcγRIIB, relative to a molecule comprising no Fc Region or comprising a wild-type Fc Region. In some embodiments, the invention encompasses multivalent DR5-Binding Molecules comprising a variant Fc Region, which variant Fc Region does not show a detectable binding to any FcγR, relative to a comparable molecule comprising the wild-type Fc Region. In other embodiments, the invention encompasses multivalent DR5-Binding Molecules comprising a variant Fc Region, which variant Fc Region only binds a single FcγR, preferably one of FcγRIIA, FcγRIIB, or FcγRIIIA Alternatively, the multivalent DR5-Binding Molecules of the invention comprise a Fc Region which inherently exhibits reduce affinity and/or affidity to FcγRs and/or reduced ADCC activity (relative to the binding exhibited by the wild-type IgG1 Fc Region is utilized, e.g., an Fc Region from IgG2 (SEQ ID NO:154) or IgG4 (SEQ ID NO:103). Any such change in affinity and/or avidity is preferably assessed by measuring in vitro the extent of detectable binding to the FcγR or FcγR-related activity in cells that express low levels of the FcγR when binding activity of the parent molecule (without the modified Fc Region) cannot be detected in the cells. In other embodiments, the modified molecule exhibits detectable binding in cells which express non-FcγR receptor target antigens at a density of 30,000 to 20,000 molecules/cell, at a density of 20,000 to 10,000 molecules/cell, at a density of 10,000 to 5,000 molecules/cell, at a density of 5,000 to 1,000 molecules/cell, at a density of 1,000 to 200 molecules/cell or at a density of 200 molecules/cell or less (but at least 10, 50, 100 or 150 molecules/cell).

The multivalent DR5-Binding Molecules of the present invention may comprise altered affinities for an activating and/or inhibitory Fcγ receptor. In one embodiment, the multivalent DR5-Binding Molecule comprises a variant Fc Region that has increased affinity for FcγRIIB and decreased affinity for FcγRIIIA and/or FcγRIIA, relative to a comparable molecule with a wild-type Fc Region. In another embodiment, the multivalent DR5-Binding Molecule of the present invention comprise a variant Fc Region, which has decreased affinity for FcγRIIB and increased affinity for FcγRIIIA and/or FcγRIIA, relative to a comparable molecule with a wild-type Fc Region. In yet another embodiment, the multivalent DR5-Binding Molecules of the present invention comprise a variant Fc Region that has decreased affinity for FcγRIIB and decreased affinity for FcγRIIIA and/or FcγRIIA, relative to a comparable molecule with a wild-type Fc Region. In still another embodiment, the multivalent DR5-Binding Molecules of the present invention comprise a variant Fc Region, which has unchanged affinity for FcγRIIB and decreased (or increased) affinity for FcγRIIIA and/or FcγRIIA, relative to a comparable molecule with a wild-type Fc Region.

In certain embodiments, the multivalent DR5-Binding Molecules of the present invention comprise a variant Fc Region having an altered affinity for FcγRIIIA and/or FcγRIIA such that the immunoglobulin has an enhanced effector function, e.g., antibody dependent cell mediated cytotoxicity. Non-limiting examples of effector cell functions include antibody dependent cell mediated cytotoxicity (ADCC), antibody dependent phagocytosis, phagocytosis, opsonization, opsonophagocytosis, cell binding, rosetting, C1q binding, and complement dependent cell mediated cytotoxicity.

In a preferred embodiment, the alteration in affinity or effector function is at least 2-fold, preferably at least 4-fold, at least 5-fold, at least 6-fold, at least 7-fold, at least 8-fold, at least 9-fold, at least 10-fold, at least 50-fold, or at least 100-fold, relative to a comparable molecule comprising a wild-type Fc Region. In other embodiments of the invention, the variant Fc Region immunospecifically binds one or more FcRs with at least 65%, preferably at least 70%, 75%, 80%, 85%, 90%, 95%, 100%, 125%, 150%, 175%, 200%, 225%, or 250% greater affinity relative to a molecule comprising a wild-type Fc Region. Such measurements can be in vivo or in vitro assays, and in a preferred embodiment are in vitro assays such as ELISA or surface plasmon resonance assays.

In different embodiments, the multivalent DR5-Binding Molecules of the present invention comprise a variant Fc Region that agonizes at least one activity of an FcγR receptor, or antagonizes at least one activity of an FcγR receptor. In a preferred embodiment, the molecules comprise a variant Fc Region that antagonizes one or more activities of FcγRIIB, for example, B cell receptor-mediated signaling, activation of B cells, B cell proliferation, antibody production, intracellular calcium influx of B cells, cell cycle progression, FcγRIIB-mediated inhibition of FcεRI signaling, phosphorylation of FcγRIIB, SHIP recruitment, SHIP phosphorylation and association with Shc, or activity of one or more downstream molecules (e.g., MAP kinase, JNK, p38, or Akt) in the FcγRIIB signal transduction pathway. In another embodiment, the multivalent DR5-Binding Molecules of the present invention comprise a variant Fc Region that agonizes one or more activities of FcεRI, for example, mast cell activation, calcium mobilization, degranulation, cytokine production, or serotonin release.

In certain embodiments, the molecules comprise an Fc Region comprising regions from two or more IgG isotypes (e.g., IgG1, IgG2, IgG3 and IgG4). The various IgG isotypes exhibit differing physical and functional properties including serum half-life, complement fixation, FcγR binding affinities and effector function activities (e.g., ADCC, CDC, etc.) due to differences in the amino acid sequences of their hinge and/or Fc Regions, for example as described in Flesch and Neppert (1999) J. Clin. Lab. Anal. 14:141-156; Chappel et al. (1993) J. Biol. Chem. 33:25124-25131; Chappel et al. (1991) Proc. Natl. Acad. Sci. (U.S.A.) 88:9036-9040; or Bruggemann et al. (1987) J. Exp. Med 166:1351-1361. This type of variant Fc Region may be used alone, or in combination with an amino acid modification, to affect Fc-mediated effector function and/or binding activity. In combination, the amino acid modification and IgG hinge/Fc Region may display similar functionality (e.g., increased affinity for FcγRIIA) and may act additively or, more preferably, synergistically to modify the effector functionality in the molecule of the invention, relative to a molecule of the invention comprising a wild-type Fc Region. In other embodiments, the amino acid modification and IgG Fc Region may display opposite functionality (e.g., increased and decreased affinity for FcγRIIA, respectively) and may act to selectively temper or reduce a specific functionality in the molecule of the invention, relative to a molecule of the invention not comprising an Fc Region or comprising a wild-type Fc Region of the same isotype.

In a preferred specific embodiment, the multivalent DR5-Binding Molecules of the present invention comprise a variant Fc Region, wherein said variant Fc Region comprises at least one amino acid modification relative to a wild-type Fc Region, such that said molecule has an altered affinity for an FcR, provided that said variant Fc Region does not have a substitution at positions that make a direct contact with FcγR based on crystallographic and structural analysis of Fc-FcR interactions such as those disclosed by Sondermann et al. (2000) Nature 406:267-73. Examples of positions within the Fc Region that make a direct contact with FcγR are amino acid residues 234-239 (hinge region), amino acid residues 265-269 (B/C loop), amino acid residues 297-299 (C'/E loop), and amino acid residues 327-332 (F/G loop). In some embodiments, the molecules of the invention comprise variant Fc Regions comprise modification of at least one residue that does not make a direct contact with an FcγR based on structural and crystallographic analysis, e.g., is not within the Fc-FcγR binding site.

Variant Fc Regions are well known in the art, and any known Fc variant may be used in the present invention to confer or modify the effector function exhibited by a molecule of the invention comprising an Fc Region (or portion thereof) as functionally assayed, e.g., in an NK dependent or macrophage dependent assay. For example, Fc Region variants identified as altering effector function are disclosed in the Antibody Engineering Technology Art, and any suitable variant disclosed therein may be used in the present molecules.

In certain embodiments, the multivalent DR5-Binding Molecules of the present invention comprise a variant Fc Region, having one or more amino acid modifications in one or more regions, which modification(s) alter (relative to a wild-type Fc Region) the Ratio of Affinities of the variant Fc Region to an activating FcγR (such as FcγRIIA or FcγRIIIA) relative to an inhibiting FcγR (such as FcγRIIB):

Ratio of Affinities=

$$\frac{\text{Wild-Type to Variant Change in Affinity to } Fc\gamma R_{Activating}}{\text{Wild-Type to Variant Change in Affinity to } Fc\gamma R_{Inhibiting}}$$

Particularly preferred are multivalent DR5-Binding Molecules of the present invention that possess a variant Fc Region (relative to the wild-type Fc Region) in which the Fc variant has a Ratio of Affinities greater than 1. Such molecules have particular use in providing a therapeutic or prophylactic treatment of a disease, disorder, or infection, or the amelioration of a symptom thereof, where an enhanced efficacy of effector cell function (e.g., ADCC) mediated by FcγR is desired, e.g., cancer or infectious disease. In contrast, an Fc variant having a Ratio of Affinities less than 1 mediates decreased efficacy of effector cell function. Table 1 lists exemplary single, double, triple, quadruple and quintuple mutations by whether their Ratio of Affinities is greater than or less than 1.

TABLE 1

Exemplary Single and Multiple Mutations Listed by Ratio of Affinities

| Single | Double | Triple | Quadruple | Quintuple |
|---|---|---|---|---|
| Ratio of Affinities > 1 | | | | |
| F243L | F243L & R292P | F243L, P247L & N421K | L234F, F243L, R292P & Y300L | L235V, F243L, R292P, Y300L & P396L |
| D270E | F243L & Y300L | F243L, R292P & Y300L | L235I, F243L, R292P & Y300L | |
| R292G | F243L & P396L | F243L, R292P & V305I | L235Q, F243L, R292P & Y300L | L235P, F243L, Y300L & P396L |
| R292P | D270E & P396L | F243L, R292P & P396L | F243L, P247L, D270E & N421K | R292P, Y300L & P396L |
|  | R292P & Y300L | F243L, Y300L & P396L | F243L, R255L, D270E & P396L | F243L, R292P, V305I, & P396L |
|  | R292P & V305I | P247L, D270E & N421K | F243L, D270E, G316D & R416G | |
|  | R292P & P396L | R255L, D270E & P396L | F243L, D270E, K392T & P396L | |
|  | Y300L & P396L | D270E, G316D & R416G | F243L, D270E, P396L & Q419H | |
|  | P396L & Q419H | D270E, K392T & P396L | F243L, R292P, Y300L, & P396L | |
|  |  | D270E, P396L & Q419H | F243L, R292P, V305I & P396L | |
|  |  | V284M, R292L & K370N | P247L, D270E, Y300L & N421K | |
|  |  | R292P, Y300L & P396L | R255L, D270E, R292G & P396L | |
|  |  |  | R255L, D270E, Y300L & P396L | |
|  |  |  | D270E, G316D, P396L & R416G | |
| Ratio of Affinities < 1 | | | | |
| Y300L | F243L & P396L | F243L, R292P & V305I | | |
| P396L | P247L & N421K | | | |
|  | R255L & P396L | | | |
|  | R292P & V305I | | | |
|  | K392T & P396L | | | |
|  | P396L & Q419H | | | |

In a specific embodiment, in variant Fc Regions, any amino acid modifications (e.g., substitutions) at any of positions 235, 240, 241, 243, 244, 247, 262, 263, 269, 298, 328, or 330 and preferably one or more of the following residues: A240, I240, L241, L243, H244, N298, I328 or V330. In a different specific embodiment, in variant Fc Regions, any amino acid modifications (e.g., substitutions) at any of positions 268, 269, 270, 272, 276, 278, 283, 285, 286, 289, 292, 293, 301, 303, 305, 307, 309, 331, 333, 334, 335, 337, 338, 340, 360, 373, 376, 416, 419, 430, 434, 435, 437, 438 or 439 and preferably one or more of the following residues: H280, Q280, Y280, G290, 5290, T290, Y290, N294, K295, P296, D298, N298, P298, V298, I300 or L300.

In a preferred embodiment, in variant Fc Regions that bind an FcγR with an altered affinity, any amino acid modifications (e.g., substitutions) at any of positions 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438 or 439. Preferably, the variant Fc Region has any of the following residues: A256, N268, Q272, D286, Q286, S286, A290, S290, A298, M301, A312, E320, M320, Q320, R320, E322, A326, D326, E326, N326, S326, K330, T339, A333, A334, E334, H334, L334, M334, Q334, V334, K335, Q335, A359, A360 or A430.

In a different embodiment, in variant Fc Regions that bind an FcγR (via its Fc Region) with a reduced affinity, any amino acid modifications (e.g., substitutions) at any of positions 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438, or 439.

In a different embodiment, in variant Fc Regions that bind an FcγR (via its Fc Region) with an enhanced affinity, any amino acid modifications (e.g., substitutions) at any of positions 280, 283, 285, 286, 290, 294, 295, 298, 300, 301, 305, 307, 309, 312, 315, 331, 333, 334, 337, 340, 360, 378, 398, or 430. In a different embodiment, in variant Fc Regions that binds FcγRIIA with an enhanced affinity, any of the following residues: A255, A256, A258, A267, A268, N268, A272, Q272, A276, A280, A283, A285, A286, D286, Q286, 5286, A290, 5290, M301, E320, M320, Q320, R320, E322, A326, D326, E326, 5326, K330, A331, Q335, A337 or A430.

Preferred variants include one or more modifications at any of positions: 228, 230, 231, 232, 233, 234, 235, 239, 240, 241, 243, 244, 245, 247, 262, 263, 264, 265, 266, 271, 273, 275, 281, 284, 291, 296, 297, 298, 299, 302, 304, 305, 313, 323, 325, 326, 328, 330 or 332.

Particularly preferred variants include one or more modifications selected from groups A-AI:

| | |
|---|---|
| A | 228E, 228K, 228Y or 228G; |
| B | 230A, 230E, 230Y or 230G; |
| C | 231E, 231K, 231Y, 231P or 231G; |
| D | 232E, 232K, 232Y, 232G; |
| E | 233D; |
| F | 234I or 234F; |
| G | 235D, 235Q, 235P, 235I or 235V; |
| H | 239D, 239E, 239N or 239Q; |
| I | 240A, 240I, 240M or 240T; |
| J | 243R, 243, 243Y, 243L, 243Q, 243W, 243H or 243I; |
| K | 244H; |
| L | 245A; |
| M | 247G, 247V or 247L; |
| N | 262A, 262E, 262I, 262T, 262E or 262F; |
| O | 263A, 263I, 263M or 263T; |
| P | 264F, 264E, 264R, 264I, 264A, 264T or 264W; |
| Q | 265F, 265Y, 265H, 265I, 265L, 265T, 265V, 265N or 265Q; |
| R | 266A, 266I, 266M or 266T; |

| | |
|---|---|
| S | 271D, 271E, 271N, 271Q, 271K, 271R, 271S, 271T, 271H, 271A, 271V, 271L, 271I, 271F, 271M, 271Y, 271W or 271G; |
| T | 273I; |
| U | 275L or 275W; |
| V | 281D, 281K, 281Y or 281P; |
| W | 284E, 284N, 284T, 284L, 284Y or 284M; |
| X | 291D, 291E, 291Q, 291T, 291H, 291I or 291G; |
| Y | 299A, 299D, 299E, 299F, 299G, 299H, 299I, 299K, 299L, 299M, 299N, 299P, 299Q, 299R, 299S, 299V, 299W or 299Y; |
| Z | 302I; |
| AA | 304D, 304N, 304T, 304H or 304L |
| AB | 305I; |
| AC | 313F; |
| AD | 323I; |
| AE | 325A, 325D, 325E, 325G, 325H, 325I, 325L, 325K, 325R, 325S, 325F, 325M, 325T, 325V, 325Y, 325W or 325P; |
| AF | 328D, 328Q, 328K, 328R, 328S, 328T, 328V, 328I, 328Y, 328W, 328P, 328G, 328A, 328E, 328F, 328H, 328M or 328N; |
| AG | 330L, 330Y, 330I or 330V; |
| AH | 332A, 332D, 332E, 332H, 332N, 332Q, 332T, 332K, 332R, 332S, 332V, 332L, 332F, 332M, 332W, 332P, 332G or 332Y; and |
| AT | 336E, 336K or 336Y |

Still more particularly preferred variants include one or more modifications selected from Groups 1-105:

| Group | Variant |
|---|---|
| 1 | A330L/I332E |
| 2 | D265F/N297E/I332E |
| 3 | D265Y/N297D/I332E |
| 4 | D265Y/N297D/T299L/I332E |
| 5 | F241E/F243Q/V262T/V264F |
| 6 | F241E/F243Q/V262T/V264E/I332E |
| 7 | F241E/F243R/V262E/V264R |
| 8 | F241E/F243R/V262E/V264R/I332E |
| 9 | F241E/F243Y/V262T/V264R |
| 10 | F241E/F243Y/V262T/V264R/I332E |
| 11 | F241L/F243L/V262I/V264I |
| 12 | F241L/V262I |
| 13 | F241R/F243Q/V262T/V264R |
| 14 | F241R/F243Q/V262T/V264R/I332E |
| 15 | F241W/F243W/V262A/V264A |
| 16 | F241Y/F243Y/V262T/V264T |
| 17 | F241Y/F243Y/V262T/V264T/N297D/I332E |
| 18 | F243L/V262I/V264W |
| 19 | P243L/V264I |
| 20 | L328D/I332E |
| 21 | L328E/I332E |
| 22 | L328H/I332E |
| 23 | L328I/I332E |
| 24 | L328M/I332E |
| 25 | L328N/I332E |
| 26 | L328Q/I332E |
| 27 | L328T/I332E |
| 28 | L328V/I332E |
| 29 | N297D/A330Y/I332E |
| 30 | N297D/I332E |
| 31 | N297D/I332E/S239D/A330L |
| 32 | N297D/S298A/A330Y/I332E |
| 33 | N297D/T299L/I332E |
| 34 | N297D/T299F/I332E/N297D/T299H/I332E |
| 35 | N297D/T299I/I332E |
| 36 | N297D/T299L/I332E |
| 37 | N297D/T299V/I332E |
| 38 | N297E/I332E |
| 39 | N297S/I332E |
| 40 | P230A/E233D/I332E |
| 41 | P244H/P245A/P247V |
| 42 | S239D/A330L/I332E |
| 43 | S239D/A330Y/I332E |
| 44 | S239D/A330Y/I332E/K326E |
| 45 | S239D/A330Y/I332E/K326T |
| 46 | S239D/A330Y/I332E/L234I |
| 47 | S239D/A330Y/I332E/L235D |
| 48 | S239D/A330Y/I332E/V240I |
| 49 | S239D/A330Y/I332E/V264T |

| Group | Variant |
|---|---|
| 50 | S239D/A330Y/I332E/V266I |
| 51 | S239D/D265F/N297D/I332E |
| 52 | S239D/D265H/N297D/I332E |
| 53 | S239D/D265I/N297D/I332E |
| 54 | S239D/D265L/N297D/I332E |
| 55 | S239D/D265T/N297D/I332E |
| 56 | S239D/D265V/N297D/I332E |
| 57 | S239D/D265Y/N297D/I332E |
| 58 | S239D/I332D |
| 59 | S239D/I332E |
| 60 | S239D/I332E/A330I |
| 61 | S239D/I332N |
| 62 | S239D/I332Q |
| 63 | S239D/N297D/I332E |
| 64 | S239D/N297D/I332E/A330Y |
| 65 | S239D/N297D/I332E/A330Y/F241S/F243H/V262T/V264T |
| 66 | S239D/N297D/I332E/K326E |
| 67 | S239D/N297D/I332E/L235D |
| 68 | S239D/S298A/I332E |
| 69 | S239D/V264I/A330L/I332E |
| 70 | S239D/V264I/I332E |
| 71 | S239D/V264I/S298A/I332E |
| 72 | S239E/D265N |
| 73 | S239E/D265Q |
| 74 | S239E/I332D |
| 75 | S239E/I332E |
| 76 | S239E/I332N |
| 77 | S239E/I332Q |
| 78 | S239E/N297D/I332E |
| 79 | S239E/V264I/A330Y/I332 E |
| 80 | S239E/V264I/I332 E |
| 81 | S239E/V264I/S298A/A330Y/I332E |
| 82 | S239N/A330L/I332E |
| 83 | S239N/A330Y/I332E |
| 84 | S239N/I332D |
| 85 | S239N/I332E |
| 86 | S239N/I332N |
| 87 | S239N/I332Q |
| 88 | S239N1S298A/I332E |
| 89 | S239Q/I332D |
| 90 | S239Q/I332E |
| 91 | S239Q/I332N |
| 92 | S239Q/I332Q |
| 93 | S239Q/V264I/I332E |
| 94 | S298A/I332E |
| 95 | V264E/N297D/I332E |
| 96 | V264I/A330L/I332E |
| 97 | V264I/A330Y/I332E |
| 98 | V264I/I332E |
| 99 | V264I/S298A/I332E |
| 100 | Y296D/N297D/I332E |
| 101 | Y296E/N297D/I332E |
| 102 | Y296H/N297D/I332E |
| 103 | Y296N/N297D/I332E |
| 104 | Y296Q/N297I/I332E |
| 105 | Y296T/N297D/I332E. |

In one embodiment, a multivalent DR5-Binding Molecule of the invention will comprise a variant Fc Region having at least one modification in the Fc Region. In certain embodiments, the variant Fc Region comprises at least one substitution selected from the group consisting of L235V, F243L, R292P, Y300L, V305I, and P396L, wherein said numbering is that of the EU index as in Kabat.

In a specific embodiment, the variant Fc Region comprises:

A) at least one substitution selected from the group consisting of F243L, R292P, Y300L, V305I, and P396L;

(B) at least two substitutions selected from the group consisting of:
(1) F243L and P396L;
(2) F243L and R292P; and
(3) R292P and V305I;

(C) at least three substitutions selected from the group consisting of:
(1) F243L, R292P and Y300L;
(2) F243L, R292P and V305I;
(3) F243L, R292P and P396L; and
(4) R292P, V305I and P396L;

(D) at least four substitutions selected from the group consisting of:
(1) F243L, R292P, Y300L and P396L; and
(2) F243L, R292P, V305I and P396L; or (E) at least the five substitutions selected from the group consisting of:
(1) F243L, R292P, Y300L, V305I and P396L; and
(2) L235V, F243L, R292P, Y300L and P396L.

In another specific embodiment, the variant Fc Region comprises substitutions of:
(A) F243L, R292P, and Y300L;
(B) L235V, F243L, R292P, Y300L, and P396L; or
(C) F243L, R292P, Y300L, V305I, and P396L.

In other embodiments, the invention encompasses the use of any Fc variant known in the art, such as those disclosed in Jefferis, B. J. et al. (2002) "*Interaction Sites On Human IgG-Fc For FcgammaR: Current Models,*" Immunol. Lett. 82:57-65; Presta, L. G. et al. (2002) "*Engineering Therapeutic Antibodies For Improved Function,*" Biochem. Soc. Trans. 30:487-90; Idusogie, E. E. et al. (2001) "*Engineered Antibodies With Increased Activity To Recruit Complement,*" J. Immunol. 166:2571-75; Shields, R. L. et al. (2001) "*High Resolution Mapping Of The Binding Site On Human IgG1 For Fc Gamma RI, Fc Gamma RII, Fc Gamma RIII, And FcRn And Design Of IgG1 Variants With Improved Binding To The Fc gamma R,*" J. Biol. Chem. 276:6591-6604; Idusogie, E. E. et al. (2000) "*Mapping Of The C1q Binding Site On Rituxan, A Chimeric Antibody With A Human IgG Fc,*" J. Immunol. 164:4178-84; Reddy, M. P. et al. (2000) "*Elimination Of Fc Receptor-Dependent Effector Functions Of A Modified IgG4 Monoclonal Antibody To Human CD4,*" J. Immunol. 164:1925-1933; Xu, D. et al. (2000) "*In Vitro Characterization of Five Humanized OKT3 Effector Function Variant Antibodies,*" Cell. Immunol. 200:16-26; Armour, K. L. et al. (1999) "*Recombinant human IgG Molecules Lacking Fcgamma Receptor I Binding And Monocyte Triggering Activities,*" Eur. J. Immunol. 29:2613-24; Jefferis, R. et al. (1996) "*Modulation Of Fc(Gamma)R And Human Complement Activation By IgG3-Core Oligosaccharide Interactions,*" Immunol. Lett. 54:101-04; Lund, J. et al. (1996) "*Multiple Interactions Of IgG With Its Core Oligosaccharide Can Modulate Recognition By Complement And Human Fc Gamma Receptor I And Influence The Synthesis Of Its Oligosaccharide Chains,*" J. Immunol. 157:4963-4969; Hutchins et al. (1995) "*Improved Biodistribution, Tumor Targeting, And Reduced Immunogenicity In Mice With A Gamma 4 Variant Of Campath-1H,*" Proc. Natl. Acad. Sci. (U.S.A.) 92:11980-84; Jefferis, R. et al. (1995) "*Recognition Sites On Human IgG For Fc Gamma Receptors: The Role Of Glycosylation,*" Immunol. Lett. 44:111-17; Lund, J. et al. (1995) "*Oligosaccharide-Protein Interactions In IgG Can Modulate Recognition By Fc Gamma Receptors,*" FASEB J. 9:115-19; Alegre, M. L. et al. (1994) "*A Non-Activating "Humanized" Anti-CD3 Monoclonal Antibody Retains Immunosuppressive Properties In Vivo,*" Transplantation 57:1537-1543; Lund et al. (1992) "*Multiple Binding Sites On The CH2 Domain Of IgG For Mouse Fc Gamma R*11," Mol. Immunol. 29:53-59; Lund et al. (1991) "*Human Fc Gamma RI And Fc Gamma RII Interact With Distinct But Overlapping Sites On Human IgG,*" J. Immunol. 147:2657-2662; Duncan, A. R. et al. (1988) "*Localization Of The Binding Site For The Human High-Affinity Fc Receptor On IgG,*" Nature 332:563-564; U.S. Pat. Nos. 5,624,821; 5,885,573; 6,194,551; 7,276,586; and 7,317,091; and PCT Publications WO 00/42072 and PCT WO 99/58572.

In some embodiments, the molecules of the invention further comprise one or more glycosylation sites, so that one or more carbohydrate moieties are covalently attached to the molecule. Preferably, the molecules of the invention with one or more glycosylation sites and/or one or more modifications in the Fc Region confer or have an enhanced antibody mediated effector function, e.g., enhanced ADCC activity, compared to to the unmodified molecule. In some embodiments, the invention further comprises molecules comprising one or more modifications of amino acids that are directly or indirectly known to interact with a carbohydrate moiety of the Fc Region, including but not limited to amino acids at positions 241, 243, 244, 245, 245, 249, 256, 258, 260, 262, 264, 265, 296, 299, and 301. Amino acids that directly or indirectly interact with a carbohydrate moiety of an Fc Region are known in the art, see, e.g., Jefferis et al., 1995 *Immunology Letters,* 44: 111-7, which is incorporated herein by reference in its entirety.

In another embodiment, the invention encompasses molecules that have been modified by introducing one or more glycosylation sites into one or more sites of the molecules, preferably without altering the functionality of the molecules, e.g., binding activity to target antigen or FcγR. Glycosylation sites may be introduced into the variable and/or constant region of the molecules of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., senile, threonine. The molecules of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention is the amino acid sequence: Asn-X-Thr/Ser, wherein X may be any amino acid and Thr/Ser indicates a threonine or a serine. Such a site or sites may be introduced into a molecule of the invention using methods well known in the art to which this invention pertains (see for example, IN VITRO MUTAGENESIS, RECOMBINANT DNA: A SHORT COURSE, J. D. Watson, et al. W. H. Freeman and Company, New York, 1983, chapter 8, pp. 106-116, which is incorporated herein by reference in its entirety. An exemplary method for introducing a glycosylation site into a molecule of the invention may comprise: modifying or mutating an amino acid sequence of the molecule so that the desired Asn-X-Thr/Ser sequence is obtained.

In some embodiments, the invention encompasses methods of modifying the carbohydrate content of a molecule of the invention by adding or deleting a glycosylation site. Methods for modifying the carbohydrate content of antibodies (and molecules comprising antibody domains, e.g., Fc Domain) are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety. In other embodiments, the invention encompasses methods of modifying the carbohydrate content of a molecule of the invention by deleting one or more endogenous carbohydrate moieties of the molecule. In a specific embodiment, the invention encompasses shifting the glycosylation site of the Fc Region of an antibody, by modifying positions adjacent to 297. In a specific embodiment, the invention encompasses modifying position 296 so that position 296 and not position 297 is glycosylated.

Effector function can also be modified by techniques such as by introducing one or more cysteine residues into the Fc Region, thereby allowing interchain disulfide bond formation in this region to occur, resulting in the generation of a homodimeric antibody that may have improved internalization capability and/or increased complement-mediated cell killing and ADCC (Caron, P. C. et al. (1992) "*Engineered Humanized Dimeric Forms Of IgG Are More Effective Antibodies*," J. Exp. Med. 176:1191-1195; Shopes, B. (1992) "*A Genetically Engineered Human IgG Mutant With Enhanced Cytolytic Activity*," J. Immunol. 148(9):2918-2922. Homodimeric antibodies with enhanced antitumor activity may also be prepared using heterobifunctional cross-linkers as described in Wolff, E. A. et al. (1993) "*Monoclonal Antibody Homodimers: Enhanced Antitumor Activity In Nude Mice*," Cancer Research 53:2560-2565. Alternatively, an antibody can be engineered which has dual Fc Regions and may thereby have enhanced complement lysis and ADCC capabilities (Stevenson, G. T. et al. (1989) "*A Chimeric Antibody With Dual Fc Regions (bisFabFc) Prepared By Manipulations At The IgG Hinge*," Anti-Cancer Drug Design 3:219-230).

E. Multivalent DR5-Binding Molecules Comprising Diabodies

1. Multivalent DR5-Binding Molecules Comprising Diabodies Lacking Fc Regions

One embodiment of the present invention relates to multivalent DR5-Binding Molecules comprising or consisting of bispecific diabodies that are capable of binding to a first epitope ("Epitope 1") and a second epitope ("Epitope 2"), wherein the first epitope is an epitope of human DR5 and the second epitope is a different epitope of DR5. Preferably, such diabodies comprise, and most preferably are composed of, a first polypeptide chain and a second polypeptide chain, whose sequences permit the polypeptide chains to covalently bind to each other to form a covalently associated complex that is capable of simultaneously binding to a first DR5 epitope and the second DR5 epitope. Accordingly, such diabodies may bind the first and second epitope on a single DR5 polypeptide (i.e., bind intramolecularly), or they may bind the first epitope on a one DR5 polypeptide and the second epitope on another DR5 polypeptide (i.e., bind intermolecularly). Preferably, such diabodies cross-link DR5 molecules that are arrayed on the surface of a cell.

In one embodiment, the first polypeptide chain of such bispecific diabodies comprises, in the N-terminal to C-terminal direction, an N-terminus, the VL Domain of a first monoclonal antibody capable of binding to either the first or second epitope (i.e., either $VL_{Epitope\ 1}$ or $VL_{Epitope\ 2}$), a first intervening spacer peptide (Linker 1), a VH Domain of a second monoclonal antibody capable of binding to either the second epitope (if such first polypeptide chain contains $VL_{Epitope\ 1}$) or the first epitope (if such first polypeptide chain contains $VL_{Epitope\ 2}$), a second intervening spacer peptide (Linker 2) optionally containing a cysteine residue, a heterodimer-promoting Domain and a C-terminus (FIG. 1). The notation "VL1" and "VL1" denote respectively, the Variable Light Chain Domain and Variable Heavy Chain Domain of the first monoclonal antibody. Similarly, the notation "VL2" and "VH2" denote respectively, the Variable Light Chain Domain and Variable Heavy Chain Domain of the second antibody.

The second polypeptide chain of this embodiment of bispecific diabodies comprises, in the N-terminal to C-terminal direction, an N-terminus, a VL Domain of a monoclonal antibody capable of binding to either the first or the second epitope (i.e., either $VL_{Epitope\ 1}$ or $VL_{Epitope\ 2}$, and being the VL Domain not selected for inclusion in the first polypeptide chain of the diabody), an intervening linker peptide (Linker 1), a VH Domain of a monoclonal antibody capable of binding to either the second epitope (if such second polypeptide chain contains $VL_{Epitope\ 1}$) or to the first epitope (if such second polypeptide chain contains $VL_{Epitope\ 2}$), a spacer peptide (Linker 2) optionally containing a cysteine residue, a heterodimer-promoting Domain, and a C-terminus (FIG. 1).

The VL Domain of the first polypeptide chain interacts with the VH Domain of the second polypeptide chain to form a first functional antigen-binding site that is specific for DR5 (i.e., either the first or the second epitope). Likewise, the VL Domain of the second polypeptide chain interacts with the VH Domain of the first polypeptide chain in order to form a second functional antigen-binding site that is also specific for DR5 (i.e., either the second epitope or the first epitope). Thus, the selection of the VL and VH Domains of the first and second polypeptide chains is coordinated, such that the two polypeptide chains of the diabody collectively comprise VL and VH Domains capable of binding to both a first epitope of DR5 and to a second epitope of DR5 (i.e., they comprise $VL_{Epitope\ 1}/VL_{Epitope\ 1}$ and $VL_{Epitope\ 2}/VH_{Epitope\ 2}$).

Most preferably, the length of the intervening linker peptide (Linker 1, which separates such VL and VH Domains) is selected to substantially or completely prevent the VL and VH Domains of the polypeptide chain from binding to one another. Thus the VL and VH Domains of the first polypeptide chain are substantially or completely incapable of binding to one another. Likewise, the VL and VH Domains of the second polypeptide chain are substantially or completely incapable of binding to one another. A preferred intervening spacer peptide (Linker 1) has the sequence (SEQ ID NO:33): GGGSGGGG.

The second intervening spacer peptide (Linker 2) will optionally contain 1, 2, 3 or more cysteines. A preferred cysteine-containing spacer peptide (Linker 2) has the sequence is SEQ ID NO:34: GGCGGG. Alternatively, Linker 2 does not comprise a cysteine and a Cysteine-Containing Heterodimer-Promoting Domain, as described below is used. Optionally, both a cysteine-containing Linker 2 and a cysteine-containing Heterodimer-Promoting Domain are used.

The Heterodimer-Promoting Domains may be GVEPKSC (SEQ ID NO:35) VEPKSC (SEQ ID NO:36) or AEPKSC (SEQ ID NO:169) on one polypeptide chain and GFNRGEC (SEQ ID NO:37) or FNRGEC (SEQ ID NO:38) on the other polypeptide chain (US2007/0004909).

More preferably, however, the Heterodimer-Promoting Domains of such diabodies are formed from one, two, three or four tandemly repeated coil domains of opposing charge that comprise a sequence of at least six, at least seven or at least eight charged amino acid residues (Apostolovic, B. et al. (2008) "*pH-Sensitivity of the E3/K3 Heterodimeric*

*Coiled Coil,"* Biomacromolecules 9:3173-3180; Arndt, K. M. et al. (2001) *"Helix-stabilized Fv (hsFv) Antibody Fragments: Substituting the Constant Domains of a Fab Fragment for a Heterodimeric Coiled-coil Domain,"* J. Molec. Biol. 312:221-228; Arndt, K. M. et al. (2002) *"Comparison of In Vivo Selection and Rational Design of Heterodimeric Coiled Coils,"* Structure 10:1235-1248; Boucher, C. et al. (2010) *"Protein Detection By Western Blot Via Coiled-Coil Interactions,"* Analytical Biochemistry 399:138-140; Cachia, P. J. et al. (2004) *"Synthetic Peptide Vaccine Development: Measurement Of Polyclonal Antibody Affinity And Cross-Reactivity Using A New Peptide Capture And Release System For Surface Plasmon Resonance Spectroscopy,"* J. Mol. Recognit. 17:540-557; De Crescenzo, G. D. et al. (2003) *"Real-Time Monitoring of the Interactions of Two-Stranded de novo Designed Coiled-Coils: Effect of Chain Length on the Kinetic and Thermodynamic Constants of Binding,"* Biochemistry 42:1754-1763; Fernandez-Rodriquez, J. et al. (2012) *"Induced Heterodimerization And Purification Of Two Target Proteins By A Synthetic Coiled-Coil Tag,"* Protein Science 21:511-519; Ghosh, T. S. et al. (2009) *"End-To-End And End-To-Middle Interhelical Interactions: New Classes Of Interacting Helix Pairs In Protein Structures,"* Acta Crystallographica D65:1032-1041; Grigoryan, G. et al. (2008) *"Structural Specificity In Coiled-Coil Interactions,"* Curr. Opin. Struc. Biol. 18:477-483; Litowski, J. R. et al. (2002) *"Designing Heterodimeric Two-Stranded a-Helical Coiled-Coils: The Effects Of Hydrophobicity And a-Helical Propensity On Protein Folding, Stability, And Specificity,"* J. Biol. Chem. 277:37272-37279; Steinkruger, J. D. et al. (2012) *"The d'--d--d' Vertical Triad is Less Discriminating Than the a'--a--a' Vertical Triad in the Antiparallel Coiled-coil Dimer Motif,"* J. Amer. Chem. Soc. 134(5):2626-2633; Straussman, R. et al. (2007) *"Kinking the Coiled Coil—Negatively Charged Residues at the Coiled-coil Interface,"* J. Molec. Biol. 366:1232-1242; Tripet, B. et al. (2002) *"Kinetic Analysis of the Interactions between Troponin C and the C-terminal Troponin I Regulatory Region and Validation of a New Peptide Delivery/Capture System used for Surface Plasmon Resonance,"* J. Molec. Biol. 323:345-362; Woolfson, D. N. (2005) *"The Design Of Coiled-Coil Structures And Assemblies,"* Adv. Prot. Chem. 70:79-112; Zeng, Y. et al. (2008) *"A Ligand-Pseudoreceptor System Based On de novo Designed Peptides For The Generation Of Adenoviral Vectors With Altered Tropism,"* J. Gene Med. 10:355-367).

Such repeated coil domains may be exact repeats or may have substitutions. For example, the Heterodimer-Promoting Domain of the first polypeptide chain may comprise a sequence of eight negatively charged amino acid residues and the Heterodimer-Promoting Domain of the second polypeptide chain may comprise a sequence of eight negatively charged amino acid residues. It is immaterial which coil is provided to the first or second polypeptide chains, provided that a coil of opposite charge is used for the other polypeptide chain. The positively charged amino acid may be lysine, arginine, histidine, etc. and/or the negatively charged amino acid may be glutamic acid, aspartic acid, etc. The positively charged amino acid is preferably lysine and/or the negatively charged amino acid is preferably glutamic acid. It is possible for only a single Heterodimer-Promoting Domain to be employed (since such domain will inhibit homodimerization and thereby promote heterodimerization), however, it is preferred for both the first and second polypeptide chains of the diabodies of the present invention to contain Heterodimer-Promoting Domains.

In a preferred embodiment, one of the Heterodimer-Promoting Domains will comprise four tandem "E-coil" helical domains (SEQ ID NO:39: EVAALEK-EVAALEK-EVAALEK-EVAALEK), whose glutamate residues will form a negative charge at pH 7, while the other of the Heterodimer-Promoting Domains will comprise four tandem "K-coil" domains (SEQ ID NO:40: KVAALKE-KVAALKE-KVAALKE-KVAALKE), whose lysine residues will form a positive charge at pH 7. The presence of such charged domains promotes association between the first and second polypeptides, and thus fosters heterodimer formation. Especially preferred is a Heterodimer-Promoting Domain in which one of the four tandem "E-coil" helical domains of SEQ ID NO:39 has been modified to contain a cysteine residue: EVAACEK-EVAALEK-EVAALEK-EVAALEK (SEQ ID NO:41). Likewise, especially preferred is a Heterodimer-Promoting Domain in which one of the four tandem "K-coil" helical domains of SEQ ID NO:40 has been modified to contain a cysteine residue: KVAACKE-KVAALKE-KVAALKE-KVAALKE (SEQ ID NO:42).

As disclosed in WO 2012/018687, in order to improve the in vivo pharmacokinetic properties of diabodies, a diabody may be modified to contain a polypeptide portion of a serum-binding protein at one or more of the termini of the diabody. Most preferably, such polypeptide portion of a serum-binding protein will be installed at the C-terminus of the diabody. Albumin is the most abundant protein in plasma and has a half-life of 19 days in humans. Albumin possesses several small molecule binding sites that permit it to non-covalently bind to other proteins and thereby extend their serum half-lives. The Albumin-Binding Domain 3 (ABD3) of protein G of *Streptococcus* strain G148 consists of 46 amino acid residues forming a stable three-helix bundle and has broad albumin-binding specificity (Johansson, M. U. et al. (2002) *"Structure, Specificity, And Mode Of Interaction For Bacterial Albumin-Binding Modules,"* J. Biol. Chem. 277(10):8114-8120. Thus, a particularly preferred polypeptide portion of a serum-binding protein for improving the in vivo pharmacokinetic properties of a diabody is the Albumin-Binding Domain (ABD) from streptococcal protein G, and more preferably, the Albumin-Binding Domain 3 (ABD3) of protein G of *Streptococcus* strain G148 (SEQ ID NO:43): LAEAKVLANR ELDKYGVSDY YKNLID-NAKS AEGVKALIDE ILAALP.

As disclosed in WO 2012/162068 (herein incorporated by reference), "deimmunized" variants of SEQ ID NO:43 have the ability to attenuate or eliminate MHC class II binding. Based on combinational mutation results, the following combinations of substitutions are considered to be preferred substitutions for forming such a deimmunized albumin-binding domain: 66S/70S+71A; 66S/70S+79A; 64A/65A/71A+66S; 64A/65A/71A+66D; 64A/65A/71A+66E; 64A/65A/79A+66S; 64A/65A/79A+66D; 64A/65A/79A+66E. Variant ABDs having the modifications L64A, I65A and D79A or the modifications N66S, T70S and D79A. Variant deimmunized ABD having the amino acid sequence:

(SEQ ID NO: 44)
LAEAKVLANR ELDKYGVSDY YKNA$_{64}$A$_{65}$NNAKT VEGVKALIA$_{79}$E

ILAALP, or the amino acid sequence:

LAEAKVLANR ELDKYGVSDY YKNLI$\underline{S}_{66}$NAK$\underline{S}_{70}$ VEGVKALI$\underline{A}_{79}$E ILAALP, (SEQ ID NO: 45)

are particularly preferred as such deimmunized Albumin-Binding Domains exhibit substantially wild-type binding while providing attenuated MHC class II binding. Thus, the first polypeptide chain of such a diabody having an Albumin-Binding Domain contains a third linker (Linker 3) preferably positioned C-terminally to the E-coil (or K-coil) Domain of such polypeptide chain so as to intervene between the E-coil (or K-coil) Domain and the Albumin-Binding Domain (which is preferably a deimmunized Albumin-Binding Domain). A preferred sequence for such Linker 3 is SEQ ID NO:46: GGGS.

Another embodiment of the present invention relates to multivalent DR5-Binding Molecules comprising or consisting of monospecific diabodies capable of binding to one epitope of DR5. Preferably, such diabodies comprise, and most preferably are composed of, a first polypeptide chain and a second polypeptide chain, whose sequences permit the polypeptide chains to covalently bind to each other to form a covalently associated complex having two binding domains, each capable of binding to the same DR5 epitope. Preferably, such diabodies are capable of simultaneously binding to the same DR5 epitope on two separate DR5 polypeptides. Preferably, such diabodies cross-link DR5 on the surface of a cell.

Monospecific diabodies may readily be generated from homodimerization of polypeptide chains comprising, in the N-terminal to C-terminal direction, an N-terminus, the VL Domain of a monoclonal antibody capable of binding to an epitope of DR5 a first intervening spacer peptide (Linker 1), a VH Domain of a monoclonal antibody capable of binding to the epitope of DR5. As detailed above, the length of the intervening linker peptide (Linker 1, which separates such VL and VH Domains) is selected to substantially or completely prevent the VL and VH Domains of the polypeptide chain from binding to one another. The polypeptide chains may optionally comprise a cysteine-containing peptide which can form a covalent disulfide linkage between the pair of polypeptides.

Alternatively, monospecific bivalent diabodies may readily be generated by heterodimerization of a first and second polypeptide as detailed above, for example, if the first monoclonal antibody and the second monoclonal antibody recognize the same epitope, or the same VL and VH Domains are used on both the first and the second polypeptide chains.

2. Fc Region-Containing, Multivalent DR5-Binding Molecules

One embodiment of the present invention relates to Fc Region-containing, multivalent, DR5-Binding Molecules. The addition of IgG CH2-CH3 Domains to one or both of the diabody polypeptide chains, such that the complexing of the diabody chains results in the formation of an Fc Region, increases the biological half-life and/or alters the valency of the diabody.

Figure 2:
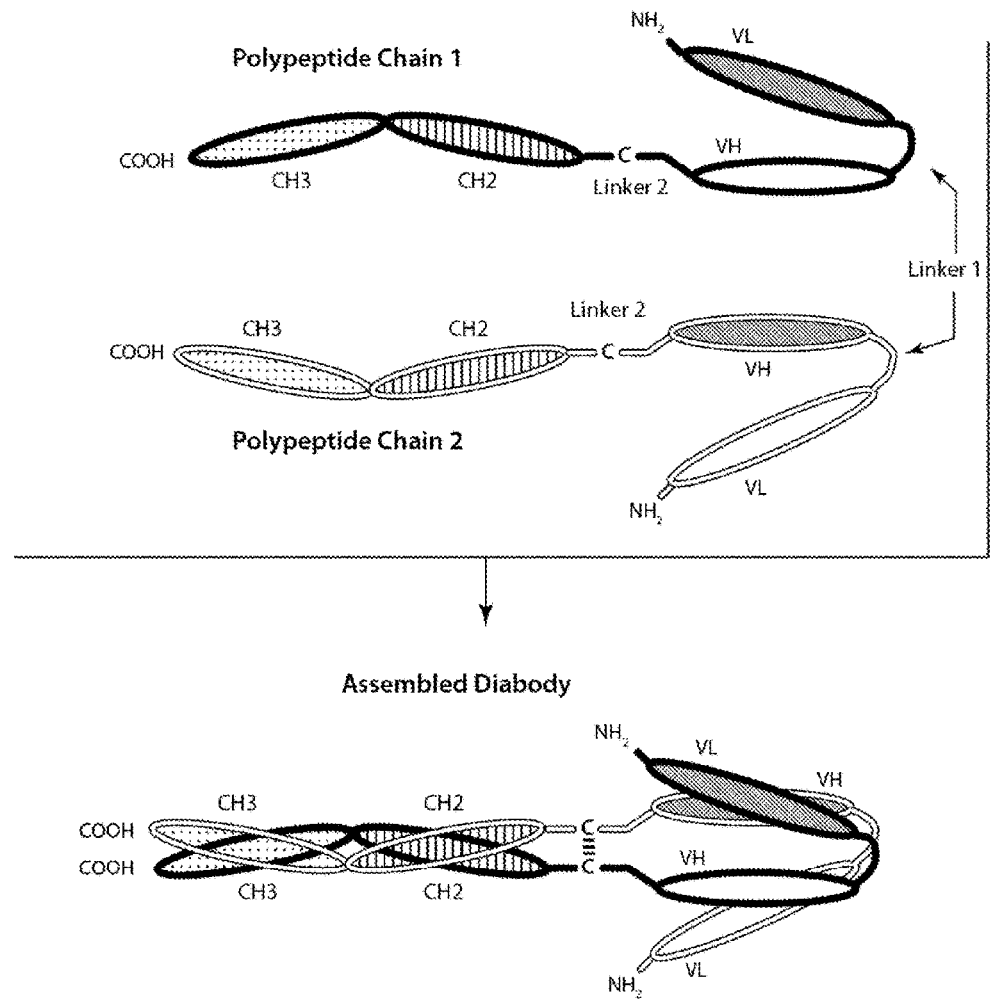
FIG. 2 provides a schematic of a representative covalently bonded diabody molecule having two epitope binding sites composed of two polypeptide chains, each having a CH2 and CH3 Domain, such that the associated chains form an Fc Region that comprises all or part of a naturally occurring Fc Region. VL and VH Domains that recognize the same epitope are shown using the same shading. In certain embodiments, the epitopes are different epitopes of the same antigen resulting in a bispecific molecule that is monovalent for each epitope, but is bivalent with respect to the antigen (e.g., DR5). In certain embodiments the epitopes are the same epitope (e.g., the same VL Domain CDRs and VH Domain CDRs are used on each chain) resulting in a monospecific molecule that is bivalent.

Incorporating IgG CH2-CH3 Domains onto both of the diabody polypeptides will permit a two-chain Fc-containing diabody to form (FIG. 2). As noted above, such a diabody will be bispecific or monospecific for DR5 epitopes depending on the selection of the VL and VH Domains, and will be bivalent with respect to the DR5 antigen.

Alternatively, incorporating an IgG CH2-CH3 domain onto only one of the diabody polypeptides will permit a four-chain Fc Region-containing diabody to form (FIG. 3 and FIG. 4). Where each diabody portion is bispecific and monovalent for different DR5 epitopes the resulting four-chain molecule will be bispecific and bivalent with respect to each of two different DR5 epitopes, and tetravalent with respect to the DR5 antigen (FIG. 4). Alternatively, if two different bispecific monovalent diabodies are combined, the resulting four-chain molecule will be tetraspecific and monovalent with respect to four different DR5 epitopes and tetravalent with respect to the DR5 antigen (FIG. 3). Where each diabody portion is monospecific and bivalent for one DR5 epitope the resulting four-chain molecule will be monospecific and tetravalent with respect to one DR5 epitope and with respect to the DR5 antigen. Although FIG. 3 shows diabodies possessing the Constant Light (CL) Domain and the Constant Heavy-1 (CH1) Domain, fragments of such domains as well as other polypeptides may alternatively be employed as Heterodimer-Promoting Domains as shown schematically in FIG. 4 (see., e.g., United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538). Thus, for example, in lieu of the CH1 domain, one may employ a peptide having the amino acid sequence GVEPKSC (SEQ ID NO:35) or VEPKSC (SEQ ID NO:36), derived from the hinge domain of a human IgG, and in lieu of the CL domain, one may employ the C-terminal 6 amino acids of the human kappa light chain, GFNRGEC (SEQ ID NO:37) or FNRGEC (SEQ ID NO:38). A representative peptide containing four-chain diabody is shown in FIG. 4A. Alternatively, or in addition, one may employ a peptide comprising tandem coil domains of opposing charge such as the "E-coil" helical domains (SEQ ID NO:39: $\underline{E}$VAAL$\underline{E}$K-$\underline{E}$VAAL$\underline{E}$K-$\underline{E}$VAAL$\underline{E}$K-$\underline{E}$VAAL$\underline{E}$K or SEQ ID NO:41: $\underline{E}$VAA$\underline{C}$$\underline{E}$K-$\underline{E}$VAAL$\underline{E}$K-$\underline{E}$VAAL$\underline{E}$K-$\underline{E}$VAAL$\underline{E}$K); and the "K-coil" domains (SEQ ID NO:40: $\underline{K}$VAAL$\underline{K}$E-$\underline{K}$VAAL$\underline{K}$E-$\underline{K}$VAAL$\underline{K}$E-$\underline{K}$VAAL$\underline{K}$E or SEQ ID NO:42: $\underline{K}$VAA$\underline{C}$$\underline{K}$E-$\underline{K}$VAAL$\underline{K}$E-$\underline{K}$VAAL$\underline{K}$E-$\underline{K}$VAAL$\underline{K}$E). A representative coil domain containing four-chain diabody is shown in FIG. 4B.

Additional or alternative linkers that may be employed in the Fc Region-containing diabody molecules of the present invention include: ASTKG (SEQ ID NO:47), DKTHTCPPCP (SEQ ID NO:48), LEPKSS (SEQ ID NO:49), and APSSSPME (SEQ ID NO:50), GGC, and GGG. SEQ ID NO:49 may be used in lieu of GGG or GGC for ease of cloning. Additionally, SEQ ID NO:49 may be immediately followed by SEQ ID NO:47 to form an alternate linker (LEPKSSDKTHTCPPCP; SEQ ID NO:51).

As provided in FIG. 3, and FIG. 4A-4B, diabodies of the invention may comprise four different chains. The first and third polypeptide chains of such a diabody contain three domains: (i) a VL1-containing Domain, (ii) a VH2-containing Domain, (iii) Heterodimer-Promoting Domain and (iv) a Domain containing a CH2-CH3 sequence. The second and fourth polypeptide contain: (i) a VL2-containing Domain, (ii) a VH1-containing Domain and (iii) a Heterodimer-Promoting Domain, where the Heterodimer-Promoting Domains promote the dimerization of the first/third chains with the second/fourth chains. The VL and/or VH Domains of the third and fourth polypeptide chains, and VL and/or VH Domains of the first and second polypeptide chains may be the same or different so as to permit tetravalent binding that is either monospecific, bispecific or tetraspecific. The general structure of the polypeptide chains of a representative four-chain Fc Region-containing diabodies of invention is provided in Table 2:

TABLE 2

| | | |
|---|---|---|
| Bispecific | 2$^{nd}$ Chain | NH$_2$-VL2-VH1-Heterodimer-Promoting Domain-COOH |
| | 1$^{st}$ Chain | NH$_2$-VL1-VH2-Heterodimer-Promoting Domain-CH2—CH3—COOH |
| | 1$^{st}$ Chain | NH$_2$-VL1-VH2-Heterodimer-Promoting Domain-CH2—CH3—COOH |
| | 2$^{nd}$ Chain | NH$_2$-VL2-VH1-Heterodimer-Promoting Domain-COOH |
| Tetraspecific | 2$^{nd}$ Chain | NH$_2$-VL2-VH1-Heterodimer-Promoting Domain-COOH |
| | 1$^{st}$ Chain | NH$_2$-VL1-VH2-Heterodimer-Promoting Domain-CH2—CH3—COOH |
| | 3$^{rd}$ Chain | NH$_2$-VL3-VH4-Heterodimer-Promoting Domain-CH2—CH3—COOH |
| | 4$^{th}$ Chain | NH$_2$-VL4-VH3-Heterodimer-Promoting Domain-COOH |

The structure of the first and second polypeptide chains of representative Fc Region-containing diabodies of invention tetravalent for DR5 (i.e., having four antigen-binding domains each capable of binding human DR5) are provided in Table 3. Each Fc Region-containing diabody comprises two pairs of covalently bonded first and second polypeptide chains such that:

(a) the VL1 Domain of said first polypeptide chain and the VH1 Domain of said second polypeptide chain form an Antigen-Binding Domain capable of specific binding to a first epitope of DR5;

(b) said VH2 Domain of said first polypeptide chain and said VL1 Domain of said second polypeptide chain form an Antigen-Binding Domain capable of specific binding to a second epitope of DR5; and (c) the CH2-CH3 portions of the pair of first polypeptide chains form an IgG Fc Region.

As described herein, the Fc Region (i.e., CH2-CH3 domains of an IgG heavy chain) may be a variant Fc Region having altered affinity for an FcγR and/or altered effector function and/or altered serum half-life. In some embodiments, the Fc Region is a variant lacking the C-terminal residue.

TABLE 3

| | |
|---|---|
| Diabody DR5 Binding Molecules comprising E/K-Coil Heterodimer-Promoting Domains | |
| 1$^{st}$ Polypeptide Chain | NH$_2$-[VL1 Domain]-[Linker 1]-[VH2 Domain]-[Linker 2]-[Heterodimer-Promoting domain]-[Linker 3]-[CH2-CH3 Domain]-COOH<br>Wherein:<br>[VL1 Domain] comprises the VL Domain from an anti-DR5 antibody binding to a first DR5 epitope;<br>[Linker 1] is SEQ ID NO: 33;<br>[VH2 Domain] comprises the VH Domain from an anti-DR5 antibody binding to a second DR5 epitope;<br>[Linker 2] comprises the amino acids "GGG," or "GGC," or is selected from ASTKG (SEQ ID NO: 47) and GGCGGG (SEQ ID NO: 34);<br>[Heterodimer-Promoting Domain] is an E-coil Domain (SEQ ID NO: 39 or 41), or a K-coil Domain (SEQ ID NO: 40 or 42);<br>[Linker 3] comprises the amino acids "GGG," or "GGC," or is selected from DKTHTCPPCP (SEQ ID NO: 48), LEPKSS (SEQ ID NO: 49), APSSSPME (SEQ ID NO: 50) and LEPKSSDKTHTCPPCP (SEQ ID NO: 51); and<br>[CH2-CH3 Domain] comprises the CH2-CH3 domains of an IgG starting from reside 231 according to EU numbering, optionally lacking the C-terminal amino acid residue. |
| 2$^{nd}$ Polypeptide Chain | NH$_2$-[VL1 Domain]-[Linker 1]-[VH2 Domain]-[Linker 2]-[Heterodimer-Promoting Domain]-COOH<br>Wherein:<br>[VL1 Domain] comprises the VL Domain from the anti-DR5 antibody binding to the first DR5 epitope;<br>[Linker 1] is SEQ ID NO: 33;<br>[VH2 Domain] comprises the VH Domain from the anti-DR5 antibody binding to the second DR5 epitope;<br>[Linker 2] comprises the amino acids "GGG," or "GGC," or is selected from ASTKG (SEQ ID NO: 47) and GGCGGG (SEQ ID NO: 34); and<br>[Heterodimer-Promoting Domain] is an E-coil Domain (SEQ ID NO: 39 or 41), or a K-coil Domain (SEQ ID NO: 40 or 42), wherein the [Heterodimer-Promoting Domain] of the first polypeptide chain and the [Heterodimer-Promoting Domain] of the second polypeptide chain are not both E-coil Domains or both K-coil Domains. |
| Diabody DR5 Binding Molecules Comprising Peptide Heterodimer-Promoting Domains | |
| 1$^{st}$ Polypeptide Chain | NH$_2$-[VL1 Domain]-[Linker 1]-[VH2 Domain]-[Linker 2]-[Heterodimer-Promoting Domain]-[Linker 3]-[CH2-CH3 Domain]-COOH<br>Wherein:<br>[VL1 Domain] comprises the VL Domain from an anti-DR5 antibody binding to a first DR5 epitope;<br>[Linker 1] is SEQ ID NO: 33;<br>[VH2 Domain] comprises the VH Domain from an anti-DR5 antibody binding to a second DR5 epitope; |

TABLE 3-continued

| | |
|---|---|
| | [Linker 2] comprises the amino acids "GGG," or "GGC," or is selected from ASTKG (SEQ ID NO: 47) and GGCGGG (SEQ ID NO: 34);<br>[Heterodimer-Promoting Domain] is ] is (i) an GVEPKSC (SEQ ID NO: 35) or VEPKSC (SEQ ID NO: 36); or (ii) GFNRGEC (SEQ ID NO: 37) or FNRGEC (SEQ ID NO: 38);<br>[Linker 3] comprises the amino acids "GGG," or "GGC," or is selected from DKTHTCPPCP (SEQ ID NO: 48), LEPKSS (SEQ ID NO: 49), APSSSPME (SEQ ID NO: 50) and LEPKSSDKTHTCPPCP (SEQ ID NO: 51); and<br>[CH2-CH3 Domain] comprises the CH2-CH3 domains of an IgG starting from reside 231 according to EU numbering, optionally lacking the C-terminal amino acid residue. |
| 2$^{nd}$ Polypeptide Chain | NH$_2$-[VL1 Domain]-[Linker 1]-[VH2 Domain]-[Linker 2]-[Heterodimer-Promoting Domain]-COOH<br>Wherein:<br>[VL1 Domain] comprises the VL Domain from the anti-DR5 antibody binding to the first DR5 epitope;<br>[Linker 1] is SEQ ID NO: 33;<br>[VH2 Domain] comprises the VH Domain from the anti-DR5 antibody binding to the second DR5 epitope;<br>[Linker 2] comprises the amino acids "GGG," or "GGC," or is selected from ASTKG (SEQ ID NO: 47) and GGCGGG (SEQ ID NO: 34); and<br>[Heterodimer-Promoting Domain] is (i) GVEPKSC (SEQ ID NO: 35) or VEPKSC (SEQ ID NO: 36); or (ii) GFNRGEC (SEQ ID NO: 37) or FNRGEC (SEQ ID NO: 38);<br>wherein in [Heterodimer-Promoting Domain] of the first polypeptide chain and the [Heterodimer-Promoting Domain] of the second polypeptide chain are not both selected from (i) or (ii). |
| Diabody DR5 Binding Molecules Comprising IgG Constant Domains | |
| 1$^{st}$ Polypeptide Chain | NH$_2$-[VL1 Domain]-[Linker 1]-[VH2 Domain]-[Linker 2]-[CH1-H-CH2-CH3 Domain]-COOH<br>Wherein:<br>[VL1 Domain] comprises the VL Domain from an anti-DR5 antibody binding to a first DR5 epitope;<br>[Linker 1] is SEQ ID NO: 33;<br>[VH2 Domain] comprises the VH Domain from an anti-DR5 antibody binding to a second DR5 epitope;<br>[Linker 2] comprises the amino acids "GGG," or "GGC," or is selected from ASTKG (SEQ ID NO: 47) and GGCGGG (SEQ ID NO: 34);<br>[CH1-H-CH2-CH3 Domain] comprises the constant domains (CH1 to CH3) of an IgG heavy chain, optionally lacking the C-terminal amino acid residue. |
| 2$^{nd}$ Polypeptide Chain | NH$_2$-[VL1 Domain]-[Linker 1]-[VH2 Domain]-[Linker 2]-[CL Domain]-COOH<br>Wherein:<br>[VL1 Domain] comprises the VL Domain from the anti-DR5 antibody binding to the first DR5 epitope;<br>[Linker 1] is SEQ ID NO: 33;<br>[VH2 Domain] comprises the VH Domain from the anti-DR5 antibody binding to the second DR5 epitope;<br>[Linker 2] comprises the amino acids "GGG," or "GGC," or is selected from ASTKG (SEQ ID NO: 47) and GGCGGG (SEQ ID NO: 34); and<br>[CL Domain] comprises the CL domain of an IgG light chain. |

The Fc Region of the Fc Region-containing diabodies of the present invention may be either a complete Fc Region (e.g., a complete IgG Fc Region) or only a fragment of a complete Fc Region. Although the Fc Region of the Fc Region-containing diabodies of the present invention may possess the ability to bind to one or more Fc receptors (e.g., FcγR(s)), more preferably such Fc Region will cause altered binding to FcγRIA (CD64), FcγRIIA (CD32A), FcγRIIB (CD32B), FcγRIIIA (CD16a) or FcγRIIIB (CD16b) (relative to the binding exhibited by a wild-type Fc Region) or will substantially eliminate the ability of such Fc Region to bind to inhibitory receptor(s). Thus, the Fc Region of the Fc Region-containing diabodies of the present invention may include some or all of the CH2 Domain and/or some or all of the CH3 Domain of a complete Fc Region, or may comprise a variant CH2 and/or a variant CH3 sequence (that may include, for example, one or more insertions and/or one or more deletions with respect to the CH2 or CH3 Domains of a complete Fc Region). Such Fc Regions may comprise non-Fc polypeptide portions, or may comprise portions of non-naturally complete Fc Regions, or may comprise non-naturally occurring orientations of CH2 and/or CH3 Domains (such as, for example, two CH2 Domains or two CH3 Domains, or in the N-terminal to C-terminal direction, a CH3 Domain linked to a CH2 Domain, etc.).

In particular, it is preferred for the CH2-CH3 domains of the polypeptide chains of the Fc Region-containing diabodies of the present invention to exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type IgG1 Fc Region (SEQ ID NO:1). Fc variants and mutant forms capable of mediating such altered binding are described above. In a specific embodiment, the CH2-CH3 domains of the polypeptide chains of the Fc Region-containing diabodies of the present invention comprise an IgG Fc Region that mediates little or no ADCC effector function. In a preferred embodiment the CH2-CH3 Domain of the first and/or third polypeptide chains of such diabodies include any 1, 2, or 3, of the substitutions: L234A, L235A, D265A, N297Q, and N297G. In another embodiment, the human IgG1 Fc Region variant contains an N297Q substitution, an N297G substitution, L234A and L235A substitutions or a D265A substitution, as these mutations abolish FcR binding.

The amino acid sequence of the CH2-CH3 Domain of an exemplary human IgG1 comprising the L234A/L235A substitutions is (SEQ ID NO:102):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGK
```

Alternatively, a CH2-CH3 domain which inherently exhibits decreased (or substantially no) binding to FcγRIIIA (CD16a) and/or reduced effector function (relative to the binding exhibited by the wild-type IgG1 Fc Region (SEQ ID NO:1)) is utilized. In a specific embodiment, the Fc Region-containing diabodies of the present invention comprise an IgG2 Fc Region (SEQ ID NO:164) or an IgG4 Fc Region (SEQ ID NO:103), optionally lacking the C-terminal amino acid residues. Where an IgG4 Fc Region in utilized the instant invention also encompasses the introduction of a stabilizing mutation such as S228P, as numbered by the EU index as set forth in Kabat (Lu et al., (2008) "*The Effect Of A Point Mutation On The Stability Of Igg4 As Monitored By Analytical Ultracentrifugation*," J Pharmaceutical Sciences 97:960-969) to reduce the incidence of strand exchange. Other stabilizing mutations known in the art may be introduced into an IgG4 Fc Region (Peters, P et al., (2012) "*Engineering an Improved IgG4 Molecule with Reduced Disulfide Bond Heterogeneity and Increased Fab Domain Thermal Stability*," J. Biol. Chem. 287:24525-24533; PCT Patent Publication No: WO 2008/145142). Since the N297G, N297Q, L234A, L235A and D265A substitutions abolish effector function, in circumstances in which effector function is desired, these substitutions would preferably not be employed. As described above, in some embodiments, the Fc Region lacks the C-terminal amino acid residue.

The CH2 and/or CH3 Domains of such polypeptide chains need not be identical in sequence, and advantageously are modified to foster complexing between the two polypeptide chains. For example, an amino acid substitution (preferably a substitution with an amino acid comprising a bulky side group forming a "knob", e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., "the hole" (e.g., a substitution with glycine). Such sets of mutations can be engineered into any pair of polypeptides comprising CH2-CH3 Domains that form an Fc Region. Methods of protein engineering to favor heterodimerization over homodimerization are well known in the art, in particular with respect to the engineering of immunoglobulin-like molecules, and are encompassed herein (see e.g., Ridgway et al. (1996) "'*Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety). Preferably the "knob" is engineered into the CH2-CH3 Domains of one first polypeptide chain and the "hole" is engineered into the CH2-CH3 Domains of the third polypeptide chain. Thus, the "knob" will help in preventing the first polypeptide chains from homodimerizing via its CH2 and/or CH3 Domains. As the third polypeptide chain preferably contains the "hole" substitution it will heterodimerize with the first polypeptide chain comprising the "knob" as well as homodimerize with itself.

A preferred knob is created by modifying a native IgG Fc Region to contain the modification T366W. A preferred hole is created by modifying a native IgG Fc Region to contain the modification T366S, L368A and Y407V. To aid in purifying the homodimers from the final heterodimer Fc Region-containing diabody, the protein A binding site of the CH2 and CH3 Domains of one chain is preferably mutated by amino acid substitution at position 435 (H435R) on the third polypeptide containing the "hole" substitutions. Thus, the homodimer of third polypeptide chains containing the "hole" substitutions will not bind to protein A, whereas the heterodimer will retain its ability to bind protein A via the protein A binding site on the first polypeptide chain.

A preferred sequence for the CH2 and CH3 Domains of the first polypeptide chain of an Fc Region-containing diabody of the present invention will have the "knob-bearing" sequence (SEQ ID NO:52):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGK
```

A preferred sequence for the CH2 and CH3 Domains of the second polypeptide chain of an Fc Region-containing diabody of the present invention having two polypeptide chains (or the third polypeptide chain of an Fc Region-containing diabody having three polypeptide chains) will have the "hole-bearing" sequence (SEQ ID NO:53):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGK
```

As will be noted, the CH2-CH3 Domains of SEQ ID NO:52 and SEQ ID NO:53 include a substitution at position 234 with alanine and 235 with alanine, and thus form an Fc Region exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc Region (SEQ ID NO:1). The C-terminal residue is optionally included.

It is preferred that the first polypeptide chain will have a "knob-bearing" CH2-CH3 sequence, such as that of SEQ ID NO:52. However, as will be recognized, a "hole-bearing" CH2-CH3 Domain (e.g., SEQ ID NO:53) could be employed in the first polypeptide chain, in which case, a "knob-bearing" CH2-CH3 Domain (e.g., SEQ ID NO:52) would be employed in the second polypeptide chain of an Fc Region-containing diabody of the present invention having two polypeptide chains (or the third polypeptide chain of an Fc Region-containing diabody having three or four polypeptide chains). The C-terminal residue of SEQ ID NO: 52 and/or SEQ ID NO:53, is optionally included.

V. REFERENCE ANTIBODIES

A. Reference Anti-Human CD3 Antibodies

CD3 is a T cell co-receptor composed of four distinct chains (Wucherpfennig, K. W. et al. (2010) "*Structural Biology Of The T-Cell Receptor: Insights Into Receptor Assembly, Ligand Recognition, And Initiation Of Signaling*," Cold Spring Harb. Perspect. Biol. 2(4):a005140; pages 1-14). In mammals, the complex contains a CD3γ chain, a CD3δ chain, and two CD3ε chains. These chains associate with a molecule known as the T cell receptor (TCR) in order to generate an activation signal in T lymphocytes. In the absence of CD3, TCRs do not assemble properly and are degraded (Thomas, S. et al. (2010) "*Molecular Immunology Lessons From Therapeutic T-Cell Receptor Gene Transfer*," Immunology 129(2):170-177). CD3 is found bound to the membranes of all mature T cells, and in virtually no other cell type (see, Janeway, C. A. et al. (2005) In: IMMUNOBIOLOGY: THE IMMUNE SYSTEM IN HEALTH AND DISEASE," 6th ed. Garland Science Publishing, NY, pp. 214-216; Sun, Z. J. et al. (2001) "*Mechanisms Contributing To T Cell Receptor Signaling And Assembly Revealed By The Solution Structure Of An Ectodomain Fragment Of The CD3ε:γ Heterodimer*," Cell 105(7):913-923; Kuhns, M. S. et al. (2006) "*Deconstructing The Form And Function Of The TCR/CD3 Complex*," Immunity. 2006 February; 24(2):133-139).

As discussed below, in order to illustrate the present invention, bispecific anti-human CD3×anti-human DR5-Binding Molecules were produced. An anti-human CD3 antibody used for such constructs is designated herein as "CD3 mAb 2." The amino acid sequence of the VL Domain of CD3 mAb 2 (SEQ ID NO:104) is shown below (CDR$_L$ residues are shown underlined):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG
```

CDR$_L$1 of CD3 mAb 2:
(SEQ ID NO: 105)
RSSTGAVTTSNYAN

CDR$_L$2 of CD3 mAb 2:
(SEQ ID NO: 106)
GTNKRAP

CDR$_L$3 of CD3 mAb 2:
(SEQ ID NO: 107)
ALWYSNLWV

The amino acid sequence of the VH Domain of CD3 mAb 2 (SEQ ID NO:108) is shown below (CDR$_H$ residues are shown underlined):

```
EVQLVESGGG LVQPGGSLRL SCAASGFTFS TYAMNWVRQA

PGKGLEWVGR IRSKYNNYAT YYADSVKDRF

LYLQMNSLKT EDTAVYYCVR HGNFGNSYVS WFAYWGQGIL VTVSS
```

CDR$_H$1 of CD3 mAb 2:
(SEQ ID NO: 109)
TYAMN

CDR$_H$2 of CD3 mAb 2:
(SEQ ID NO: 110)
RIRSKYNNYATYYADSVKD

CDR$_H$3 of CD3 mAb 2:
(SEQ ID NO: 111)
HGNFGNSYVSWFAY

In some of the CD3 constructs, a variant VH Domain was employed for CD3 mAb 2. The variant VH Domain possesses a D65G substitution, thus having the amino acid sequence shown below (SEQ ID NO:112) (CDR$_H$ residues are shown underlined):

```
EVQLVESGGG LVQPGGSLRL SCAASGFTFS TYAMNWVRQA

PGKGLEWVGR IRSKYNNYAT YYADSVKGRF TISRDDSKNS

LYLQMNSLKT EDTAVYYCVR HGNFGNSYVS WFAYWGQGTL VTVSS
```

The substitution causes the CDR$_H$2 to have the amino acid sequence (SEQ ID NO:113) RIRSKYNNYATYYADSVKG. The substituted position (D65G) is shown in double underline.

A second anti-CD3 antibody used herein is antibody Muromonab-CD3 "OKT3" (Xu et al. (2000) "*In Vitro Characterization Of Five Humanized OKT3 Effector Function Variant Antibodies*," Cell. Immunol. 200:16-26); Norman, D. J. (1995) "*Mechanisms Of Action And Overview Of OKT3*," Ther. Drug Monit. 17(6):615-620; Canafax, D. M. et al. (1987) "*Monoclonal Antilymphocyte Antibody (OKT3) Treatment Of Acute Renal Allograft Rejection*," Pharmacotherapy 7(4):121-124; Swinnen, L. J. et al. (1993) "*OKT3 Monoclonal Antibodies Induce Interleukin-6 And Interleukin-10: A Possible Cause Of Lymphoproliferative Disorders Associated With Transplantation*," Curr. Opin. Nephrol. Hypertens. 2(4):670-678). The amino acid sequence of the VL Domain of OKT3 (SEQ ID NO:166) is shown below (CDR$_L$ residues are shown underlined):

```
QIVLTQSPAI MSASPGEKVT MTCSASSSVS YMNWYQQKSG

TSPKRWIYDT SKLASGVPAH FRGSGSGTSY SLTISGMEAE

DAATYYCQQW SSNPFTFGSG TKLEINR
```

The amino acid sequence of the VH Domain of OKT3 (SEQ ID NO:167) is shown below (CDR$_H$ residues are shown underlined):

```
QVQLQQSGAE LARPGASVKM SCKASGYTFT RYTMHWVKQR

PGQGLEWIGY INPSRGYTNY NQKFKDKATL TTDKSSSTAY

MQLSSLTSED SAVYYCARYY DDHYCLDYWG QGTTLTVSSA

KTTAPSVYPL APVCGDTTGS SVTLGCLVKG YFPEPVTLTW

NSGSLSSGVH TFPAVLQSDL YTLSSSVTVT SS
```

B. Reference Anti-Fluorescein Antibody

The anti-fluorescein antibody 4-4-20 (Gruber, M. et al. (1994) "*Efficient Tumor Cell Lysis Mediated By A Bispecific Single Chain Antibody Expressed In Escherichia coli*," J. Immunol. 152(11):5368-5374; Bedzyk, W. D. et al. (1989) "*Comparison Of Variable Region Primary Structures Within An Anti-Fluorescein Idiotype Family*," J. Biol. Chem. 264 (3): 1565-1569) was used in control diabodies. The amino acid sequences of the variable light and variable heavy Domains of anti-fluorescein antibody 4-4-20 are as follows:

Amino Acid Sequence Of The Variable Light Chain Domain Of Anti-Fluorescein Antibody 4-4-20 (SEQ ID NO:114) (CDR$_L$ residues are underlined):

```
DVVMTQTPFS LPVSLGDQAS ISCRSSQSLV HSNGNTYLRW

YLQKPGQSPK VLIYKVSNRF SGVPDRFSGS GSGTDFTLKI

SRVEAEDLGV YFCSQSTHVP WTFGGGTKLE IK
```

Amino Acid Sequence Of The Variable Heavy Chain Domain Of Anti-Fluorescein Antibody 4-4-20 (SEQ ID NO:115) (CDR$_H$ residues are underlined):

```
EVKLDETGGG LVQPGRPMKL SCVASGFTFS DYWMNWVRQS

PEKGLEWVAQ IRNKPYNYET YYSDSVKGRF TISRDDSKSS

VYLQMNNLRV EDMGIYYCTG SYYGMDYWGQ GTSVTVSS
```

VI. EXEMPLARY MULTIVALENT DR5-BINDING MOLECULES

As described above multivalent DR5-Binding Molecules possessing at least two, and preferably, at least four DR5 binding sites may have a variety of structures. In particular, structures comprising the antigen-binding portions of immunoglobulins, including, but not limited to, IgG-based bispecific antibodies, and molecules comprising diabodies are preferred. Specific, non-limiting, examples of multivalent DR5-Binding Molecules comprising diabodies are provided. However, alternative structures, including those disclosed above (see, e.g., FIGS. 1-4) or otherwise apparent to one of skill in the art are encompassed by the instant invention.

A. DR5xDR5 Bispecific Fc Region-Containing Diabodies Tetravalent For DR5

1. DR5 mAb 1xDR5 mAb 2 Fc Region-Containing Diabodies

Exemplary bispecific Fc Region-Containing diabodies tetravalent for DR5 composed of two pairs of polypeptide chains are constructed having the VL and VH Domains of anti-human DR5 antibody DR5 mAb 1 and the VL and VH Domains of DR5 mAb 2. One Fc Region-Containing diabody designated "DR5 mAb 1xDR5 mAb 2 Fc diabody," contains a wild-type IgG1 Fc Region. The amino acid sequence of the first polypeptide chain of this Fc Region-Containing diabody is (SEQ ID NO:116):

```
DIVLTQSPAS LAVSLGQRAT ISCRASKSVS SSGYSYMHWY

QQKPGQPPKV LIFLSSNLDS GVPARFSGSG SGTDFTLNIH

PVEDGDAATY YCQHSRDLPP TFGGGTKLEI KGGGSGGGGK

VQLQQSGAEL VKPGASVKLS CKASGYTFTE YILHWVKQKS

GQGLEWIGWF YPGNNNIKYN EKFKDKATLT ADKSSSTVYM

ELSRLTSEDS AVYFCARHEQ GPGYFDYWGQ GTTLTVSSAS

TKGEVAACEK EVAALEKEVA ALEKEVAALE KLEPKSSDKT

HTCPPCPAPE LLGGPSVFLF PPKPKDTLMI SRTPEVTCVV

VDVSHEDPEV KFNWYVDGVE VHNAKTKPRE EQYNSTYRVV

SVLTVLHQDW LNGKEYKCKV SNKALPAPIE KTISKAKGQP

REPQVYTLPP SREEMTKNQV SLTCLVKGFY PSDIAVEWES

NGQPENNYKT TPPVLDSDGS FFLYSKLTVD KSRWQQGNVF

SCSVMHEALH NHYTQKSLSL SPG
```

In SEQ ID NO:116, amino acid residues 1-111 correspond to the amino acid sequence of the VL Domain of DR5 mAb 1 (SEQ ID NO:3), residues 112-119 correspond to the intervening spacer peptide GGGSGGGG (Linker 1) (SEQ ID NO:33), residues 120-238 correspond to the amino acid sequence of the VH Domain of DR5 mAb 2 (SEQ ID NO:18), residues 239-243 correspond to an ASTKG linker (SEQ ID NO:47) residues 244-271 correspond to a cysteine-containing E-coil Domain (SEQ ID NO:41), residues 272-277 correspond to a LEPKSS linker (SEQ ID NO: 49), residues 278-287 correspond to a linker (DKTHTCPPCP; SEQ ID NO:48) derived from an IgG1 hinge domain, and residues 288-503 correspond to a wild-type IgG1 Fc Region (SEQ ID NO:1, lacking the C-terminal amino acid residue). A polynucleotide that encodes SEQ ID NO:116 is SEQ ID NO:117:

```
gacattgtgc tgacacagtc tcctgcttcc ttagctgtat ctctcgggca gagggccacc atctcatgca gggccagcaa aagtgtcagt tcctctggct atagttatat gcactggtac caacagaaac caggacagcc acccaaagtc ctcatctttc tttcatccaa cctagattct ggggtccctg ccaggttcag tggcagtggg tctgggacag acttcaccct caacatccat cctgtggagg atggggatgc tgcaacctat tactgtcagc acagtaggga tcttcctccg acgttcggtg gaggcaccaa gctggaaatc aaaggaggcg gatccggcgg cggaggcaag gtccagctgc agcagtctgg agctgaactg gtgaaacccg gggcatcagt gaagctgtcc tgcaaggctt ctgggtacac cttcactgag tatattttac actgggtaaa gcagaagtct ggacagggtc ttgagtggat tgggtggttt tatcctggaa ataataatat aaagtacaat gagaaattca aggacaaggc cacactgact gcggacaaat cctccagcac agtctatatg gaacttagta gattgacatc tgaagactct gcggtctatt
```

```
tctgtgcaag acacgaacaa ggaccaggtt actttgacta ctggggccaa ggcaccactc tcacagtctc ctccgcctcc accaagggcg aagtggccgc atgtgagaaa gaggttgctg ctttggagaa ggaggtcgct gcacttgaaa aggaggtcgc agccctggag aaactggagc ccaaatcttc tgacaaaact cacacatgcc caccgtgccc agcacctgaa ctcctggggg gaccgtcagt cttcctcttc cccccaaaac ccaaggacac cctcatgatc tcccgaccc ctgaggtcac atgcgtggtg gtggacgtga gccacgaaga ccctgaggtc aagttcaact ggtacgtgga cggcgtggag gtgcataatg ccaagacaaa gccgcgggag gagcagtaca acagcacgta ccgtgtggtc agcgtcctca ccgtcctgca ccaggactgg ctgaatggca aggagtacaa gtgcaaggtc tccaacaaag ccctcccagc ccccatcgag aaaaccatct ccaaagccaa agggcagccc cgagaaccac aggtgtacac cctgccccca tcccgggagg agatgaccaa gaaccaggtc agcctgacct gcctggtcaa aggcttctat cccagcgaca tcgccgtgga gtgggagagc aatgggcagc cggagaacaa ctacaagacc acgcctcccg tgctggactc cgacggctcc ttcttcctct acagcaagct caccgtggac aagagcaggt ggcagcaggg gaacgtcttc tcatgctccg tgatgcatga ggctctgcac aaccactaca cgcagaagag cctctccctg tctccgggt
```

The amino acid sequence of the second polypeptide chain of DR5 mAb 1×DR5 mAb 2 Fc diabody is (SEQ ID NO:118):

```
DIVMTQSHKF MSTSVGDRVS ITCKASQDVN TAVAWYQQKP

GQSPKLLIYW ASTRHTGVPD RFTGSGSGTD YTLTIKSVQA

EDLTLYYCQQ HYITPWTFGG GTKLEIKGGG SGGGGEVKFL

ESGGGLVQPG GSLKLSCVAS GFDFSRYWMS WVRQAPGKGL

EWIGEINPDS NTINYTPSLK DKFIISRDNA KNTLYLQMTK

VRSEDTALYY CTRRAYYGNP AWFAYWGQGT LVTVSAASTK

GKVAACKEKV AALKEKVAAL KEKVAALKE
```

In SEQ ID NO:118, amino acid residues 1-107 correspond to the amino acid sequence of the VL Domain of DR5 mAb 2 (SEQ ID NO:13), residues 108-115 correspond to the intervening spacer peptide GGGSGGGG (Linker 1) (SEQ ID NO:33), residues 116-236 correspond to the amino acid sequence of the VH Domain of DR5 mAb 1 (SEQ ID NO:8), except that the C-terminal serine residue of SEQ ID NO:8 has been replaced with an alanine residue, residues 237-241 correspond to an ASTKG linker (SEQ ID NO:47), and residues 242-269 correspond to a cysteine-containing K-coil Domain (SEQ ID NO:42). A polynucleotide that encodes SEQ ID NO:118 is SEQ ID NO:119:

```
gacattgtga tgacccagtc tcacaaattc atgtccactt cagtaggaga cagggtcagc atcacctgca aggccagtca ggatgtgaat actgctgtag cctggtatca acaaaaacca gggcaatctc ctaaactact gatttactgg gcatccaccc ggcacactgg agtccctgat cgcttcacag gcagtggatc tgggacagat tatacactca ccatcaaaag tgtgcaggct gaagacctga cactttatta ctgtcagcaa cactatatca ctccgtggac gttcggtgga ggcaccaagc tggaaatcaa aggaggcgga tccggcggcg gaggcgaggt gaagtttctc gagtctggag gtggcctggt gcagcctgga ggatccctga aactctcctg tgtagcctca ggattcgatt ttagtagata ctggatgagt tgggtccggc aggctccagg aaagggcta gaatggattg gagaaattaa tccagatagc aatacgataa actatacgcc atctctaaag gataaattca tcatctccag agacaacgcc aaaaatacgg tgtatctgca aatgaccaaa gtgagatctg aggacacagc cctttattat tgtacaagaa gggcctacta tggtaaccg gcctggtttg cttactgggg ccaagggact ctggtcactg tctctgcagc ctccaccaag ggcaaagtgg ccgcatgtaa ggagaaagtt gctgctttga aagagaaggt cgccgcactt aaggaaaagg tcgcagccct gaaagag
```

Another Fc Region-containing diabody, designated "DR5 mAb 1×DR5 mAb 2 Fc diabody (AA)," is identical to DR5 mAb 1×DR5 mAb 2 Fc diabody except the Fc Region is a variant having a L234A/L235A double mutation (underlined) which reduces/eliminates binding to FcγRIIIA and reduces/eliminates effector functions. The amino acid sequence of the first polypeptide chain of this Fc Region-Containing diabody is (SEQ ID NO:120):

```
DIVLTQSPAS LAVSLGQRAT ISCRASKSVS SSGYSYMHWY

QQKPGQPPKV LIFLSSNLDS GVPARFSGSG SGTDFTLNIH

PVEDGDAATY YCQHSRDLPP TFGGGTKLEI KGGGSGGGGK

VQLQQSGAEL VKPGASVKLS CKASGYTFTE YILHWVKQKS

GQGLEWIGWF YPGNNNIKYN EKFKDKATLT ADKSSSTVYM

ELSRLTSEDS AVYFCARHEQ GPGYFDYWGQ GTTLTVSSAS

TKGEVAACEK EVAALEKEVA ALEKEVAALE KLEPKSSDKT

HTCPPCPAPE AAGGPSVFLF PPKPKDTLMI SRTPEVTCVV

VDVSHEDPEV KFNWYVDGVE VHNAKTKPRE EQYNSTYRVV

SVLTVLHQDW LNGKEYKCKV SNKALPAPIE KTISKAKGQP

REPQVYTLPP SREEMTKNQV SLTCLVKGFY PSDIAVEWES

NGQPENNYKT TPPVLDSDGS FFLYSKLTVD KSRWQQGNVF

SCSVMHEALH NHYTQKSLSL SPG
```

A polynucleotide that encodes SEQ ID NO:120 is SEQ ID NO:121:

```
gacattgtgc tgacacagtc tcctgcttcc ttagctgtat ctctcgggca gagggccacc atctcatgca gggccagcaa aagtgtcagt tcctctggct atagttatat gcactggtac caacagaaac caggacagcc acccaaagtc ctcatctttc tttcatccaa cctagattct ggggtccctg ccaggttcag tggcagtggg tctgggacag acttcaccct caacatccat cctgtggagg atggggatgc tgcaacctat tactgtcagc acagtaggga tcttcctccg acgttcggtg gaggcaccaa gctggaaatc aaaggaggcg gatccggcgg cggaggcaag gtccagctgc agcagtctgg agctgaactg gtgaaacccg gggcatcagt gaagctgtcc tgcaaggctt ctgggtacac cttcactgag tatattttac actgggtaaa gcagaagtct ggacagggtc ttgagtggat tgggtggttt tatcctggaa ataataatat aaagtacaat gagaaattca aggacaaggc cacactgact gcggacaaat cctccagcac agtctatatg gaacttagta gattgacatc tgaagactct gcggtctatt tctgtgcaag acacgaacaa ggaccaggtt actttgacta ctggggccaa ggcaccactc tcacagtctc ctccgcctcc accaagggcg aagtggccgc atgtgagaaa gaggttgctg ctttggagaa ggaggtcgct gcacttgaaa aggaggtcgc agccctggag aaactggagc ccaaatcttc tgacaaaact cacacatgcc caccgtgccc agcacctgaa ctcctggggg gaccgtcagt cttcctcttc ccccaaaac ccaaggacac cctcatgatc tcccgaccc ctgaggtcac atgcgtggtg gtggacgtga gccacgaaga ccctgaggtc aagttcaact ggtacgtgga cggcgtggag gtgcataatg ccaagacaaa gccgcgggag gagcagtaca acagcacgta ccgtgtggtc agcgtcctca ccgtcctgca ccaggactgg ctgaatggca aggagtacaa gtgcaaggtc tccaacaaag ccctcccagc ccccatcgag aaaaccatct ccaaagccaa agggcagccc cgagaaccac aggtgtacac cctgccccca tcccgggagg agatgaccaa gaaccaggtc agcctgacct gcctggtcaa aggcttctat cccagcgaca tcgccgtgga gtgggagagc aatgggcagc cggagaacaa ctacaagacc acgcctcccg tgctggactc cgacggctcc ttcttcctct acagcaagct caccgtggac aagagcaggt ggcagcaggg gaacgtcttc tcatgctccg tgatgcatga ggctctgcac aaccactaca cgcagaagag cctctccctg tctccgggt
```

The second polypeptide chain of DR5 mAb 1×DR5 mAb 2 Fc diabody (AA) is also SEQ ID NO:118 (encoded by SEQ ID NO:119), described in detail above.

Alternatively, where reduced/eliminated binding to FcγRIIIA and/or reduced/eliminated effector functions is desired, the CH2-CH3 region of IgG2 or IgG4 may be used. In such an Fc Region-Containing diabody, amino acid residues 288-504 of SEQ ID NOs:116 or 120 will be replaced with SEQ ID NO:164 (CH2-CH3 of IgG2) or SEQ ID NO:103 (CH2-CH3 of IgG4), optionally lacking the C-terminal amino acid residue.

2. DR5 mAb 2×DR5 mAb 1 Fc Region-Containing Diabodies

Exemplary bispecific Fc Region-Containing diabodies tetravalent for DR5 composed of two pairs of polypeptide chains are constructed having the VL and VH Domains of anti-human DR5 antibody DR5 mAb 2 and the VL and VH Domains of DR5 mAb 1. One Fc Region-Containing diabody designated "DR5 mAb 2×DR5 mAb 1 Fc diabody," contains a wild-type IgG1 Fc Region. The amino acid sequence of the first polypeptide chain of this Fc Region-Containing diabody is (SEQ ID NO:122):

DIVMTQSHKF MSTSVGDRVS ITCKASQDVN TAVAWYQQKP

GQSPKLLIYW ASTRHTGVPD RFTGSGSGTD YTLTIKSVQA

EDLTLYYCQQ HYITPWTFGG GTKLEIKGGG SGGGGEVKFL

ESGGGLVQPG GSLKLSCVAS GFDFSRYWMS WVRQAPGKGL

EWIGEINPDS NTINYTPSLK DKFIISRDNA KNTLYLQMTK

VRSEDTALYY CTRRAYYGNP AWFAYWGQGT LVTVSAASTK

GEVAACEKEV AALEKEVAAL EKEVAALEKL EPKSSDKTHT

CPPCPAPELL GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP G

In SEQ ID NO:122, amino acid residues 1-107 correspond to the amino acid sequence of the VL Domain of DR5 mAb 2 (SEQ ID NO:13), residues 108-115 correspond to the intervening spacer peptide GGGSGGGG (Linker 1) (SEQ ID NO:33), residues 116-236 correspond to the amino acid sequence of the VH Domain of DR5 mAb 1 (SEQ ID NO:8) except that the C-terminal serine residue of SEQ ID NO:8 has been replaced with an alanine residue, residues 237-241 correspond to an ASTKG linker (SEQ ID NO:47) residues 242-269 correspond to a cysteine-containing E-coil Domain (SEQ ID NO:41), residues 270-275 correspond to a LEPKSS linker (SEQ ID NO: 49), residues 276-285 correspond to a linker (DKTHTCPPCP; SEQ ID NO:48) derived from an IgG1 hinge domain, and residues 286-501 correspond to a wild-type IgG1 Fc Region (SEQ ID NO:1, lacking the C-terminal amino acid residue). A polynucleotide that encodes SEQ ID NO:122 is SEQ ID NO:123:

gacattgtga tgacccagtc tcacaaattc atgtccactt cagtaggaga cagggtcagc atcacctgca aggccagtca ggatgtgaat actgctgtag cctggtatca acaaaaacca gggcaatctc ctaaactact gatttactgg gcatccaccc ggcacactgg agtccctgat cgcttcacag gcagtggatc

```
tgggacagat tatacactca ccatcaaaag tgtgcaggct gaagacctga cactttatta ctgtcagcaa cactatatca ctccgtggac gttcggtgga ggcaccaagc tggaaatcaa aggaggcgga tccggcggcg gaggcgaggt gaagtttctc gagtctggag gtggcctggt gcagcctgga ggatccctga aactctcctg tgtagcctca ggattcgatt ttagtagata ctggatgagt tgggtccggc aggctccagg gaagggcta gaatggattg gagaaattaa tccagatagc aatacgataa actatacgcc atctctaaag gataaattca tcatctccag agacaacgcc aaaaatacgc tgtatctgca aatgaccaaa gtgagatctg aggacacagc cctttattat tgtacaagaa gggcctacta tggtaacccg gcctggtttg cttactgggg ccaagggact ctggtcactg tctctgcagc ctccaccaag ggcgaagtgg ccgcatgtga aaagaggtt gctgctttgg agaaggaggt cgctgcactt gaaaaggagg tcgcagccct ggagaaactg gagcccaaat cttctgacaa aactcacaca tgcccaccgt gcccagcacc tgaactcctg ggggaccgt cagtcttcct cttcccccca aaacccaagg acaccctcat gatctcccgg acccctgagg tcacatgcgt ggtggtggac gtgagccacg aagacctga ggtcaagttc aactggtacg tggacggcgt ggaggtgcat aatgccaaga caaagccgcg ggaggagcag tacaacagca cgtaccgtgt ggtcagcgtc ctcaccgtcc tgcaccagga ctggctgaat ggcaaggagt acaagtgcaa ggtctccaac aaagccctcc cagcccccat cgagaaaacc atctccaaag ccaaagggca gccccgagaa ccacaggtgt acaccctgcc cccatcccgg gaggagatga ccaagaacca ggtcagcctg acctgcctg tcaaaggctt ctatcccagc gacatcgccg tggagtggga gagcaatggg cagccggaga acaactacaa gaccacgcct cccgtgctgg actccgacgg ctccttcttc ctctacagca agctcaccgt ggacaagagc aggtggcagc aggggaacgt cttctcatgc tccgtgatgc atgaggctct gcacaaccac tacacgcaga agagcctctc cctgtctccg ggt
```

The amino acid sequence of the second polypeptide chain of DR5 mAb 2×DR5 mAb 1 Fc diabody is (SEQ ID NO:124):

```
DIVLTQSPAS LAVSLGQRAT ISCRASKSVS SSGYSYMHWY
QQKPGQPPKV LIFLSSNLDS GVPARFSGSG SGTDFTLNIH
PVEDGDAATY YCQHSRDLPP TFGGGTKLEI KGGGSGGGGK
VQLQQSGAEL VKPGASVKLS CKASGYTFTE YILHWVKQKS
```

-continued

```
GQGLEWIGWF YPGNNNIKYN EKFKDKATLT ADKSSSTVYM
ELSRLTSEDS AVYFCARHEQ GPGYFDYWGQ GTTLTVSSAS
TKGKVAACKE KVAALKEKVA ALKEKVAALK E
```

In SEQ ID NO:124, amino acid residues 1-111 correspond to the amino acid sequence of the VL Domain of DR5 mAb 1 (SEQ ID NO:3), residues 112-119 correspond to the intervening spacer peptide GGGSGGGG (Linker 1) (SEQ ID NO:33), residues 120-238 correspond to the amino acid sequence of the VH Domain of DR5 mAb 2 (SEQ ID NO:18), residues 239-243 correspond to an ASTKG linker (SEQ ID NO:47) residues 244-271 correspond to a cysteine-containing K-coil Domain (SEQ ID NO:42). A polynucleotide that encodes SEQ ID NO:124 is SEQ ID NO:125:

```
gacattgtgc tgacacagtc tcctgcttcc ttagctgtat
ctctcgggca gagggccacc atctcatgca gggccagcaa
aagtgtcagt tcctctggct atagttatat gcactggtac
caacagaaac caggacagcc acccaaagtc ctcatctttc
tttcatccaa cctagattct ggggtccctg ccaggttcag
tggcagtggg tctgggacag acttcaccct caacatccat
cctgtggagg atggggatgc tgcaacctat tactgtcagc
acagtaggga tcttcctccg acgttcggtg gaggcaccaa
gctggaaatc aaaggaggcg gatccggcgg cggaggcaag
gtccagctgc agcagtctgg agctgaactg gtgaaacccg
gggcatcagt gaagctgtcc tgcaaggctt ctgggtacac
cttcactgag tatattttac actgggtaaa gcagaagtct
ggacagggtc ttgagtggat tgggtggttt tatcctggaa
ataataatat aaagtacaat gagaaattca aggacaaggc
cacactgact gcggacaaat cctccagcac agtctatatg
gaacttagta gattgacatc tgaagactct gcggtctatt
tctgtgcaag acacgaacaa ggaccaggtt actttgacta
ctggggccaa ggcaccactc tcacagtctc ctccgcctcc
accaagggca aagtggccgc atgtaaggag aaagttgctg
ctttgaaaga gaaggtcgcc gcacttaagg aaaaggtcgc
agccctgaaa gag
```

Another Fc Region-containing diabody, designated "DR5 mAb 2×DR5 mAb 1 Fe diabody (AA)," is identical to DR5 mAb 2×DR5 mAb 1 Fc diabody except the Fc Region is a variant having a L234A/L235A double mutation (bolded) which reduces/eliminates binding to FcγRIIIA and reduces/eliminates effector functions. The amino acid sequence of the first polypeptide chain of this Fc Region-Containing diabody is (SEQ ID NO:126):

```
DIVMTQSHKF MSTSVGDRVS ITCKASQDVN TAVAWYQQKP
GQSPKLLIYW ASTRHTGVPD RFTGSGSGTD YTLTIKSVQA
EDLTLYYCQQ HYITPWTFGG GTKLEIKGGG SGGGGEVKFL
```

```
ESGGGLVQPG GSLKLSCVAS GFDFSRYWMS WVRQAPGKGL

EWIGEINPDS NTINYTPSLK DKFIISRDNA KNTLYLQMTK

VRSEDTALYY CTRRAYYGNP AWFAYWGQGT LVTVSAASTK

GEVAACEKEV AALEKEVAAL EKEVAALEKL EPKSSDKTHT

CPPCPAPEAA GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR EEMTKNQVSL TCLVKGFYPS DIAVEWESNG

QPENNYKTTP PVLDSDGSFF LYSKLTVDKS RWQQGNVFSC

SVMHEALHNH YTQKSLSLSP G
```

A polynucleotide that encodes SEQ ID NO:126 is SEQ ID NO:127:

```
gacattgtga tgacccagtc tcacaaattc atgtccactt cagtaggaga cagggtcagc atcacctgca aggccagtca ggatgtgaat actgctgtag cctggtatca acaaaaacca gggcaatctc ctaaactact gatttactgg gcatccaccc ggcacactgg agtccctgat cgcttcacag gcagtggatc tgggacagat tatacactca ccatcaaaag tgtgcaggct gaagacctga cactttatta ctgtcagcaa cactatatca ctccgtggac gttcggtgga ggcaccaagc tggaaatcaa aggaggcgga tccggcggcg gaggcgaggt gaagtttctc gagtctggag gtggcctggt gcagcctgga ggatccctga aactctcctg tgtagcctca ggattcgatt ttagtagata ctggatgagt tgggtccggc aggctccagg gaaagggcta gaatggattg gagaaattaa tccagatagc aatacgataa actatacgcc atctctaaag gataaattca tcatctccag agacaacgcc aaaaatacgc tgtatctgca aatgaccaaa gtgagatctg aggacacagc ccttttattat tgtacaagaa gggcctacta tggtaacccg gcctggtttg cttactgggg ccaagggact ctggtcactg tctctgcagc ctccaccaag ggcgaagtgg ccgcatgtga gaaagaggtt gctgctttgg agaaggaggt cgctgcactt gaaaaggagg tcgcagccct ggagaaactg gagcccaaat cttctgacaa aactcacaca tgcccaccgt gcccagcacc tgaactcctg gggggaccgt cagtcttcct cttccccca aacccaagg acaccctcat gatctcccgg accctgagg tcacatgcgt ggtggtggac gtgagccacg aagacctga ggtcaagttc aactggtacg tggacggcgt ggaggtgcat aatgccaaga caaagccgcg ggaggagcag tacaacagca cgtaccgtgt ggtcagcgtc ctcaccgtcc tgcaccagga ctggctgaat ggcaaggagt
```

```
acaagtgcaa ggtctccaac aaagccctcc cagccccat cgagaaaacc atctccaaag ccaaagggca gccccgagaa ccacaggtgt acaccctgcc cccatcccgg gaggagatga ccaagaacca ggtcagcctg acctgcctgg tcaaaggctt ctatcccagc gacatcgccg tggagtggga gagcaatggg cagccggaga caactacaa gaccacgcct cccgtgctgg actccgacgg ctccttcttc ctctacagca agctcaccgt ggacaagagc aggtggcagc aggggaacgt cttctcatgc tccgtgatgc atgaggctct gcacaaccac tacacgcaga agagcctctc cctgtctccg ggt
```

The second polypeptide chain of DR5 mAb 1×DR5 mAb 2 Fc diabody (AA) is also SEQ ID NO:124 (encoded by SEQ ID NO:125), described in detail above.

Alternatively, where reduced/eliminated binding to FcγRIIIA and/or reduced/eliminated effector functions is desired, the CH2-CH3 region of IgG2 or IgG4 may be used. In such an Fc Region-Containing diabody, amino acid residues 286-502 of SEQ ID NOs:122 or 126 will be replaced with SEQ ID NO:164 (CH2-CH3 of IgG2) or SEQ ID NO:103 (CH2-CH3 of IgG4), optionally lacking the C-terminal amino acid residue.

B. DR5×DR5 Bispecific Diabodies Bivalent For DR5

1. DR5 mAb 1×DR5 mAb 2 Diabody

Exemplary bispecific diabodies bispecific for DR5 lacking an Fc Region composed of two polypeptide chains are constructed having the VL and VH Domains of anti-human DR5 antibody DR5 mAb 1 and the VL and VH Domains of DR5 mAb 2. The amino acid sequence of the first polypeptide chain of this diabody comprises amino acid residues 1-271 of SEQ ID NO:116 described above. The amino acid sequence of the second polypeptide chain of this diabody comprises SEQ ID NO:118 described above.

Other exemplary bispecific diabodies bispecific for DR5 comprising an Fc Region composed of two polypeptide chains are constructed having the VL and VH Domains of anti-human DR5 antibody DR5 mAb 1 and the VL and VH Domains of DR5 mAb 2. The amino acid sequence of the first polypeptide chain of this diabody comprises SEQ ID NO:116 or SEQ ID NO:120 described above. The amino acid sequence of the second polypeptide chain of this diabody comprises SEQ ID NO:118, and further comprises a linker having the amino acid residues LEPKSSDKTH-TCPPCP; SEQ ID NO:51, and an IgG1 Fc Region have the amino acid sequence of SEQ ID NO:1 or SEQ ID NO:102, optionally lacking the C-terminal amino acid residue.

2. DR5 mAb 2×DR5 mAb 1 Diabody

Exemplary bispecific diabodies bivalent for DR5 lacking an Fc Region composed of two polypeptide chains are constructed having the VL and VH Domains of anti-human DR5 antibody DR5 mAb 2 and the VL and VH Domains of DR5 mAb 1. The amino acid sequence of the first polypeptide chain of this diabody comprises amino acid residues 1-269 of SEQ ID NO:122 described above. The amino acid sequence of the second polypeptide chain of this diabody comprises SEQ ID NO:124 described above.

Other exemplary bispecific diabodies bivalent for DR5 containing an Fc Region composed of two polypeptide chains are constructed having the VL and VH Domains of anti-human DR5 antibody DR5 mAb 2 and the VL and VH Domains of DR5 mAb 1. The amino acid sequence of the first polypeptide chain of this diabody comprises SEQ ID NO:122 or SEQ ID NO:126 described above. The amino acid sequence of the second polypeptide chain of this diabody comprises SEQ ID NO:124, and further comprises a linker having the amino acid residues LEPKSSDKTH-TCPPCP; SEQ ID NO:51, and an IgG1 Fc Region have the amino acid sequence of SEQ ID NO:1 or SEQ ID NO:102, optionally lacking the C-terminal amino acid residue.

C. DR5×DR5 Monospecific Fc Region-Containing Diabodies Tetravalent For DR5

1. DR5 mAb 1×DR5 mAb 1 Fc Region-Containing Diabodies

Exemplary monospecific Fc Region-Containing diabodies tetravalent for DR5 composed of two pairs of polypeptide chains are constructed having the VL and VH Domains of anti-human DR5 antibody DR5 mAb 1. One Fc Region-Containing diabody designated "DR5 mAb 1×DR5 mAb 1 Fc diabody," contains a wild-type IgG1 Fc Region. The amino acid sequence of the first polypeptide chain of this Fc Region-Containing diabody is (SEQ ID NO:128):

```
DIVLTQSPAS LAVSLGQRAT ISCRASKSVS SSGYSYMHWY
QQKPGQPPKV LIFLSSNLDS GVPARFSGSG SGTDFTLNIH
PVEDGDAATY YCQHSRDLPP TFGGGTKLEI KGGGSGGGGE
VKFLESGGGL VQPGGSLKLS CVASGFDFSR YWMSWVRQAP
GKGLEWIGEI NPDSNTINYT PSLKDKFIIS RDNAKNTLYL
QMTKVRSEDT ALYYCTRRAY YGNPAWFAYW GQGTLVTVSA
ASTKGEVAAC EKEVAALEKE VAALEKEVAA LEKLEPKSSD
KTHTCPPCPA PELLGGPSVF LFPPKPKDTL MISRTPEVTC
VVVDVSHEDP EVKFNWYVDG VEVHNAKTKP REEQYNSTYR
VVSVLTVLHQ DWLNGKEYKC KVSNKALPAP IEKTISKAKG
QPREPQVYTL PPSREEMTKN QVSLTCLVKG FYPSDIAVEW
ESNGQPENNY KTTPPVLDSD GSFFLYSKLT VDKSRWQQGN
VFSCSVMHEA LHNHYTQKSL SLSPG
```

In SEQ ID NO:128, amino acid residues 1-111 correspond to the amino acid sequence of the VL Domain of DR5 mAb 1 (SEQ ID NO:3), residues 112-119 correspond to the intervening spacer peptide GGGSGGGG (Linker 1) (SEQ ID NO:33), residues 120-240 correspond to the amino acid sequence of the VH Domain of DR5 mAb 1 (SEQ ID NO:8) except that the C-terminal serine residue of SEQ ID NO:8 has been replaced with an alanine residue, residues 241-245 correspond to an ASTKG linker (SEQ ID NO:47) residues 246-273 correspond to a cysteine-containing E-coil Domain (SEQ ID NO:41), residues 274-279 correspond to a LEPKSs linker (SEQ ID NO: 49), residues 280-289 correspond to a linker (DKTHTCPPCP; SEQ ID NO:48) derived from an IgG1 hinge domain, and residues 290-505 correspond to a wild-type IgG1 Fc Region (SEQ ID NO:1, lacking the C-terminal amino acid residue). A polynucleotide that encodes SEQ ID NO:128 is SEQ ID NO:129:

```
gacattgtgc tgacacagtc tcctgcttcc ttagctgtat
ctctcgggca gagggccacc atctcatgca gggccagcaa
aagtgtcagt tcctctggct atagttatat gcactggtac
caacagaaac caggacagcc acccaaagtc ctcatctttc
tttcatccaa cctagattct ggggtccctg ccaggttcag
tggcagtggg tctgggacag acttcaccct caacatccat
cctgtggagg atggggatgc tgcaacctat tactgtcagc
acagtaggga tcttcctccg acgttcggtg gaggcaccaa
gctggaaatc aaaggaggcg gatccggcgg cggaggcgag
gtgaagtttc tcgagtctgg aggtggcctg gtgcagcctg
gaggatccct gaaactctcc tgtgtagcct caggattcga
ttttagtaga tactggatga gttgggtccg gcaggctcca
gggaaagggc tagaatggat tggagaaatt aatccagata
gcaatacgat aaactatacg ccatctctaa aggataaatt
catcatctcc agagacaacg ccaaaaatac gctgtatctg
caaatgacca aagtgagatc tgaggacaca gcccttattt
attgtacaag aagggcctac tatggtaacc cggcctggtt
tgcttactgg ggccaaggga ctctggtcac tgtctctgca
gcctccacca agggcgaagt ggccgcatgt gagaaagagg
ttgctgcttt ggagaaggag gtcgctgcac ttgaaaagga
ggtcgcagcc ctggagaaac tggagcccaa atcttctgac
aaaactcaca catgcccacc gtgcccagca cctgaactcc
tggggggacc gtcagtcttc ctcttccccc caaaacccaa
ggacaccctc atgatctccc ggacccctga ggtcacatgc
gtggtggtgg acgtgagcca cgaagaccct gaggtcaagt
tcaactggta cgtggacggc gtggaggtgc ataatgccaa
gacaaagccg cgggaggagc agtacaacag cacgtaccgt
gtggtcagcg tcctcaccgt cctgcaccag gactggctga
atggcaagga gtacaagtgc aaggtctcca acaaagccct
cccagccccc atcgagaaaa ccatctccaa agccaaaggg
cagccccgag aaccacaggt gtacaccctg cccccatccc
gggaggagat gaccaagaac caggtcagcc tgacctgcct
ggtcaaaggc ttctatccca gcgacatcgc cgtggagtgg
gagagcaatg ggcagccgga gaacaactac aagaccacgc
ctcccgtgct ggactccgac ggctccttct tcctctacag
caagctcacc gtggacaaga gcaggtggca gcaggggaac
gtcttctcat gctccgtgat gcatgaggct ctgcacaacc
actacacgca gaagagcctc tccctgtctc cgggt
```

The amino acid sequence of the second polypeptide chain of DR5 mAb 1×DR5 mAb 1 Fc diabody is (SEQ ID NO:130):

```
DIVLTQSPAS LAVSLGQRAT ISCRASKSVS SSGYSYMHWY
QQKPGQPPKV LIFLSSNLDS GVPARFSGSG SGTDFTLNIH
```

-continued
```
PVEDGDAATY YCQHSRDLPP TFGGGTKLEI KGGGSGGGGE

VKFLESGGGL VQPGGSLKLS CVASGFDFSR YWMSWVRQAP

GKGLEWIGEI NPDSNTINYT PSLKDKFIIS RDNAKNTLYL

QMTKVRSEDT ALYYCTRRAY YGNPAWFAYW GQGTLVTVSA

ASTKGKVAAC KEKVAALKEK VAALKEKVAA LKE
```

In SEQ ID NO:130, amino acid residues 1-111 correspond to the amino acid sequence of the VL Domain of DR5 mAb 1 (SEQ ID NO:3), residues 112-119 correspond to the intervening spacer peptide GGGSGGGG (Linker 1) (SEQ ID NO:33), residues 120-240 correspond to the amino acid sequence of the VH Domain of DR5 mAb 1 (SEQ ID NO:8) except that the C-terminal serine residue of SEQ ID NO:8 has been replaced with an alanine residue, residues 241-245 correspond to an ASTKG linker (SEQ ID NO:47) residues 246-273 correspond to a cysteine-containing K-coil Domain (SEQ ID NO:42). A polynucleotide that encodes SEQ ID NO:130 is SEQ ID NO:131:

```
gacattgtgc tgacacagtc tcctgcttcc ttagctgtat ctctcgggca gagggccacc atctcatgca gggccagcaa aagtgtcagt tcctctggct atagttatat gcactggtac caacagaaac caggacagcc acccaaagtc ctcatctttc tttcatccaa cctagattct ggggtccctg ccaggttcag tggcagtggg tctgggacag acttcaccct caacatccat cctgtggagg atggggatgc tgcaacctat tactgtcagc acagtaggga tcttcctccg acgttcggtg gaggcaccaa gctggaaatc aaaggaggcg gatccggcgg cggaggcgag gtgaagtttc tcgagtctgg aggtggcctg gtgcagcctg gaggatccct gaaactctcc tgtgtagcct caggattcga ttttagtaga tactggatga gttgggtccg gcaggctcca gggaaagggc tagaatggat tggagaaatt aatccagata gcaatacgat aaactatacg ccatctctaa aggataaatt catcatctcc agagacaacg ccaaaaatac gctgtatctg caaatgacca aagtgagatc tgaggacaca gcccttt att attgtacaag aagggcctac tatggtaacc cggcctggtt tgcttactgg ggccaaggga ctctggtcac tgtctctgca gcctccacca agggcaaagt ggccgcatgt aaggagaaag ttgctgcttt gaaagagaag gtcgccgcac ttaaggaaaa ggtcgcagcc ctgaaagag
```

Another Fc Region-containing diabody, designated "DR5 mAb 1×DR5 mAb 1 Fc diabody (AA)," is identical DR5 mAb 1×DR5 mAb 1 Fc diabody except the Fc Region is a variant having a L234A/L235A double mutation (underlined) which reduces/eliminates binding to FcγRIIIA and reduces/eliminates effector functions. The amino acid sequence of the first polypeptide chain of this Fc Region-Containing diabody is (SEQ ID NO:132):

```
DIVLTQSPAS LAVSLGQRAT ISCRASKSVS SSGYSYMHWY

QQKPGQPPKV LIFLSSNLDS GVPARFSGSG SGTDFTLNIH

PVEDGDAATY YCQHSRDLPP TFGGGTKLEI KGGGSGGGGE

VKFLESGGGL VQPGGSLKLS CVASGFDFSR YWMSWVRQAP

GKGLEWIGEI NPDSNTINYT PSLKDKFIIS RDNAKNTLYL

QMTKVRSEDT ALYYCTRRAY YGNPAWFAYW GQGTLVTVSA

ASTKGEVAAC EKEVAALEKE VAALEKEVAA LEKLEPKSSD

KTHTCPPCPA PEAAGGPSVF LFPPKPKDTL MISRTPEVTC

VVVDVSHEDP EVKFNWYVDG VEVHNAKTKP REEQYNSTYR

VVSVLTVLHQ DWLNGKEYKC KVSNKALPAP IEKTISKAKG

QPREPQVYTL PPSREEMTKN QVSLTCLVKG FYPSDIAVEW

ESNGQPENNY KTTPPVLDSD GSFFLYSKLT VDKSRWQQGN

VFSCSVMHEA LHNHYTQKSL SLSPG
```

A polynucleotide that encodes SEQ ID NO:132 is SEQ ID NO:133:

```
gacattgtgc tgacacagtc tcctgcttcc ttagctgtat ctctcgggca gagggccacc atctcatgca gggccagcaa aagtgtcagt tcctctggct atagttatat gcactggtac caacagaaac caggacagcc acccaaagtc ctcatctttc tttcatccaa cctagattct ggggtccctg ccaggttcag tggcagtggg tctgggacag acttcaccct caacatccat cctgtggagg atggggatgc tgcaacctat tactgtcagc acagtaggga tcttcctccg acgttcggtg gaggcaccaa gctggaaatc aaaggaggcg gatccggcgg cggaggcgag gtgaagtttc tcgagtctgg aggtggcctg gtgcagcctg gaggatccct gaaactctcc tgtgtagcct caggattcga ttttagtaga tactggatga gttgggtccg gcaggctcca gggaaagggc tagaatggat tggagaaatt aatccagata gcaatacgat aaactatacg ccatctctaa aggataaatt catcatctcc agagacaacg ccaaaaatac gctgtatctg caaatgacca aagtgagatc tgaggacaca gcccttt att attgtacaag aagggcctac tatggtaacc cggcctggtt tgcttactgg ggccaaggga ctctggtcac tgtctctgca gcctccacca agggcgaagt ggccgcatgt gagaaagagg ttgctgcttt ggagaaggag gtcgctgcac ttgaaaagga ggtcgcagcc ctggagaaac tggagcccaa atcttctgac aaaactcaca catgcccacc gtgcccagca cctgaagccg cgggggggacc gtcagtcttc ctcttccccc caaaacccaa ggacaccctc atgatctccc ggacccctga ggtcacatgc gtggtggtgg acgtgagcca cgaagaccct gaggtcaagt
```

```
tcaactggta cgtggacggc gtggaggtgc ataatgccaa gacaaagccg cgggaggagc agtacaacag cacgtaccgt gtggtcagcg tcctcaccgt cctgcaccag gactggctga atggcaagga gtacaagtgc aaggtctcca acaaagccct cccagccccc atcgagaaaa ccatctccaa agccaagggg cagccccgag aaccacaggt gtacaccctg cccccatccc gggaggagat gaccaagaac caggtcagcc tgacctgcct ggtcaaaggc ttctatccca gcgacatcgc cgtggagtgg gagagcaatg ggcagccgga gaacaactac aagaccacgc ctcccgtgct ggactccgac ggctccttct tcctctacag caagctcacc gtggacaaga gcaggtggca gcagggggaac gtcttctcat gctccgtgat gcatgaggct ctgcacaacc actacacgca gaagagcctc tccctgtctc cgggt
```

The second polypeptide chain of DR5 mAb 1×DR5 mAb 1 Fc diabody (AA) is also SEQ ID NO:130 (encoded by SEQ ID NO:131), described in detail above.

Alternatively, where reduced/eliminated binding to FcγRIIIA and/or reduced/eliminated effector functions is desired, the CH2-CH3 region of IgG2 or IgG4 may be used. In such an Fc Region-Containing diabody, amino acid residues 290-506 of SEQ ID NOs:128 or 132 will be replaced with SEQ ID NO:164 (CH2-CH3 of IgG2) or SEQ ID NO:103 (CH2-CH3 of IgG4), optionally lacking the C-terminal amino acid residue.

2. DR5 mAb 2×DR5 mAb 2 Fc Region-Containing Diabodies

Exemplary monospecific Fc Region-Containing diabodies tetravalent for DR5 composed of two pairs of polypeptide chains are constructed having the VL and VH Domains of anti-human DR5 antibody DR5 mAb 2. The first Fc Region-Containing diabody designated "DR5 mAb 2×DR5 mAb 2 Fc diabody," contains a wild-type IgG1 Fc Region. The amino acid sequence of the first polypeptide chain of this Fc Region-Containing diabody is (SEQ ID NO:134):

```
DIVMTQSHKF MSTSVGDRVS ITCKASQDVN TAVAWYQQKP

GQSPKLLIYW ASTRHTGVPD RFTGSGSGTD YTLTIKSVQA

EDLTLYYCQQ HYITPWTFGG GTKLEIKGGS GGGGKVQLQ

QSGAELVKPG ASVKLSCKAS GYTFTEYILH WVKQKSGQGL

EWIGWFYPGN NNIKYNEKFK DKATLTADKS SSTVYMELSR

LTSEDSAVYF CARHEQGPGY FDYWGQGTTL TVSSASTKGE

VAACEKEVAA LEKEVAALEK EVAALEKLEP KSSDKTHTCP

PCPAPELLGG PSVFLFPPKP KDTLMISRTP EVTCVVVDVS

HEDPEVKFNW YVDGVEVHNA KTKPREEQYN STYRVVSVLT

VLHQDWLNGK EYKCKVSNKA LPAPIEKTIS KAKGQPREPQ

VYTLPPSREE MTKNQVSLTC LVKGFYPSDI AVEWESNGQP

ENNYKTTPPV LDSDGSFFLY SKLTVDKSRW QQGNVFSCSV

MHEALHNHYT QKSLSLSPG
```

In SEQ ID NO:134, amino acid residues 1-107 correspond to the amino acid sequence of the VL Domain of DR5 mAb 2 (SEQ ID NO:13), residues 108-115 correspond to the intervening spacer peptide GGGSGGGG (Linker 1) (SEQ ID NO:33), residues 116-237 correspond to the amino acid sequence of the VH Domain of DR5 mAb 2 (SEQ ID NO:18), residues 235-239 correspond to an ASTKG linker (SEQ ID NO:47) residues 240-267 correspond to a cysteine-containing E-coil Domain (SEQ ID NO:41), residues 268-273 correspond to a LEPKSS linker (SEQ ID NO: 49), residues 274-283 correspond to a linker (DKTHTCPPCP; SEQ ID NO:48) derived from an IgG1 hinge domain, and residues 284-499 correspond to a wild-type IgG1 Fc Region (SEQ ID NO:1, lacking the C-terminal amino acid residue). A polynucleotide that encodes SEQ ID NO:134 is SEQ ID NO:135:

```
gacattgtga tgacccagtc tcacaaattc atgtccactt cagtaggaga cagggtcagc atcacctgca aggccagtca ggatgtgaat actgctgtag cctggtatca acaaaaacca gggcaatctc ctaaactact gatttactgg gcatccaccc ggcacactgg agtccctgat cgcttcacag gcagtggatc tgggacagat tatacactca ccatcaaaag tgtgcaggct gaagacctga cactttatta ctgtcagcaa cactatatca ctccgtggac gttcggtgga ggcaccaagc tggaaatcaa aggaggcgga tccggcggcg gaggcaaggt ccagctgcag cagtctggag ctgaactggt gaaacccggg gcatcagtga agctgtcctg caaggcttct gggtacacct tcactgagta tattttacac tgggtaaagc agaagtctgg acagggtctt gagtggattg ggtggtttta tcctggaaat aataatataa agtacaatga gaaattcaag gacaaggcca cactgactgc ggacaaatcc tccagcacag tctatatgga acttagtaga ttgacatctg aagactctgc ggtctatttc tgtgcaagac acgaacaagg accaggttac tttgactact ggggccaagg caccactctc acagtctcct ccgcctccac caagggcgaa gtggccgcat gtgagaaaga ggttgctgct ttggagaagg aggtcgctgc acttgaaaag gaggtcgcag ccctggagaa actggagccc aaatcttctg acaaaactca cacatgccca ccgtgcccag cacctgaact cctgggggga ccgtcagtct tcctcttccc cccaaaaccc aaggacaccc tcatgatctc ccggacccct gaggtcacat gcgtggtggt ggacgtgagc cacgaagacc ctgaggtcaa gttcaactgg tacgtggacg gcgtggaggt gcataatgcc aagacaaagc cgcgggagga gcagtacaac agcacgtacc gtgtggtcag cgtcctcacc gtcctgcacc aggactggct gaatggcaag gagtacaagt gcaaggtctc caacaaagcc ctcccagccc ccatcgagaa aaccatctcc aaagccaaag gcagccccg agaaccacag gtgtacaccc tgcccccatc ccgggaggag atgaccaaga
```

```
accaggtcag cctgacctgc ctggtcaaag gcttctatcc cagcgacatc gccgtggagt gggagagcaa tgggcagccg gagaacaact acaagaccac gcctccgtg ctggactccg acggctcctt cttcctctac agcaagctca ccgtggacaa gagcaggtgg cagcagggga acgtcttctc atgctccgtg atgcatgagg ctctgcacaa ccactacacg cagaagagcc tctccctgtc tccgggt
```

The amino acid sequence of the second polypeptide chain of DR5 mAb 2×DR5 mAb 2 Fc diabody is (SEQ ID NO:136):

```
DIVMTQSHKF MSTSVGDRVS ITCKASQDVN TAVAWYQQKP
GQSPKLLIYW ASTRHTGVPD RFTGSGSGTD YTLTIKSVQA
EDLTLYYCQQ HYITPWTFGG GTKLEIKGGG SGGGGKVQLQ
QSGAELVKPG ASVKLSCKAS GYTFTEYILH WVKQKSGQGL
EWIGWFYPGN NNIKYNEKFK DKATLTADKS SSTVYMELSR
LTSEDSAVYF CARHEQGPGY FDYWGQGTTL TVSSASTKGK
VAACKEKEVAA LKEKVAALKE KVAALKE
```

In SEQ ID NO:136, amino acid residues 1-107 correspond to the amino acid sequence of the VL Domain of DR5 mAb 2 (SEQ ID NO:13), residues 108-115 correspond to the intervening spacer peptide GGGSGGGG (Linker 1) (SEQ ID NO:33), residues 116-237 correspond to the amino acid sequence of the VH Domain of DR5 mAb 2 (SEQ ID NO:18), residues 235-239 correspond to an ASTKG linker (SEQ ID NO:47) residues 240-267 correspond to a cysteine-containing K-coil Domain (SEQ ID NO:42). A polynucleotide that encodes SEQ ID NO:136 is SEQ ID NO:137:

```
gacattgtga tgacccagtc tcacaaattc atgtccactt cagtaggaga cagggtcagc atcacctgca aggccagtca ggatgtgaat actgctgtag cctggtatca acaaaaacca gggcaatctc ctaaactact gatttactgg gcatccaccc ggcacactgg agtccctgat cgcttcacag gcagtggatc tgggacagat tatacactca ccatcaaaag tgtgcaggct gaagacctga cactttatta ctgtcagcaa cactatatca ctccgtggac gttcggtgga ggcaccaagc tggaaatcaa aggaggcgga tccggcggcg gaggcaaggt ccagctgcag cagtctggag ctgaactggt gaaacccggg gcatcagtga agctgtcctg caaggcttct gggtacacct tcactgagta tattttacac tgggtaaagc agaagtctgg acagggtctt gagtggattg ggtggtttta tcctggaaat aataatataa agtacaatga gaaattcaag gacaaggcca cactgactgc ggacaaatcc tccagcacag tctatatgga acttagtaga ttgacatctg aagactctgc ggtctatttc tgtgcaagac
```

```
acgaacaagg accaggttac tttgactact ggggccaagg caccactctc acagtctcct ccgcctccac caagggcaaa gtggccgcat gtaaggagaa agttgctgct ttgaaagaga aggtcgccgc acttaaggaa aaggtcgcag ccctgaaaga g
```

Another Fc Region-containing diabody, designated "DR5 mAb 2×DR5 mAb 2 Fc diabody (AA)," is identical to DR5 mAb 2×DR5 mAb 2 Fc diabody except the Fc Region is a variant having a L234A/L235A double mutation (underlined) which reduces/eliminates binding to FcγRIIIA and reduces/eliminates effector functions. The amino acid sequence of the first polypeptide chain of this Fc Region-Containing diabody is (SEQ ID NO:138):

```
DIVMTQSHKF MSTSVGDRVS ITCKASQDVN TAVAWYQQKP
GQSPKLLIYW ASTRHTGVPD RFTGSGSGTD YTLTIKSVQA
EDLTLYYCQQ HYITPWTFGG GTKLEIKGGG SGGGGKVQLQ
QSGAELVKPG ASVKLSCKAS GYTFTEYILH WVKQKSGQGL
EWIGWFYPGN NNIKYNEKFK DKATLTADKS SSTVYMELSR
LTSEDSAVYF CARHEQGPGY FDYWGQGTTL TVSSASTKGE
VAACEKEVAA LEKEVAALEK EVAALEKLEP KSSDKTHTCP
PCPAPEAAGG PSVFLFPPKP KDTLMISRTP EVTCVVVDVS
HEDPEVKFNW YVDGVEVHNA KTKPREEQYN STYRVVSVLT
VLHQDWLNGK EYKCKVSNKA LPAPIEKTIS KAKGQPREPQ
VYTLPPSREE MTKNQVSLTC LVKGFYPSDI AVEWESNGQP
ENNYKTTPPV LDSDGSFFLY SKLTVDKSRW QQGNVFSCSV
MHEALHNHYT QKSLSLSPG
```

A polynucleotide that encodes SEQ ID NO:138 is SEQ ID NO:139:

```
gacattgtga tgacccagtc tcacaaattc atgtccactt cagtaggaga cagggtcagc atcacctgca aggccagtca ggatgtgaat actgctgtag cctggtatca acaaaaacca gggcaatctc ctaaactact gatttactgg gcatccaccc ggcacactgg agtccctgat cgcttcacag gcagtggatc tgggacagat tatacactca ccatcaaaag tgtgcaggct gaagacctga cactttatta ctgtcagcaa cactatatca ctccgtggac gttcggtgga ggcaccaagc tggaaatcaa aggaggcgga tccggcggcg gaggcaaggt ccagctgcag cagtctggag ctgaactggt gaaacccggg gcatcagtga agctgtcctg caaggcttct gggtacacct tcactgagta tattttacac tgggtaaagc agaagtctgg acagggtctt gagtggattg ggtggtttta tcctggaaat aataatataa agtacaatga gaaattcaag gacaaggcca cactgactgc
```

-continued

```
ggacaaatcc tccagcacag tctatatgga acttagtaga ttgacatctg aagactctgc ggtctatttc tgtgcaagac acgaacaagg accaggttac tttgactact ggggccaagg caccactctc acagtctcct ccgcctccac caagggcgaa gtggccgcat gtgagaaaga ggttgctgct ttggagaagg aggtcgctgc acttgaaaag gaggtcgcag ccctggagaa actggagccc aaatcttctg acaaaactca cacatgccca ccgtgcccag cacctgaagc cgcgggggga ccgtcagtct tcctcttccc cccaaaaccc aaggacaccc tcatgatctc ccggacccct gaggtcacat gcgtggtggt ggacgtgagc cacgaagacc ctgaggtcaa gttcaactgg tacgtggacg gcgtggaggt gcataatgcc aagacaaagc cgcgggagga gcagtacaac agcacgtacc gtgtggtcag cgtcctcacc gtcctgcacc aggactggct gaatggcaag gagtacaagt gcaaggtctc caacaaagcc ctcccagccc ccatcgagaa aaccatctcc aaagccaaag ggcagccccg agaaccacag gtgtacaccc tgcccccatc ccggggaggag atgaccaaga accaggtcag cctgacctgc ctggtcaaag gcttctatcc cagcgacatc gccgtggagt gggagagcaa tgggcagccg gagaacaact acaagaccac gcctcccgtg ctggactccg acggctcctt cttcctctac agcaagctca ccgtggacaa gagcaggtgg cagcaggga acgtcttctc atgctccgtg atgcatgagg ctctgcacaa ccactacacg cagaagagcc tctccctgtc tccgggt
```

The second polypeptide chain of DR5 mAb 2×DR5 mAb 2 Fc diabody (AA) is also SEQ ID NO:136 (encoded by SEQ ID NO:137), described in detail above.

Alternatively, where reduced/eliminated binding to FcγRIIIA and/or reduced/eliminated effector functions is desired, the CH2-CH3 region of IgG2 or IgG4 may be used. In such an Fc Region-Containing diabody, amino acid residues 284-500 of SEQ ID NOs:134 or 138 will be replaced with SEQ ID NO:164 (CH2-CH3 of IgG2) or SEQ ID NO:103 (CH2-CH3 of IgG4), optionally lacking the C-terminal amino acid residue.

3. hDR5 mAb 2.2×hDR5 mAb 2.2 Fc Region-Containing Diabodies

Exemplary monospecific Fc Region-Containing diabodies tetravalent for DR5 composed of two pairs of polypeptide chains are constructed having the VL Domain of anti-human DR5 antibody hDR5 mAb 2 VL-2 and the VH Domain of anti-human DR5 antibody hDR5 mAb 2 VH-2. The first Fc Region-Containing diabody designated "hDR5 mAb 2.2×hDR5 mAb 2.2 Fc diabody," contains a wild-type IgG1 Fc Region. The amino acid sequence of the first polypeptide chain of this Fc Region-Containing diabody is (SEQ ID NO:140):

```
DIQMTQSPSF LSASVGDRVT ITCKASQDVN TAVAWYQQKP

GKAPKLLIYW ASTRHTGVPS RFSGSGSGTD FTLTISSLQP

EDVATYYCQQ HYITPWTFGG GTKLEIKGGG SGGGGQVQLV

QSGAEVKKPG ASVKVSCKAS GYTFTEYILH WVRQAPGQGL

EWMGWFYPGN NNIKYNEKFK DRVTITADKS TSTVYMELSS

LRSEDTAVYY CARHEQGPGY FDYWGQGTLV TVSSASTKGE

VAACEKEVAA LEKEVAALEK EVAALEKLEP KSSDKTHTCP

PCPAPELLGG PSVFLFPPKP KDTLMISRTP EVTCVVVDVS

HEDPEVKFNW YVDGVEVHNA KTKPREEQYN STYRVVSVLT

VLHQDWLNGK EYKCKVSNKA LPAPIEKTIS KAKGQPREPQ

VYTLPPSREE MTKNQVSLTC LVKGFYPSDI AVEWESNGQP

ENNYKTTPPV LDSDGSFFLY SKLTVDKSRW QQGNVFSCSV

MHEALHNHYT QKSLSLSPG
```

In SEQ ID NO:140, amino acid residues 1-107 correspond to the amino acid sequence of the VL Domain of hDR5 mAb 2 VL-2 (SEQ ID NO:23), residues 108-115 correspond to the intervening spacer peptide GGGSGGGG (Linker 1) (SEQ ID NO:33), residues 116-237 correspond to the amino acid sequence of the VH Domain of hDR5 mAb 2 VH-2 (SEQ ID NO:31), residues 235-239 correspond to an ASTKG linker (SEQ ID NO:47) residues 240-267 correspond to a cysteine-containing E-coil Domain (SEQ ID NO:41), residues 268-273 correspond to a LEPKSS linker (SEQ ID NO: 49), residues 274-283 correspond to a linker (DKTHTCPPCP; SEQ ID NO:48) derived from an IgG1 hinge domain, and residues 284-499 correspond to a wild-type IgG1 Fc Region (SEQ ID NO:1, lacking the C-terminal amino acid residue). A polynucleotide that encodes SEQ ID NO:140 is SEQ ID NO:141:

```
gatattcaga tgacccagag tccctcattt ctgtccgcct ccgtcggtga ccgcgtgact attacttgta aagcttctca ggatgtcaac accgccgtgg cttggtacca gcagaagccc ggtaaagcac ctaagctgct gatctattgg gccagcactc ggcacaccgg agtcccatct aggttctctg gcagtggatc agggacagac tttaccctga caattagctc cctgcagccc gaggatgtgg ctacttacta ttgtcagcag cactacatca ctccttggac cttcggcggg ggcacaaaac tggaaatcaa aggaggcgga tccggcggcg gaggccaggt ccagctggtg cagagtgggg cagaggtgaa aaagccaggg gcatcagtga aagtgtcttg taaagcatca ggttatacat ttactgagta catcctgcac tgggtgcgac aggcaccagg acagggactg gaatggatgg ggtggttcta ccctggcaac aacaacatta agtacaacga gaagtttaaa gaccgggtga ccatcacagc ggataagtct accagtacag tctatatgga gctgagctcc ctgagaagcg aagacaccgc cgtctactat tgcgctcgcc acgaacaggg tccaggttac tttgattatt ggggcaggg
```

```
aactctggtc acagtcagct ccgcctccac caagggcgaa gtggccgcat gtgagaaaga ggttgctgct ttggagaagg aggtcgctgc acttgaaaag gaggtcgcag ccctggagaa actggagccc aaatcttctg acaaaactca cacatgccca ccgtgcccag cacctgaact cctgggggga ccgtcagtct tcctcttccc cccaaaaccc aaggacaccc tcatgatctc ccggacccct gaggtcacat gcgtggtggt ggacgtgagc cacgaagacc ctgaggtcaa gttcaactgg tacgtggacg gcgtggaggt gcataatgcc aagacaaagc cgcgggagga gcagtacaac agcacgtacc gtgtggtcag cgtcctcacc gtcctgcacc aggactggct gaatggcaag gagtacaagt gcaaggtctc caacaaagcc ctcccagccc ccatcgagaa aaccatctcc aaagccaaag gcagccccga gaaccacag gtgtacaccc tgcccccatc ccgggaggag atgaccaaga accaggtcag cctgacctgc ctggtcaaag gcttctatcc cagcgacatc gccgtggagt gggagagcaa tgggcagccg gagaacaact acaagaccac gcctcccgtg ctggactccg acggctcctt cttcctctac agcaagctca ccgtggacaa gagcaggtgg cagcagggga acgtcttctc atgctccgtg atgcatgagg ctctgcacaa ccactacacg cagaagagcc tctccctgtc tccgggt
```

The amino acid sequence of the second polypeptide chain of hDR5 mAb 2.2×hDR5 mAb 2.2 Fc diabody is (SEQ ID NO:142):

```
DIQMTQSPSF LSASVGDRVT ITCKASQDVN TAVAWYQQKP

GKAPKLLIYW ASTRHTGVPS RFSGSGSGTD FTLTISSLQP

EDVATYYCQQ HYITPWTFGG GTKLEIKGGG SGGGGQVQLV

QSGAEVKKPG ASVKVSCKAS GYTFTEYILH WVRQAPGQGL

EWMGWFYPGN NNIKYNEKFK DRVTITADKS TSTVYMELSS

LRSEDTAVYY CARHEQGPGY FDYWGQGTLV TVSSASTKGK

VAACKEKVAA LKEKVAALKE KVAALKE
```

In SEQ ID NO:142, amino acid residues 1-107 correspond to the amino acid sequence of the VL Domain of hDR5 mAb 2 VL-2 (SEQ ID NO:23), residues 108-115 correspond to the intervening spacer peptide GGGSGGGG (Linker 1) (SEQ ID NO:33), residues 116-237 correspond to the amino acid sequence of the VH Domain of hDR5 mAb 2 VH-2 (SEQ ID NO:31), residues 235-239 correspond to an ASTKG linker (SEQ ID NO:47) residues 240-267 correspond to a cysteine-containing K-coil Domain (SEQ ID NO:42). A polynucleotide that encodes SEQ ID NO:142 is SEQ ID NO:143:

```
gatattcaga tgacccagag tccctcattt ctgtccgcct ccgtcggtga ccgcgtgact attacttgta aagcttctca
```

```
ggatgtcaac accgccgtgg cttggtacca gcagaagccc ggtaaagcac ctaagctgct gatctattgg gccagcactc ggcacaccgg agtcccatct aggttctctg gcagtggatc agggacagac tttaccctga caattagctc cctgcagccc gaggatgtgg ctacttacta ttgtcagcag cactacatca ctccttggac cttcggcggg ggcacaaaac tggaaatcaa aggaggcgga tccggcggcg gaggccaggt ccagctggtg cagagtgggg cagaggtgaa aaagccaggg gcatcagtga aagtgtcttg taaagcatca ggttatacat ttactgagta catcctgcac tgggtgcgac aggcaccagg cagggactg gaatggatgg ggtggttcta ccctggcaac aacaacatta agtacaacga gaagtttaaa gaccgggtga ccatcacagc ggataagtct accagtacag tctatatgga gctgagctcc ctgagaagcg aagacaccgc cgtctactat tgcgctcgcc acgaacaggg tccaggttac tttgattatt gggggcaggg aactctggtc acagtcagct ccgcctccac caagggcaaa gtggccgcat gtaaggagaa agttgctgct ttgaaagaga aggtcgccgc acttaaggaa aaggtcgcag ccctgaaaga g
```

Another Fc Region-containing diabody, designated "hDR5 mAb 2.2×hDR5 mAb 2.2 Fc diabody (AA)," is identical to hDR5 mAb 2.2×hDR5 mAb 2.2 Fc diabody except the Fc Region is a variant having a L234A/L235A double mutation (underlined) which reduces/eliminates binding to FcγRIIIA and reduces/eliminates effector functions. The amino acid sequence of the first polypeptide chain of this Fc Region-Containing diabody is (SEQ ID NO:144):

```
DIQMTQSPSF LSASVGDRVT ITCKASQDVN TAVAWYQQKP

GKAPKLLIYW ASTRHTGVPS RFSGSGSGTD FTLTISSLQP

EDVATYYCQQ HYITPWTFGG GTKLEIKGGG SGGGGQVQLV

QSGAEVKKPG ASVKVSCKAS GYTFTEYILH WVRQAPGQGL

EWMGWFYPGN NNIKYNEKFK DRVTITADKS TSTVYMELSS

LRSEDTAVYY CARHEQGPGY FDYWGQGTLV TVSSASTKGE

VAACEKEVAA LEKEVAALEK EVAALEKLEP KSSDKTHTCP

PCPAPEAAGG PSVFLFPPKP KDTLMISRTP EVTCVVVDVS

HEDPEVKFNW YVDGVEVHNA KTKPREEQYN STYRVVSVLT

VLHQDWLNGK EYKCKVSNKA LPAPIEKTIS KAKGQPREPQ

VYTLPPSREE MTKNQVSLTC LVKGFYPSDI AVEWESNGQP

ENNYKTTPPV LDSDGSFFLY SKLTVDKSRW QQGNVFSCSV

MHEALHNHYT QKSLSLSPG
```

A polynucleotide that encodes SEQ ID NO:144 is SEQ ID NO:145:

```
gatattcaga tgacccagag tccctcattt ctgtccgcct ccgtcggtga ccgcgtgact attacttgta aagcttctca ggatgtcaac accgccgtgg cttggtacca gcagaagccc ggtaaagcac ctaagctgct gatctattgg gccagcactc ggcacaccgg agtcccatct aggttctctg gcagtggatc agggacagac tttaccctga caattagctc cctgcagccc gaggatgtgg ctacttacta ttgtcagcag cactacatca ctccttggac cttcggcggg ggcacaaaac tggaaatcaa aggaggcgga tccggcgcg gaggccaggt ccagctggtg cagagtgggg cagaggtgaa aaagccaggg gcatcagtga aagtgtcttg taaagcatca ggttatacat ttactgagta catcctgcac tgggtgcgac aggcaccagg acagggactg gaatggatgg ggtggttcta ccctggcaac aacaacatta agtacaacga gaagtttaaa gaccgggtga ccatcacagc ggataagtct accagtacag tctatatgga gctgagctcc ctgagaagcg aagacaccgc cgtctactat tgcgctcgcc acgaacaggg tccaggttac tttgattatt gggggcaggg aactctggtc acagtcagct ccgcctccac caagggcgaa gtggccgcat gtgagaaaga ggttgctgct ttggagaagg aggtcgctgc acttgaaaag gaggtcgcag ccctggagaa actggagccc aaatcttctg acaaaactca cacatgccca ccgtgcccag cacctgaagc cgcggggggga ccgtcagtct tcctcttccc cccaaaaccc aaggacaccc tcatgatctc ccggacccct gaggtcacat gcgtggtggt ggacgtgagc cacgaagacc ctgaggtcaa gttcaactgg tacgtggacg gcgtggaggt gcataatgcc aagacaaagc cgcgggagga gcagtacaac agcacgtacc gtgtggtcag cgtcctcacc gtcctgcacc aggactggct gaatggcaag gagtacaagt gcaaggtctc caacaaagcc ctcccagccc ccatcgagaa aaccatctcc aaagccaaag ggcagccccg agaaccacag gtgtacaccc tgcccccatc ccgggaggag atgaccaaga accaggtcag cctgacctgc ctggtcaaag gcttctatcc cagcgacatc gccgtggagt gggagagcaa tgggcagccg gagaacaact acaagaccac gcctcccgtg ctggactccg acggctcctt cttcctctac agcaagctca ccgtggacaa gagcaggtgg cagcagggga acgtcttctc atgctccgtg atgcatgagg ctctgcacaa ccactacacg cagaagagcc tctccctgtc tccgggt
```

The second polypeptide chain of hDR5 mAb 2.2×hDR5 mAb 2.2 Fc diabody (AA) is also SEQ ID NO:142 (encoded by SEQ ID NO:143), described in detail above.

Alternatively, where reduced/eliminated binding to FcγRIIIA and/or reduced/eliminated effector functions is desired, the CH2-CH3 region of IgG2 or IgG4 may be used. In such an Fc Region-Containing diabody, amino acid residues 284-500 of SEQ ID NOs:140 or 144 will be replaced with SEQ ID NO:164 (CH2-CH3 of IgG2) or SEQ ID NO:103 (CH2-CH3 of IgG4), optionally lacking the C-terminal amino acid residue.

4. hDR5 mAb 2.3×hDR5 mAb 2.3 Fc Region-Containing Diabodies

Exemplary monospecific Fc Region-Containing diabodies tetravalent for DR5 composed of two pairs of polypeptide chains are constructed having the VL Domain of anti-human DR5 antibody hDR5 mAb 2 VL-3 and the VH Domain of anti-human hDR5 antibody hDR5 mAb 2 VH-3. The first Fc Region-Containing diabody designated "hDR5 mAb 2.3×hDR5 mAb 2.3 Fc diabody," contains a wild-type IgG1 Fc Region. The amino acid sequence of the first polypeptide chain of this Fc Region-Containing diabody is (SEQ ID NO:146):

```
DIQMTQSPSF LSASVGDRVT ITCRASQDVN TAVAWYQQKP

GKAPKLLIYW ASTRHTGVPD RFSGSGSGTD FTLTISSLQP

EDVATYYCQQ HYITPWTFGG GTKLEIKGGG SGGGGQVQLV

QSGAEVKKPG ASVKVSCKAS GYTFTEYILH WVRQAPGQGL

EWMGWFYPGN NNIKYNEKFK DRVTITADKS TSTVYMELSS

LRSEDTAVYY CARHEQGPGY FDYWGQGTLV TVSSASTKGE

VAACEKEVAA LEKEVAALEK EVAALEKLEP KSSDKTHTCP

PCPAPELLGG PSVFLFPPKP KDTLMISRTP EVTCVVVDVS

HEDPEVKFNW YVDGVEVHNA KTKPREEQYN STYRVVSVLT

VLHQDWLNGK EYKCKVSNKA LPAPIEKTIS KAKGQPREPQ

VYTLPPSREE MTKNQVSLTC LVKGFYPSDI AVEWESNGQP

ENNYKTTPPV LDSDGSFFLY SKLTVDKSRW QQGNVFSCSV

MHEALHNHYT QKSLSLSPG
```

In SEQ ID NO:146, amino acid residues 1-107 correspond to the amino acid sequence of the VL Domain of hDR5 mAb 2 VL-3 (SEQ ID NO:25), residues 108-115 correspond to the intervening spacer peptide GGGSGGGG (Linker 1) (SEQ ID NO:33), residues 116-237 correspond to the amino acid sequence of the VH Domain of hDR5 mAb 2 VH-2 (SEQ ID NO:31), residues 235-239 correspond to an ASTKG linker (SEQ ID NO:47) residues 240-267 correspond to a cysteine-containing E-coil Domain (SEQ ID NO:41), residues 268-273 correspond to a LEPKSS linker (SEQ ID NO: 49), residues 274-283 correspond to a linker (DKTHTCPPCP; SEQ ID NO:48) derived from an IgG1 hinge domain, and residues 284-499 correspond to a wild-type IgG1 Fc Region (SEQ ID NO:1, lacking the C-terminal amino acid residue). A polynucleotide that encodes SEQ ID NO:146 is SEQ ID NO:147:

```
gatattcaga tgacccagag tccctcattt ctgtccgcct ccgtcggtga ccgcgtgact attacttgtc gggcttctca ggatgtcaac accgccgtgg cttggtacca gcagaagccc ggtaaagcac ctaagctgct gatctattgg gccagcactc ggcacaccgg agtcccagat aggttctctg gcagtggatc
```

```
agggacagac tttaccctga caattagctc cctgcagccc gaggatgtgg ctacttacta ttgtcagcag cactacatca ctccttggac cttcggcggg ggcacaaaac tggaaatcaa aggaggcgga tccggcggcg gaggccaggt ccagctggtg cagagtgggg cagaggtgaa aaagccaggg gcatcagtga aagtgtcttg taaagcatca ggttatacat ttactgagta catcctgcac tgggtgcgac aggcaccagg cagggactg gaatggatgg ggtggttcta ccctggcaac aacaacatta agtacaacga gaagtttaaa gaccgggtga ccatcacagc ggataagtct accagtacag tctatatgga gctgagctcc ctgagaagcg aagacaccgc cgtctactat tgcgctcgcc acgaacaggg tccaggttac tttgattatt gggggcaggg aactctggtc acagtcagct ccgcctccac caagggcgaa gtggccgcat gtgagaaaga ggttgctgct ttggagaagg aggtcgctgc acttgaaaag gaggtcgcag ccctggagaa actggagccc aaatcttctg acaaaactca cacatgccca ccgtgcccag cacctgaact cctgggggga ccgtcagtct tcctcttccc cccaaaaccc aaggacaccc tcatgatctc ccggacccct gaggtcacat gcgtggtggt ggacgtgagc cacgaagacc ctgaggtcaa gttcaactgg tacgtggacg gcgtggaggt gcataatgcc aagacaaagc cgcgggagga gcagtacaac agcacgtacc gtgtggtcag cgtcctcacc gtcctgcacc aggactggct gaatggcaag gagtacaagt gcaaggtctc caacaaagcc ctcccagccc ccatcgagaa aaccatctcc aaagccaaag ggcagccccg agaaccacag gtgtacaccc tgcccccatc ccgggaggag atgaccaaga accaggtcag cctgacctgc ctggtcaaag gcttctatcc cagcgacatc gccgtggagt gggagagcaa tgggcagccg gagaacaact acaagaccac gcctcccgtg ctggactccg acggctcctt cttcctctac agcaagctca ccgtggacaa gagcaggtgg cagcagggga acgtcttctc atgctccgtg atgcatgagg ctctgcacaa ccactacacg cagaagagcc tctccctgtc tccggt
```

The amino acid sequence of the second polypeptide chain of hDR5 mAb 2.3×hDR5 mAb 2.3 Fc diabody is (SEQ ID NO:148):

```
DIQMTQSPSF LSASVGDRVT ITCRASQDVN TAVAWYQQKP
GKAPKLLIYW ASTRHTGVPD RFSGSGSGTD FTLTISSLQP
EDVATYYCQQ HYITPWTFGG GTKLEIKGGG SGGGGQVQLV
QSGAEVKKPG ASVKVSCKAS GYTFTEYILH WVRQAPGQGL
EWMGWFYPGN NNIKYNEKFK DRVTITADKS TSTVYMELSS
LRSEDTAVYY CARHEQGPGY FDYWGQGTLV TVSSASTKGK
VAACKEKVAA LKEKVAALKE KVAALKE
```

In SEQ ID NO:148, amino acid residues 1-107 correspond to the amino acid sequence of the VL Domain of hDR5 mAb 2 VL-3 (SEQ ID NO:25), residues 108-115 correspond to the intervening spacer peptide GGGSGGGG (Linker 1) (SEQ ID NO:33), residues 116-237 correspond to the amino acid sequence of the VH Domain of hDR5 mAb 2 VH-2 (SEQ ID NO:31), residues 235-239 correspond to an ASTKG linker (SEQ ID NO:47) residues 240-267 correspond to a cysteine-containing K-coil Domain (SEQ ID NO:42). A polynucleotide that encodes SEQ ID NO:148 is SEQ ID NO:149:

```
gatattcaga tgacccagag tcccctcattt ctgtccgcct ccgtcggtga ccgcgtgact attacttgtc gggcttctca ggatgtcaac accgccgtgg cttggtacca gcagaagccc ggtaaagcac ctaagctgct gatctattgg gccagcactc ggcacaccgg agtcccagat aggttctctg gcagtggatc agggacagac tttaccctga caattagctc cctgcagccc gaggatgtgg ctacttacta ttgtcagcag cactacatca ctccttggac cttcggcggg ggcacaaaac tggaaatcaa aggaggcgga tccggcggcg gaggccaggt ccagctggtg cagagtgggg cagaggtgaa aaagccaggg gcatcagtga aagtgtcttg taaagcatca ggttatacat ttactgagta catcctgcac tgggtgcgac aggcaccagg cagggactg gaatggatgg ggtggttcta ccctggcaac aacaacatta agtacaacga gaagtttaaa gaccgggtga ccatcacagc ggataagtct accagtacag tctatatgga gctgagctcc ctgagaagcg aagacaccgc cgtctactat tgcgctcgcc acgaacaggg tccaggttac tttgattatt gggggcaggg aactctggtc acagtcagct ccgcctccac caagggcaaa gtggccgcat gtaaggagaa agttgctgct ttgaaagaga aggtcgccgc acttaaggaa aaggtcgcag ccctgaaaga g
```

Another Fc Region-containing diabody, designated "hDR5 mAb 2.3×hDR5 mAb 2.3 Fc diabody (AA)," is identical to hDR5 mAb 2.3×hDR5 mAb 2.3 Fc diabody except the Fc Region is a variant having a L234A/L235A double mutation (underlined) which reduces/eliminates binding to FcγRIIIA and reduces/eliminates effector functions. The amino acid sequence of the first polypeptide chain of this Fc Region-Containing diabody is (SEQ ID NO:150):

```
DIQMTQSPSF LSASVGDRVT ITCRASQDVN TAVAWYQQKP
GKAPKLLIYW ASTRHTGVPD RFSGSGSGTD FTLTISSLQP
```

```
EDVATYYCQQ HYITPWTFGG GTKLEIKGGG SGGGGQVQLV

QSGAEVKKPG ASVKVSCKAS GYTFTEYILH WVRQAPGQGL

EWMGWFYPGN NNIKYNEKFK DRVTITADKS TSTVYMELSS

LRSEDTAVYY CARHEQGPGY FDYWGQGTLV TVSSASTKGE

VAACEKEVAA LEKEVAALEK EVAALEKLEP KSSDKTHTCP

PCPAPEAAGG PSVFLFPPKP KDTLMISRTP EVTCVVVDVS

HEDPEVKFNW YVDGVEVHNA KTKPREEQYN STYRVVSVLT

VLHQDWLNGK EYKCKVSNKA LPAPIEKTIS KAKGQPREPQ

VYTLPPSREE MTKNQVSLTC LVKGFYPSDI AVEWESNGQP

ENNYKTTPPV LDSDGSFFLY SKLTVDKSRW QQGNVFSCSV

MHEALHNHYT QKSLSLSPG
```

A polynucleotide that encodes SEQ ID NO:150 is SEQ ID NO:151:

```
gatattcaga tgacccagag tccctcattt ctgtccgcct
ccgtcggtga ccgcgtgact attacttgtc gggcttctca
ggatgtcaac accgcgtgg cttggtacca gcagaagccc
ggtaaagcac ctaagctgct gatctattgg gccagcactc
ggcacaccgg agtcccagat aggttctctg gcagtggatc
agggacagac tttaccctga caattagctc cctgcagccc
gaggatgtgg ctacttacta ttgtcagcag cactcatca
ctccttggac cttcggcggg ggcacaaaac tggaaatcaa
aggaggcgga tccggcggcg gaggccaggt ccagctggtg
cagagtgggg cagaggtgaa aaagccaggg gcatcagtga
aagtgtcttg taaagcatca ggttatacat ttactgagta
catcctgcac tgggtgcgac aggcaccagg acagggactg
gaatggatgg ggtggttcta ccctggcaac aacaacatta
agtacaacga gaagtttaaa gacgggtga ccatcacagc
ggataagtct accagtacag tctatatgga gctgagctcc
ctgagaagcg aagacaccgc cgtctactat tgcgctcgcc
acgaacaggg tccaggttac tttgattatt gggggcaggg
aactctggtc acagtcagct ccgcctccac caagggcgaa
gtggccgcat gtgagaaaga ggttgctgct ttggagaagg
aggtcgctgc acttgaaaag gaggtcgcag ccctggagaa
actggagccc aaatcttctg acaaaactca cacatgccca
ccgtgcccag cacctgaagc cgcgggggga ccgtcagtct
tcctcttccc cccaaaaccc aaggacaccc tcatgatctc
ccggacccct gaggtcacat gcgtggtggt ggacgtgagc
cacgaagacc ctgaggtcaa gttcaactgg tacgtggacg
gcgtggaggt gcataatgcc aagacaaagc cgcgggagga
gcagtacaac agcacgtacc gtgtggtcag cgtcctcacc
gtcctgcacc aggactggct gaatggcaag gagtacaagt
gcaaggtctc caacaaagcc ctcccagccc ccatcgagaa
aaccatctcc aaagccaaag ggcagccccg agaaccacag
gtgtacaccc tgcccccatc ccgggaggag atgaccaaga
accaggtcag cctgacctgc ctggtcaaag gcttctatcc
cagcgacatc gccgtggagt gggagagcaa tgggcagccg
gagaacaact acaagaccac gcctcccgtg ctggactccg
acggctcctt cttcctctac agcaagctca ccgtggacaa
gagcaggtgg cagcagggga acgtcttctc atgctccgtg
atgcatgagg ctctgcacaa ccactacacg cagaagagcc
tctccctgtc tccgggt
```

The second polypeptide chain of hDR5 mAb 2.3×hDR5 mAb 2.3 Fc diabody (AA) is also SEQ ID NO:148 (encoded by SEQ ID NO:149), described in detail above.

Alternatively, where reduced/eliminated binding to FcγRIIIA and/or reduced/eliminated effector functions is desired, the CH2-CH3 region of IgG2 or IgG4 may be used. In such an Fc Region-Containing diabody, amino acid residues 284-500 of SEQ ID NOs:146 or 150 will be replaced with SEQ ID NO:164 (CH2-CH3 of IgG2) or SEQ ID NO:103 (CH2-CH3 of IgG4), optionally lacking the C-terminal amino acid residue.

5. hDR5 mAb 2.4×hDR5 mAb 2.4 Fc Region-Containing Diabodies

Exemplary monospecific Fc Region-Containing diabodies tetravalent for DR5 composed of two pairs of polypeptide chains are constructed having the VL Domain of anti-human DR5 antibody hDR5 mAb 2 VL-4 and the VH Domain of anti-human hDR5 antibody hDR5 mAb 2 VH-4. The first Fc Region-Containing diabody designated "hDR5 mAb 2.4×hDR5 mAb 2.4 Fc diabody," contains a wild-type IgG1 Fc Region. The amino acid sequence of the first polypeptide chain of this Fc Region-Containing diabody is (SEQ ID NO:152

```
DIQMTQSPSF LSASVGDRVT ITCRASQDVN TAVAWYQQKP

GKAPKLLIYW ASTRHTGVPS RFSGSGSGTD FTLTISSLQP

EDIATYYCQQ HYITPWTFGG GTKLEIKGGG SGGGGQVQLV

QSGAEVKKPG ASVKVSCKAS GYTFTEYILH WVRQAPGQGL

EWMGWFYPGN NNIKYNEKFK DRVTITADKS TSTVYMELSS

LRSEDTAVYY CARHEQGPGY FDYWGQGTLV TVSSASTKGE

VAACEKEVAA LEKEVAALEK EVAALEKLEP KSSDKTHTCP

PCPAPELLGG PSVFLFPPKP KDTLMISRTP EVTCVVVDVS

HEDPEVKFNW YVDGVEVHNA KTKPREEQYN STYRVVSVLT

VLHQDWLNGK EYKCKVSNKA LPAPIEKTIS KAKGQPREPQ

VYTLPPSREE MTKNQVSLTC LVKGFYPSDI AVEWESNGQP

ENNYKTTPPV LDSDGSFFLY SKLTVDKSRW QQGNVFSCSV

MHEALHNHYT QKSLSLSPG
```

In SEQ ID NO:152, amino acid residues 1-107 correspond to the amino acid sequence of the VL Domain of hDR5 mAb 2 VL-4 (SEQ ID NO:27), residues 108-115 correspond to the intervening spacer peptide GGGSGGGG (Linker 1) (SEQ ID NO:33), residues 116-237 correspond to the amino acid sequence of the VH Domain of hDR5 mAb 2 VH-2 (SEQ ID NO:31), residues 235-239 correspond to an ASTKG linker (SEQ ID NO:47) residues 240-267 correspond to a cysteine-containing E-coil Domain (SEQ ID NO:41), residues 268-273 correspond to a LEPKSS linker (SEQ ID NO: 49), residues 274-283 correspond to a linker (DKTHTCPPCP; SEQ ID NO:48) derived from an IgG1 hinge domain, and residues 284-499 correspond to a wild-type IgG1 Fc Region (SEQ ID NO:1, lacking the C-terminal amino acid residue). A polynucleotide that encodes SEQ ID NO:152 is SEQ ID NO:153:

```
gatattcaga tgacccagag tccctcattt ctgtccgcct
ccgtcggtga ccgcgtgact attacttgtc gggcttctca
ggatgtcaac accgcgtgg cttggtacca gcagaagccc
ggtaaagcac ctaagctgct gatctattgg gccagcactc
ggcacaccgg agtcccatct aggttctctg gcagtggatc
agggacagac tttaccctga caattagctc cctgcagcca
gaggatatcg ctacatacta ttgtcagcag cactacatca
ctccttggac cttcggcggg ggcacaaaac tggaaatcaa
aggaggcgga tccggcggcg gaggccaggt ccagctggtg
cagagtgggg cagaggtgaa aaagccaggg gcatcagtga
aagtgtcttg taaagcatca ggttatacat ttactgagta
catcctgcac tgggtgcgac aggcaccagg acagggactg
gaatggatgg ggtggttcta ccctggcaac aacaacatta
agtacaacga gaagtttaaa gacccgggtga ccatcacagc
ggataagtct accagtacag tctatatgga gctgagctcc
ctgagaagcg aagacaccgc cgtctactat tgcgctcgcc
acgaacaggg tccaggttac tttgattatt gggggcaggg
aactctggtc acagtcagct ccgcctccac caagggcgaa
gtggccgcat gtgagaaaga ggttgctgct ttggagaagg
aggtcgctgc acttgaaaag gaggtcgcag ccctggagaa
actggagccc aaatcttctg acaaaactca cacatgccca
ccgtgcccag cacctgaact cctgggggga ccgtcagtct
tcctcttccc cccaaaaccc aaggacaccc tcatgatctc
ccggacccct gaggtcacat gcgtggtggt ggacgtgagc
cacgaagacc ctgaggtcaa gttcaactgg tacgtggacg
gcgtggaggt gcataatgcc aagacaaagc cgcgggagga
gcagtacaac agcacgtacc gtgtggtcag cgtcctcacc
gtcctgcacc aggactggct gaatggcaag gagtacaagt
gcaaggtctc caacaaagcc ctcccagccc ccatcgagaa
aaccatctcc aaagccaaag gcagccccg agaaccacag
gtgtacaccc tgcccccatc ccgggaggag atgaccaaga
```

```
accaggtcag cctgacctgc ctggtcaaag gcttctatcc
cagcgacatc gccgtggagt gggagagcaa tgggcagccg
gagaacaact acaagaccac gcctcccgtg ctggactccg
acggctcctt cttcctctac agcaagctca ccgtggacaa
gagcaggtgg cagcagggga acgtcttctc atgctccgtg
atgcatgagg ctctgcacaa ccactacacg cagaagagcc
tctccctgtc tccgggt
```

The amino acid sequence of the second polypeptide chain of hDR5 mAb 2×hDR5 mAb 2 Fc diabody is (SEQ ID NO:154):

```
DIQMTQSPSF LSASVGDRVT ITCRASQDVN TAVAWYQQKP
GKAPKLLIYW ASTRHTGVPS RFSGSGSGTD FTLTISSLQP
EDIATYYCQQ HYITPWTFGG GTKLEIKGGG SGGGGQVQLV
QSGAEVKKPG ASVKVSCKAS GYTFTEYILH WVRQAPGQGL
EWMGWFYPGN NNIKYNEKFK DRVTITADKS TSTVYMELSS
LRSEDTAVYY CARHEQGPGY FDYWGQGTLV TVSSASTKGK
VAACKEKVAA LKEKVAALKE KVAALKE
```

In SEQ ID NO:154, amino acid residues 1-107 correspond to the amino acid sequence of the VL Domain of hDR5 mAb 2 VL-4 (SEQ ID NO:17), residues 108-115 correspond to the intervening spacer peptide GGGSGGGG (Linker 1) (SEQ ID NO:33), residues 116-237 correspond to the amino acid sequence of the VH Domain of hDR5 mAb 2 VH-2 (SEQ ID NO:31), residues 235-239 correspond to an ASTKG linker (SEQ ID NO:47) residues 240-267 correspond to a cysteine-containing K-coil Domain (SEQ ID NO:42). A polynucleotide that encodes SEQ ID NO:154 is SEQ ID NO:155:

```
gatattcaga tgacccagag tccctcattt ctgtccgcct
ccgtcggtga ccgcgtgact attacttgtc gggcttctca
ggatgtcaac accgcgtgg cttggtacca gcagaagccc
ggtaaagcac ctaagctgct gatctattgg gccagcactc
ggcacaccgg agtcccatct aggttctctg gcagtggatc
agggacagac tttaccctga caattagctc cctgcagcca
gaggatatcg ctacatacta ttgtcagcag cactacatca
ctccttggac cttcggcggg ggcacaaaac tggaaatcaa
aggaggcgga tccggcggcg gaggccaggt ccagctggtg
cagagtgggg cagaggtgaa aaagccaggg gcatcagtga
aagtgtcttg taaagcatca ggttatacat ttactgagta
catcctgcac tgggtgcgac aggcaccagg acagggactg
gaatggatgg ggtggttcta ccctggcaac aacaacatta
agtacaacga gaagtttaaa gacccgggtga ccatcacagc
ggataagtct accagtacag tctatatgga gctgagctcc
ctgagaagcg aagacaccgc cgtctactat tgcgctcgcc
```

```
acgaacaggg tccaggttac tttgattatt gggggcaggg aactctggtc acagtcagct ccgcctccac caagggcaaa gtggccgcat gtaaggagaa agttgctgct ttgaaagaga aggtcgccgc acttaaggaa aaggtcgcag ccctgaaaga g
```

Another Fc Region-containing diabody, designated "hDR5 mAb 2.4×hDR5 mAb 2.4 Fc diabody (AA)," is identical to hDR5 mAb 2.4×hDR5 mAb 2.4 Fc diabody except the Fc Region is a variant having a L234A/L235A double mutation (underlined) which reduces/eliminates binding to FcγRIIIA and reduces/eliminates effector functions. The amino acid sequence of the first polypeptide chain of this Fc Region-Containing diabody is (SEQ ID NO:156):

```
DIQMTQSPSF LSASVGDRVT ITCRASQDVN TAVAWYQQKP

GKAPKLLIYW ASTRHTGVPS RFSGSGSGTD FTLTISSLQP

EDIATYYCQQ HYITPWTFGG GTKLEIKGGG SGGGGQVQLV

QSGAEVKKPG ASVKVSCKAS GYTFTEYILH WVRQAPGQGL

EWMGWFYPGN NNIKYNEKFK DRVTITADKS TSTVYMELSS

LRSEDTAVYY CARHEQGPGY FDYWGQGTLV TVSSASTKGE

VAACEKEVAA LEKEVAALEK EVAALEKLEP KSSDKTHTCP

PCPAPEAAGG PSVFLFPPKP KDTLMISRTP EVTCVVVDVS

HEDPEVKFNW YVDGVEVHNA KTKPREEQYN STYRVVSVLT

VLHQDWLNGK EYKCKVSNKA LPAPIEKTIS KAKGQPREPQ

VYTLPPSREE MTKNQVSLTC LVKGFYPSDI AVEWESNGQP

ENNYKTTPPV LDSDGSFFLY SKLTVDKSRW QQGNVFSCSV

MHEALHNHYT QKSLSLSPG
```

A polynucleotide that encodes SEQ ID NO:156 is SEQ ID NO:157:

```
gatattcaga tgacccagag tccctcattt ctgtccgcct ccgtcggtga ccgcgtgact attacttgtc gggcttctca ggatgtcaac accgccgtgg cttggtacca gcagaagccc ggtaaagcac ctaagctgct gatctattgg gccagcactc ggcacaccgg agtccatct aggttctctg gcagtggatc agggacagac tttaccctga caattagctc cctgcagcca gaggatatcg ctacatacta ttgtcagcag cactacatca ctccttggac cttcggcggg ggcacaaaac tggaaatcaa aggaggcgga tccggcggcg gaggccaggt ccagctggtg cagagtgggg cagaggtgaa aaagccaggg gcatcagtga aagtgtcttg taaagcatca ggttatacat ttactgagta catcctgcac tgggtgcgac aggcaccagg acagggactg gaatggatgg ggtggttcta ccctggcaac aacaacatta agtacaacga gaagtttaaa gacccggtga ccattcacagc
```

```
ggataagtct accagtacag tctatatgga gctgagctcc ctgagaagcg aagacaccgc cgtctactat tgcgctcgcc acgaacaggg tccaggttac tttgattatt gggggcaggg aactctggtc acagtcagct ccgcctccac caagggcgaa gtggccgcat gtgagaaaga ggttgctgct ttggagaagg aggtcgctgc acttgaaaag gaggtcgcag ccctggagaa actggagccc aaatcttctg acaaaactca cacatgccca ccgtgcccag cacctgaagc cgcggggga ccgtcagtct tcctcttccc cccaaaaccc aaggacaccc tcatgatctc ccggacccct gaggtcacat gcgtggtggt ggacgtgagc cacgaagacc ctgaggtcaa gttcaactgg tacgtggacg gcgtggaggt gcataatgcc aagacaaagc cgcgggagga gcagtacaac agcacgtacc gtgtggtcag cgtcctcacc gtcctgcacc aggactggct gaatggcaag gagtacaagt gcaaggtctc caacaaagcc ctcccagccc ccatcgagaa aaccatctcc aaagccaaag ggcagccccg agaaccacag gtgtacaccc tgcccccatc ccgggaggag atgaccaaga accaggtcag cctgacctgc ctggtcaaag gcttctatcc cagcgacatc gccgtggagt gggagagcaa tgggcagccg gagaacaact acaagaccac gcctcccgtg ctggactccg acggctcctt cttcctctac agcaagctca ccgtggacaa gagcaggtgg cagcaggga acgtcttctc atgctccgtg atgcatgagg ctctgcacaa ccactacacg cagaagagcc tctccctgtc tccgggt
```

The second polypeptide chain of hDR5 mAb 2×hDR5 mAb 2 Fc diabody (AA) is also SEQ ID NO:154 (encoded by SEQ ID NO:155), described in detail above.

Alternatively, where reduced/eliminated binding to FcγRIIIA and/or reduced/eliminated effector functions is desired, the CH2-CH3 region of IgG2 or IgG4 may be used. In such an Fc Region-Containing diabody, amino acid residues 284-500 of SEQ ID NOs:152 or 156 will be replaced with SEQ ID NO:164 (CH2-CH3 of IgG2) or SEQ ID NO:103 (CH2-CH3 of IgG4), optionally lacking the C-terminal amino acid residue.

6. hDR5 mAb 2.5×hDR5 mAb 2.5 Fe Region-Containing Diabodies

Exemplary monospecific Fc Region-Containing diabodies tetravalent for DR5 composed of two pairs of polypeptide chains are constructed having the VL Domain of anti-human DR5 antibody hDR5 mAb 2 VL-5 and the VH Domain of anti-human hDR5 antibody hDR5 mAb 2 VH-2. The first Fc Region-Containing diabody designated "hDR5 mAb 2.5×hDR5 mAb 2.5 Fe diabody," contains a wild-type IgG1 Fc Region. The amino acid sequence of the first polypeptide chain of this Fc Region-Containing diabody is (SEQ ID NO:158):

```
DIQMTQSPSF LSASVGDRVT ITCRASQDVN TAVAWYQQKP

GKAPKLLIYW ASTRHTGVPD RFSGSGSGTD FTLTISSLQP
```

```
EDIATYYCQQ HYITPWTFGG GTKLEIKGGG SGGGGQVQLV

QSGAEVKKPG ASVKVSCKAS GYTFTEYILH WVRQAPGQGL

EWMGWFYPGN NNIKYNEKFK DRVTITADKS TSTVYMELSS

LRSEDTAVYY CARHEQGPGY FDYWGQGTLV TVSSASTKGE

VAACEKEVAA LEKEVAALEK EVAALEKLEP KSSDKTHTCP

PCPAPELLGG PSVFLFPPKP KDTLMISRTP EVTCVVVDVS

HEDPEVKFNW YVDGVEVHNA KTKPREEQYN STYRVVSVLT

VLHQDWLNGK EYKCKVSNKA LPAPIEKTIS KAKGQPREPQ

VYTLPPSREE MTKNQVSLTC LVKGFYPSDI AVEWESNGQP

ENNYKTTPPV LDSDGSFFLY SKLTVDKSRW QQGNVFSCSV

MHEALHNHYT QKSLSLSPG
```

In SEQ ID NO:158, amino acid residues 1-107 correspond to the amino acid sequence of the VL Domain of hDR5 mAb 2 VL-5 (SEQ ID NO:29), residues 108-115 correspond to the intervening spacer peptide GGGSGGGG (Linker 1) (SEQ ID NO:33), residues 116-237 correspond to the amino acid sequence of the VH Domain of hDR5 mAb 2 VH-2 (SEQ ID NO:31), residues 235-239 correspond to an ASTKG linker (SEQ ID NO:47) residues 240-267 correspond to a cysteine-containing E-coil Domain (SEQ ID NO:41), residues 268-273 correspond to a LEPKSS linker (SEQ ID NO:49), residues 274-283 correspond to a linker (DKTHTCPPCP; SEQ ID NO:48) derived from an IgG1 hinge domain, and residues 284-499 correspond to a wild-type IgG1 Fc Region (SEQ ID NO:1, lacking the C-terminal amino acid residue). A polynucleotide that encodes SEQ ID NO:158 is SEQ ID NO:159:

```
gatattcaga tgacccagag tccctcattt ctgtccgcct ccgtcggtga ccgcgtgact attacttgtc gggcttctca ggatgtcaac accgccgtgg cttggtacca gcagaagccc ggtaaagcac ctaagctgct gatctattgg gccagcactc ggcacaccgg agtcccagat aggttctctg gcagtggatc agggacagac tttaccctga caattagctc cctgcagccc gaggatatcg ctacttacta ttgtcagcag cactacatca ctccttggac cttcggcggg ggcacaaaac tggaaatcaa aggaggcgga tccggcgcg gaggccaggt ccagctggtg cagagtgggg cagaggtgaa aaagccaggg gcatcagtga aagtgtcttg taaagcatca ggttatacat ttactgagta catcctgcac tgggtgcgac aggcaccagg acagggactg gaatggatgg ggtggttcta ccctggcaac aacaacatta agtacaacga aagtttaaa gacccgggtga ccatcacagc ggataagtct accagtacag tctatatgga gctgagctcc ctgagaagcg aagacaccgc cgtctactat tgcgctcgcc acgaacaggg tccaggttac tttgattatt gggggcaggg aactctggtc acagtcagct ccgcctccac caagggcgaa
```

```
gtggccgcat gtgagaaaga ggttgctgct ttggagaagg aggtcgctgc acttgaaaag gaggtcgcag ccctggagaa actggagccc aaatcttctg acaaaactca cacatgccca ccgtgcccag cacctgaact cctgggggga ccgtcagtct tcctcttccc cccaaaaccc aaggacaccc tcatgatctc ccggacccct gaggtcacat gcgtggtggt ggacgtgagc cacgaagacc ctgaggtcaa gttcaactgg tacgtggacg gcgtggaggt gcataatgcc aagacaaagc cgcgggagga gcagtacaac agcacgtacc gtgtggtcag cgtcctcacc gtcctgcacc aggactggct gaatggcaag gagtacaagt gcaaggtctc caacaaagcc ctcccagccc ccatcgagaa aaccatctcc aaagccaaag ggcagccccg agaaccacag gtgtacaccc tgcccccatc ccgggaggag atgaccaaga accaggtcag cctgacctgc ctggtcaaag gcttctatcc cagcgacatc gccgtggagt gggagagcaa tgggcagccg gagaacaact acaagaccac gcctcccgtg ctggactccg acggctcctt cttcctctac agcaagctca ccgtggacaa gagcaggtgg cagcagggga acgtcttctc atgctccgtg atgcatgagg ctctgcacaa ccactacacg cagaagagcc tctccctgtc tccgggt
```

The amino acid sequence of the second polypeptide chain of hDR5 mAb 2×hDR5 mAb 2 Fc diabody is (SEQ ID NO:160):

```
DIQMTQSPSF LSASVGDRVT ITCRASQDVN TAVAWYQQKP

GKAPKLLIYW ASTRHTGVPD RFSGSGSGTD FTLTISSLQP

EDIATYYCQQ HYITPWTFGG GTKLEIKGGG SGGGGQVQLV

QSGAEVKKPG ASVKVSCKAS GYTFTEYILH WVRQAPGQGL

EWMGWFYPGN NNIKYNEKFK DRVTITADKS TSTVYMELSS

LRSEDTAVYY CARHEQGPGY FDYWGQGTLV TVSSASTKGK

VAACKEKVAA LKEKVAALKE KVAALKE
```

In SEQ ID NO:160, amino acid residues 1-107 correspond to the amino acid sequence of the VL Domain of hDR5 mAb 2 VL-5 (SEQ ID NO:29), residues 108-115 correspond to the intervening spacer peptide GGGSGGGG (Linker 1) (SEQ ID NO:33), residues 116-237 correspond to the amino acid sequence of the VH Domain of hDR5 mAb 2 VH-2 (SEQ ID NO:31), residues 235-239 correspond to an ASTKG linker (SEQ ID NO:47) residues 240-267 correspond to a cysteine-containing K-coil Domain (SEQ ID NO:42). A polynucleotide that encodes SEQ ID NO:160 is SEQ ID NO:161:

```
gatattcaga tgacccagag tccctcattt ctgtccgcct ccgtcggtga ccgcgtgact attacttgtc gggcttctca
```

```
ggatgtcaac accgccgtgg cttggtacca gcagaagccc
ggtaaagcac ctaagctgct gatctattgg gccagcactc
ggcacaccgg agtcccagat aggttctctg gcagtggatc
agggacagac tttaccctga caattagctc cctgcagccc
gaggatatcg ctacttacta ttgtcagcag cactacatca
ctccttggac cttcggcggg ggcacaaaac tggaaatcaa
aggaggcgga tccggcggcg gaggccaggt ccagctggtg
cagagtgggg cagaggtgaa aaagccaggg gcatcagtga
aagtgtcttg taaagcatca ggttatacat ttactgagta
catcctgcac tgggtgcgac aggcaccagg acagggactg
gaatggatgg ggtggttcta ccctggcaac aacaacatta
agtacaacga gaagtttaaa gaccgggtga ccatcacagc
ggataagtct accagtacag tctatatgga gctgagctcc
ctgagaagcg aagacaccgc cgtctactat tgcgctcgcc
acgaacaggg tccaggttac tttgattatt gggggcaggg
aactctggtc acagtcagct ccgcctccac caagggcaaa
gtggccgcat gtaaggagaa agttgctgct ttgaaagaga
aggtcgccgc acttaaggaa aaggtcgcag ccctgaaaga
g
```

Another Fc Region-containing diabody, designated "hDR5 mAb 2.5×hDR5 mAb 2.5 Fc diabody (AA)," is identical to hDR5 mAb 2.5×hDR5 mAb 2.5 Fc diabody except the Fc Region is a variant having a L234A/L235A double mutation (underlined) which reduces/eliminates binding to FcγRIIIA and reduces/eliminates effector functions. The amino acid sequence of the first polypeptide chain of this Fc Region-Containing diabody is (SEQ ID NO:162):

```
DIQMTQSPSF LSASVGDRVT ITCRASQDVN TAVAWYQQKP
GKAPKLLIYW ASTRHTGVPD RFSGSGSGTD FTLTISSLQP
EDIATYYCQQ HYITPWTFGG GTKLEIKGGG SGGGGQVQLV
QSGAEVKKPG ASVKVSCKAS GYTFTEYILH WVRQAPGQGL
EWMGWFYPGN NNIKYNEKFK DRVTITADKS TSTVYMELSS
LRSEDTAVYY CARHEQGPGY FDYWGQGTLV TVSSASTKGE
VAACEKEVAA LEKEVAALEK EVAALEKLEP KSSDKTHTCP
PCPAPEAAGG PSVFLFPPKP KDTLMISRTP EVTCVVVDVS
HEDPEVKFNW YVDGVEVHNA KTKPREEQYN STYRVVSVLT
VLHQDWLNGK EYKCKVSNKA LPAPIEKTIS KAKGQPREPQ
VYTLPPSREE MTKNQVSLTC LVKGFYPSDI AVEWESNGQP
ENNYKTTPPV LDSDGSFFLY SKLTVDKSRW QQGNVFSCSV
MHEALHNHYT QKSLSLSPG
```

A polynucleotide that encodes SEQ ID NO:162 is SEQ ID NO:163:

```
gatattcaga tgacccagag tccctcattt ctgtccgcct
ccgtcggtga ccgcgtgact attacttgtc gggcttctca
ggatgtcaac accgccgtgg cttggtacca gcagaagccc
ggtaaagcac ctaagctgct gatctattgg gccagcactc
ggcacaccgg agtcccagat aggttctctg gcagtggatc
agggacagac tttaccctga caattagctc cctgcagccc
gaggatatcg ctacttacta ttgtcagcag cactacatca
ctccttggac cttcggcggg ggcacaaaac tggaaatcaa
aggaggcgga tccggcggcg gaggccaggt ccagctggtg
cagagtgggg cagaggtgaa aaagccaggg gcatcagtga
aagtgtcttg taaagcatca ggttatacat ttactgagta
catcctgcac tgggtgcgac aggcaccagg acagggactg
gaatggatgg ggtggttcta ccctggcaac aacaacatta
agtacaacga gaagtttaaa gaccgggtga ccatcacagc
ggataagtct accagtacag tctatatgga gctgagctcc
ctgagaagcg aagacaccgc cgtctactat tgcgctcgcc
acgaacaggg tccaggttac tttgattatt gggggcaggg
aactctggtc acagtcagct ccgcctccac caagggcgaa
gtggccgcat gtgagaaaga ggttgctgct ttggagaagg
aggtcgctgc acttgaaaag gaggtcgcag ccctggagaa
actggagccc aaatcttctg acaaaactca cacatgccca
ccgtgcccag cacctgaagc gcgggggga ccgtcagtct
tcctcttccc cccaaaaccc aaggacaccc tcatgatctc
ccggacccct gaggtcacat gcgtggtggt ggacgtgagc
cacgaagacc ctgaggtcaa gttcaactgg tacgtggacg
gcgtggaggt gcataatgcc aagacaaagc cgcgggagga
gcagtacaac agcacgtacc gtgtggtcag cgtcctcacc
gtcctgcacc aggactggct gaatggcaag gagtacaagt
gcaaggtctc caacaaagcc ctcccagccc catcgagaa
aaccatctcc aaagccaaag gcagccccg agaaccacag
gtgtacaccc tgccccccatc ccgggaggag atgaccaaga
accaggtcag cctgacctgc ctggtcaaag gcttctatcc
cagcgacatc gccgtggagt gggagagcaa tgggcagccg
gagaacaact acaagaccac gcctcccgtg ctggactccg
acggctcctt cttcctctac agcaagctca ccgtggacaa
gagcaggtgg cagcagggga acgtcttctc atgctccgtg
atgcatgagg ctctgcacaa ccactacacg cagaagagcc
tctccctgtc tccgggt
```

The second polypeptide chain of hDR5 mAb 2×hDR5 mAb 2 Fc diabody (AA) is also SEQ ID NO:160 (encoded by SEQ ID NO:161), described in detail above.

Alternatively, where reduced/eliminated binding to FcγRIIIA and/or reduced/eliminated effector functions is desired, the CH2-CH3 region of IgG2 or IgG4 may be used. In such an Fc Region-Containing diabody, amino acid residues 284-500 of SEQ ID NOs:158 or 162 will be replaced with SEQ ID NO:164 (CH2-CH3 of IgG2) or SEQ ID NO:103 (CH2-CH3 of IgG4), optionally lacking the C-terminal amino acid residue.

D. DR5×DR5 Monospecific Diabodies Bivalent For DR5

1. DR5 mAb 1×DR5 mAb 1 Diabody

Exemplary monospecific diabodies bivalent for DR5 lacking an Fc Region composed of two polypeptide chains are constructed having the VL and VH Domains of anti-human DR5 antibody DR5 mAb 1 and the VL and VH Domains of DR5 mAb 1. The amino acid sequence of the first polypeptide chain of this diabody comprises amino acid residues 1-273 of SEQ ID NO:128 described above. The amino acid sequence of the second polypeptide chain of this diabody comprises SEQ ID NO:130 described above.

Other exemplary monospecific diabodies bivalent for DR5 containing an Fc Region composed of two polypeptide chains are constructed having the VL and VH Domains of anti-human DR5 antibody DR5 mAb 1 and the VL and VH Domains of DR5 mAb 1. The amino acid sequence of the first polypeptide chain of this diabody comprises SEQ ID NO:128 or SEQ ID NO:132 described above. The amino acid sequence of the second polypeptide chain of this diabody comprises SEQ ID NO:130 and further comprises a linker having the amino acid residues LEPKSSDKTHTCP-PCP; SEQ ID NO:51, and an IgG1 Fc region have the amino acid sequence of SEQ ID NO:1 or SEQ ID NO:102, optionally lacking the C-terminal amino acid residue.

2. DR5 mAb 2×DR5 mAb 2 Diabody

Exemplary monospecific diabodies bivalent for DR5 lacking an Fc Region composed of two polypeptide chains are constructed having the VL and VH Domains of anti-human DR5 antibody DR5 mAb 2 and the VL and VH Domains of DR5 mAb 2. The amino acid sequence of the first polypeptide chain of this diabody comprises amino acid residues 1-267 of SEQ ID NO:134 described above. The amino acid sequence of the second polypeptide chain of this diabody comprises SEQ ID NO:136 described above.

Other exemplary monospecific diabodies bivalent for DR5 containing an Fc Region composed of two polypeptide chains are constructed having the VL and VH Domains of anti-human DR5 antibody DR5 mAb 2 and the VL and VH Domains of DR5 mAb 2. The amino acid sequence of the first polypeptide chain of this diabody comprises SEQ ID NO:134 or SEQ ID NO:138. The amino acid sequence of the second polypeptide chain of this diabody comprises SEQ ID NO:136, and further comprises a linker having the amino acid residues LEPKSSDKTHTCPPCP; SEQ ID NO:51, and an IgG1 Fc Region have the amino acid sequence of SEQ ID NO:1 or SEQ ID NO:102, optionally lacking the C-terminal amino acid residue.

3. DR5 mAb 2.2×DR5 mAb 2.2 Diabody

Exemplary monospecific diabodies bivalent for DR5 lacking an Fc Region composed of two polypeptide chains are constructed having the VL and VH Domains of anti-human DR5 antibody DR5 mAb 2 VL-2 and the VL and VH Domains of DR5 mAb 2 VH-2. The amino acid sequence of the first polypeptide chain of this diabody comprises amino acid residues 1-267 of SEQ ID NO:140, described above. The amino acid sequence of the second polypeptide chain of this diabody comprises SEQ ID NO:142, described above.

Other exemplary monospecific diabodies bivalent for DR5 containing an Fc Region composed of two polypeptide chains are constructed having the VL and VH Domains of anti-human DR5 antibody DR5 mAb 2 VL-2 and the VL and VH Domains of DR5 mAb 2 VH-2. The amino acid sequence of the first polypeptide chain of this diabody comprises SEQ ID NO:140 or SEQ ID NO:144. The amino acid sequence of the second polypeptide chain of this diabody comprises SEQ ID NO:142 and further comprises a linker having the amino acid residues LEPKSSDKTHTCP-PCP; SEQ ID NO:51, and an IgG1 Fc Region have the amino acid sequence of SEQ ID NO:1 or SEQ ID NO:102, optionally lacking the C-terminal amino acid residue.

4. DR5 mAb 2.3×DR5 mAb 2.3 Diabody

Exemplary monospecific diabodies bivalent for DR5 lacking an Fc Region composed of two polypeptide chains are constructed having the VL and VH Domains of anti-human DR5 antibody DR5 mAb 2 VL-3 and the VL and VH Domains of DR5 mAb 2 VH-2. The amino acid sequence of the first polypeptide chain of this diabody comprises amino acid residues 1-267 of SEQ ID NO:146 described above. The amino acid sequence of the second polypeptide chain of this diabody comprises SEQ ID NO:148 described above.

Other exemplary monospecific diabodies bivalent for DR5 containing an Fc Region composed of two polypeptide chains are constructed having the VL and VH Domains of anti-human DR5 antibody DR5 mAb 2 VL-3 and the VL and VH Domains of DR5 mAb 2 VH-2. The amino acid sequence of the first polypeptide chain of this diabody comprises SEQ ID NO:146 or SEQ ID NO:150. The amino acid sequence of the second polypeptide chain of this diabody comprises SEQ ID NO:148 and further comprises a linker having the amino acid residues LEPKSSDKTHTCP-PCP; SEQ ID NO:51, and an IgG1 Fc Region have the amino acid sequence of SEQ ID NO:1 or SEQ ID NO:102, optionally lacking the C-terminal amino acid residue.

5. DR5 mAb 2.4×DR5 mAb 2.4 Diabody

Exemplary monospecific diabodies bivalent for DR5 lacking an Fc Region composed of two polypeptide chains are constructed having the VL and VH Domains of anti-human DR5 antibody DR5 mAb 2 VL-4 and the VL and VH Domains of DR5 mAb 2 VH-2. The amino acid sequence of the first polypeptide chain of this diabody comprises amino acid residues 1-267 of SEQ ID NO:152 described above. The amino acid sequence of the second polypeptide chain of this diabody comprises SEQ ID NO:154 described above.

Other exemplary monospecific diabodies bivalent for DR5 containing an Fc Region composed of two polypeptide chains are constructed having the VL and VH Domains of anti-human DR5 antibody DR5 mAb 2 VL-4 and the VL and VH Domains of DR5 mAb 2 VH-2. The amino acid sequence of the first polypeptide chain of this diabody comprises SEQ ID NO:152 or SEQ ID NO:156. The amino acid sequence of the second polypeptide chain of this diabody comprises SEQ ID NO:154 and further comprises a linker having the amino acid residues LEPKSSDKTHTCP-PCP; SEQ ID NO:51, and an IgG1 Fc Region have the amino acid sequence of SEQ ID NO:1 or SEQ ID NO:102, optionally lacking the C-terminal amino acid residue.

6. DR5 mAb 2.5×DR5 mAb 2.5 Diabody

Exemplary monospecific diabodies bivalent for DR5 lacking an Fc Region composed of two polypeptide chains are constructed having the VL and VH Domains of anti-human DR5 antibody DR5 mAb 2 VL-5 and the VL and VH Domains of DR5 mAb 2 VH-2. The amino acid sequence of the first polypeptide chain of this diabody comprises amino acid residues 1-267 of SEQ ID NO:158 described above. The amino acid sequence of the second polypeptide chain of this diabody comprises SEQ ID NO:160 described above.

Other exemplary monospecific diabodies bivalent for DR5 containing an Fc Region composed of two polypeptide chains are constructed having the VL and VH Domains of anti-human DR5 antibody DR5 mAb 2 VL-5 and the VL and VH Domains of DR5 mAb 2 VH-2. The amino acid sequence of the first polypeptide chain of this diabody comprises SEQ ID NO:158 or SEQ ID NO:162. The amino acid sequence of the second polypeptide chain of this diabody comprises SEQ ID NO:160 and further comprises a linker having the amino acid residues LEPKSSDKTHTCP-PCP; SEQ ID NO:51, and an IgG1 Fc Region have the amino acid sequence of SEQ ID NO:1 or SEQ ID NO:102, optionally lacking the C-terminal amino acid residue.

E. Additional DR5×DR5 Diabodies

In alternative embodiments, the DR5×DR5 diabodies of the invention are constructed having the VL and VH Domains of humanized anti-human DR5 antibody DR5 mAb 1 and/or the VL and VH Domains of humanized DR5 mAb 2. In a specific embodiment, the VL Domain of hDR5 mAb2 VL VL-2 (SEQ ID NO:23), hDR5 mAb2 VL VL-3 (SEQ ID NO:25), hDR5 mAb2 VL VL-4 (SEQ ID NO:27), or hDR5 mAb2 VL VL-5 (SEQ ID NO:29) is incorporated into the above constructs in place of SEQ ID NO:13, and/or the VH Domain of hDR5 mAb2 VH-2 (SEQ ID NO:31) is incorporated into the above construct in place of SEQ ID NO: 18. Alternatively, or in addition, a humanized VL Domain of DR5 mAb 1 is incorporated into the above constructs in place of SEQ ID NO:3 and/or a humanized VH Domain is incorporated into the above constructs in place of SEQ ID NO:8.

Although the exemplary multivalent DR5-Binding Molecules described above comprise three $CDR_{LS}$ of the Light Chain (VL) and three $CDR_{HS}$ of the Heavy Chain (VH) for each binding domain, it will be recognized that the invention also includes multivalent DR5-Binding Molecules that possess:

(1) at least one of the $CDR_{LS}$ of the VL Domain of the anti-human DR5 antibody DR5 mAb 1;
(2) at least two of the $CDR_{LS}$ of the VL Domain of the anti-human DR5 antibody DR5 mAb 1;
(3) the three $CDR_{LS}$ of the VL Domain of the anti-human DR5 antibody DR5 mAb 1;
(4) at least one of the $CDR_{HS}$ of the VH Domain of the anti-human DR5 antibody DR5 mAb 1;
(5) at least two of the $CDR_{HS}$ of the VH Domain of the anti-human DR5 antibody DR5 mAb 1;
(6) the three $CDR_{HS}$ of the VH Domain of the anti-human DR5 antibody DR5 mAb 1;
(7) at least one of the $CDR_{LS}$ of the VL Domain of the anti-human DR5 antibody DR5 mAb 1 and at least one of the $CDR_{HS}$ of the VH Domain of the anti-human DR5 antibody DR5 mAb 1;
(8) at least two of the $CDR_{LS}$ of the VL Domain of the anti-human DR5 antibody DR5 mAb 1 and at least two of the $CDR_{HS}$ of the VH Domain of the anti-human DR5 antibody DR5 mAb 1;
(9) the three $CDR_{LS}$ of the VL Domain of the anti-human DR5 antibody DR5 mAb 1 and the three $CDR_{HS}$ of the VH Domain of the anti-human DR5 antibody DR5 mAb 1;
(10) the VL Domain of the anti-human DR5 antibody DR5 mAb 1;
(11) the VH Domain of the anti-human DR5 antibody DR5 mAb 1;
(12) the VL and VH Domains of the anti-human DR5 antibody DR5 mAb 1;
(13) or may compete with anti-human DR5 antibody DR5 mAb 1 for binding to human DR5;
or
(14) compete with any of (1)-(13) for binding to human DR5.

Similarly, it will be recognized that the invention also includes multivalent DR5-Binding Molecules that possess:
(15) at least one of the $CDR_{LS}$ of the VL Domain of the anti-human DR5 antibody DR5 mAb 2;
(16) at least two of the $CDR_{LS}$ of the VL Domain of the anti-human DR5 antibody DR5 mAb 2;
(17) the three $CDR_{LS}$ of the VL Domain of the anti-human DR5 antibody DR5 mAb 2;
(18) at least one of the $CDR_{HS}$ of the VH Domain of the anti-human DR5 antibody DR5 mAb 2;
(19) at least two of the $CDR_{HS}$ of the VH Domain of the anti-human DR5 antibody DR5 mAb 2;
(20) the three $CDR_{HS}$ of the VH Domain of the anti-human DR5 antibody DR5 mAb 2;
(21) at least one of the $CDR_{LS}$ of the VL Domain of the anti-human DR5 antibody DR5 mAb 2 and at least one of the $CDR_{HS}$ of the VH Domain of the anti-human DR5 antibody DR5 mAb 2;
(22) at least two of the $CDR_{LS}$ of the VL Domain of the anti-human DR5 antibody DR5 mAb 2 and at least two of the $CDR_{HS}$ of the VH Domain of the anti-human DR5 antibody DR5 mAb 2;
(23) the three $CDR_{LS}$ of the VL Domain of the anti-human DR5 antibody DR5 mAb 2 and the three $CDR_{HS}$ of the VH Domain of the anti-human DR5 antibody DR5 mAb 2;
(24) the VL Domain of the anti-human DR5 antibody DR5 mAb 2;
(25) the VH Domain of the anti-human DR5 antibody DR5 mAb 2;
(26) the VL and VH Domains of the anti-human DR5 antibody DR5 mAb 2;
(27) compete with anti-human DR5 antibody DR5 mAb 2 for binding to human DR5;
or
(28) or that compete with any of (15)-(27) for binding to human DR5.

VII. METHODS OF PRODUCTION

A multivalent DR5-Binding Molecule, and other DR5 agonists, antagonists and modulators can be created from the polynucleotides and/or sequences of the DR5 mAb 1 or DR5 mAb 2 antibodies by methods known in the art, for example, synthetically or recombinantly. One method of producing such peptide agonists, antagonists and modulators involves chemical synthesis of the polypeptide, followed by treatment under oxidizing conditions appropriate to obtain the native conformation, that is, the correct disulfide bond linkages. This can be accomplished using methodologies well known to those skilled in the art (see, e.g., Kelley, R. F. et al. (1990) In: GENETIC ENGINEERING PRINCIPLES AND METHODS, Setlow, J. K. Ed., Plenum Press, N.Y., vol. 12, pp 1-19; Stewart, J. M et al. (1984) SOLID PHASE PEPTIDE SYNTHESIS, Pierce Chemical Co., Rockford, Ill.; see also U.S. Pat. Nos. 4,105,603; 3,972,859; 3,842,067; and 3,862,925).

Polypeptides of the invention may be conveniently prepared using solid phase peptide synthesis (Merrifield, B. (1986) "*Solid Phase Synthesis*," Science 232(4748):341-347; Houghten, R. A. (1985) "*General Method For The Rapid Solid-Phase Synthesis Of Large Numbers Of Peptides: Specificity Of Antigen-Antibody Interaction At The Level Of Individual Amino Acids*," Proc. Natl. Acad. Sci.

(U.S.A.) 82(15):5131-5135; Ganesan, A. (2006) "*Solid-Phase Synthesis In The Twenty-First Century*," Mini Rev. Med. Chem. 6(1):3-10).

In yet another alternative, fully human antibodies having one or more of the CDRs of DR5 mAb 1 or DR5 mAb 2 or which compete with DR5 mAb 1 or DR5 mAb 2 for binding to human DR5 or a soluble form thereof may be obtained through the use of commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are XENOMOUSE™ (Abgenix, Inc., Fremont, Calif.) and HuMAB-MousE® and TC MousE™ (both from Medarex, Inc., Princeton, N.J.).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Suitable methods for expressing antibodies recombinantly in plants or milk have been disclosed (see, for example, Peeters et al. (2001) "*Production Of Antibodies And Antibody Fragments In Plants*," Vaccine 19:2756; Lonberg, N. et al. (1995) "*Human Antibodies From Transgenic Mice*," Int. Rev. Immunol 13:65-93; and Pollock et al. (1999) "*Transgenic Milk As A Method For The Production Of Recombinant Antibodies*," J. Immunol Methods 231:147-157). Suitable methods for making derivatives of antibodies, e.g., humanized, single-chain, etc. are known in the art. In another alternative, antibodies may be made recombinantly by phage display technology (see, for example, U.S. Pat. Nos. 5,565,332; 5,580,717; 5,733,743; 6,265,150; and Winter, G. et al. (1994) "*Making Antibodies By Phage Display Technology*," Annu. Rev. Immunol. 12.433-455).

The antibodies or protein of interest may be subjected to sequencing by Edman degradation, which is well known to those of skill in the art. The peptide information generated from mass spectrometry or Edman degradation can be used to design probes or primers that are used to clone the protein of interest.

An alternative method of cloning the protein of interest is by "panning" using purified DR5 or portions thereof for cells expressing an antibody or protein of interest that possesses one or more of the CDRs of DR5 mAb 1 or DR5 mAb 2 or that competes with DR5 mAb 1 or DR5 mAb 2 for binding to human DR5. The "panning" procedure may be conducted by obtaining a cDNA library from tissues or cells that express DR5, overexpressing the cDNAs in a second cell type, and screening the transfected cells of the second cell type for a specific binding to DR5 in the presence or absence of DR5 mAb 1 or DR5 mAb 2. Detailed descriptions of the methods used in cloning mammalian genes coding for cell surface proteins by "panning" can be found in the art (see, for example, Aruffo, A. et al. (1987) "*Molecular Cloning Of A CD28 cDNA By A High-Efficiency COS Cell Expression System*," Proc. Natl. Acad. Sci. (U.S.A.) 84:8573-8577 and Stephan, J. et al. (1999) "*Selective Cloning Of Cell Surface Proteins Involved In Organ Development: Epithelial Glycoprotein Is Involved In Normal Epithelial Differentiation*," Endocrinol. 140:5841-5854).

Vectors containing polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cell capable of overexpressing heterologous DNAs can be used for the purpose of isolating the genes encoding the antibody, polypeptide or protein of interest. Non-limiting examples of suitable mammalian host cells include but are not limited to COS, HeLa, and CHO cells. Preferably, the host cells express the cDNAs at a level of about 5-fold higher, more preferably 10-fold higher, even more preferably 20-fold higher than that of the corresponding endogenous antibody or protein of interest, if present, in the host cells. Screening the host cells for a specific binding to DR5 is effected by an immunoassay or FACS. A cell overexpressing the antibody or protein of interest can be identified.

The invention includes polypeptides comprising an amino acid sequence of the antibodies of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an anti-DR5 polypeptide could be produced by an automated polypeptide synthesizer employing the solid phase method.

The invention includes modifications to DR5 mAb 1 or DR5 mAb 2 antibodies and their polypeptide fragments that bind to DR5 and the agonists, antagonists, and modulators of such molecules, including functionally equivalent antibodies and fusion polypeptides that do not significantly affect the properties of such molecules as well as variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues that can be conservatively substituted for one another include but are not limited to: glycine/alanine; serine/threonine; valine/isoleucine/leucine; asparagine/glutamine; aspartic acid/glutamic acid; lysine/arginine; and phenylalanine/tyrosine. These polypeptides also include glycosylated and non-glycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention encompasses fusion proteins comprising one or more of the polypeptides or DR5 mAb 1 or DR5 mAb 2 antibodies of this invention. In one embodiment, a fusion polypeptide is provided that comprises a light chain, a heavy chain or both a light and heavy chain. In another embodiment, the fusion polypeptide contains a heterologous immunoglobulin constant region. In another embodiment, the fusion polypeptide contains a Light Chain Variable Domain and a Heavy Chain Variable Domain of an antibody produced from a publicly-deposited hybridoma. For purposes of this invention, an antibody fusion protein contains one or more polypeptide domains that specifically bind to DR5 and another amino acid sequence to which it is not attached in the native molecule, for example, a heterologous sequence or a homologous sequence from another region.

VIII. USES OF THE MULTIVALENT DR5-BINDING MOLECULES OF THE PRESENT INVENTION

The present invention encompasses compositions, including pharmaceutical compositions, comprising the multivalent DR5-Binding Molecules of the present invention (e.g., multivalent DR5-Binding Molecules comprising antigen-binding domains from anti-DR5 antibodies, such as DR5 mAb 1 and DR5 mAb 2, or their humanized derivatives), polypeptides derived from such molecules, polynucleotides comprising sequences encoding such molecules or polypeptides, and other agents as described herein.

As discussed above, activation of DR5 by the TRAIL cytokine results in the highly selective recognition and killing of tumor cells. The multivalent DR5-Binding Molecules of the present invention have the ability to act as agonist agents, mimicking TRAIL, and thus leading to the activation of DR5. As such, the multivalent DR5-Binding Molecules comprising antigen-binding domains from anti-DR5 antibodies, such as DR5 mAb 1 and DR5 mAb 2, and their humanized derivatives, may be used as surrogates for TRAIL so as to promote the death of tumor cells that express DR5. Since DR5 is ubiquitously distributed in tumor cell lines, the multivalent DR5-Binding Molecules of the present invention provide a general therapy for cancer. The cancers that may be treated by such molecules include cancers characterized by the presence of a cancer cell selected from the group consisting of a cell of: an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

In particular, the multivalent DR5-Binding Molecules of the present invention may be used in the treatment of colorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer and rectal cancer.

In some embodiments the multivalent DR5-Binding Molecules of the present invention may be used to promote the death of tumor cells which are human cancer stem cells. Cancer stem cells (CSCs) have been hypothesized to play a role in tumor growth and metastasis (Ghotra, V. P. et al. (2009) "*The Cancer Stem Cell Microenvironment And Anti-Cancer Therapy*," Int. J. Radiat. Biol. 85(11):955-962; Gupta, P. B. et al. (2009) "*Cancer Stem Cells: Mirage Or Reality?*" Nat. Med. 15(9):1010-1012; Lawson, J. C. et al. (2009) "*Cancer Stem Cells In Breast Cancer And Metastasis*," Breast Cancer Res. Treat. 118(2):241-254; Hermann, P. C. et al. (2009) "*Pancreatic Cancer Stem Cells—Insights And Perspectives*," Expert Opin. Biol. Ther. 9(10):1271-1278; Schatton, T. et al. (2009) "*Identification And Targeting Of Cancer Stem Cells*," Bioessays 31(10):1038-1049; Mittal, S. et al. (2009) "*Cancer Stem Cells: The Other Face Of Janus*," Amer. J. Med. Sci. 338(2):107-112; Alison, M. R. et al. (2009) "*Stem Cells And Lung Cancer: Future Therapeutic Targets?*" Expert Opin. Biol. Ther. 9(9):1127-1141; Charafe-Jauffret, E. et al. (2009) "*Breast Cancer Stem Cells: Tools And Models To Rely On*," BMC Cancer 9:202; Scopelliti, A. et al. (2009) "*Therapeutic Implications Of Cancer Initiating Cells*," Expert Opin. Biol. Ther. 9(8):1005-1016; PCT Publication WO 2008/091908). Under this hypothesis, the CSCs comprise a small, distinct subset of cells within each tumor that are capable of indefinite self-renewal and of developing into the more adult tumor cell(s) that are relatively limited in replication capacity. It has been hypothesized that cancer stem cells might be more resistant to chemotherapeutic agents, radiation or other toxic conditions, and thus, might persist after clinical therapies and later grow into secondary tumors, metastases or be responsible for relapse. It has been suggested that CSCs can arise either from 'normal' tissue stem cells or from more differentiated tissue progenitor cells. As demonstrated herein, the multivalent DR5-Binding Molecules of the present invention are cytotoxic to cells that appear like cancer stem cells (i.e. cancer stem cell-like (CSCL) cells). Accordingly, the multivalent DR5-Binding Molecules of the invention may be used to promote the death of human cancer stem cells.

In addition, Histone deacetylase (HDAC) inhibitors, such as vorinostat, have been reported to sensitize tumor cells to apoptosis induced via the DR5 pathway (Nakata et al. (2004) "*Histone deacetylase inhibitors upregulate death receptor 5/TRAIL-R2 and sensitize apoptosis induced by TRAIL/APO2-L in human malignant tumor cells*," Oncogene 19:6261-71; Butler et al. (2006) "*The histone deacetylase inhibitor, suberoylanilide hydroxamic acid, overcomes resistance of human breast cancer cells to Apo2L/TRAIL*," Int J Cancer. 15:944-54; Shankar et al. (2009) "*Suberoylanilide* hydroxamic acid (Zolinza/vorinostat) sensitizes TRAIL-resistant breast cancer cells orthotopically implanted in BALB/c nude mice," Mol Cancer Ther. 8:1596-605). As demonstrated herein, the ability of the multivalent DR5-Binding Molecules of the present invention to promote cell death is augmented by treatment in combination with an HDAC inhibitor (e.g., vorinostat). Accordingly, the use of an HDAC inhibitor in combination with multivalent DR5-Binding Molecules is particularly useful for the treatment of cancers expressing DR5 which are not sensitive to treatment with a multivalent DR5-Binding Molecule as a single agent.

In addition to their utility in therapy, the multivalent DR5-Binding Molecules of the present invention may be detectably labeled and used in the diagnosis of cancer or in the imaging of tumors and tumor cells.

IX. PHARMACEUTICAL COMPOSITIONS

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of the multivalent DR5-Binding Molecules of the present invention, or a combination of such agents and a pharmaceutically acceptable carrier. Preferably, compositions of the invention comprise a prophylactically or therapeutically effective amount of the multivalent DR5-Binding Molecules of the present invention and a pharmaceutically acceptable carrier. The invention particularly encompasses such pharmaceutical compositions in which the multivalent DR5-Binding Molecule comprises antigen-binding domains from anti-DR5 antibodies, such as: DR5 mAb 1, a DR5 mAb 2 antibody, a humanized DR5 mAb 1, a humanized DR5 mAb 2 antibody, or a DR5-binding fragment of any such antibody. Especially encompassed are such molecules that comprise: the 3 $CDR_{LS}$ and the 3 $CDR_{HS}$ of DR5 mAb 1; the 3 $CDR_{LS}$ and the 3 $CDR_{HS}$ of DR5 mAb 2; and/or the 3 $CDR_{HS}$ and the 3 $CDR_{HS}$ of hDR5 mAb 2 VL-3.

The invention encompasses compositions comprising a multivalent DR5-Binding Molecule of the present invention, and a pharmaceutically acceptable carrier. The invention also encompasses such pharmaceutical compositions that additionally include a second therapeutic antibody (e.g., tumor specific monoclonal antibody) that is specific for a particular cancer antigen, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers filled with a multivalent DR5-Binding Molecule of the present invention (and more preferably, a tetravalent Fc Region-containing diabody comprising the CDRs of DR5 mAb 1, and/or DR5 mAb 2 antibody, and/or a humanized DR5 mAb 1, and/or humanized DR5 mAb 2 antibody (especially, a tetravalent E-coil/K-coil-Fc Region-containing diabody). Especially encompassed are such molecules that comprise: the 3 $CDR_{LS}$ and the 3 $CDR_{LS}$ of DR5 mAb 1; the 3 $CDR_{LS}$ and the 3 $CDR_{LS}$ of DR5 mAb 2; and/or the 3 $CDR_{LS}$ and the 3 $CDR_{LS}$ of hDR5 mAb 2 V-3, alone or with such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. A kit can comprise any of the multivalent DR5-Binding Molecules of the present invention. The kit can further comprise one or more other prophylactic and/or therapeutic agents useful for the treatment of cancer, in one or more containers; and/or the kit can further comprise one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

X. METHODS OF ADMINISTRATION

The compositions of the present invention may be provided for the treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or a conjugated molecule of the invention. In a preferred aspect, such compositions are substantially purified (i.e., substantially free from substances that limit its effect or produce undesired side effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) "Receptor-Mediated In Vitro Gene Transformation By A Soluble DNA Carrier System," J. Biol. Chem. 262: 4429-4432), construction of a nucleic acid as part of a retroviral or other vector, etc.

Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the multivalent DR5-Binding Molecules of the present invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the multivalent DR5-Binding Molecules of the present invention are packaged in a hermetically sealed container such as an ampoule or sachette indicating the quantity of the molecule. In one embodiment, such molecules are supplied as a dry sterilized lyophilized powder or water free concentrate in a hermetically sealed container and can be reconstituted, e.g., with water or saline to the appropriate concentration for administration to a subject. Preferably, the multivalent DR5-Binding Molecules of the present invention are supplied as a dry sterile lyophilized powder in a hermetically sealed container at a unit dosage of at least 5 µg, more preferably at least 10 µg, at least 15 µg, at least 25 µg, at least 50 µg, at least 100 µg, or at least 200 µg.

The lyophilized multivalent DR5-Binding Molecules of the present invention should be stored at between 2 and 8° C. in their original container and the molecules should be administered within 12 hours, preferably within 6 hours, within 5 hours, within 3 hours, or within 1 hour after being reconstituted. In an alternative embodiment, such molecules are supplied in liquid form in a hermetically sealed container indicating the quantity and concentration of the molecule, fusion protein, or conjugated molecule. Preferably, such multivalent DR5-Binding Molecules when provided in liquid form are supplied in a hermetically sealed container in which the molecules are present at a concentration of least 1 µg/ml, more preferably at least 2.5 µg/ml, at least 5 µg/ml, at least 10 µg/ml, at least 50 µg/ml, or at least 100 µg/ml.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For the multivalent DR5-Binding Molecules encompassed by the invention, the dosage administered to a patient is preferably determined based upon the body weight (kg) of the recipient subject. The dosage administered is typically from at least about 0.3 ng/kg per day to about 0.9 ng/kg per day, from at least about 1 ng/kg per day to about 3 ng/kg per day, from at least about 3 ng/kg per day to about 9 ng/kg per day, from at least about 10 ng/kg per day to about 30 ng/kg per day, from at least about 30 ng/kg per day to about 90 ng/kg per day, from at least about 100 ng/kg per day to about 300 ng/kg per day, from at least about 200 ng/kg per day to about 600 ng/kg per day, from at least about 300 ng/kg per day to about 900 ng/kg per day, from at least about 400 ng/kg per day to about 800 ng/kg per day, from at least about 500 ng/kg per day to about 1000 ng/kg per day, from at least about 600 ng/kg per day to about 1000 ng/kg per day, from at least about 700 ng/kg per day to about 1000 ng/kg per day, from at least about 800 ng/kg per day to about 1000 ng/kg per day, from at least about 900 ng/kg per day to about 1000 ng/kg per day, or at least about 1,000 ng/kg per day. The calculated dose will be administered based on the patient's body weight at baseline. Significant (≥10%) change in body weight from baseline or established plateau weight should prompt recalculation of dose.

In another embodiment, the patient is administered a treatment regimen comprising one or more doses of such prophylactically or therapeutically effective amount of a multivalent DR5-Binding Molecule of the present invention, wherein the treatment regimen is administered over 2 days, 3 days, 4 days, 5 days, 6 days or 7 days. In certain embodiments, the treatment regimen comprises intermittently administering doses of the prophylactically or therapeutically effective amount of the multivalent DR5-Binding Molecules of the present invention (for example, administering a dose on day 1, day 2, day 3 and day 4 of a given week and not administering doses of the prophylactically or therapeutically effective amount of the multivalent DR5-Binding Molecule (and particularly, a tetravalent Fc Region-containing diabody comprising the CDRs of DR5 mAb 1, and/or DR5 mAb 2 antibody, and/or a humanized DR5 mAb 1, and/or humanized DR5 mAb 2 antibody (especially, a tetravalent E-coil/K-coil-Fc Region-containing diabody). Especially encompassed is the administration (on day 5, day 6, and day 7 of the same week) of molecules that comprise: the 3 $CDR_{LS}$ and the 3 $CDR_{HS}$ of DR5 mAb 1; the 3 $CDR_{LS}$ and the 3 $CDR_{HS}$ of DR5 mAb 2; and/or the 3 $CDR_{LS}$ and the 3 $CDR_{HS}$ of hDR5 mAb 2 V-3. Typically, there are 1, 2, 3, 4, 5 or more courses of treatment. Each course may be the same regimen or a different regimen.

In another embodiment, the administered dose escalates over the first quarter, first half or first two-thirds or three-quarters of the regimen(s) (e.g., over the first, second, or third regimens of a 4 course treatment) until the daily prophylactically or therapeutically effective amount of the multivalent DR5-Binding Molecule is achieved. Table 4 provides 5 examples of different dosing regimens described above for a typical course of treatment.

TABLE 4

| Regimen | Day | Diabody Dosage (ng diabody per kg subject weight per day) | | | | |
|---|---|---|---|---|---|---|
| 1 | 1, 2, 3, 4 | 100 | 100 | 100 | 100 | 100 |
|   | 5, 6, 7 | none | none | none | none | none |
| 2 | 1, 2, 3, 4 | 300 | 500 | 700 | 900 | 1,000 |
|   | 5, 6, 7 | none | none | none | none | none |
| 3 | 1, 2, 3, 4 | 300 | 500 | 700 | 900 | 1,000 |
|   | 5, 6, 7 | none | none | none | none | none |
| 4 | 1, 2, 3, 4 | 300 | 500 | 700 | 900 | 1,000 |
|   | 5, 6, 7 | none | none | none | none | none |

The dosage and frequency of administration of a multivalent DR5-Binding Molecule of the present invention may be reduced or altered by enhancing uptake and tissue penetration of the molecule by modifications such as, for example, lipidation.

The dosage of a multivalent DR5-Binding Molecule of the invention administered to a patient may be calculated for use as a single agent therapy. Alternatively, the molecule may be used in combination with other therapeutic compositions and the dosage administered to a patient are lower than when said molecules are used as a single agent therapy.

The pharmaceutical compositions of the invention may be administered locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

The compositions of the invention can be delivered in a vesicle, in particular a liposome (See Langer (1990) "*New Methods Of Drug Delivery*," Science 249:1527-1533); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 3 17-327).

The compositions of the invention can be delivered in a controlled-release or sustained-release system. Any technique known to one of skill in the art can be used to produce sustained-release formulations comprising one or more of the multivalent DR5-Binding Molecule(s) of the invention. See, e.g., U.S. Pat. No. 4,526,938; PCT publication WO 91/05548; PCT publication WO 96/20698; Ning et al. (1996) "*Intratumoral Radioimmunotheraphy Of A Human Colon Cancer Xenograft Using A Sustained-Release Gel*," Radiotherapy & Oncology 39:179-189, Song et al. (1995) "*Antibody Mediated Lung Targeting Of Long-Circulating Emulsions*," PDA Journal of Pharmaceutical Science & Technology 50:372-397; Cleek et al. (1997) "*Biodegradable Polymeric Carriers For A bFGF Antibody For Cardiovascular Application*," Pro. Intl. Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety. In one embodiment, a pump may be used in a controlled-release system (See Langer, supra; Sefton, (1987) "*Implantable Pumps*," CRC Crit. Rev. Biomed. Eng. 14:201-240; Buchwald et al. (1980) "*Long-Term, Continuous Intravenous Heparin Administration By An Implantable Infusion Pump In Ambulatory Patients With Recurrent Venous Thrombosis*," Surgery 88:507-516; and Saudek et al. (1989) "*A Preliminary Trial Of The Programmable Implantable Medication System For Insulin Delivery*," N. Engl. J. Med. 321:574-579). In another embodiment, polymeric materials can be used to achieve controlled-release of the molecules (see e.g., MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Levy et al. (1985) "*Inhibition Of Calcification Of Bioprosthetic Heart Valves By Local Controlled-Release Diphosphonate*," Science 228: 190-192; During et al. (1989) "*Controlled Release Of Dopamine From A Polymeric Brain Implant: In Vivo Characterization*," Ann. Neurol. 25:351-356; Howard et al. (1989) "*Intracerebral Drug Delivery In Rats With Lesion-Induced Memory Deficits*," J. Neurosurg. 7(1):105-112); U.S. Pat. Nos. 5,679,377; 5,916,597; 5,912,015; 5,989,463; 5,128, 326; PCT Publication No. WO 99/15154; and PCT Publication No. WO 99/20253). Examples of polymers used in sustained-release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. A controlled-release system can be placed in proximity of the therapeutic target (e.g., the lungs), thus requiring only a fraction of the systemic dose (see, e.g., Goodson, in MEDICAL APPLICATIONS OF CONTROLLED RELEASE, supra, vol. 2, pp. 115-138 (1984)). Polymeric compositions useful as controlled-release implants can be used according to Dunn et al. (See U.S. Pat. No. 5,945,155). This particular method is based upon the therapeutic effect of the in situ controlled-release of the bioactive material from the polymer system. The implantation can generally occur anywhere within the body of the patient in need of therapeutic treatment. A non-polymeric sustained delivery system can be used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled-release systems are discussed in the review by Langer (1990, "*New Methods Of Drug Delivery*," Science 249:1527-1533). Any technique known to one of skill in the art can be used to produce sustained-release formulations comprising one or more therapeutic agents of the invention. See, e.g., U.S. Pat. No. 4,526,938; International Publication Nos. WO 91/05548 and WO 96/20698; Ning et al. (1996) "*Intratumoral Radioimmunotheraphy Of A Human Colon Cancer Xenograft Using A Sustained-Release Gel*," Radiotherapy & Oncology 39:179-189, Song et al. (1995) "*Antibody Mediated Lung Targeting Of Long-Circulating Emulsions*," PDA Journal of Pharmaceutical Science & Technology 50:372-397; Cleek et al. (1997) "*Biodegradable Polymeric Carriers For A bFGF Antibody For Cardiovascular Application*," Pro. Intl Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety.

Where the composition of the invention is a nucleic acid encoding a multivalent DR5-Binding Molecule of the present invention, the nucleic acid can be administered in vivo to promote expression of its encoded multivalent DR5-Binding Molecule by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (See e.g., Joliot et al. (1991) "*Antennapedia Homeobox Peptide Regulates Neural Morphogenesis*," Proc. Natl. Acad. Sci. (U.S.A.) 88:1864-1868), etc. Alternatively, a nucleic acid can be introduced intracellularly and incorporated within host cell DNA for expression by homologous recombination.

Treatment of a subject with a therapeutically or prophylactically effective amount of a multivalent DR5-Binding Molecule of the present invention can include a single treatment or, preferably, can include a series of treatments. In a preferred example, a subject is treated with such a diabody one time per week for between about 1 to 10 weeks, preferably between 2 to 8 weeks, more preferably between about 3 to 7 weeks, and even more preferably for about 4, 5, or 6 weeks. The pharmaceutical compositions of the invention can be administered once a day, twice a day, or three times a day. Alternatively, the pharmaceutical compositions can be administered once a week, twice a week, once every two weeks, once a month, once every six weeks, once every two months, twice a year or once per year. It will also be appreciated that the effective dosage of the molecules used for treatment may increase or decrease over the course of a particular treatment.

XI. EXAMPLES

Having now generally described the invention, the same will be more readily understood through reference to the following examples, which are provided by way of illustration and are not intended to be limiting of the present invention unless specified. It will be apparent to those skilled in the art that many modifications, both to materials and methods, can be practiced without departing from the scope of the present disclosure.

A. Example 1: Characterization of Anti-Human DR5 Monoclonal Antibodies DR5 mAb 1 and DR5 mAb 2

Two monoclonal antibodies were isolated as being capable of immuno specifically binding to human DR5, and accorded the designations "DR5 mAb 1" and "DR5 mAb 2". As discussed above, the CDRs of these antibodies were found to differ. In order to determine whether the antibodies bound to different DR5 epitopes, a human DR5-Fc fusion protein was prepared and was coated to an immobilized surface. DR5 mAb 1 (1 µg/mL) was biotinylated and incubated with either a control IgG or with DR5 mAb 2 (10 µg/mL), and the ability of the IgG or DR5 mAb 2 antibody to compete for binding (to human DR5-Fc fusion protein) with DR5 mAb 1 was assessed by measuring the amount of immobilized biotinylated antibody. Additionally, the ability of the IgG or DR5 mAb 1 antibody to compete for binding with biotinylated DR5 mAb 2 was assessed. The results of this experiment are shown in Table 5.

TABLE 5

| 1 µg/mL DR5-Fc Fusion coat | | 10 µg/mL Competitor mAb | | |
|---|---|---|---|---|
| | | mIgG | DR5 mAb 1 | DR5 mAb 2 |
| 1 µg/mL biotinylated DR5 mAb | DR5 mAb 1 | 2.162 | self | 0.826 |
| | DR5 mAb 2 | 2.102 | 2.377 | self |

The results of this experiment indicate that the biotinylated antibody was capable of binding to the DR5 protein even in the presence of excess amounts of the non-biotinylated antibody. Thus, the results show that DR5 mAb 1 and DR5 mAb 2 bind to different epitopes of DR5.

In order to further characterize the DR5 mAb 1 and DR mAb 2 antibodies, their ability to block binding between DR5 and the TRAIL ligand as assessed. Thus, biotinylated DR5 mAb 1, biotinylated DR5 mAb 2 or biotinylated DR5-Fc fusion (each at 2 µg/mL) were separately incubated with immobilized DR5-Fc fusion (1 µg/mL) in the presence of either buffer or histidine tagged TRAIL (20 µg/mL). The amount of immobilized biotinylated antibody was assessed. The results of this experiment are shown in Table 6.

TABLE 6

| 2 µg/mL | 1 µg/mL DR5-Fc fusion coat | | |
|---|---|---|---|
| Biotinylated DR5 mAb | 20 µg/mL TRAIL-His | Buffer | 1 µg/mL TRAIL-His coat |
| DR5 mAb 1 | 1.939 | 2.118 | 0.007 |
| DR5 mAb 2 | 2.052 | 2.052 | 0.008 |
| DR5-Fc fusion | — | — | 0.288 |

The results show that the amount of DR5 mAb 1 or DR5 mAb 2 bound to the immobilized DR5-Fc was not affected by the presence of the histidine tagged TRAIL, thus indicating that neither DR5 mAb 1 nor DR5 mAb 2 block the TRAIL ligand binding site of DR5. Additionally, neither antibody was capable of binding to the histidine tagged TRAIL ligand.

B. Example 2: Species Specificity of Anti-Human DR5 Monoclonal Antibodies DR5 mAb 1 and DR5 mAb 2

Figure 5:
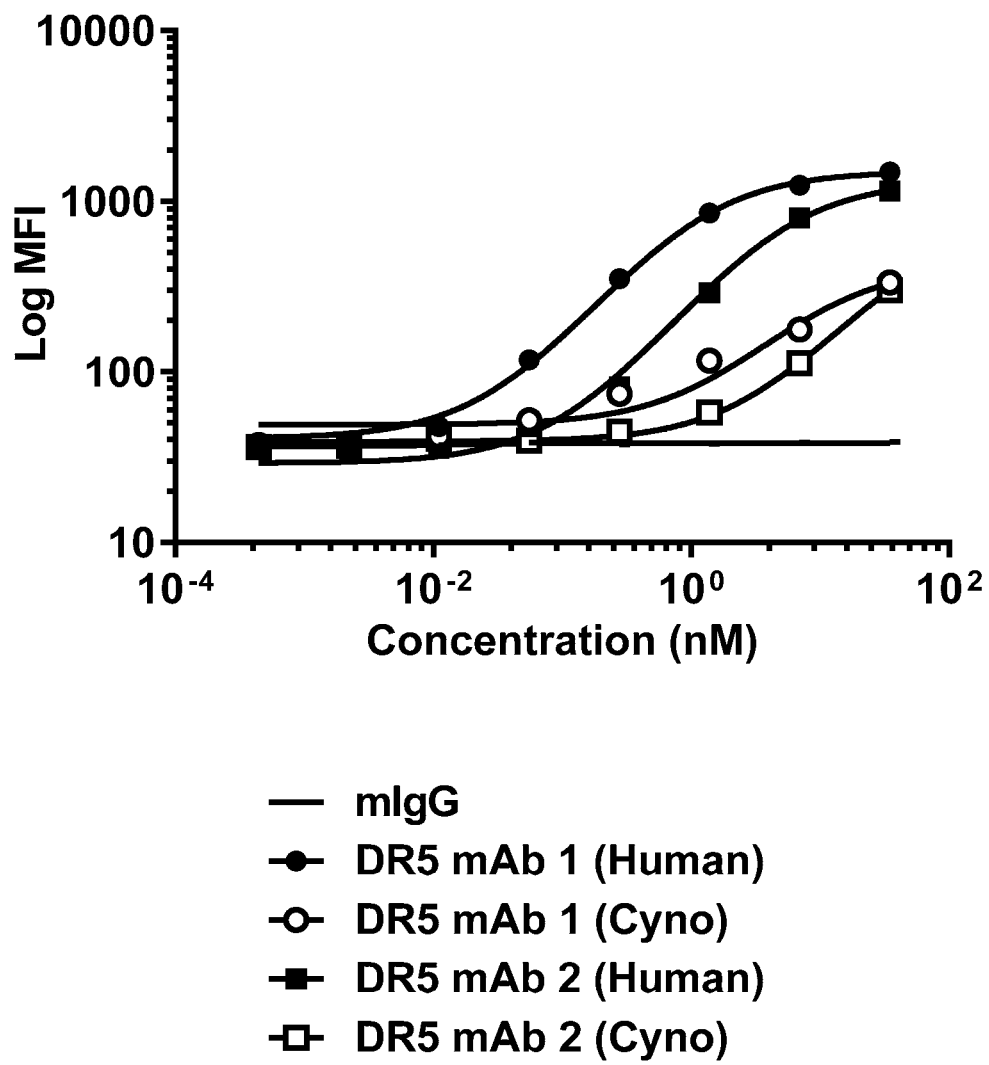
FIG. 5 shows the ability of anti-human DR5 monoclonal antibodies DR5 mAb 1 and DR5 mAb 2 to bind to human DR5 and to the DR5 of cynomolgus monkey.

In order to assess the species specificity of anti-human DR5 monoclonal antibodies DR5 mAb 1 and DR5 mAb 2, the ability of the antibodies to bind to human DR5 was compared with their ability to bind cynomolgus monkey (*Macaca fascicularis*) DR5. The results of this experiment are shown in FIG. 5. The results show that both antibodies are capable of binding to cynomolgus monkey DR5, but that they each exhibit higher binding affinity for human DR5.

Figure 6:
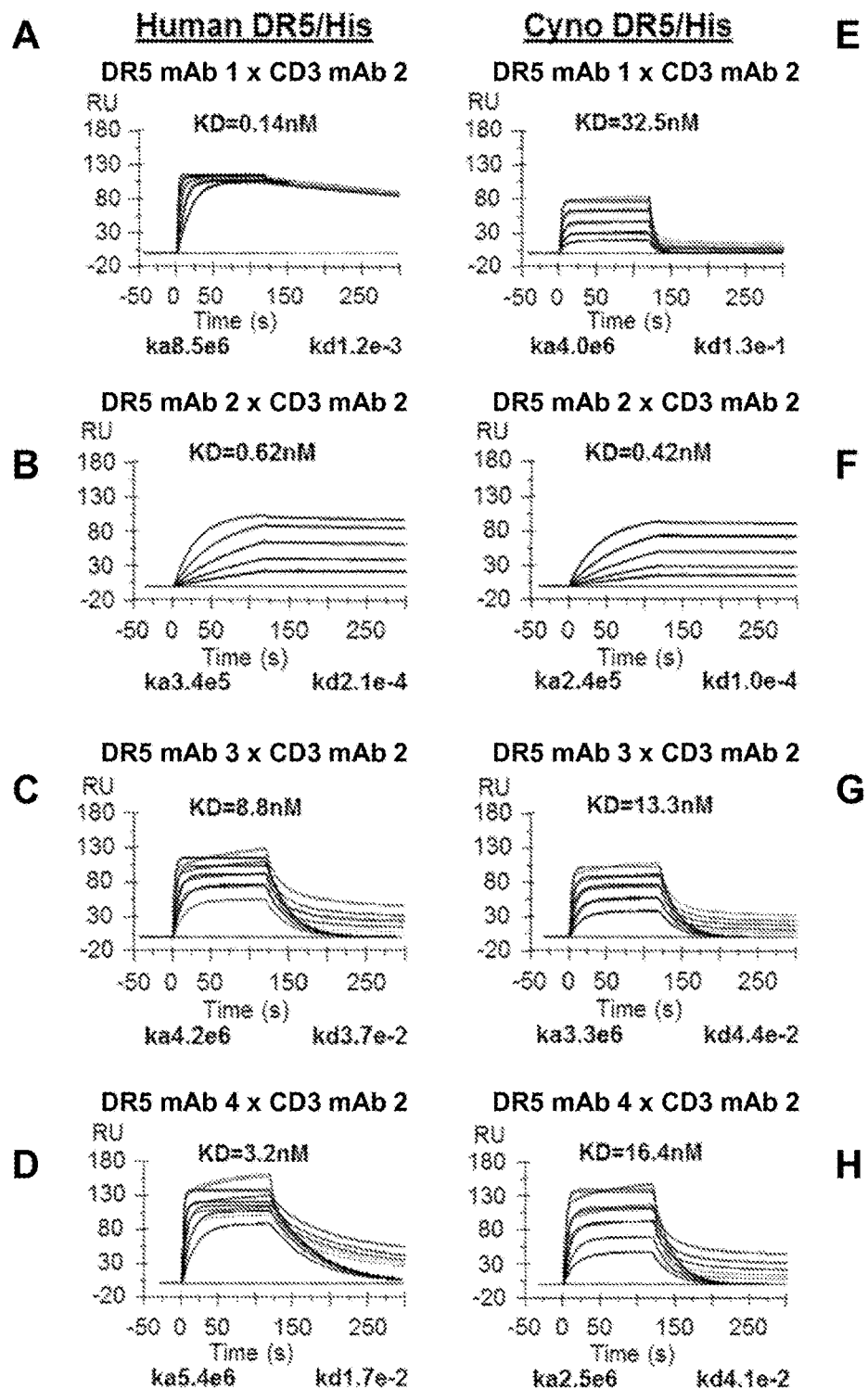
FIG. 6, Panels A-H, show the kinetics of binding of DR5 mAb 1 (Panels A and E), DR5 mAb 2 (Panels B and F), DR5 mAb 3 (Panels C and G) and DR5 mAb 4 (Panels D and H) for human DR5 (Panels A-D) and for cynomolgus monkey DR5 (Panels E-H).

The kinetics of binding was investigated using Biacore Analysis, as shown in FIG. 6. Bispecific DR5×CD3 diabodies were incubated with His-tagged DR5 and the kinetics of binding was determined via Biacore analysis. The diabodies employed were DR5 mAb 1×CD3 mAb 2 (FIG. 6, Panels A and E), DR5 mAb 2×CD3 mAb 2 (FIG. 6, Panels B and F), DR5 mAb 3×CD3 mAb 2 (FIG. 6, Panels C and G), and DR5 mAb 4×CD3 mAb 2 (FIG. 6, Panels D and H). FIG. 6, Panels A-D show the results for human DR5. FIG. 6, Panels E-H show the results for cynomolgus monkey DR5. The calculated ka, kd and KD are presented in Table 7.

TABLE 7

| Anti-DR Antibody | Human | | | Cynomolgus Monkey | | |
|---|---|---|---|---|---|---|
| | ka | kd | KD (nM) | ka | kd | KD (nM) |
| DR mAb 1 | $8.5 \times 10^6$ | $1.2 \times 10^{-3}$ | 0.14 | $4.0 \times 10^6$ | $1.3 \times 10^{-1}$ | 32.5 |
| DR mAb 2 | $3.4 \times 10^5$ | $2.1 \times 10^{-4}$ | 0.62 | $2.4 \times 10^5$ | $1.0 \times 10^{-4}$ | 0.42 |
| DR mAb 3 | $4.2 \times 10^6$ | $3.7 \times 10^{-2}$ | 8.8 | $3.3 \times 10^6$ | $4.4 \times 10^{-2}$ | 13.3 |
| DR mAb 4 | $5.4 \times 10^6$ | $1.7 \times 10^{-2}$ | 3.2 | $2.5 \times 10^6$ | $4.1 \times 10^{-2}$ | 16.4 |

The results demonstrate that DR5 mAb 1 and DR5 mAb 2 exhibit altered kinetics of binding relative to reference antibodies DR5 mAb 3 and DR5 mAb 4.

C. Example 3: Tumor Cell Specificity of Anti-Human DR5 Monoclonal Antibodies DR5 mAb 1 and DR5 mAb 2

The tumor cell specificity of anti-human DR5 monoclonal antibodies DR5 mAb 1 and DR5 mAb 2 were investigated. Normal tissue was contacted with DR5 mAb 1 or with an isotype control (5 µg/mL) and the extent of staining was visualized. As shown in FIG. 7A, Panels A-L, DR5 mAb 1 and the isotype control both failed to label cells of the normal tissue. In contrast, DR5 mAb 1 was found to strongly label cells of colon cancer tissue (FIG. 7B, Panel A) and lung cancer tissue (FIG. 7B, Panel B). In contrast, the isotype control failed to label either tissue (FIG. 7B, Panels C-D). The results presented in FIGS. 7A-7B thus indicate that DR5 mAb 1 was capable of specifically binding to cancer cells.

Similarly, normal tissue was contacted with DR5 mAb 2 (5 µg/mL) and the extent of staining was visualized. As shown in FIG. 8A, Panels A-F, DR5 mAb 2 failed to label cells of the normal tissue. In contrast, DR5 mAb 2 was found to strongly label cells of colon cancer tissue (FIG. 8B, Panel A) and lung cancer tissue (FIG. 8B, Panel C). In contrast, the isotype control failed to label either tissue (FIG. 8B, Panels B and D). The results presented in FIGS. 8A-8B thus indicate that DR5 mAb 2 was capable of specifically binding to cancer cells.

D. Example 4: Tumor Cell Cytotoxicity of DR5 mAb 2×CD3 mAb 2 Diabody

The ability of DR5-Binding Molecules of the present invention to mediate cytotoxicity was assessed by incubating a bispecific DR5×CD3 diabody or a control diabody in the presence of a target tumor cell and peripheral blood mononuclear cells (PBMC) for 24 hours at an effector to target cell ratio of 30:1 or 20:1. The percentage cytotoxicity was determined by measuring the release of lactate dehydrogenase (LDH) into the media by damaged cells.

For this investigation, an exemplary bispecific diabody designated "DR5 mAb 2×CD3 mAb 2" having the structure shown in FIG. 1 was constructed having the VL and VH Domains of anti-human DR5 antibody DR5 mAb 2 and the VL and VH Domains of CD3 mAb 2 (this diabody is monovalent for DR5 and CD3). The diabody was composed of two polypeptide chains. The first polypeptide chain of the diabody comprises amino acid residues 1-107 correspond to the amino acid sequence of the VL Domain of DR5 mAb 2 (SEQ ID NO:13), residues 108-115 correspond to intervening spacer peptide (Linker 1) (SEQ ID NO:33), residues 116-240 correspond to the amino acid sequence of the VH Domain of CD3 mAb 2 having the D65G substitution (SEQ ID NO:112), residues 241-245 correspond to an ASTKG linker (SEQ ID NO:47) and residues 246-273 correspond to a cysteine-containing E-coil Domain (SEQ ID NO:41).

The second polypeptide chain of the DR5 mAb 2×CD3 mAb 2 diabody comprises amino acid residues 1-110 correspond to the amino acid sequence of the VL Domain of CD3 mAb 2 (SEQ ID NO:104), residues 111-118 correspond to the intervening spacer peptide GGGSGGGG (Linker 1) (SEQ ID NO:33), residues 119-237 correspond to the amino acid sequence of the VH Domain of DR5 mAb 2 (SEQ ID NO:18), residues 238-242 correspond to an ASTKG linker (SEQ ID NO:47), and residues 243-270 correspond to a cysteine-containing K-coil Domain (SEQ ID NO:42).

The employed control diabody contained the VL and VH Domains of anti-fluorescein antibody 4-4-20 (respectively, SEQ ID NOs:114 and 115) and the VL and VH Domains of CD3 mAb 2 (respectively, SEQ ID NOs:102 and 108), and was designated as the anti-fluorescein×anti-CD3 control diabody "4-4-20×CD3 mAb 2." The diabody was composed of two polypeptide chains. The first polypeptide chain of the diabody comprises amino acid residues 1-112 corresponding to the VL Domain of anti-fluorescein antibody 4-4-20 (SEQ ID NO:114), residues 113-120 corresponding to the intervening spacer peptide GGGSGGGG (Linker 1) (SEQ ID NO:33), residues 121-245 corresponding to the VH Domain of CD3 mAb 2 (SEQ ID NO:108), residues 246-251 are a cysteine-containing spacer peptide (GGCGGG) (SEQ ID NO:34), and residues 252-280 corresponding to an E-coil Domain (SEQ ID NO:39).

The second polypeptide chain of the 4-4-20×CD3 mAb 2 diabody comprises amino acid residues 1-110 corresponding to the VL Domain of CD3 mAb 2 (SEQ ID NO:114), residues 111-118 corresponding to the intervening spacer peptide GGGSGGGG (Linker 1) (SEQ ID NO:33), residues 119-236 corresponding to the VH Domain of anti-fluorescein antibody 4-4-20 (SEQ ID NO:115), residues 237-242 are a cysteine-containing spacer peptide (GGCGGG) (SEQ ID NO:34), and residues 243-270 corresponding to a K-coil Domain (SEQ ID NO:40).

The results of this investigation are shown in FIGS. 9A-9K. The employed target tumor cells were: 786 0 renal cell adenocarcinoma cells (FIG. 9A), A498 kidney carcinoma cells (FIG. 9B), AsPC1 pancreatic adenocarcinoma cells (FIG. 9C), LNCap androgen-sensitive human prostate adenocarcinoma cells (FIG. 9D), SW48 colorectal adenocarcinoma cells (FIG. 9E), A549 adenocarcinomic human alveolar basal epithelial cells (FIG. 9F), SKMES human lung cancer cells (FIG. 9G), DU145 human prostate cancer cells (FIG. 9H), A375 human malignant melanoma cells (FIG. 9I), SKBR3 human HER2-overexpressing breast carcinoma cells (FIG. 9J) and JIMT human breast carcinoma cells (FIG. 9K). The results indicate that the DR5 mAb 2×CD3 mAb 2 diabody was capable of mediating a potent cytotoxic attack on the cancer cells.

E. Example 5: Unexpected Superiority of DR5 mAb 1 and DR5 mAb 2

The ability of DR5-Binding Molecules DR5 mAb 1 and DR5 mAb 2 of the present invention to mediate cytotoxicity was compared with that of the reference anti-DR5 antibodies: DR5 mAb 3 and DR5 mAb 4. In order to make such a comparison, a bispecific DR5×CD3 diabody having the structure shown in FIG. 1 containing the VL and VH Domains of these anti-DR5 antibodies and the VL and VH Domains of CD3 mAb 2 were prepared essentially as described above. The first and second The prepared diabodies were designated "DR5 mAb 1×CD3 mAb 2"; "DR5 mAb 2×CD3 mAb 2"; "DR5 mAb 3×CD3 mAb 2"; and "DR5 mAb 4×CD3 mAb 2".

Target tumor cells were incubated with one of these diabodies or with the control diabody (4-4-20×CD3 mAb 2) in the presence of peripheral blood mononuclear cells (PBMC) and target tumor cells for 24 hours at an effector to target cell ratio of 20:1. The percentage cytotoxicity was determined by measuring the release of lactate dehydrogenase (LDH) into the media by damaged cells.

The results of this investigation are shown in FIGS. 10A-10F. The employed target tumor cells were: A549 adenocarcinomic human alveolar basal epithelial cells (FIG. 10A), SKMES human lung cancer cells (FIG. 10B), DU145 human prostate cancer cells (FIG. 10C), A375 human malignant melanoma cells (FIG. 10D), SKBR3 human HER2-overexpressing breast carcinoma cells (FIG. 10E), and JIMT human breast carcinoma cells (FIG. 10F). The results indicate that the VL and VH Domains of DR5 mAb 1 and DR5 mAb 2 are significantly and unexpectedly more potent in inducing cytotoxicity than those of the reference DR5 mAbs.

F. Example 6: Dual and Simultaneous Binding of DR5 mAb 1 and DR5 mAb 2

In order to demonstrate the ability of the DR5×CD3 diabodies of the present invention to simultaneously bind to DR5 and to CD3, soluble human DR5 (tagged with histidine) was coated to a support surface. The support was then incubated with DR5 mAb 2×CD3 mAb 2 diabody or one of its humanized derivatives: hDR5 mAb 2 (2.2)×CD3 mAb 2, hDR5 mAb 2 (2.3)×CD3 mAb 2, hDR5 mAb 2 (2.4)×CD3 mAb 2, or hDR5 mAb 2 (2.5)×CD3 mAb 2. Thereafter, CD3, conjugated with biotin, was provided and the amount of CD3 immobilized to the support was measured.

The results of this experiment are shown in FIG. 11. All of the diabodies were found to be capable of simultaneously binding to both DR5 and CD3.

G. Example 7: Cytotoxicity of Humanized Derivatives of DR5 mAb 2

In order to demonstrate the ability of the humanized DR5 mAb 2×CD3 diabodies of the present invention to mediate cytotoxicity, DR5 mAb 2×CD3 mAb 2 diabody or one of its humanized derivatives: hDR5 mAb 2 (2.2)×CD3 mAb 2, hDR5 mAb 2 (2.3)×CD3 mAb 2, hDR5 mAb 2 (2.4)×CD3 mAb 2, or hDR5 mAb 2 (2.5)×CD3 mAb 2 was incubated for 24 hours with pan T cells and target Colo206 colorectal carcinoma cells that had been engineered to express the luciferase (luc) reporter gene (Colo205-Luc cells) (effector to target ratio of 10:1). Cytotoxicity was measured by the increase in luminescence caused by the release of luciferase upon cell lysis.

The results of this investigation are shown in FIG. 12. Each of the DR5 mAb 2×CD3 diabodies was found to be capable of mediating the cytotoxicity of the colorectal carcinoma cells.

H. Example 8: Cytotoxicity of DR5 mAbs Alone, Cross-Linked or in Combination The cytotoxicity of the DR5-Binding Molecules DR5 mAb 1 and DR5 mAb 2 of the present invention was examined in a number of cell lines using a non-radioactive cell proliferation assay. The activity of DR5 mAb 1 and DR5 mAb 2 alone, cross-linked, or in combination was examined.

Cell lines obtained from ATCC were cultured under standard tissue culture conditions. Each cell line was plated at ~2×10$^4$ cells/well (in 96-well plates), and incubated overnight in F12/DMEM media supplemented with 10% FBS. Separate wells (in triplicate) were treated with 0, or 1 µg/ml of DR5 mAb 1 or DR5 mAb 2±10 µg/ml goat anti-mouse IgG Fc antibody (designated "αmFc") added one hour after the DR5 antibody to cross-link the DR5 mAbs, or with 1 µg/ml each DR5 mAb 1 and DR5 mAb 2 (total of 2 µg/ml anti-DR5 antibody) and incubated for two days. Cell viability was determined using Promega CellTiter 96® AQeous Non-Radioactive Cell Proliferation Assay (Cat # G5430) essentially as described in the manufacturer's instructions to assay the amount of soluble formazan produced by cellular reduction of the MTS, which is a measure of the number of viable cells in the culture. Briefly, MTS/PMS regent was added to the wells and the absorbance at 490 nm (referenced at 650 mm) was read in a Molecular Devices ThermoMax microplate reader.

Cell viability of cells treated with the test articles is normalized to the negative control (medium only) which is set to 100% to give the "% Medium Ctrl." The % inhibition=100%−% Medium Ctrl, and is provided in Table 8, where larger values indicate a greater inhibition of growth reflecting the cytotoxicity of the test article. Similar studies were performed over a range of anti-DR5 mAb concentrations from ~10$^{-3}$ nM to ~10$^2$ nM. The data for COLO205 cells is provided in FIG. 13, and are representative of cell lines sensitive to the antibodies of the invention.

The results indicate that neither DR5 mAb 1, nor DR5 mAb 2 alone is capable of inhibiting cell growth in any of cell lines examined, suggesting that neither antibody alone is an agonist. However, each of DR5 mAb 1 and DR5 mAb 2 showed potent cytotoxicity in a number of cell lines when cross-linked by goat anti-mouse IgG Fc antibody. In particular, the growth of COLO205, SW48, SW948, A498 and SKMES cell lines were dramatically reduced when treated with cross-linked DR5 mAbs of the invention.

Surprisingly, the combination of DR5 mAb 1 and DR5 mAb 2 was also seen to significantly inhibit the growth of several cell lines (e.g., COLO205 and SW948) in the absence of cross-linking. Thus, the combination of DR5 mAb 1 and DR5 mAb 2 exhibits an agonist activity not seen with either antibody alone. These data indicate that a combination of anti-DR5 antibodies can be used to agonize DR5 in a therapeutic setting where a single antibody would be ineffective.

TABLE 8

| | % Inhibition (Average) | DR5 mAb 1 | DR5 mAb 1 + αmFc | DR5 mAb 2 | DR5 mAb 2 + αmFc | DR5 mAb 1 + DR5 mAb 2 |
|---|---|---|---|---|---|---|
| Breast | BT474 | 2.26 | 16.13 | 2.84 | 12.84 | 4.98 |
| | MCF7 | 2.47 | 12.59 | 3.98 | 11.2 | 2.96 |
| | MDA-MB-175VII | 1.6 | 10.83 | 1.09 | 10.99 | 2.78 |
| | MDA-MB-231 | 1.79 | 20.78 | 4.47 | 12.59 | 10.14 |
| | MDA-MB-361 | 1.54 | 16.8 | 1.98 | 11.51 | 3.39 |
| | SKBR3 | 1.97 | 23.91 | 2.55 | 10.98 | 6.12 |
| Stomach | NCI-N87 | 1.6 | 16.99 | 0.67 | 10.78 | 1.46 |
| | Hs746T | 2.83 | 11.02 | 1.25 | 10.6 | 4.62 |
| Pancreas | AsPC1 | 1.73 | 18.38 | 0.13 | 10.65 | 2.87 |
| | HPAFII | 2.86 | 12.1 | 2.68 | 10.63 | 2.4 |
| | Hs700T | 1.21 | 20.54 | 0.99 | 16.12 | 7.14 |
| Colon | COLO205 | 3.5 | 89.06 | 3.61 | 69.73 | 29.31 |
| | HT29 | 0.68 | 22.47 | 0.87 | 14.58 | 4.15 |
| | SW48 | 2.65 | 60.95 | 2.44 | 58.12 | 14.63 |
| | SW948 | 3.53 | 79.23 | 1.76 | 71.26 | 50.48 |
| Kidney | 786O | 0.91 | 11.09 | 1.79 | 10.54 | 9.03 |
| | A498 | 0.89 | 78.9 | 1.92 | 50.35 | 10.4 |
| | CaKi2 | 0.55 | 30.09 | 2.64 | 11.08 | 2.5 |
| Lung | A549 | 2.79 | 10.89 | 4.25 | 10.71 | 0.79 |
| | Calu3 | 2.86 | 12.79 | 2.06 | 10.02 | 5.46 |
| | SKMES | 1.75 | 77.59 | 1.28 | 69.93 | 18.67 |
| Ovary | ES2 | 3.31 | 14.83 | 1.88 | 13.7 | 5.92 |
| | SKOV3 | 3.16 | 19.28 | 2.02 | 15.11 | 3.35 |
| Prostate | 22RV1 | 3.03 | 10.92 | 3.89 | 10.8 | 1.64 |
| | DU145 | 1.66 | 18.77 | 2.09 | 15.93 | 2.75 |
| | LNCap | 2.1 | 20.17 | 1.72 | 19.26 | 10.37 |
| | PC3 | 2.79 | 16.1 | 2.19 | 13.84 | 5.16 |

I. Example 9: Cytotoxicity of DR5 mAb 1 and DR5 mAb 2 is Apoptosis

The cytotoxic mechanism of DR5 mAb 1 and DR5 mAb 2 was investigated. Specifically, three different measurements of apoptosis: (i) nucleosome enrichment, (ii) PARP cleavage, and (iii) active caspase 3, were employed on COLO205 cells treated with DR5 mAb 1 or DR5 mAb 2 alone or in the presence of αmFc to cross-link the DR5 mAbs.

For all assays COLO205 cells were plated at ~$10^4$ cells/well (in 96-well plates), and incubated overnight in F12/DMEM media supplemented with 10% FBS. Separate wells were treated (in triplicate) with 0, or 1 µg/ml of DR5 mAb 1 or DR5 mAb 2±10 µg/ml αmFc (added one hour after the DR5 antibody) and incubated for four hours.

Nucleosome enrichment (FIG. 14A) was determined using Roche Cell Death Detection ELISA$^{PLUS}$ assay (Cat#1774425) essentially as described in the manufacturer's instructions to assay. Briefly, after the incubation, cells were lysed in lysis buffer and cleared. The cleared lysates were incubated with anti-histone-biotin/anti-DNA-POD antibody cocktail in a streptavidin-coated ELISA plate, the plate was then washed and ABTS reagent was added and the absorbance at 405 nm (referenced at 490 nm) was read in a Molecular Devices ThermoMax microplate reader. The enrichment factor (a measure of nucleosomes released into the cytoplasm) calculated using the formula: enrichment factor=mU of the sample (dying/dead cells)/mU of the corresponding negative control (cells without antibody treatment), where mU=absorbance $[10^{-3}]$ is plotted in FIG. 14A.

PARP cleavage and Active Caspase 3 (FIGS. 14B and 14C, respectively) were determined using MILLIPLEX MAP Human Late Apoptosis Magnetic Bead 3-Plex Kit-Cell Signaling Multiplex Assay (Cat. #48-670) essentially as described in the manufacturer's instructions to assay. Briefly, after the incubation, Briefly, after the incubation, cells were lysed in lysis buffer and cleared. The cleared lysates were incubated with the reference bead-conjugated primary then washed, and incubated with the respective biotinylated secondary antibodies. The plate was then incubated with streptavidin-PE (SAPE) then washed, assay buffer was added to each well and the plate was read in a Luminex LX-100 system with XY platform. The results are plotted in FIG. 14B (cleaved PARP) and FIG. 14A (Active Caspase 3).

All three measurements of apoptosis are increased in cell cultures treated with cross-linked DR5 mAb 1 or DR5 mAb 2 demonstrating that the cytotoxicity seen is the result of apoptosis.

J. Example 10: Tetravalent DR5-Binding Molecules

To examine the impact of valency on DR5-Binding Molecules, molecule tetravalent for DR5 are generated. In this example E-coil/K-coil-Fc Region-containing diabodies are prepared. Several of these E-coil/K-coil-Fc Region-containing diabodies characterized in the following examples. Each multivalent DR5-Binding Molecule is composed of two pairs of polypeptide chains.

The first polypeptide chain has the general sequence: [VL1 Domain]-[GGGSGGGG]-[VH2 Domain]-[ASTKG]-[EVAACEK(EVAALEK)$_3$]-[LEPKSS]-[DKTHTCPPCP]-Fc Region (Wild-Type or L234A/L235A double mutant) starting from 231 EU numbering), where VL1 is from an anti-DR5 antibody, [GGGSGGGG] is SEQ ID NO:33, VH2 is from an anti-DR5 antibody, [ASTKG] is SEQ ID NO:47, [EVAACEK(EVAALEK)$_3$] is SEQ ID NO:41, [LEPKSS] is SEQ ID NO:49, [DKTHTCPPCP] is SEQ ID NO:48, and the Fc Region is SEQ ID NO:1 (wild-type) or SEQ ID NO:102 (L234A/L235L mutant) and optionally lacks the C-terminal amino acid residue.

The second polypeptide chain has the general sequence: [VL2 Domain]-[GGGSGGGG]-[VH1 Domain]-[ASTKG]-[KVAACKE(KVAALKE)$_3$], where VL2 is from an anti-DR5 antibody, [GGGSGGGG] is SEQ ID NO:33, VH1 is from an anti-DR5 antibody, [ASTKG] is SEQ ID NO:47, [KVAACKE(KVAALKE)₃] is SEQ ID NO:42.

The chains assemble as shown in FIG. 4B. The VL1 Domain of the first polypeptide chain interacts with the VH1 Domain of the second polypeptide chain to form a first functional antigen-binding site that is specific for DR5. Likewise, the VL2 Domain of the second polypeptide chain interacts with the VH2 Domain of the first polypeptide chain in order to form a second functional antigen-binding site that is also specific for DR5. Thus, the selection of the VL and VH Domains of the first and second polypeptide chains is coordinated, such that the two polypeptide chains of the diabody collectively comprise VL and VH Domains capable of binding to at least one epitope of DR5. Molecules having all the same VL and VH Domains (e.g., all VL and VH Domains are from DR5 mAb 1 or from DR5 mAb 2) are monospecific (i.e., bind a single epitope of DR5) and tetravalent for DR5. Molecules having VL and VH Domains of DR5 mAb 1 and DR5 mAb 2 are bispecific (i.e., binds two different epitopes of DR5) but are still tetravalent for DR5. Exemplary E-coil/K-coil-Fc Region-containing diabodies comprising the VL and VH Domains of DR5 mAb 1 and DR5 mAb 2 are provided. However, it will be understood that E-coil/K-coil-Fc Region-containing diabodies which are tetravalent for DR5 may be prepared using the VL and VH Domains of any anti-DR5 antibody. Similarly, alternative constructs such as those disclosed above comprising the VL and VH Domains of one or more anti-DR5 antibody such as those disclosed herein may be prepared.

The VL, VH and Fc Region, as well as the SEQ ID NOs: (polypeptide), of the first and second chains for each E-coil/K-coil-Fc Region-containing diabody are summarized in Table 9. Also provided is the unique designator for the assembled molecule. The complete sequence for the polypeptide chains and the polynucleotides encoding the same is provided above." While several of the molecules provided in Table 9 are bispecific, that is they bind two different DR5 epitopes, all are tetravalent with respect to DR5.

TABLE 9

| Designation | Portion | First Chain | Second Chain |
|---|---|---|---|
| Molecules Binding Two Different DR5 Epitopes | | | |
| DR5 mAb 1 × DR5 mAb 2 Fc diabody | VL | DR5 mAb 1 [SEQ ID NO: 3] | DR5 mAb 2 [SEQ ID NO: 13] |
| | VH | DR5 mAb 2 [SEQ ID NO: 18] | DR5 mAb 1 [SEQ ID NO: 8] |
| | Fc | Wild-Type [SEQ ID NO: 1] | n/a |
| | Polypeptide Sequence | [SEQ ID NO: 116] | [SEQ ID NO: 118] |
| DR5 mAb 1 × DR5 mAb 2 Fc diabody (AA) | VL | DR5 mAb 1 [SEQ ID NO: 3] | DR5 mAb 2 [SEQ ID NO: 13] |
| | VH | DR5 mAb 2 [SEQ ID NO: 18] | DR5 mAb 1 [SEQ ID NO: 8] |
| | Fc | L234A/L235A [SEQ ID NO: 102] | n/a |
| | Polypeptide Sequence | [SEQ ID NO: 120] | [SEQ ID NO: 118] |
| DR5 mAb 2 × DR5 mAb 1 Fc diabody | VL | DR5 mAb 2 [SEQ ID NO: 13] | DR5 mAb 1 [SEQ ID NO: 3] |
| | VH | DR5 mAb 1 [SEQ ID NO: 8] | DR5 mAb 2 [SEQ ID NO: 18] |
| | Fc | Wild-Type [SEQ ID NO: 1] | n/a |
| | Polypeptide Sequence | [SEQ ID NO: 122] | [SEQ ID NO: 124] |

TABLE 9-continued

| Designation | Portion | First Chain | Second Chain |
|---|---|---|---|
| DR5 mAb 2 × DR5 mAb 1 Fc diabody (AA) | VL | DR5 mAb 2 [SEQ ID NO: 13] | DR5 mAb 1 [SEQ ID NO: 3] |
| | VH | DR5 mAb 1 [SEQ ID NO: 8] | DR5 mAb 2 [SEQ ID NO: 18] |
| | Fc | L234A/L235A [SEQ ID NO: 102] | n/a |
| | SEQ ID NOs: | [SEQ ID NO: 126] | [SEQ ID NO: 124] |
| Molecules Binding One DR5 Epitope | | | |
| DR5 mAb 1 × DR5 mAb 1 Fc diabody | VL | DR5 mAb 1 [SEQ ID NO: 3] | DR5 mAb 1 [SEQ ID NO: 3] |
| | VH | DR5 mAb 1 [SEQ ID NO: 8] | DR5 mAb 1 [SEQ ID NO: 8] |
| | Fc | Wild-Type [SEQ ID NO: 1] | n/a |
| | Polypeptide Sequence | [SEQ ID NO: 128] | [SEQ ID NO: 130] |
| DR5 mAb 1 × DR5 mAb 1 Fc diabody (AA) | VL | DR5 mAb 1 [SEQ ID NO: 3] | DR5 mAb 1 [SEQ ID NO: 3] |
| | VH | DR5 mAb 1 [SEQ ID NO: 8] | DR5 mAb 1 [SEQ ID NO: 8] |
| | Fc | L234A/L235A [SEQ ID NO: 102] | n/a |
| | Polypeptide Sequence | [SEQ ID NO: 132] | [SEQ ID NO: 130] |
| DR5 mAb 2 × DR5 mAb 2 Fc diabody | VL | DR5 mAb 2 [SEQ ID NO: 13] | DR5 mAb 2 [SEQ ID NO: 13] |
| | VH | DR5 mAb 2 [SEQ ID NO: 18] | DR5 mAb 2 [SEQ ID NO: 18] |
| | Fc | Wild-Type [SEQ ID NO: 1] | n/a |
| | Polypeptide Sequence | [SEQ ID NO: 134] | [SEQ ID NO: 136] |
| DR5 mAb 2 × DR5 mAb 2 Fc diabody (AA) | VL | DR5 mAb 2 [SEQ ID NO: 13] | DR5 mAb 2 [SEQ ID NO: 13] |
| | VH | DR5 mAb 2 [SEQ ID NO: 18] | DR5 mAb 2 [SEQ ID NO: 18] |
| | Fc | L234A/L235A [SEQ ID NO: 102] | n/a |
| | Polypeptide Sequence | [SEQ ID NO: 138] | [SEQ ID NO: 136] |
| hDR5 mAb 2.2 × hDR5 mAb 2.2 Fc diabody | VL | hDR5 mAb 2 VL-2 [SEQ ID NO: 23] | hDR5 mAb 2 VL-2 [SEQ ID NO: 23] |
| | VH | hDR5 mAb 2 VH-2 [SEQ ID NO: 31] | hDR5 mAb 2 VH-2 [SEQ ID NO: 31] |
| | Fc | Wild-Type [SEQ ID NO: 1] | n/a |
| | Polypeptide Sequence | [SEQ ID NO: 140] | [SEQ ID NO: 142] |
| hDR5 mAb 2.2 × hDR5 mAb 2.2 Fc diabody (AA) | VL | hDR5 mAb 2 VL-2 [SEQ ID NO: 23] | hDR5 mAb 2 VL-2 [SEQ ID NO: 23] |
| | VH | hDR5 mAb 2 VH-2 [SEQ ID NO: 31] | hDR5 mAb 2 VH-2 [SEQ ID NO: 31] |
| | Fc | L234A/L235A [SEQ ID NO: 102] | n/a |
| | Polypeptide Sequence | [SEQ ID NO: 144] | [SEQ ID NO: 142] |
| hDR5 mAb 2.3 × hDR5 mAb 2.3 Fc diabody | VL | hDR5 mAb 2 VL-3 [SEQ ID NO: 25] | hDR5 mAb 2 VL-3 [SEQ ID NO: 25] |
| | VH | hDR5 mAb 2 VH-2 [SEQ ID NO: 31] | hDR5 mAb 2 VH-2 [SEQ ID NO: 31] |
| | Fc | Wild-Type [SEQ ID NO: 1] | n/a |
| | Polypeptide Sequence | [SEQ ID NO: 146] | [SEQ ID NO: 148] |
| hDR5 mAb 2.3 × hDR5 mAb 2.3 Fc diabody (AA) | VL | hDR5 mAb 2 VL-3 [SEQ ID NO: 25] | hDR5 mAb 2 VL-3 [SEQ ID NO: 25] |
| | VH | hDR5 mAb 2 VH-2 [SEQ ID NO: 31] | hDR5 mAb 2 VH-2 [SEQ ID NO: 31] |
| | Fc | L234A/L235A | n/a |

TABLE 9-continued

| Designation | Portion | First Chain | Second Chain |
|---|---|---|---|
| | Poly-peptide Sequence | [SEQ ID NO: 102]<br>[SEQ ID NO: 150] | [SEQ ID NO: 148] |
| hDR5 mAb 2.4 ×<br>hDR5 mAb 2.4<br>Fc diabody | VL<br>VH<br>Fc | hDR5 mAb 2 VL-4<br>[SEQ ID NO: 27]<br>hDR5 mAb 2 VH-2<br>[SEQ ID NO: 31]<br>Wild-Type<br>[SEQ ID NO: 1] | hDR5 mAb 2 VL-4<br>[SEQ ID NO: 27]<br>hDR5 mAb 2 VH-2<br>[SEQ ID NO: 31]<br>n/a |
| | Poly-peptide Sequence | [SEQ ID NO: 152] | [SEQ ID NO: 154] |
| hDR5 mAb 2.4 ×<br>hDR5 mAb 2.4<br>Fc diabody (AA) | VL<br>VH<br>Fc | hDR5 mAb 2 VL-4<br>[SEQ ID NO: 27]<br>hDR5 mAb 2 VH-2<br>[SEQ ID NO: 31]<br>L234A/L235A<br>[SEQ ID NO: 102] | hDR5 mAb 2 VL-4<br>[SEQ ID NO: 27]<br>hDR5 mAb 2 VH-2<br>[SEQ ID NO: 31]<br>n/a |
| | Poly-peptide Sequence | [SEQ ID NO: 156] | [SEQ ID NO: 154] |
| hDR5 mAb 2.5 ×<br>hDR5 mAb 2.5<br>Fc diabody | VL<br>VH<br>Fc | hDR5 mAb 2 VL-5<br>[SEQ ID NO: 29]<br>hDR5 mAb 2 VH-2<br>[SEQ ID NO: 31]<br>Wild-Type<br>[SEQ ID NO: 1] | hDR5 mAb 2 VL-5<br>[SEQ ID NO: 29]<br>hDR5 mAb 2 VH-2<br>[SEQ ID NO: 31]<br>n/a |
| | Poly-peptide Sequence | [SEQ ID NO: 158] | [SEQ ID NO: 160] |
| hDR5 mAb 2.5 ×<br>hDR5 mAb 2.5<br>Fc diabody (AA) | VL<br>VH<br>Fc | hDR5 mAb 2 VL-5<br>[SEQ ID NO: 29]<br>hDR5 mAb 2 VH-2<br>[SEQ ID NO: 31]<br>L234A/L235A<br>[SEQ ID NO: 102] | hDR5 mAb 2 VL-5<br>[SEQ ID NO: 29]<br>hDR5 mAb 2 VH-2<br>[SEQ ID NO: 31]<br>n/a |
| | Poly-peptide Sequence | [SEQ ID NO: 162] | [SEQ ID NO: 160] |

K. Example 11: Tumor Cell Specificity of a Bispecific Tetravalent DR5-Binding Molecules Containing DR5 mAb 1 and DR5 mAb 2

The tumor cell specificity of a representative bispecific tetravalent DR5-Binding Molecule (DR5 mAb 2×DR5 mAb 1 Fc diabody) was investigated. Normal tissue was contacted with labeled DR5 mAb 2×DR5 mAb 1 Fc diabody or with a labeled control diabody (4-4-20×CD3 mAb 2, described in Example 4) at 0.625 µg/mL and the extent of staining was visualized. As shown in FIG. 15A-B, DR5 mAb 2×DR5 mAb 1 Fc diabody and the control diabody both failed to label cells of the normal tissue. Similar results were seen in additional samples of normal tissues, including liver as shown in FIG. 15B. In contrast, DR5 mAb 2×DR5 mAb 1 Fc diabody was found to strongly label cells of breast cancer tissue (FIG. 16, Panel A), colon cancer tissue (FIG. 16, Panel B), lung cancer tissue (FIG. 16, Panel C) and prostate cancer tissue (FIG. 16, Panel D). In contrast, the control diabody failed to label either tissue (FIG. 16, Panels E-H). A summary of the histology observations is provided in Table 10. The results presented in FIGS. 15A-15B, 16, and Table 10, thus indicate that a tetravalent DR5-Binding Molecule (bispecific for two epitopes of DR5) was capable of specifically binding to cancer cells.

TABLE 10

| Tissue/Cells | DR5 mAb 2 × DR5 mAb 1 Fc diabody 0.625 ug/mL | Control DART 0.625 ug/mL |
|---|---|---|
| Colon (6N) | — | ±/— |
| Lung (6N) | Macrophage 2+ (c) rare; endo 2+ (c) very rare; others (—) | — |
| Liver (6N) | — | — |
| Kidney (6N) | — | — |
| Heart (6N) | — | — |
| Pancreas (6N) | Secreted acinar epi ± (c) very rare | ±/— |
| COLO205 | 4+ (m) | — |
| CHO | — | — |
| MDA-MB-175VII | 1+ | — |
| MDA-MD-231 | 3+ (c, m) | — |
| Liver (3N) | — | — |
| Lung | Endo 1+ (c) very rare; others (—) | — |
| Lung | Macrophage 3+ (c, m) occasional; possible type II pneumocytes 2-3+ (c, m) rare | — |
| Lung | Macrophage 3+ (c) occasional mixed with type II pneumocytes | — |

L. Example 12: Cytotoxicity of Tetravalent DR5-Binding Molecules

The cytotoxicity of tetravalent DR5-Binding Molecules of the present invention was investigated. The activity of two exemplary bispecific tetravalent E-coil/K-coil-Fc Region-containing diabodies (DR5 mAb 1×DR5 mAb 2 Fc diabody; and DR5 mAb 2×DR5 mAb 1 Fc diabody), and four exemplary monospecific tetravalent E-coil/K-coil-Fc Region-containing diabodies (DR5 mAb 1×DR5 mAb 1 Fc diabody; DR5 mAb 1×DR5 mAb 1 Fc diabody (AA); DR5 mAb 2×DR5 mAb 2 Fc diabody; and DR5 mAb 2×DR5 mAb 2 Fc diabody (AA), where "AA" refers to the L234A/L235A mutation), on a number of cell lines was examined using the non-radioactive cell proliferation assay essentially as described above except that no cross-linking antibody was added to any of the test samples. His-tagged TRAIL (R&D systems) was used as a positive control.

Cell viability of cells treated with the test articles is normalized to the negative control (medium only) which is set to 100% to give the "% Medium Ctrl." The % inhibition=100%–% Medium Ctrl, and is provided in Table 11, where larger values indicate a greater inhibition of growth reflecting the cytotoxicity of the test article. Similar studies were performed over a range of anti-DR5 mAb concentrations from ~$10^{-3}$ nM to ~$10^2$ nM. FIG. 17 shows the data for several responsive cell lines, COLO205 (FIG. 17A), A498 (FIG. 17B), and SKMES (FIG. 17C).

TABLE 11

| % Inhibition (Average) | | DR5 mAb 1 × DR5 mAb 2 Fc diabody | DR5 mAb 2 × DR5 mAb 1 Fc diabody |
|---|---|---|---|
| Breast | BT474 | 3.96 | 2.62 |
| | MCF7 | 6.03 | 6.27 |
| | MDA-MB-175VII | 3.36 | 2.96 |
| | MDA-MB-231 | 15.24 | 14.03 |
| | MDA-MB-361 | 5.35 | 3.61 |
| | SKBR3 | 13.07 | 8.47 |
| Stomach | NCI-N87 | 10.62 | 5.01 |
| | Hs746T | 5.94 | 5.09 |
| Pancreas | AsPC1 | 15.01 | 12.7 |
| | HPAFII | 10.05 | 10.1 |
| | Hs700T | 17.89 | 13.38 |

TABLE 11-continued

| % Inhibition (Average) | | DR5 mAb 1 ×<br>DR5 mAb 2 Fc<br>diabody | DR5 mAb 2 ×<br>DR5 mAb 1 Fc<br>diabody |
|---|---|---|---|
| Colon | COLO205 | 88.89 | 88.53 |
|  | HT29 | 16.2 | 11.02 |
|  | SW48 | 39.81 | 33.53 |
|  | SW948 | 78.33 | 77.91 |
| Kidney | 786O | 5.62 | 5.13 |
|  | A498 | 81.47 | 74.27 |
|  | CaKi2 | 36.9 | 31.66 |
| Lung | A549 | 2.63 | 2.8 |
|  | Calu3 | 15.18 | 18.01 |
|  | SKMES | 75.6 | 68.97 |
| Ovary | ES2 | 8.44 | 12.25 |
|  | SKOV3 | 13.02 | 9.95 |
| Prostate | 22RV1 | 1.83 | 2.95 |
|  | DU145 | 12.14 | 12.34 |
|  | LNCap | 11.82 | 12.71 |
|  | PC3 | 10.54 | 10.79 |

The results indicate that all the tetravalent DR5-Binding Molecules have potent cytotoxicity in a number of cell lines. Indeed, all the tetravalent DR5-Binding Molecules were more potent than TRAIL itself. In particular, the growth of COLO205, SW48, SW948, A498, CaKi2 and SKMES were dramatically reduced when treated with tetravalent DR5-Binding Molecules of the invention. Tetravalent DR5-Binding Molecules possessing the L234A/L235A Fc Region exhibited similar, or slightly higher cytotoxicity as the counter part molecules possessing a wild-type Fc Region, indicating that Fc Regions having reduced binding to FcγRs and/or reduced effector function can be incorporated into tetravalent DR5-Binding Molecules where binding to FcγRs and/or effector function is not required and/or desirable.

M. Example 13: Tetravalent DR5-Binding Molecules Induce Apoptosis

The ability of tetravalent DR5-Binding Molecules of the present invention to induce apoptosis was investigated. The activity of two exemplary bispecific tetravalent E-coil/K-coil-Fc Region-containing diabodies (DR5 mAb 1×DR5 mAb 2 Fc diabody; and DR5 mAb 2×DR5 mAb 1 Fc diabody), and two exemplary monospecific tetravalent E-coil/K-coil-Fc Region-containing diabodies (DR5 mAb 1×DR5 mAb 1 Fc diabody; and DR5 mAb 2×DR5 mAb 2 Fc diabody), was examined in the COLO205, A496, SKMES, LNCap, MDA-MB-231 and Hs700T cell lines, This investigation was performed using the nucleosome enrichment assay essentially as described above except that no cross-linking antibody was added to the test samples. His-tagged TRAIL (R&D systems) was used as a positive control. The enrichment factor (calculated as described above) is plotted in FIG. 18.

The results indicate that all the tetravalent DR5-Binding Molecules are potent inducers of Apoptosis. Indeed, all the tetravalent DR5-Binding Molecules had an enrichment factor similar to that seen for the positive control in the same cell line.

N. Example 14: Cytotoxicity of Tetravalent DR5-Binding Molecules

The cytotoxicity of multivalent DR5-Binding Molecules of the present invention was compared to that of the previously reported antibodies DR5 mAb 8 (KMTR2) and DR5 mAb 4 (conatumumab) in a cell proliferation assay. The activity of one exemplary bispecific tetravalent E-coil/K-coil-Fc Region-containing diabody (DR5 mAb 1×DR5 mAb 2 Fc diabody (AA)); two exemplary monospecific tetravalent E-coil/K-coil-Fc Region-containing diabodies (DR5 mAb 1×DR5 mAb 1 Fc diabody (AA); and DR5 mAb 2×DR5 mAb 2 Fc diabody (AA)); the anti-DR5 antibody DR5 mAb 8 (AA) (KMTR2); and the anti-DR5 antibody DR5 mAb 4 (AA) (conatumumab) with and without cross-linking (where "AA" refers to the L234A/L235A mutation) on COLO205 was examined over a range of concentrations from approximately $10^{-3}$ nM to approximately $10^2$ nM, using the non-radioactive cell proliferation assay essentially as described above except that cross-linking antibody was added only to one test sample of DR5 mAb 4. His-tagged TRAIL (R&D systems) was used as a positive control.

Cell viability of cells treated with the test articles is normalized to the negative control (medium only) which is set to 100% to give the "% Medium Ctrl." The % inhibition=100%−% Medium Ctrl is plotted in FIG. 19.

The results indicate that all the tetravalent DR5-Binding Molecules tested have potent cytotoxicity that is independent of cross-linking and are more potent than the previously described anti-DR5 antibodies DR5 mAb 8 (KMTR2); and DR5 mAb 4 (conatumumab). In particular, the tetravalent DR5-Binding Molecules were significantly more potent than even cross-linked DR5 mAb 4.

O. Example 15: Cytotoxicity of Tetravalent DR5-Binding Molecules On Cancer Stem Cell-Like (CSCL) Cells The cytotoxicity of multivalent DR5-Binding Molecules of the present invention on cancer stem cell-like (CSLC) cells was investigated. RECA0201 are CSCL cells isolated from a moderately differentiated rectal adenocarcinoma (mutated APC and KRAS; CD44hi, CD133+ and A33+). RECA0201 cells are tumorigenic and capable to recapitulate tumor morphology and multi-lineage differentiation in vivo or organoid formation in vitro.

The cytotoxic activity of one exemplary bispecific tetravalent E-coil/K-coil-Fc Region-containing diabody (DR5 mAb 1×DR5 mAb 2 Fc diabody (AA)); two exemplary monospecific tetravalent E-coil/K-coil-Fc Region-containing diabodies (DR5 mAb 1×DR5 mAb 1 Fc diabody (AA); and DR5 mAb 2×DR5 mAb 2 Fc diabody (AA)); two anti-DR5 antibodies (DR5 mAb 8 (AA) (KMTR2); and DR5 mAb 4 (AA) (conatumumab), (where "AA" refers to the L234A/L235A mutation) on RECA0201 cells was examined over a range of concentrations, using a non-radioactive cytotoxicity assay. Briefly, 20,000 cells RECA0201 colon cancer CSCL cells stably transfected with constitutively expressed luciferase are plated per well and exposed to indicated concentrations of test article. After 48 hours the level of cell viability is determined through measurement of luciferase using Promega STEADY GLO® substrate reagent on a Victor Plate reader, essentially as described by the manufacturer. The results are plotted in FIG. 20.

As shown in FIG. 20, the tetravalent DR5-Binding Molecules displayed potent cytotoxicity on CSCL RECA0201 cells. Indeed, the results indicate that all the tetravalent DR5-Binding Molecules are more potent than the previously described anti-DR5 antibodies DR5 mAb 8 (KMTR2); and DR5 mAb 4 (conatumumab), and are more potent than TRAIL itself.

P. Example 16: Inhibition of Tumor Growth by a Tetravalent DR5-Binding Molecule in Mice Implanted with COLO205 Tumor Cells The anti-tumor activity of an exemplary monospecific tetravalent E-coil/K-coil-Fe Region-containing diabody (DR5 mAb 1×DR5 mAb 1 Fc diabody (AA)); and two anti-DR5 antibodies (DR5 mAb 8 (AA) (KMTR2), and DR5 mAb 4 (AA) (conatumumab)) (where "AA" refers to the L234A/L235A mutation) were evaluated in a xenograft tumor model. Briefly, female hCD16A FOX N1 mice (n=7/group) were implanted subcutaneously (SC) with 5 million COLO205 cells suspended in 200 µL of Ham's F12 medium mixed 1:1 with Matrigel on Day 0. The tumors were measured every 3-4 days with calipers. On Study Day 3, the mice were randomized based on tumor size and treated twice a week (intravenous (IV) injection) with the indicated dose levels of test article or vehicle (sterile saline containing 0.5% bovine serum albumin). Tumor volume was monitored over the course of the study and is plotted in FIG. 21 as a group mean±SEM. The tetravalent DR5-Binding Molecule was seen to dramatically inhibit tumor growth over the course of the study and the tumors were seen to regress in the 0.5 and 0.05 mg/kg treatment groups.

Q. Histone deacetylase Inhibitors Synergizes with Tetravalent DR5-Binding Molecules Histone deacetylase (HDAC) inhibitors, such as vorinostat, have been reported to sensitize tumor cells to apoptosis induced via the DR5. The cytotoxic activity of DR5 mAb 1, DR5 mAb 2, and several tetravalent DR5-Binding Molecules in combination with the HDAC inhibitor vorinostat was investigated using a non-radioactive cell proliferation assay.

The activity of DR5 mAb 1, DR5 mAb 2, two exemplary bispecific tetravalent E-coil/K-coil-Fc Region-containing diabodies (DR5 mAb 1×DR5 mAb 2 Fc diabody; and DR5 mAb 2×DR5 mAb 1 Fc diabody), and two exemplary monospecific tetravalent E-coil/K-coil-Fc Region-containing diabodies (DR5 mAb 1×DR5 mAb 1 Fc diabody; and DR5 mAb 2×DR5 mAb 2 Fc diabody) was examined in these studies. His-tagged TRAIL (R&D systems) was used as a positive control.

For the first study COLO205 cells were plated at $2\times10^4$ cells/well (in 96-well plates), and incubated overnight in F12/DMEM media supplemented with 10% FBS. Separate wells (in triplicate) were treated with 0, or 1 µg/ml of DR5 mAb 1 or DR5 mAb 2, 10 ng/ml tetravalent DR5-Binding Molecule (100 fold less then used in the previous cytotoxicity study), or His-tagged TRAIL±0.1 or 1 µM vorinostat and incubated for one day. Cell viability was determined using Promega CELLTITER-GLO® Luminescent Cell Viability Assay (Cat # G5430) essentially as described in the manufacturer's instructions to assay the amount of ATP present, which is a measure of the number of viable cells in the culture. Briefly, an CELLTITER-GLO® Reagent was added to the wells and mixed for two minutes to induce lysis and the luminescence was read in a in PerkinElmer EnVision multilabel plate reader.

Cell viability of cells treated with the test articles is is normalized to the corresponding negative control (medium±vorinostat) which is set to 100% and reported in Table 12 as % of control for each test agent alone or % control for each test agent in combination with vorinostat. % of control values less than 100% indicate a reduction in viability and reflect the cytotoxicity of the test article alone or in combination with vorinostat.

TABLE 12

| COLO205 | Vorinostat | | |
|---|---|---|---|
| Average % Ctrl | 0 µM‡ | 0.1 µM§ | 1 µM§ |
| 10% FBS | 100% | 100% | 100% |
| DR5 mAb 1 × DR5 mAb 2 Fc diabody | 64.4% | 52.6% | 44.8% |
| DR5 mAb 2 × DR5 mAb 1 Fc diabody | 84.1% | 70.7% | 48.9% |
| DR5 mAb 1 × DR5 mAb 1 Fc diabody | 64.2% | 49.7% | 42.9% |
| DR5 mAb 2 × DR5 mAb 2 Fc diabody | 75.0% | 50.8% | 45.6% |
| DR5 mAb 1 | 96.8% | 96.4% | 93.3% |
| DR5 mAb 2 | 96.4% | 96.5% | 95.5% |
| R&D TRAIL/His | 68.7% | 54.1% | 44.8% |

‡% Medium Ctrl (10% FBS)
§% Medium Ctrl (1/10 µM vorinostat)

The Net Gain (Average % Growth Inhibition)=% Medium Ctrl (10% FBS)−% Medium Ctrl (1/10 µM vorinostat), and represents increased cytotoxicity of the test article in combination with vorinostat over cells treated with vorinostat alone. The net gain for the first study is provided in Table 13.

TABLE 13

| COLO205 | Vorinostat | |
|---|---|---|
| Net Gain (Average % Growth Inhibition) | 0.1 µM | 1 µM |
| 10% FBS | 0 | 0 |
| DR5 mAb 1 × DR5 mAb 2 Fc diabody | 12 | 20 |
| DR5 mAb 2 × DR5 mAb 1 Fc diabody | 13 | 35 |
| DR5 mAb 1 × DR5 mAb 1 Fc diabody | 15 | 21 |
| DR5 mAb 2 × DR5 mAb 2 Fc diabody | 24 | 29 |
| DR5 mAb 1 | 0 | 3 |
| DR5 mAb 2 | 0 | 1 |
| R&D TRAIL/His | 15 | 24 |

The results indicate that the HDAC inhibitor vorinostat synergizes with low dose tetravalent DR5-Binding Molecules to enhance their cytotoxicity in cells sensitive to tetravalent DR5-Binding Molecules. However, vorinostat did not synergize with non-cross-linked antibodies DR5 mAb 1 and DR5 mAb 2.

For the second study DR5 mAb 1, DR5 mAb 2, and several tetravalent DR5-Binding Molecules in combination with vorinostat were tested on a number of cell lines including several previously shown to be insensitive to multivalent DR5-Binding Molecules. The assay was perform essentially as described above except that the cells were treated with 0, or 1 µg/ml of DR5 mAb 1 or DR5 mAb 2 or tetravalent DR5-Binding Molecule, or His-tagged TRAIL±1 or 10 µM vorinostat.

For this study the Net Gain (calculated as described above) in growth inhibition is reported in Table 14 (treatment in combination with 10 µM vorinostat) and Table 15 (treatment in combination with 1 µM vorinostat).

TABLE 14

(10 μM Vorinostat)

| Net Gain (Average % Growth Inhibition) | | DR5 mAb 1 × DR5 mAb 2 Fc DART | DR5 mAb 2 × DR5 mAb 1 Fc DART | DR5 mAb 1 × DR5 mAb 1 Fc DART | DR5 mAb 2 × DR5 mAb 2 Fc DART | DR5 mAb 1 | DR5 mAb 2 | R&D TRAIL/ His |
|---|---|---|---|---|---|---|---|---|
| Breast | BT474 | 75.26 | 64.18 | 71.80 | 54.94 | 2.15 | 2.23 | 50.24 |
|  | MCF7 | 4.96 | 4.35 | 4.00 | 8.76 | 4.55 | 5.00 | 0.79 |
|  | MDA-MB-361 | 83.21 | 80.65 | 87.06 | 62.67 | 5.11 | 5.11 | 64.85 |
| Stomach | Hs746T | 38.78 | 25.69 | 49.15 | 22.05 | 0.20 | 0.20 | 31.81 |
| Pancreas | HPAFII | 49.19 | 45.01 | 55.42 | 37.51 | 1.75 | 2.86 | 46.71 |
| Lung | A549 | 36.34 | 34.95 | 30.24 | 20.29 | 6.48 | 6.48 | 26.71 |
| Ovary | ES2 | 87.60 | 89.61 | 88.11 | 74.12 | 4.17 | 4.17 | 79.12 |
| Prostate | 22RV1 | 5.36 | 6.32 | 6.81 | 7.45 | 7.49 | 7.49 | 8.91 |
|  | DU145 | 1.32 | 3.43 | 2.92 | 3.88 | 4.18 | 4.18 | 4.57 |
|  | LNCap | 20.41 | 16.63 | 20.96 | 14.37 | 3.81 | 4.49 | 28.73 |

TABLE 15

(1 μM Vorinostat)

| Net Gain (Average % Growth Inhibition) | | DR5 mAb 1 × DR5 mAb 2 Fc DART | DR5 mAb 2 × DR5 mAb 1 Fc DART | DR5 mAb 1 × DR5 mAb 1 Fc DART | DR5 mAb 2 × DR5 mAb 2 Fc DART | DR5 mAb 1 | DR5 mAb 2 | R&D TRAIL/ His |
|---|---|---|---|---|---|---|---|---|
| Breast | MDA-MB-175VII | 10.84 | 10.63 | 15.84 | 15.11 | 0.95 | 0.95 | 24.17 |
|  | SKBR3 | 38.50 | 37.04 | 42.42 | 34.85 | 0.69 | 0.69 | 43.10 |
| Stomach | NCI-N87 | 31.47 | 25.28 | 38.47 | 36.43 | 0.12 | 0.36 | 35.97 |
| Pancreas | AsPC1 | 14.27 | 12.91 | 10.71 | 12.30 | 5.11 | 5.11 | 11.86 |
|  | Hs700T | 46.91 | 43.04 | 49.75 | 48.54 | 0.22 | 0.22 | 15.83 |
| Kidney | 786O | 21.12 | 13.49 | 27.69 | 18.24 | 0.64 | 2.33 | 31.16 |
| Lung | Calu3 | 10.13 | 11.03 | 10.67 | 13.22 | 0.11 | 0.11 | 9.96 |
| Ovary | SKOV3 | 55.63 | 55.97 | 60.65 | 55.49 | 1.75 | 1.75 | 33.93 |
| Prostate | PC3 | 11.32 | 10.22 | 11.22 | 10.85 | 1.59 | 1.59 | 12.49 |

The results indicate that the HDAC inhibitor vorinostat synergizes with the tetravalent DR5-Binding Molecules to enhance their cytotoxic activity on cells, including cells insensitive to tetravalent DR5-Binding Molecules alone. In particular, nine cell lines (MDA-MB-175VII, SKBR3, NCI-N87, AsPC1, Hs700T, 786O, Calu3, SKOV3 and PC3) were seen to respond to the tetravalent DR5-Binding Molecules in combination with just 1 μM vorinostat. Another three cell line (BT474, MDA-MB-361, Hs746T, HPAFII, A549, ES2 and LNCap) were seen to respond to the tetravalent DR5-Binding Molecules in combination with 10 μM vorinostat.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A multivalent DR5-Binding Molecule that is a monospecific binding molecule, capable of binding to an epitope of human DR5, wherein said multivalent DR5-Binding Molecule comprises four antigen-binding domains each capable of binding human DR5, and wherein each of said antigen-binding domains comprise three Light Chain CDR Domains ($CDR_L1$, $CDR_L2$ and $CDR_L3$) and three Heavy Chain CDR Domains ($CDR_H1$, $CDR_H2$ and $CDR_H3$) wherein:
 (i) said $CDR_L1$ Domain, $CDR_L2$ Domain, and $CDR_L3$ Domain are the Light Chain CDRs of DR5 mAb 1, and respectively comprise the amino acid sequences: SEQ ID NO:4, SEQ ID NO:5, and SEQ ID NO:6, and said $CDR_H1$ Domain, $CDR_H2$ Domain, and $CDR_H3$ Domain are the Heavy Chain CDRs of DR5 mAb 1, and respectively comprise the amino acid sequences: SEQ ID NO:9, SEQ ID NO:10, and SEQ ID NO:11; or
 (ii) said $CDR_L1$ Domain, $CDR_L2$ Domain, and $CDR_L3$ Domain are the Light Chain CDRs of DR5 mAb 2, and, respectively comprise the amino acid sequences: SEQ ID NO:14, SEQ ID NO:15, and SEQ ID NO:16, and said $CDR_H1$ Domain, $CDR_H2$ Domain, and $CDR_H3$ Domain are the Heavy Chain CDRs of DR5 mAb 2, and respectively comprise the amino acid sequences: SEQ ID NO:19, SEQ ID NO:20, and SEQ ID NO:21; or
 (iii) said $CDR_L1$ Domain, $CDR_L2$ Domain, and $CDR_L3$ Domain are the Light Chain CDRs of hDR5 mAb 2 VL-3, and, respectively comprise the amino acid sequences: SEQ ID NO:165, SEQ ID NO:15, and SEQ ID NO:16, and said $CDR_H1$ Domain, $CDR_H2$ Domain, and $CDR_H3$ Domain are the Heavy Chain CDRs of hDR5 mAb 2 VH-3, and respectively comprise the amino acid sequences: SEQ ID NO:19, SEQ ID NO:20, and SEQ ID NO:21.

2. A multivalent DR5-binding molecule having a VL Domain comprising a $CDR_L1$ Domain, a $CDR_L2$ Domain, and a $CDR_L3$ Domain, and a VH Domain comprising a $CDR_H1$ Domain, a $CDR_H2$ Domain and a $CDR_H3$ Domain, wherein:
 (i) said $CDR_L1$ Domain, $CDR_L2$ Domain, and $CDR_L3$ Domain are the Light Chain CDRs of DR5 mAb 1, and respectively comprise the amino acid sequences: SEQ ID NO:4, SEQ ID NO:5, and SEQ ID NO:6, and said $CDR_H1$ Domain, $CDR_H2$ Domain, and $CDR_H3$ Domain are the Heavy Chain CDRs of DR5 mAb 1, and respectively comprise the amino acid sequences: SEQ ID NO:9, SEQ ID NO:10, and SEQ ID NO:11; or
 (ii) said $CDR_L1$ Domain, $CDR_L2$ Domain, and $CDR_L3$ Domain are the Light Chain CDRs of DR5 mAb 2, and, respectively comprise the amino acid sequences: SEQ ID NO:14, SEQ ID NO:15, and SEQ ID NO:16, and said $CDR_H1$ Domain, $CDR_H2$ Domain, and $CDR_H3$ Domain are the Heavy Chain CDRs of DR5 mAb 2, and respectively comprise the amino acid sequences: SEQ ID NO:19, SEQ ID NO:20, and SEQ ID NO:21; or
 (iii) said $CDR_L1$ Domain, $CDR_L2$ Domain, and $CDR_L3$ Domain are the Light Chain CDRs of hDR5 mAb 2 VL-3, and, respectively comprise the amino acid sequences: SEQ ID NO: 165, SEQ ID NO:15, and SEQ ID NO:16, and said $CDR_H1$ Domain, $CDR_H2$ Domain, and $CDR_H3$ Domain are the Heavy Chain CDRs of hDR5 mAb 2 VH-3, and respectively comprise the amino acid sequences: SEQ ID NO:19, SEQ ID NO:20, and SEQ ID NO:21.

3. A composition comprising the multivalent DR5-Binding Molecule of claim 2 and an excipient.

4. The multivalent DR5-Binding Molecule of claim 2, wherein said multivalent DR5-Binding Molecule is an Fc Region-containing diabody, said diabody being a covalently bonded complex that comprises two pairs of polypeptides, wherein each pair comprises a first polypeptide chain and a second polypeptide chain.

5. The multivalent DR5-Binding Molecule of claim 4, wherein said Fc Region comprises one or more amino acid modifications that reduce the affinity of the variant Fc Region for an FcγR or stabilizes said Fc Region.

6. The multivalent DR5-Binding Molecule of claim 5, wherein said modifications comprise the substitution of L234A; L235A; or L234A and L235A, wherein said numbering is that of the EU index as in Kabat.

7. A multivalent DR5-Binding Molecule that is a bispecific binding molecule, capable of simultaneously binding to two different epitopes of human Death Receptor 5 (DR5), wherein said multivalent DR5-Binding Molecule comprises four antigen-binding domains each capable of binding human DR5, and wherein at least one of said antigen-binding domains comprises three Light Chain CDR Domains ($CDR_L1$, CDRL2 and $CDR_L3$) and three Heavy Chain CDR Domains ($CDR_H1$, $CDR_H2$ and $CDR_H3$) wherein:
 (i) said $CDR_L1$ Domain, $CDR_L2$ Domain, and $CDR_L3$ Domain are the Light Chain CDRs of DR5 mAb 1, and respectively comprise the amino acid sequences: SEQ ID NO:4, SEQ ID NO:5, and SEQ ID NO:6, and said $CDR_H1$ Domain, $CDR_H2$ Domain, and $CDR_H3$ Domain are the Heavy Chain CDRs of DR5 mAb 1, and respectively comprise the amino acid sequences: SEQ ID NO:9, SEQ ID NO:10, and SEQ ID NO:11; or (ii) said $CDR_L1$ Domain, $CDR_L2$ Domain, and $CDR_L3$ Domain are the Light Chain CDRs of DR5 mAb 2, and, respectively comprise the amino acid sequences: SEQ ID NO:14, SEQ ID NO:15, and SEQ ID NO:16, and said $CDR_H1$ Domain, $CDR_H2$ Domain, and $CDR_H3$ Domain are the Heavy Chain CDRs of DR5 mAb 2, and respectively comprise the amino acid sequences: SEQ ID NO:19, SEQ ID NO:20, and SEQ ID NO:21; or (iii) said $CDR_L1$ Domain, $CDR_L2$ Domain, and $CDR_L3$ Domain are the Light Chain CDRs of hDR5 mAb 2 VL-3, and, respectively comprise the amino acid sequences: SEQ ID NO:165, SEQ ID NO:15, and SEQ ID NO:16, and said $CDR_H1$ Domain, $CDR_H2$ Domain, and $CDR_H3$ Domain are the Heavy Chain CDRs of hDR5 mAb 2 VH-3, and respectively comprise the amino acid sequences: SEQ ID NO:19, SEQ ID NO:20, and SEQ ID NO:21.

8. The multivalent DR5-Binding Molecule of claim 1, wherein said multivalent DR5-Binding Molecule is capable of simultaneously binding to two, three, or four human DR5 polypeptides.

9. The multivalent DR5-Binding Molecule of claim 1, wherein said multivalent DR5-Binding Molecule is an Fc Region-containing diabody, said diabody being a covalently bonded complex that comprises two pairs of polypeptides, wherein each pair comprises a first polypeptide chain and a second polypeptide chain.

10. The multivalent DR5-Binding Molecule of claim 9, wherein:

(A) the first polypeptide chain comprises, in the N-terminal to C-terminal direction:
  (i) a variable light chain (VL) Domain of a monoclonal antibody capable of binding to a first DR5 epitope (VL1);
  (ii) a first peptide linker (Linker 1);
  (iii) a variable heavy chain (VH) Domain of a monoclonal antibody capable of binding to a second DR5 epitope (VH2);
  (iv) a second peptide linker (Linker 2);
  (v) a Heterodimer-Promoting Domain comprising a E-coil Domain or a K-coil Domain;
  (vi) a third peptide linker (Linker 3); and
  (vii) a polypeptide portion of an IgG Fc Region having CH2 and CH3 domains of an IgG immunoglobulin Fc Region; and (B) the second polypeptide chain comprises, in the N-terminal to C-terminal direction:
  (i) a VL Domain of a monoclonal antibody capable of binding to said second DR5 epitope (VL2);
  (ii) a first peptide linker (Linker 1);
  (iii) a VH Domain of a monoclonal antibody capable of binding to said first DR5 epitope (VH1);
  (iv) a second peptide linker (Linker 2); and
  (v) a Heterodimer-Promoting Domain comprising a E-coil Domain or a K-coil Domain, wherein said Heterodimer-Promoting Domain of said first polypeptide chain and said Heterodimer-Promoting Domain of said second polypeptide chain are not both E-coil Domains or both K-coil Domains;

and wherein:
(a) the VL1 Domain of said first polypeptide chain and the VH1 Domain of said second polypeptide chain form an Antigen-Binding Domain capable of specific binding to a first epitope of DR5;
(b) said VH2 Domain of said first polypeptide chain and said VL2 Domain of said second polypeptide chain form an Antigen-Binding Domain capable of specific binding to a second epitope of DR5; and
(c) the CH2-CH3 portions of the pair of first polypeptide chains form an IgG Fc Region.

11. The multivalent DR5-Binding Molecule of claim 10, wherein said VL2 comprises the $CDR_L1$ Domain, $CDR_L2$ Domain, and $CDR_L3$ Domain of DR5 mAb 1, respectively comprising the amino acid sequences of SEQ ID NO:4, SEQ ID NO:5, and SEQ ID NO:6, and said VH2 comprises the $CDR_H1$ Domain, $CDR_H2$ Domain, and $CDR_H3$ Domain of DR5 mAb 1, respectively comprising the amino acid sequences of SEQ ID NO:9, SEQ ID NO:10, and SEQ ID NO:11, and wherein said VL1 comprises a $CDR_L1$ Domain, a $CDR_L2$ Domain, and a $CDR_L3$ Domain, and said VH1 comprises a $CDR_H1$ Domain, a $CDR_H2$ Domain and a $CDR_H3$ Domain, wherein:

(i) said $CDR_L1$ Domain, $CDR_L2$ Domain, and $CDR_L3$ Domain of said VL1 are the Light Chain CDRs of DR5 mAb 1, and respectively comprise the amino acid sequences: SEQ ID NO:4, SEQ ID NO:5, and SEQ ID NO:6, and said $CDR_H1$ Domain, $CDR_H2$ Domain, and $CDR_H3$ Domain of said VH1 are the Heavy Chain CDRs of DR5 mAb 1, and respectively comprise the amino acid sequences: SEQ ID NO:9, SEQ ID NO:10, and SEQ ID NO:11; or (ii) said $CDR_L1$ Domain, $CDR_L2$ Domain, and $CDR_L3$ Domain of said VL1 are the Light Chain CDRs of DR5 mAb 2, and, respectively comprise the amino acid sequences: SEQ ID NO:14, SEQ ID NO:15, and SEQ ID NO:16, and said $CDR_H1$ Domain, $CDR_H2$ Domain, and $CDR_H3$ Domain of said VH1 are the Heavy Chain CDRs of DR5 mAb 2, and respectively comprise the amino acid sequences: SEQ ID NO:19, SEQ ID NO:20, and SEQ ID NO:21; or (iii) said $CDR_L1$ Domain, $CDR_L2$ Domain, and $CDR_L3$ Domain of said VL1 are the Light Chain CDRs of hDR5 mAb 2 VL-3, and, respectively comprise the amino acid sequences: SEQ ID NO:165, SEQ ID NO:15, and SEQ ID NO:16, and said $CDR_H1$ Domain, $CDR_H2$ Domain, and $CDR_H3$ Domain of said VH1 are the Heavy Chain CDRs of hDR5 mAb 2 VH-3, and respectively comprise the amino acid sequences: SEQ ID NO:19, SEQ ID NO:20, and SEQ ID NO:21.

12. The multivalent DR5-Binding Molecule of claim 10, wherein said VL2 comprises the $CDR_L1$ Domain, $CDR_L2$ Domain, and $CDR_L3$ Domain of DR5 mAb 2 or hDR5 mAb 2 VL-3, respectively comprising the amino acid sequences: SEQ ID NO:14 or 165, SEQ ID NO:15, and SEQ ID NO:16, and said VH2 comprises the $CDR_H1$ Domain, $CDR_H2$ Domain, and $CDR_H3$ Domain of DR5 mAb 2, respectively comprising the amino acid sequences: SEQ ID NO:19, SEQ ID NO:20, and SEQ ID NO:21, and wherein said VL1 comprises a $CDR_L1$ Domain, a $CDR_L2$ Domain, and a $CDR_L3$ Domain, and said VH1 comprises a $CDR_H1$ Domain, a $CDR_H2$ Domain and a $CDR_H3$ Domain, wherein:

(i) said $CDR_L1$ Domain, $CDR_L2$ Domain, and $CDR_L3$ Domain of said VL1 are the Light Chain CDRs of DR5 mAb 1, and respectively comprise the amino acid sequences: SEQ ID NO:4, SEQ ID NO:5, and SEQ ID NO:6, and said CDR$_H$1 Domain, CDR$_H$2 Domain, and CDR$_H$3 Domain of said VH1 are the Heavy Chain CDRs of DR5 mAb 1, and respectively comprise the amino acid sequences: SEQ ID NO:9, SEQ ID NO:10, and SEQ ID NO:11; or (ii) said CDR$_L$1 Domain, CDR$_L$2 Domain, and CDR$_L$3 Domain of said VL1 are the Light Chain CDRs of DR5 mAb 2, and, respectively comprise the amino acid sequences: SEQ ID NO:14, SEQ ID NO:15, and SEQ ID NO:16, and said CDR$_H$1 Domain, CDR$_H$2 Domain, and CDR$_H$3 Domain of said VH1 are the Heavy Chain CDRs of DR5 mAb 2, and respectively comprise the amino acid sequences: SEQ ID NO:19, SEQ ID NO:20, and SEQ ID NO:21; or (iii) said CDR$_L$1 Domain, CDR$_L$2 Domain, and CDR$_L$3 Domain of said VL1 are the Light Chain CDRs of DR5 hmAb 2 VL-3, and, respectively comprise the amino acid sequences: SEQ ID NO: 165, SEQ ID NO:15, and SEQ ID NO:16, and said CDR$_H$1 Domain, CDR$_H$2 Domain, and CDR$_H$3 Domain of said VH1 are the Heavy Chain CDRs of DR5 hmAb 2 VL-3, and respectively comprise the amino acid sequences: SEQ ID NO:19, SEQ ID NO:20, and SEQ ID NO:21.

13. The multivalent DR5-Binding Molecule of claim 12, wherein:
said VL1 comprises the Light Chain CDRs of DR5 mAb 1, and respectively comprise the amino acid sequences: SEQ ID NO:4, SEQ ID NO:5, and SEQ ID NO:6, and said VH1 comprises the Heavy Chain CDRs of DR5 mAb 1, and respectively comprise the amino acid sequences: SEQ ID NO:9, SEQ ID NO:10, and SEQ ID NO:11.

14. The multivalent DR5-Binding Molecule of claim 12, wherein:
said VL1 comprises the Light Chain CDRs of DR5 mAb 2 or hDR5 mAb2 VL-3, and, respectively have the amino acid sequences: SEQ ID NO:14 or 165, SEQ ID NO:15, and SEQ ID NO:16, and VH1 comprises the Heavy Chain CDRs of DR5 mAb 2, and respectively have the amino acid sequences: SEQ ID NO:19, SEQ ID NO:20, and SEQ ID NO:21.

15. The multivalent DR5-Binding Molecule of claim 10, wherein:
(i) said VL1 comprises the amino acid sequence of SEQ ID NO:3, and said VH1 comprises the amino acid sequence of SEQ ID NO:8; or
(ii) said VL1 comprises the amino acid sequence of SEQ ID NO:13, and said VH1 comprises the amino acid sequence of SEQ ID NO:18; or
(iii) said VL1 comprises the amino acid sequence of SEQ ID NO:23, and said VH1 comprises the amino acid sequence of SEQ ID NO:31; or
(iv) said VL1 comprises the amino acid sequence of SEQ ID NO:25, and said VH1 comprises the amino acid sequence of SEQ ID NO:31; or
(v) said VL1 comprises the amino acid sequence of SEQ ID NO:27, and said VH1 comprises the amino acid sequence of SEQ ID NO:31; or
(vi) said VL1 comprises the amino acid sequence of SEQ ID NO:29, and said VH1 comprises the amino acid sequence of SEQ ID NO:31.

16. The multivalent DR5-Binding Molecule of claim 10, wherein:
(i) said VL2 comprises the amino acid sequence of SEQ ID NO:3, and said VH2 comprises the amino acid sequence of SEQ ID NO:8; or
(ii) said VL2 comprises the amino acid sequence of SEQ ID NO:13, and said VH2 comprises the amino acid sequence of SEQ ID NO:18; or
(iii) said VL2 comprises the amino acid sequence of SEQ ID NO:23, and said VH2 comprises the amino acid sequence of SEQ ID NO:31; or
(iv) said VL2 comprises the amino acid sequence of SEQ ID NO:25, and said VH2 comprises the amino acid sequence of SEQ ID NO:31; or
(v) said VL2 comprises the amino acid sequence of SEQ ID NO:27, and said VH2 comprises the amino acid sequence of SEQ ID NO:31; or
(vi) said VL2 comprises the amino acid sequence of SEQ ID NO:29, and said VH2 comprises the amino acid sequence of SEQ ID NO:31.

17. The multivalent DR5-Binding Molecule of claim 10, wherein:
(i) said Linker 1 comprises the amino acid sequence of SEQ ID NO:33,
(ii) said Linker 2 comprises the amino acid sequence of SEQ ID NO:47,
(iii) said E-coil Domain comprises the amino acid sequence of SEQ ID NO:41,
(iv) said K-coil Domain comprises the amino acid sequence of SEQ ID NO:42,
(v) said Linker 3 comprises the amino acid sequence of SEQ ID NO:51, and
(vi) said CH2-CH3 domain comprises the amino acid sequence of SEQ ID NO:1 or SEQ ID NO:102, wherein the C-terminal residue is optionally included.

18. The multivalent DR5-Binding Molecule of claim 10, wherein said Fc Region comprises one or more amino acid modifications that reduce the affinity of the variant Fc Region for an FcγR or stabilizes said Fc Region.

19. The multivalent DR5-Binding Molecule of claim 18, wherein said modifications comprise the substitution of L234A; L235A; or L234A and L235A, wherein said numbering is that of the EU index as in Kabat.

20. The multivalent DR5-Binding Molecule of claim 10, wherein:
(i) said first polypeptide chain comprises the amino acid sequence of SEQ ID NO:116 or SEQ ID NO:120, and said second polypeptide chain comprises the amino acid sequence of SEQ ID NO:118; or
(ii) said first polypeptide chain comprises the amino acid sequence of SEQ ID NO:122 or SEQ ID NO:126, and said second polypeptide chain comprises the amino acid sequence of SEQ ID NO:124.

21. The multivalent DR5-Binding Molecule of claim 10, wherein said VL1 comprises the CDR$_L$1 Domain, CDR$_L$2 Domain, and CDR$_L$3 Domain of DR5 mAb 1, respectively comprising the amino acid sequences: SEQ ID NO:4, SEQ ID NO:5, and SEQ ID NO:6, and said VH1 comprises the CDR$_H$1 Domain, CDR$_H$2 Domain, and CDR$_H$3 Domain of DR5 mAb 1, respectively comprising the amino acid sequences: SEQ ID NO:9, SEQ ID NO:10, and SEQ ID NO:11, and wherein said VL2 comprises a CDR$_L$1 Domain, a CDR$_L$2 Domain, and a CDR$_L$3 Domain, and said VH2 comprises a CDR$_H$1 Domain, a CDR$_H$2 Domain and a CDR$_H$3 Domain, wherein:
(i) said CDR$_L$1 Domain, CDR$_L$2 Domain, and CDR$_L$3 Domain of said VL2 are the Light Chain CDRs of DR5 mAb 1, and respectively comprise the amino acid sequences: SEQ ID NO:4, SEQ ID NO:5, and SEQ ID NO:6, and said CDR$_H$1 Domain, CDR$_H$2 Domain, and CDR$_H$3 Domain of said VH2 are the Heavy Chain CDRs of DR5 mAb 1, and respectively comprise the amino acid sequences: SEQ ID NO:9, SEQ ID NO:10, and SEQ ID NO:11; or (ii) said $CDR_L1$ Domain, $CDR_L2$ Domain, and $CDR_L3$ Domain of said VL2 are the Light Chain CDRs of DR5 mAb 2, and, respectively comprise the amino acid sequences: SEQ ID NO:14, SEQ ID NO:15, and SEQ ID NO:16, and said $CDR_H1$ Domain, $CDR_H2$ Domain, and $CDR_H3$ Domain of said VH2 are the Heavy Chain CDRs of DR5 mAb 2, and respectively comprise the amino acid sequences: SEQ ID NO:19, SEQ ID NO:20, and SEQ ID NO:21; or (iii) said $CDR_L1$ Domain, $CDR_L2$ Domain, and $CDR_L3$ Domain of said VL2 are the Light Chain CDRs of DR5 mAb 2, and, respectively comprise the amino acid sequences: SEQ ID NO: 165, SEQ ID NO:15, and SEQ ID NO:16, and said $CDR_H1$ Domain, $CDR_H2$ Domain, and $CDR_H3$ Domain of said VH2 are the Heavy Chain CDRs of DR5 mAb 2, and respectively comprise the amino acid sequences: SEQ ID NO:19, SEQ ID NO:20, and SEQ ID NO:21.

22. The multivalent DR5-Binding Molecule of claim 10, wherein said VL1 comprises the $CDR_L1$ Domain, $CDR_L2$ Domain, and $CDR_L3$ Domain of DR5 mAb 2 or hDR5 mAb 2 VL-3, respectively comprising the amino acid sequences: SEQ ID NO:14 or 165, SEQ ID NO:15, and SEQ ID NO:16, and said VH1 comprises the $CDR_H1$ Domain, $CDR_H2$ Domain, and $CDR_H3$ Domain of DR5 mAb 2, respectively comprising the amino acid sequences: SEQ ID NO:19, SEQ ID NO:20, and SEQ ID NO:21, and wherein said VL2 comprises a $CDR_L1$ Domain, a $CDR_L2$ Domain, and a $CDR_L3$ Domain, and said VH2 comprises a $CDR_H1$ Domain, a $CDR_H2$ Domain and a $CDR_H3$ Domain, wherein:

(i) said $CDR_L1$ Domain, $CDR_L2$ Domain, and $CDR_L3$ Domain of said VL2 are the Light Chain CDRs of DR5 mAb 1, and respectively comprise the amino acid sequences: SEQ ID NO:4, SEQ ID NO:5, and SEQ ID NO:6, and said $CDR_H1$ Domain, $CDR_H2$ Domain, and $CDR_H3$ Domain of said VH2 are the Heavy Chain CDRs of DR5 mAb 1, and respectively comprise the amino acid sequences: SEQ ID NO:9, SEQ ID NO:10, and SEQ ID NO:11; or (ii) said $CDR_L1$ Domain, $CDR_L2$ Domain, and $CDR_L3$ Domain of said VL2 are the Light Chain CDRs of DR5 mAb 2, and, respectively comprise the amino acid sequences: SEQ ID NO:14, SEQ ID NO:15, and SEQ ID NO:16, and said $CDR_H1$ Domain, $CDR_H2$ Domain, and $CDR_H3$ Domain of said VH2 are the Heavy Chain CDRs of DR5 mAb 2, and respectively comprise the amino acid sequences: SEQ ID NO:19, SEQ ID NO:20, and SEQ ID NO:21; or (iii) said $CDR_L1$ Domain, $CDR_L2$ Domain, and $CDR_L3$ Domain of said VL2 are the Light Chain CDRs of hDR5 mAb 2 VL-3, and, respectively comprise the amino acid sequences: SEQ ID NO:165, SEQ ID NO:15, and SEQ ID NO:16, and said $CDR_H1$ Domain, $CDR_H2$ Domain, and $CDR_H3$ Domain of said VH2 are the Heavy Chain CDRs of hDR5 mAb 2 VH-3, and respectively comprise the amino acid sequences: SEQ ID NO:19, SEQ ID NO:20, and SEQ ID NO:21.

23. A composition comprising the multivalent DR5-Binding Molecule of claim 1 and an excipient.

24. A method of treating cancer comprising administering to an individual having a cancer a therapeutically effective amount of the multivalent DR5-Binding Molecule of claim 1.

25. The method of claim 24, wherein said molecule is administered to said patient in combination with a histone deacetylase inhibitor.

26. The method of claim 24, wherein said cancer is selected from the group consisting of: a breast cancer, a stomach cancer, a pancreatic cancer, a colorectal cancer, a kidney cancer, a lung cancer, an ovarian cancer, a liver cancer, a prostate cancer, and a skin cancer.

* * * * *